(12) United States Patent
Thibeault et al.

(10) Patent No.: US 9,428,504 B2
(45) Date of Patent: Aug. 30, 2016

(54) 7-HYDROXY-SPIROPIPIPERIDINE INDOLINYL ANTAGONISTS OF P2Y$_1$ RECEPTOR

(71) Applicant: BRISTOL-MYERS SQUIBB COMPANY, Princeton, NJ (US)

(72) Inventors: Carl Thibeault, Mascouche (CA); Charles G. Clark, Cherry Hill, NJ (US); Indawati DeLucca, Pennington, NJ (US); Carol Hui Hu, New Hope, PA (US); Yoon Jeon, Belle Mead, NJ (US); Patrick Y. S. Lam, Chadds Ford, PA (US); Jennifer X. Qiao, Princeton, NJ (US); Wu Yang, Princeton Junction, NJ (US); Yufeng Wang, North Brunswick, NJ (US); Tammy C. Wang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/418,011

(22) PCT Filed: Jul. 30, 2013

(86) PCT No.: PCT/US2013/052651
§ 371 (c)(1),
(2) Date: Jan. 28, 2015

(87) PCT Pub. No.: WO2014/022349
PCT Pub. Date: Feb. 6, 2014

(65) Prior Publication Data
US 2015/0166538 A1    Jun. 18, 2015

Related U.S. Application Data

(60) Provisional application No. 61/678,227, filed on Aug. 1, 2012.

(51) Int. Cl.
*C07D 471/10*  (2006.01)
*C07D 519/00*  (2006.01)

(52) U.S. Cl.
CPC ........... *C07D 471/10* (2013.01); *C07D 519/00* (2013.01)

(58) Field of Classification Search
CPC . C07D 471/10; C07D 401/04; C07D 409/04
USPC ............................................ 546/18; 514/278
See application file for complete search history.

(56) References Cited

U.S. PATENT DOCUMENTS 7,550,499 B2 * 6/2009 Tuerdi et al. ................. 514/409
7,674,828 B2 * 3/2010 Chao et al. .................... 514/596
7,728,008 B2   6/2010 Qiao et al.

FOREIGN PATENT DOCUMENTS

WO  WO 2007/002637  1/2007
WO  WO 2008/048981  4/2008

OTHER PUBLICATIONS

Abbracchio, M.P. et al., "Characterization of the UDP-glucose receptor (re-named here the P2Y$_{14}$ receptor) adds diversity to the P2Y receptor family", Trends in Pharmacological Sciences, vol. 24, No. 2, pp. 52-55 (2003).

Abbracchio, M.P. et al., "Purinoceptors: Are There Families of P2X and P2Y Purinoceptors?", Pharmac. Ther., vol. 64, pp. 445-475 (1994).

Anbazhagan, M. et al., "Direct Conversion of Amidoximes to Amidines via Transfer Hydrogenation", Synthesis, No. 16, pp. 2467-2469 (2003).

Baurand, A. et al., "The P2Y$_1$ Receptor as a Target for New Antithrombotic Drugs: A Review of the P2Y$_1$ Antagonist MRS-2179", Cardiovascular Drug Reviews, vol. 21, No. 1, pp. 67-76 (2003).

Boeynaems, J.-M. et al., "Overview of P2Y Receptors as Therapeutic Targets", Drug Development Research, vol. 52, pp. 187-189 (2001).

Boger, D.L. et al., "Benzylic Hydroperoxide Rearrangement: Observations on a Viable and Convenient Alternative to the Baeyer-Villiger Rearrangement", J. Org. Chem., vol. 51, No. 26, pp. 5436-5439 (1986).

Bundgaard, H., Chapter 5: "Design and Application of Prodrugs", A Textbook of Drug Design and Development, pp. 113-191, Krogsgaard-Larsen, P. et al,, eds., Harwood Academic Publishers, publ. (1991).

(Continued)

*Primary Examiner* — Rita Desai
(74) *Attorney, Agent, or Firm* — Barry H. Jacobsen

(57) ABSTRACT

The present invention provides compounds of Formula (I): as defined in the specification and compositions comprising any of such novel compounds. These compounds are antagonists of P2Y$_1$ receptor and may be used as medicaments in the treatment and/or prophylaxis of thromboembolic disorders.

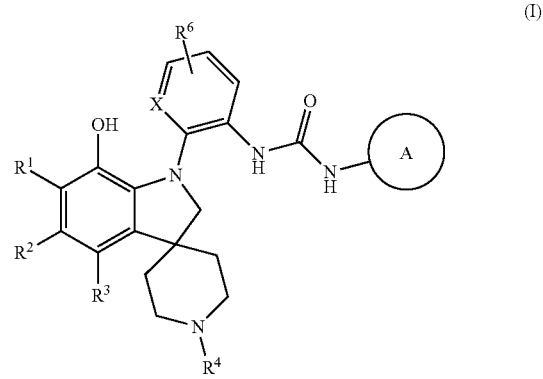

2 Claims, No Drawings

(56) References Cited

OTHER PUBLICATIONS

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

Burnstock, G. et al., "P2 Purinergic Receptors: Modulation of Cell Function and Therapeutic Potential", The Journal of Pharmacology and Experimental Therapeutics, vol. 295, No. 3, pp. 862-869 (2000).

Daniel, J.L. et al., "Molecular Basis for ADP-induced Platelet Activation: I. Evidence for Three Distinct ADP Receptors on Human Platelets", The Journal of Biological Chemistry, vol. 273, No. 4, pp. 2024-2029 (1998).

Fabre, J.-E. et al., "Decreased platelet aggregation, increased bleeding time and resistance to thromboembolism in $P2Y_1$-deficient mice", Nature Medicine, vol. 5, No. 10, pp. 1199-1202 (1999).

Gachet, C. et al., "The platelet P2 receptors in arterial thrombosis", Blood Cell, Molecules and Diseases, vol. 36, pp. 223-227 (2006).

Gennaro, A.R., ed., Remington's Pharmaceutical Sciences, 18th Edition, pp. xv-xvi, Mack Publishing Company, publ. (1990).

Greene, T.W. et al., Protective Groups in Organic Synthesis, Second Edition, pp. ix-x, John Wiley & Sons, Inc., publ. (1991).

Greene, T.W. et al., Protective Groups in Organic Synthesis, Third Edition, pp. xi-xii, John Wiley & Sons, Inc., publ. (1999).

Hassan, J. et al., "Aryl-Aryl Bond Formation One Century after the Discovery of the Ullmann Reaction", Chemical Reviews, vol. 102, No. 5, pp. 1359-1469 (2002).

Hechler, B. et al., "MRS2500 [2-Iodo-$N^6$-methyl-($N$)-methanocarba-2'-deoxyadenosine-3',5'-bisphosphate], a Potent, Selective, and Stable Antagonist of the Platelet $P2Y_1$ Receptor with Strong Antithrombotic Activity in Mice", The Journal of Pharmacology and Experimental Therapeutics, vol. 316, No. 2, pp. 556-563 (2006).

Hechler, B. et al., "The $P2Y_1$ receptor, necessary but not sufficient to support full ADP-induced platelet aggregation, is not the target of the drug clopidogrel", British Journal of Haematology, vol. 103, pp. 858-866 (1998).

Himaya, T., Chapter 10: Organosilicon Compounds in Cross-coupling Reactions, Metal-catalyzed Cross-coupling Reactions, p. 421, Diederich, F. et al., eds., Wiley-VCH Verlag GmbH, publ. (1998).

Hu, C.H. et al., "Discovery of small molecule $P2Y_1$ antagonists: Amino-heterocycles as urea mimetics in the spiropiperidine indolinyl series", Abstracts of Papers, 244th ACS National Meeting & Exposition, Philadelphia, PA, Aug. 19-23, 2012, No. MEDI-127 (2012).

Ishiyama, K. et al., "Convenient synthesis of 7-hydroxyindole", Tetrahedron Letters, vol. 46, pp. 1021-1022 (2005).

Janssens, R. et al., "Cloning and Tissue Distribution of the Human $P2Y_1$ Receptor", Biochemical and Biophysical Research Communications, vol. 221, No. 3, pp. 588-593 (1996).

Jeon, Y.T. et al., "Identification of BMS-816106, potent $P2Y_1$ antagonist as a novel antiplatelet agent", Abstracts of Papers, 244th ACS National Meeting & Exposition, Philadelphia, PA, Aug. 19-23, 2012, No. MEDI-128 (2012).

Jin, J. et al., "Coactivation of two different G protein-coupled receptors is essential for ADP-induced platelet aggregation", Proc. Natl. Acad. Sci. USA, vol. 95, pp. 8070-8074 (1998).

Jin, J. et al., "Molecular Basis for ADP-induced Platelet Activation: II. The P2Y1 Receptor Mediates ADP-Induced Intracellular Calcium Mobilization and Shape Change in Platelets", The Journal of Biological Chemistry, vol. 273, No. 4, pp. 2030-2034 (1998).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kihara, Y. et al., "Oxidative Heterocyclization Using Diethyl Azodicarboxylate", Synthesis, pp. 1020-1023 (1990).

Lenain, N. et al., "Inhibition of localized thrombosis in $P2Y_1$-deficient mice and rodents treated with MRS2179, a $P2Y_1$ receptor antagonist", Journal of Thrombosis and Haemostasis, vol. 1, pp. 1144-1149 (2003).

Léon, C. et al., "Key Role of the $P2Y_1$ Receptor in Tissue Factor-Induced Thrombin-Dependent Acute Thromboembolism: Studies in $P2Y_1$-Knockout Mice and Mice Treated with a $P2Y_1$ Antagonist", Circulation, vol. 103, pp. 718-723 (2001).

Ley, S.V. et al., "Modern Synthetic Methods for Copper-Mediated C(aryl)-O, C(aryl)-N, and C(aryl)-S Bond Formation", Angew. Chem. Int. Ed., vol. 42, pp. 5400-5449 (2003).

Liu, P. et al., "Synthesis of heterocycles via ligand-free palladium catalyzed reductive Heck cyclization", Tetrahedron Letters, vol. 48, pp. 2307-2310 (2007).

Miyaura, N. et al., "Palladium-Catalyzed Cross-Coupling Reactions of Organoboron Compounds", Chemistry Reviews, vol. 95, No. 7, pp. 2457-2483 (1995).

NCBI PubChem, CID 60150614—Compound Summary (Sep. 10, 2012).

Negishi, E., "Palladium- or Nickel-Catalyzed Cross Coupling. A New Selective Method for Carbon-Carbon Bond Formation", Acc. Chem. Res., vol. 15, pp. 340-348 (1982).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Nörenberg, W. et al., "Characterization and possible function of adenosine 5'-triphosphate receptors in activated rat microglia", Br. J. Pharmacol., vol. 111, pp. 942-950 (1994).

Qiao, J.X. et al., "Copper-Promoted Carbon-Heteroatom Bond Cross-Coupling with Boronic Acids and Derivatives", Synthesis, No. 6, pp. 829-856 (2011).

Qiao, J.X. et al., "Transformation of Anionically Activated Trifluoromethyl Groups to Heterocycles under Mild Aqueous Conditions", Organic Letters, vol. 13, No. 7, pp. 1804-1807 (2011).

Salter, M.W. et al., "ATP Causes Release of Intracellular $Ca^{2+}$ via the Phospholipase $C\beta/IP_3$ Pathway in Astrocytes from the Dorsal Spinal Cord", The Journal of Neuroscience, vol. 15, No. 4, pp. 2961-2971 (1995).

Savi, P. et al., "Role of P2Y1 purinoceptor in ADP-induced platelet activation", FEBS Letters, vol. 422, pp. 291-295 (1998).

Schumacher, W.A. et al., "Biomarker Optimization to Track the Antithrombotic and Hemostatic Effects of Clopidogrel in Rats", The Journal of Pharmacology and Experimental Therapeutics, vol. 322, No. 1, pp. 369-377 (2007).

Schwarz, O. et al., "Synthesis and biological evaluation of new antimalarial isonitriles related to marine diterpenoids", Tetrahedron Letters, vol. 43, pp. 1009-1013 (2002).

Semmelhack, M.F., ed., Comprehensive Organic Synthesis: Selectivity, Strategy & Efficiency in Modern Organic Chemistry, vol. 4: "Additions to and Substitutions at C-C π-Bonds", pp. v-vi, Pergamon Press, Inc., publ (1991).

Suzuki, A., "Synthetic studies via the cross-coupling reaction of organoboron derivatives with organic halides", Pure & App. Chem., vol. 63, No. 3, pp. 419-422 (1991).

Testa, B. et al., Hydrolysis in Drug and Prodrug Metabolism: Chemistry, Biochemistry, and Enzymology, pp. xi-xx, Wiley-VCH GmbH & Co., publ. (2003).

White, M.M. et al., Platelet Protocols: Research and Clinical Laboratory Procedures, pp. v-vii, Academic Press, publ. (1999).

Widder, K.J. et al., eds., Section III: "Prodrugs", Methods in Enzymology, vol. 112, pp. 309-396, Academic Press, Inc., publ. (1985).

Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).

Wong, P.C. et al., "Nonpeptide Factor Xa Inhibitors: II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).

(56) References Cited

OTHER PUBLICATIONS

Wong, P.C. et al., "Nonpeptide Factor Xa Inhibitors: III: Effects of DPC423, an Orally-Active Pyrazole Antithrombotic Agent, on Arterial Thrombosis in Rabbits", The Journal of Pharmacology and Experimental Therapeutics, vol. 303, No. 3, pp. 993-1000 (2002).

Yamada, Y. et al., "Preparation of 7-Halo-indoles by Thallation of N-Formylindoline and Their Attempted Use for Synthesis of the Right-Hand Segment of Chloropeptin", Chem. Pharm. Bull., vol. 54, No. 6, pp. 788-794 (2006).

* cited by examiner

7-HYDROXY-SPIROPIPIPERIDINE INDOLINYL ANTAGONISTS OF P2Y₁ RECEPTOR

The present application is a 371 application of International Application No. PCT/US2013/052651 filed on Jul. 30, 2013, which claims priority benefit of U.S. provisional application Ser. No. 61/678,227, filed Aug. 1, 2012; each of which is fully incorporated by reference herein.

FIELD OF THE INVENTION

The present invention provides novel 7-hydroxy-spiropiperidine indolinyl compounds, and analogues thereof, which are selective inhibitors of the human $P2Y_1$ receptor. The invention also provides for various pharmaceutical compositions of the same and methods for treating diseases responsive to modulation of $P2Y_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b, and A3), which bind to and are activated by the nucleoside adenosine, and the P2 receptors, which comprise a second, more diverse class of receptors which are activated by a wide variety of nucleotides including ATP, ADP, UTP, and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; $P2Y_1$, $P2Y_2$, $P2Y_4$, $P2Y_6$, $P2Y_{11}$, $P2Y_{12}$, and $P2Y_{13}$ (Boeynaems, J. M. et al., *Drug Development Research*, 52:187-189 (2001)). In addition, an eighth receptor, $P2Y_{14}$, has been considered by some to be a member of this class although it does not respond to ribosylated nucleotides and is activated by UDP-glucose (Abbracchio, M. P. et al., *Trends Pharmacol. Sci.*, 24:52-55 (2003)).

Several studies have suggested that modulators of specific members of the P2Y family of receptors could have therapeutic potential for the treatment of a variety of disorders (for review see Burnstock, G. et al., *J. Pharm. Exp. Ther.*, 295:862-869 (2000)), including diabetes, cancer, CF, and treatment of ischemia-reperfusion injury (Abbracchio M. P. et al., *Pharmacy. Ther.*, 64:445-475 (1994)). $P2Y_1$ receptors, almost ubiquitous among human organs (Janssens, R. et al., *Biochem. Biophys. Res. Comm.*, 221:588-593 (1996)) have been identified on microglia (Norenberg, W. et al., *Br. J. Pharmacol.*, 111:942-950 (1994)) and on astrocytes (Salter, M. W. et al., *J. Neurosc.*, 152961-2971 (1995)), Extracellular ATP activates microglial and/or astrocytes via P2Y receptors and leads directly to the release of inflammatory mediators, Microglia and astrocytes are believed to Play a role in the progression of Alzheimer's disease and other CNS inflammatory disorders such as stroke and multiple sclerosis.

Two members of the P2Y family, $P2Y_1$ and $P2Y_{12}$, are of particular interest as they have now both been shown to act as important receptors for ADP in platelets (Jin, J. et al., *Proc. Natl. Acad. Sci.*, 95:8070-8074 (1998)). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both $P2Y_1$ and $P2Y_{12}$ to produce two separate intracellular signals which synergize together to produce complete platelet activation (Jin, J. et al., *J. Biol. Chem.*, 273:2030-2034 (1998)). The first signal arises from ADP driven activation of the $P2Y_1$ receptor and can most easily be tracked by measuring the transitory increase in intracellular free $Ca^{+2}$. This signal appears to mediate the initial shape change reaction and to initiate the process of platelet activation. The second signal appears to be derived from ADP activation of the $P2Y_{12}$ receptor and serves to consolidate the process and produce an irreversible platelet aggregate. Using three structurally related but distinct inhibitors of $P2Y_1$ (A3P5P, A3P5PS, and A2P5P), Daniel, J. L. et al. (*J. Biol. Chem.*, 273:2024-2029 (1998)), Savi, P. et al. (*FEBS Letters*, 422:291-295 (1998)), and Hechler, B. et al. (*Br. J. Haematol.*, 103:858-866 (1998)) were the first to publish the observation that the inhibition of $P2Y_1$ activity alone could block ADP-driven aggregation independently of the $P2Y_{12}$ receptor. Although inhibition of platelet reactivity is often thought of as firm evidence of an anti-thrombotic activity, these antagonists lacked the necessary pharmacological properties for in vivo study. The first direct demonstration that inhibition of $P2Y_1$ activity could lead to an anti-thrombotic effect in vivo was reported by Leon, C. et al., *Circulation*, 103:718-723 (2001), in a model of thromboplastin induced thromboembolism using both a $P2Y_1$ knock-out mouse and the $P2Y_1$ antagonist MRS-2179 (Baurand, A. et al., *Cardiovascular Drug Reviews*, 21:67-76 (2003)). These results were subsequently extended to include the inhibition of both venous and arterial thrombosis in the rat (Lenain, N. et al., *J. Thromb. Haemost.*, 1:1144-1149 (2003)) and the confirmation of the phenotype of the $P2Y_1$ knock-out mouse in a second laboratory using an independently derived animal (Fabre, J-E. et al., *Nature Medicine*, 5:1199-1202 (1999)). These studies highlighted the need for more potent and selective $P2Y_1$ antagonists and recently, using the $P2Y_1$ antagonist MRS-2500 (Hechler, B. et al., *J. Pharmacol Exp. Ther.*, 316:556-563 (2006)) succeeded in demonstrating strong antithrombotic activity for a selective $P2Y_1$ antagonist in the mouse. Taken together, these data suggest that the discovery of novel $P2Y_1$ antagonists with improved pharmaceutical characteristics could have significant utility in the treatment of a variety of thrombotic or thromboembolic disorders (see Gachet, C. et al., *Blood Cell, Molecules and Disease*, 36:223-227 (2006) for a recent review).

U.S. Patent Publication No. 2005/0261244 A1 published Nov. 24, 2005 discloses a series of $P2Y_1$ antagonists including spiropiperidine indolinyl of the following formula:

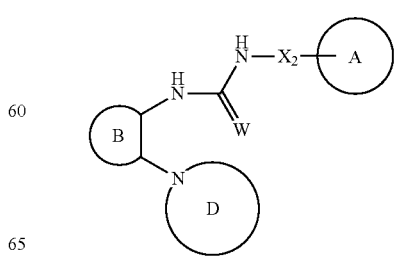

wherein ring A is $C_{6-10}$ aryl substituted with 0-5 $R^1$, or a 5- to 10-membered heterocycle comprising carbon atoms and 1-4 heteroatoms selected from N, $NR^{11}$, O, and $S(O)_p$, wherein said heterocycle is substituted with 0-5 $R^1$;

ring B is phenyl or naphthyl substituted with 0-4 $R^7$, or a 5- to 10-membered heteroaryl comprising carbon atoms and 1-4 ring heteroatoms selected from N, $NR^{11}$, $S(O)_p$, and O, wherein said heteroaryl is substituted with 0-4 $R^7$;

one of the ring D groups is

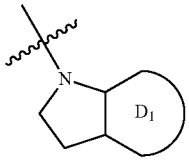

substituted with 0-5 $R^{6a}$; wherein $D_1$ is a 5- to 7-membered carbocycle or a 5- to 6-membered heterocycle comprising carbon atoms and 0-3 ring heteroatoms selected from N, $NR^{11}$, O, and $S(O)_p$, and 0-2 carbonyl groups, and 0-3 double bonds;

W is O or S;

$X_2$ is $-(CR^{16}R^{17})_s-$, or $-(CR^{16}R^{17})_tC(O)(CR^{16}R^{17})_r-$;

$R^{6a}$ is a variable defined therein;

alternatively, when two $R^{6a}$ groups are attached to the same carbon atom or silicon atom, together with the carbon atom or silicon atom to which they are attached, they form a 3- to 7-membered carbocyclic or heterocyclic ring comprising carbon atoms and 0-3 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$; and other variables are defined therein.

It is desirable to find new compounds with improved pharmacological characteristics compared with known $P2Y_1$ antagonists. For example, it is desirable to find new compounds with improved antiplatelet activity in the platelet aggregation functional assay and good binding affinity in the $P2Y_1$ binding assay.

SUMMARY OF THE INVENTION

The present disclosure provides novel 7-hydroxy-spiropiperidine indolinyl compounds and their analogues, including stereoisomers, tautomers, pharmaceutically acceptable salts, or solvates thereof, which are useful as selective inhibitors of the $P2Y_1$ receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in therapy.

The compounds of the invention may be used for the manufacture of a medicament for the treatment and/or prophylaxis of thromboembolic disorders.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

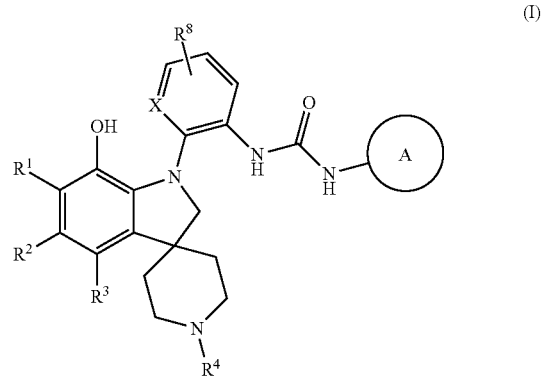

or a stereoisomer, a tautomer, a pharmaceutically acceptable salt, a solvate, or a prodrug thereof, wherein:

X is independently CH or N;

ring A is independently selected from $C_{3-6}$ carbocycle substituted with 0-3 $R^5$ and a heterocycle substituted with 0-2 $R^5$; wherein said heterocycle is selected from thienyl, thiazolyl, thiadiazolyl, pyridyl,

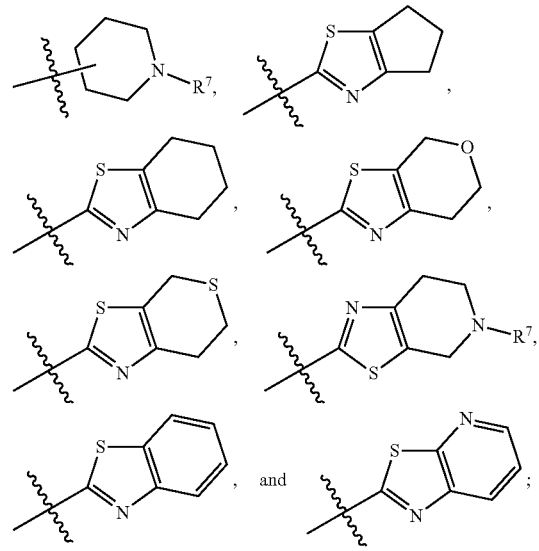

$R^1$ is independently selected from H, halogen and OH;
$R^2$ is independently H or halogen;
$R^3$ is independently selected from H, halogen, $C_{1-6}$ haloalkyl, $C_{1-4}$ haloalkoxy, CN, $C_{1-4}$ alkoxy, $C_{1-4}$ alkylthio, CHO, $CO_2(C_{1-4}$ alkyl), $SO_2N(C_{1-4}$ alkyl$)_2$, and a ring moiety substituted with 0-3 $R^6$ and selected from the group consisting of $C_{3-6}$ cycloalkyl, phenyl, thienyl, oxazolyl, isoxazolyl, thiazolyl, 1-$(C_{1-4}$ alkyl)-pyrazolyl, 1-Ph-pyrazolyl, oxadiazolyl, pyridyl, pyrimidinyl, pyrazinyl, benzoxazolyl, benzothiazolyl, 1-($C_{1-4}$ alkyl)-benzimidazolyl,

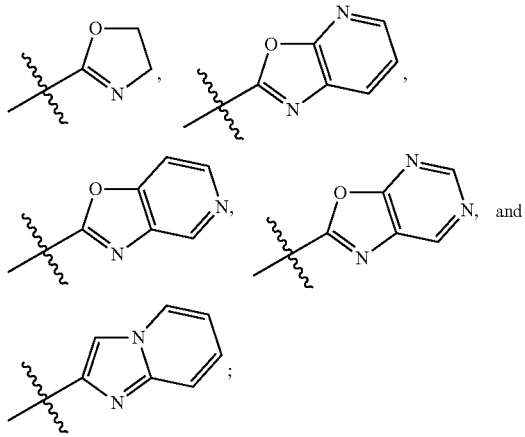

$R^4$ is independently $C_{2-6}$ alkyl substituted with 0-3 F atoms;

$R^5$ is, independently at each occurrence, selected from H, halogen, $C_{1-6}$ alkyl, $C_{1-6}$ alkoxy, $C_{1-6}$ alkylthio, $C_{1-6}$ haloalkyl, $C_{1-6}$ haloalkoxy, $CO_2(C_{1-4}$ alkyl), $NO_2$, and

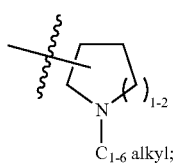

$R^6$ is, independently at each occurrence, selected from halogen, $C_{1-6}$ alkyl, $C_{2-6}$ alkenyl, $C_{1-6}$ haloalkyl, $C_{1-4}$ alkoxy, $C_{1-4}$ haloalkoxy, $C_{1-4}$ alkylthio, $CH_2OH$, CN, $CO_2(C_{1-4}$ alkyl), $N(C_{1-4}$ alkyl)$_2$, $NH(C_{1-4}$ alkyl), $CH_2N(C_{1-4}$ alkyl)$_2$, and morpholinylmethyl;

$R^7$ is independently selected from $C_{1-6}$ alkyl, $C_{1-6}$ haloalkyl, $CO(C_{1-4}$ alkyl), —$(CH_2)_{1-2}$—$C_{3-6}$ cycloalkyl, and $COCF_3$; and $R^8$ is independently selected from H, halogen and CN.

In a second aspect, the present invention includes a compound of Formula (I) or a stereoisomer, a tautomer, a pharmaceutically acceptable salt, or a solvate thereof, within the scope of the first aspect, wherein:

$R^3$ is independently selected from H, halogen, $C_{1-6}$ haloalkyl, CN, $CO_2(C_{1-4}$ alkyl), $SO_2N(C_{1-4}$ alkyl)$_2$, and a ring moiety substituted with 0-2 $R^6$ and selected from phenyl, pyridyl and benzothiazolyl;

$R^6$ is, independently at each occurrence, selected from H, halogen, $C_{1-6}$ alkyl, $C_{1-6}$ haloalkyl, CN, $CO_2(C_{1-4}$ alkyl) and $N(C_{1-4}$ alkyl)$_2$; and $R^7$ is independently selected from $C_{1-6}$ alkyl, $C_{1-6}$ haloalkyl, $CO(C_{1-4}$ alkyl), and $COCF_3$.

In a third aspect, the present invention includes a compound of Formula (I) or a stereoisomer, a tautomer, a pharmaceutically acceptable salt, or a solvate thereof, within the scope of the first or second aspect, wherein:

ring A is independently selected from

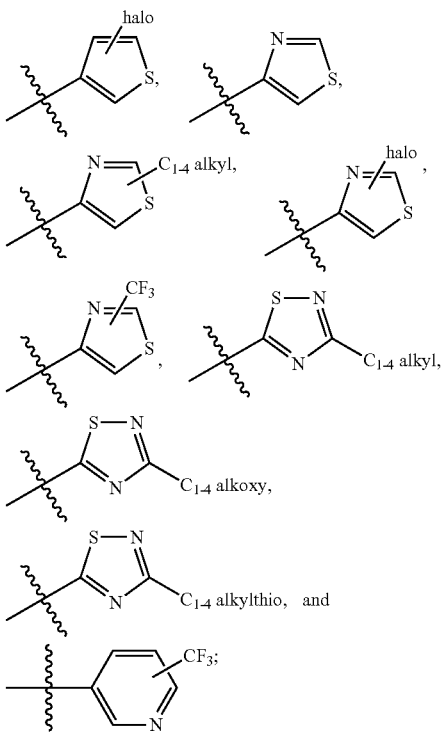

$R^1$ is independently H or halogen;
$R^2$ is independently H or halogen;
$R^3$ is independently selected from halogen, $CF_3$, CN, 4-halo-Ph, 6-$CF_3$-pyrid-3-yl, 6-$C_{1-4}$ alkoxy-bezothiazol-2-yl, 4-halo-bezothiazol-2-yl, 5-halo-bezothiazol-2-yl, 6-halo-bezothiazol-2-yl, and 7-halo-bezothiazol-2-yl;
$R^4$ is independently $C_{2-6}$ alkyl; and
$R^8$ is independently selected from H, halogen and CN.

In a fourth aspect, the present invention includes a compound of Formula (I) or a stereoisomer, a tautomer, a pharmaceutically acceptable salt, or a solvate thereof, within the scope of the first, second or third aspect, wherein:

$R^3$ is independently halogen or $CF_3$; and
$R^8$ is independently H or halogen.

In a fifth aspect, the present invention includes a compound of Formula (I) or (I), or a stereoisomer, a tautomer, a pharmaceutically acceptable salt, or a solvate thereof, within the scope of the first, second, third or fourth aspect, wherein:

ring A is independently selected from

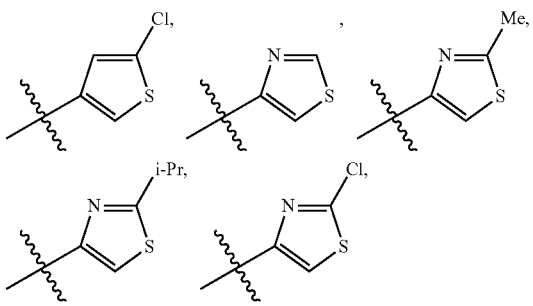

-continued

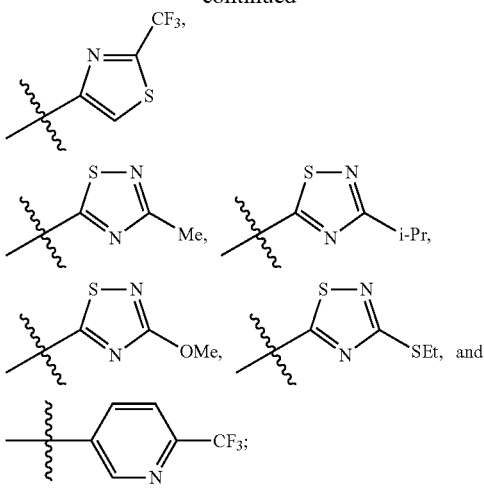

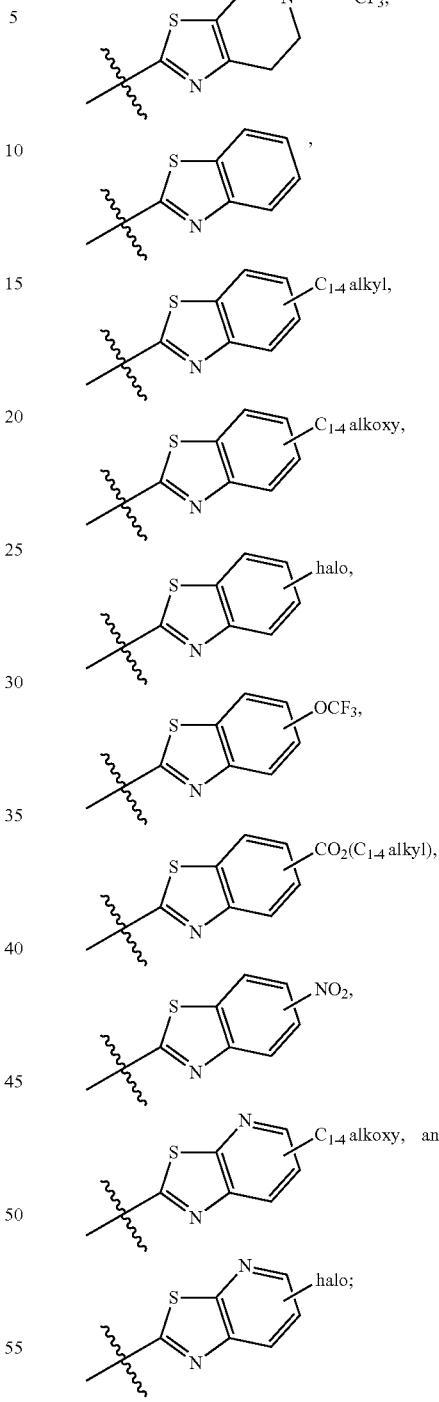

$R^1$ is independently H or F;
$R^2$ is independently H or F;
$R^3$ is independently selected from F, Cl and $CF_3$;
$R^4$ is independently i-Bu or neopentyl; and
$R^8$ is H.

In a sixth aspect, the present invention includes a compound of Formula (I), or a stereoisomer, a tautomer, a pharmaceutically acceptable salt, or a solvate thereof, within the scope of the first or second aspect, wherein:

ring A is independently selected from

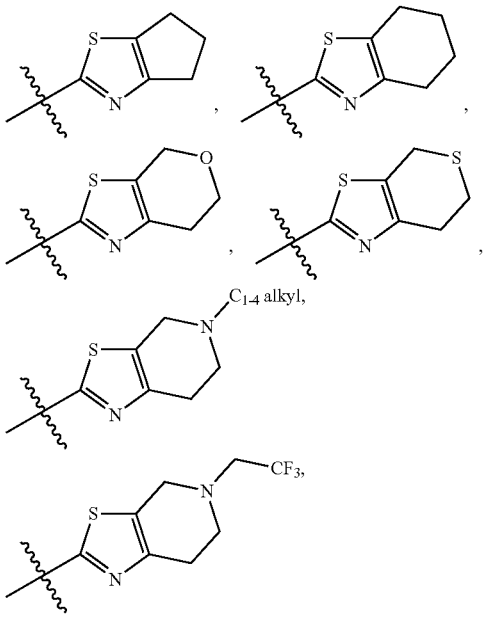

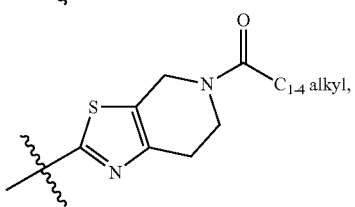

$R^1$ is independently H or halogen;
$R^2$ is independently H or halogen;
$R^3$ is independently selected from H, halogen, $CF_3$, CN, $CO_2(C_{1-4}$ alkyl), $SO_2N(C_{1-4}$ alkyl$)_2$, 4-halo-Ph, 6-$CF_3$-pyrid-3-yl, 6-$C_{1-4}$ alkoxy-bezothiazol-2-yl, 4-halo-bezothiazol-2-yl, 5-halo-bezothiazol-2-yl, 6-halo-bezothiazol-2-yl, 7-halo-bezothiazol-2-yl, and 5-$CF_3$-bezothiazol-2-yl;
$R^4$ is independently $C_{2-6}$ alkyl; and
$R^8$ is independently selected from H, halogen and CN.

In a seventh aspect, the present invention includes a compound of Formula (I), or a stereoisomer, a tautomer, a pharmaceutically acceptable salt, or a solvate thereof, within the scope of the first, second or sixth aspect, wherein:

ring A is independently selected from

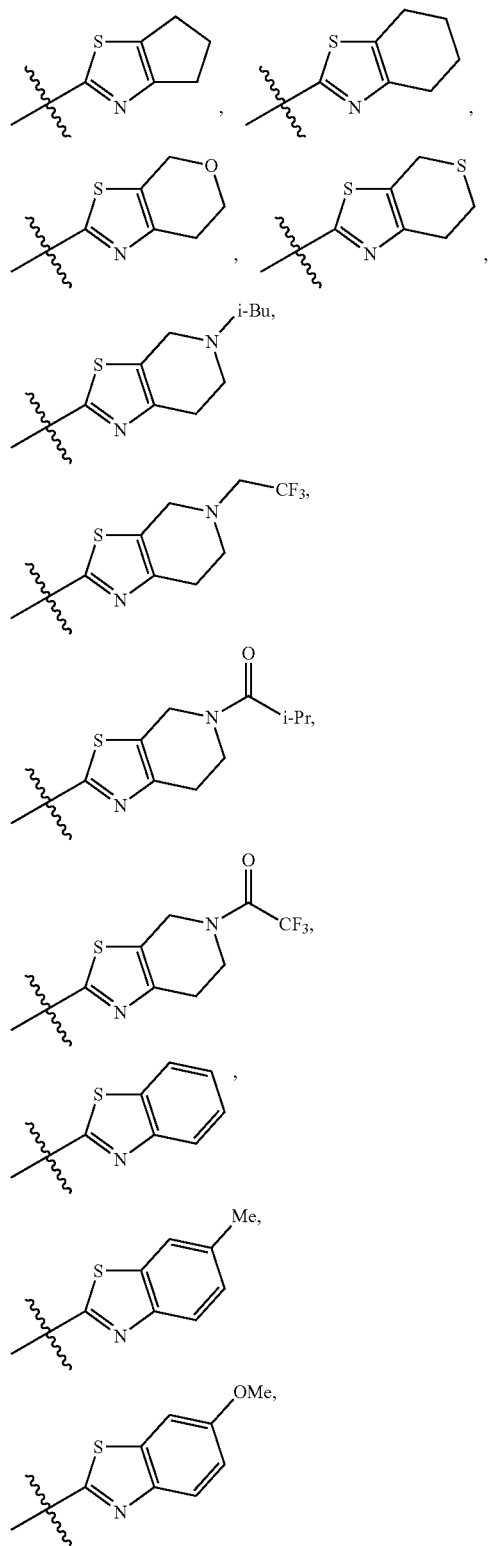

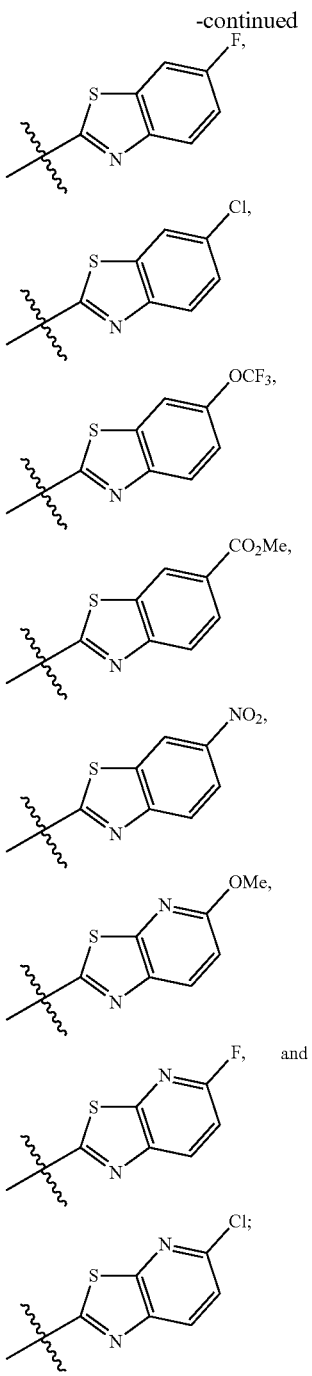

$R^1$ is independently H or F;

$R^2$ is independently H or F;

$R^3$ is independently selected from H, F, Cl, CF$_3$, CN, CO$_2$Me, SO$_2$N(Et)$_2$, 4-F-Ph, 4-Cl-Ph, 6-CF$_3$-pyrid-3-yl, 6-OMe-bezothiazol-2-yl, 5-F-bezothiazol-2-yl, 6-F-bezothiazol-2-yl, 4-Cl-bezothiazol-2-yl, 5-Cl-bezothiazol-2-yl, 6-Cl-bezothiazol-2-yl, 7-Cl-bezothiazol-2-yl, and 5-CF$_3$-bezothiazol-2-yl;

$R^4$ is independently i-Bu or neopentyl; and $R^6$ is independently selected from H, F and CN.

In an eighth aspect, the present invention includes a compound of Formula (II):

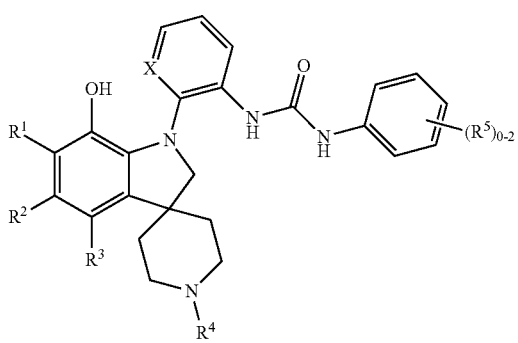

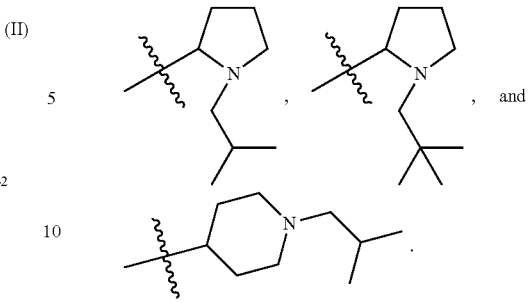

or a stereoisomer, a tautomer, a pharmaceutically acceptable salt, or a solvate thereof, within the scope of the first or second aspect, wherein:

X is independently CH or N;

$R^1$ is independently H or halogen;

$R^2$ is independently H or halogen;

$R^3$ is, independently selected from H, halogen, $C_{1-6}$ alkyl, $C_{1-6}$ haloalkyl, CN, $CO_2(C_{1-4}$ alkyl), $SO_2N(C_{1-4}$ alkyl)$_2$, 4-halo-Ph, 4-$CF_3$-Ph, 6-$CF_3$-pyrid-3-yl, 6-$C_{1-4}$ alkoxy-bezothiazol-2-yl, 4-halo-bezothiazol-2-yl, 5-halo-bezothiazol-2-yl, 6-halo-bezothiazol-2-yl, 7-halo-bezothiazol-2-yl, and 6-$N(C_{1-4}$ alkyl)$_2$-bezothiazol-2-yl;

$R^4$ is independently $C_{2-6}$ alkyl; and $R^5$ is, independently at each occurrence, selected from H, halogen, $C_{1-6}$ alkyl, $C_{1-6}$ alkoxy, $C_{1-6}$ haloalkyl, $C_{1-6}$ haloalkoxy, and

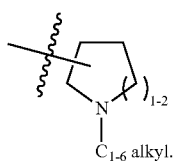

In a ninth aspect, the present invention includes a compound of Formula (II), or a stereoisomer, a tautomer, a pharmaceutically acceptable salt, or a solvate thereof, within the scope of the first, second or eighth aspect, wherein:

$R^1$ is independently H or F;

$R^2$ is independently H or F;

$R^3$ is independently selected from H, F, Cl, $CF_3$, CN, $CO_2Me$, $SO_2N(Me)_2$, $SO_2N(Et)_2$, 4-F-Ph, 4-Cl-Ph, 4-$CF_3$-Ph, 6-$CF_3$-pyrid-3-yl, 6-OMe-bezothiazol-2-yl, 5-F-bezothiazol-2-yl, 6-F-bezothiazol-2-yl, 4-Cl-bezothiazol-2-yl, 5-Cl-bezothiazol-2-yl, 6-Cl-bezothiazol-2-yl, 7-Cl-bezothiazol-2-yl, 6-Br-bezothiazol-2-yl, and 6-$N(Me)_2$-bezothiazol-2-yl;

$R^4$ is independently selected from i-Pr, i-Bu and neopentyl; and $R^5$ is, independently at each occurrence, selected from H, F, Me, t-Bu, $CF_3$, $OCHF_2$, $OCF_3$, In a tenth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the tenth aspect.

In another embodiment, the compounds of the present invention have in vitro human antiplatelet activity in the platelet aggregation assay: PA $IC_{50}$ values ≤40 μM with 10 μM ADP.

In another embodiment, the compounds of the present invention have in vitro human antiplatelet activity in the platelet aggregation assay: PA $IC_{50}$ values ≤5 μM with 10 μM ADP.

In another embodiment, the compounds of the present invention have in vitro human antiplatelet activity in the platelet aggregation assay: PA $IC_{50}$ values ≤1 μM with 10 μM ADP.

In another embodiment, the compounds of the present invention have in vitro human antiplatelet activity in the platelet aggregation assay: PA $IC_{50}$ values ≤0.2 μM with 10 μM ADP.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the modulation of platelet reactivity comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In one embodiment, the present invention provides a method for the treatment and/or prophylaxis of thromboembolic disorders, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a compound of the present invention for use in therapy.

In another embodiment, the present invention provides a compound of the present invention for use in therapy for the treatment and/or prophylaxis of thromboembolic disorders.

In another embodiment, the present invention also provides the use of a compound of the present invention for the manufacture of a medicament for the treatment and/or prophylaxis of thromboembolic disorders.

In another embodiment, the present invention provides a method for the treatment and/or prophylaxis of thromboembolic disorders, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of thromboembolic disorders.

The compounds of the present invention may be employed in combination with additional therapeutic agent(s) selected from one or more, preferably one to three, of the following therapeutic agents: potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In another embodiment, additional therapeutic agent(s) used in combined pharmaceutical compositions or combined methods or combined uses, are selected from one or more, preferably one to three, of the following therapeutic agents in treating a thromboembolic disorder: an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent.

In another embodiment, additional therapeutic agent(s) used in combined pharmaceutical compositions or combined methods or combined uses, are selected from one or more, preferably one to three, of the following therapeutic agents in treating a thromboembolic disorder: warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, apixaban, rivaroxaban, edoxaban, dabigatran, disulfatohirudin, tissue plasminogen activator, modified tissue plasminogen activator, anistreplase, urokinase, and streptokinase.

In another embodiment, additional therapeutic agent(s) used in combined pharmaceutical compositions or combined methods or combined uses, are selected from one or more, preferably one to three, of the following therapeutic agents in treating a thromboembolic disorder: an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_{12}$ antagonists, thromboxane receptor antagonists, and aspirin.

In another embodiment, the additional therapeutic agent(s) are an anti-platelet agent or a combination thereof.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" (or alkylene), is intended to include $C_1$, $C_2$, $C_3$, $C_4$, $C_5$, and $C_6$ alkyl groups. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "counter ion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112:309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.,* 8:1-38 (1992);

Nielsen, N. M. et al., *J. Pharm. Sci.,* 77:285 (1988); and

Kakeya, N. et al., *Chem. Pharm. Bull.,* 32:692 (1984).

Compounds containing a carboxy group can form physiologically hydrolyzable esters that serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
t-BuOH tert-butyl alcohol
Ph phenyl
4-NO$_2$Ph 4-nitrophenyl
Bn benzyl
MeOH methanol
EtOH ethanol
i-PrOH or IPA isopropanol
AcOH or HOAc acetic acid
2MeS-ADP 2 methylthio adenosine diphosphate
cDNA complimentary DNA
DMEM Dulbecco's modified Eagle media
FBS Fetal Bovine Serum
SCX Strong Cation Exchanger
EDC (or EDC.HCl) or 3-ethyl-3'-(dimethylamino)propylcarbodiimide hydrochloride EDCI (or EDCI.HCl) (or 1-(3-dimethylaminopropyl)-3-ethylcarbodiimide or EDAC hydrochloride)
EtOAc ethyl acetate
Et$_2$O diethyl ether
Ac$_2$O acetic anhydride
AIBN azobisisobutyronitrile
AlCl$_3$ aluminum chloride
BBr$_3$ boron tribromide
BCl$_3$ boron trichloride
BH$_3$ borane
BH$_3$.SMe$_2$ borane dimethyl sulfide complex
BF$_3$.E$_2$O ethoxyethane trifluoroborane
B(OMe)$_3$ trimethoxyborane
BINAP 2,2'-bis(diphenylphosphino)-1,1'-binaphthyl
nBuLi n-butyllithium
Bu$_3$SnCl tributyltin chloride
Bu$_3$SnH tributyltin hydride
Boc tert-butyloxycarbonyl
(Boc)$_2$O di-tert-butyl dicarbonate
t-BuOK or K-t-OBu potassium tert-butoxide
CH$_2$Cl$_2$ dichloromethane
CH$_3$CN or ACN acetonitrile
CH(COOEt)$_2$ diethyl malonate
Cs$_2$CO$_3$ cesium carbonate
Cu(OAc)$_2$ copper (II) acetate
Cu copper
CuI copper (I) iodide
Cu(PPh$_3$)Br copper triphenylphosphinebromide
CuSO$_4$.5H$_2$O copper (II) sulfate pentahydrate
DCE 1,2 dichloroethane
DCM dichloromethane
DIBAL diisobutylaluminum hydride
DIC or DIPCDI diisopropylcarbodiimide
DIEA or DIPEA N,N-diisopropylethylamine
DME 1,2-dimethoxyethane
DMF dimethyl formamide
DMSO dimethyl sulfoxide
DPPA diphenylphosphoryl azide
EDTA ethylenediaminetetraacetic acid
Fe iron
HCl hydrochloric acid
H$_2$SO$_4$ sulfuric acid
H$_2$O$_2$ hydrogen peroxide
HEPES 4-(2-hydroxyethyl)piperaxine-1-ethanesulfonic acid
Hex hexane
K$_2$CO$_3$ potassium carbonate
LAH or LiAlH$_4$ lithium aluminum hydride
LiBH$_4$ lithium borohydride
LDA lithium diisopropylamide
NH$_2$NH$_2$.H$_2$O hydrozine hydrate
D-PBS Dulbecco's Phosphate Buffered Saline
PCy$_3$ tricyclohexylphosphine
P-(t-Bu)$_3$ tri-tert-butylphosphine
Pd/C palladium on carbon
PS polystyrene
Py pyridine
Pd$_2$(dba)$_3$ tris(dibenzylideneacetone)dipalladium(0)
Pd(OAc)$_2$ palladium acetate
Pd(PPh$_3$)$_4$ tetrakis(triphenylphosphine)palladium
PTSA p-toluenesulfonic acid
RED-AL® sodium bis(2-methoxyethoxy)aluminumhydride
Rochelle's salt sodium potassium tartrate
SiO$_2$ silica oxide
SnCl$_2$ tin(II) chloride
TBAI tetra-n-butylammonium iodide
TMSCN trimethylsilyl cyanide
TEA triethylamine
TFA trifluoroacetic acid
TFAA trifluoroacetic anhydride
THF tetrahydrofuran
KOAc potassium acetate
KNO$_3$ potassium nitrate
K$_2$S$_2$O$_8$ potassium persulfate
MgSO$_4$ magnesium sulfate
MsOH or MSA methylsulfonic acid
NaCl sodium chloride
NaH sodium hydride
NaHCO$_3$ sodium bicarbonate
NaOH sodium hydroxide
Na$_2$SO$_4$ sodium sulfate
Na$_2$S$_2$O$_4$ sodium dithionite
NaBH$_4$ sodium borohydride
NaBH(OAc)$_3$ sodium triacetoxyborohydride
NaCN sodium cyanide
NaCNBH$_3$ sodium cyanoborohydride
NaO-t-Bu sodium tert-butoxide
NaNO$_2$ sodium nitrite
NH$_3$ ammonia
NH$_4$Cl ammonium chloride
NH$_4$OH ammonium hydroxide
OTs tosylate, para-toluenesulfonate
Xantphos 4,5-bis(diphenylphosphino)-9,9-dimethylxanthene
Zn zinc
ZnCl$_2$ zinc chloride
ZnI$_2$ zinc iodide Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis,* 3rd Edition, Wiley-Interscience (1999)).

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis,* Wiley and Sons (1991)).

Schemes 1 to 16 describe synthetic routes of preparing compounds of the invention with general formula I. Schemes 1 to 4 describe preparations of compounds of the invention from a key amine intermediate 1 or 4. Scheme 5 exemplifies some of the carbocyclic or heterocyclic A ring intermediates in $NH_2$-A (compound 7) or COOH-A (compound 9) that can be used to prepare compounds of the present invention. Schemes 6 to 12 describe several preparations of the amine intermediate 1 or 4 or the substituted spiropiperidinyl/spiropyrrolidinyl indoline derivative 11 via a variety of methods from commercially available starting materials or can readily be prepared from commercially available materials by methods known to one skilled in the art of organic synthesis. Schemes 13 to 15 exemplify preparations of compounds in the present invention wherein $R^3$ is a halogen (F, Cl or Br) or a trifluoromethyl group as well as elaborate further functionalization of $R^3$ and $R^4$ of the molecule. Scheme 16 illustrates the compounds of the present invention with a variety heteroaryl or aryl or alkyl type of $R^3$ substituents can be obtained from the corresponding bromo intermediates.

Scheme 1 describes a preparation of compounds of the present invention with general formula I(a), the substituted urea 3, from the key amine intermediate 1. Substituted isocyanates 2 are commercially available or can readily be prepared from commercially available materials by methods known to one skilled in the art of organic synthesis. Reaction of an isocyanate 2 with the amine 1 typically occurs at temperatures between 20° C. and 80° C. in a variety of solvents such as tetrahydrofuran, dichloroethane or dioxane. This reaction can also proceed in the presence of organic or inorganic bases, such as $Et_3N$, DMAP, or $K_2CO_3$. Alternatively, the phenolic group in amine 1 can be protected as shown in intermediate 4, wherein the protecting group can be methyl, benzyl, allyl, or silyl-based group. Urea formation between the amine 4 and the isocyanate 2, followed by deprotection to free the phenolic group of the intermediate 5 can afford the urea 3. When the protecting group on the phenol is methyl, demethylation can occur with $BBr_3$, $BCl_3$, $BBr_3.SMe$, $BCl_3.SMe$ $AlCl_3$, or $BCl_3$/TBAI (tetra-n-butylammonium iodide) at temperatures between −78° C. and refluxing in a solvent such as $CH_2Cl_2$. When heating is needed, the reaction can also occur under microwave irradiation to shorten the reaction time. When the protecting group on the phenol is a benzyl group, debenzylation can occur by using hydrogenation (such as Pd/C, $H_2$) or by using $AlCl_3$ in $CH_2Cl_2$ in a variety of solvent such as methanol, EtOAc.

Scheme 1

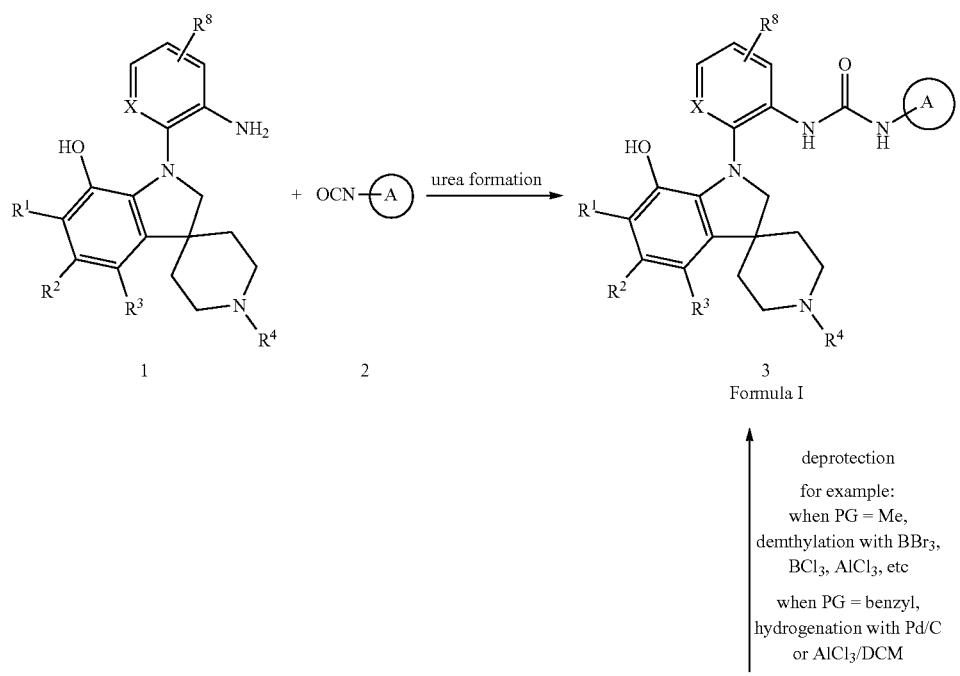

-continued

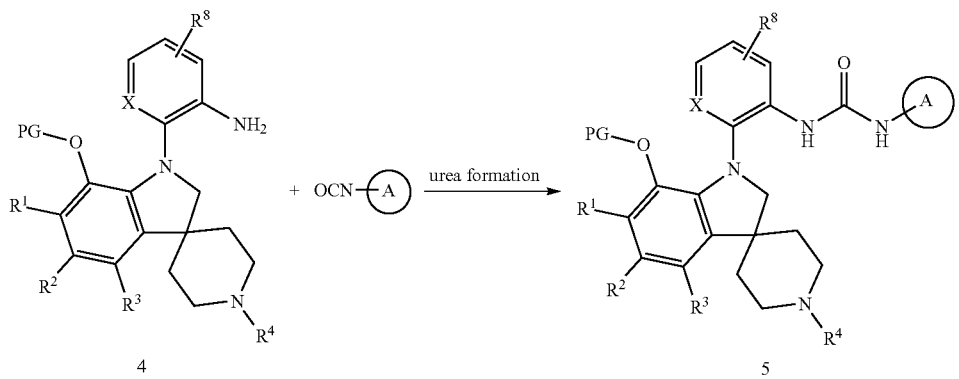

4 → 5

PG = protecting group
X = N or CH

Scheme 2 describes a step-wise preparation of compounds of the present invention with general formula I, the substituted ureas 3, from the amine intermediate 1 or 4. Substituted anilines and amino-substituted heteroaromatics 7 are commercially available or can readily be prepared from commercially available materials by methods known to one skilled in the art of organic synthesis. Reaction of intermediate 1 or 4 with chloroformate (e.g., p-nitrophenyl chloroformate, phenyl chloroformate or isopropenyl chloroformate) affords the carbonate intermediate 6 in the presence of an inorganic or an organic base, such as $Et_3N$, DMAP, or $K_2CO_3$. The carbonate 6 can be further replaced with a variety of aniline or amine 7 to afford the desired urea 3 or 5 by heating in THF, $CH_2Cl_2$, DMSO, etc at elevated temperatures or under microwave irradiation in the presence of an organic or an inorganic base, such as DMAP, $Et_3N$, N-methylpyrrolidine, $K_2CO_3$.

Scheme 2

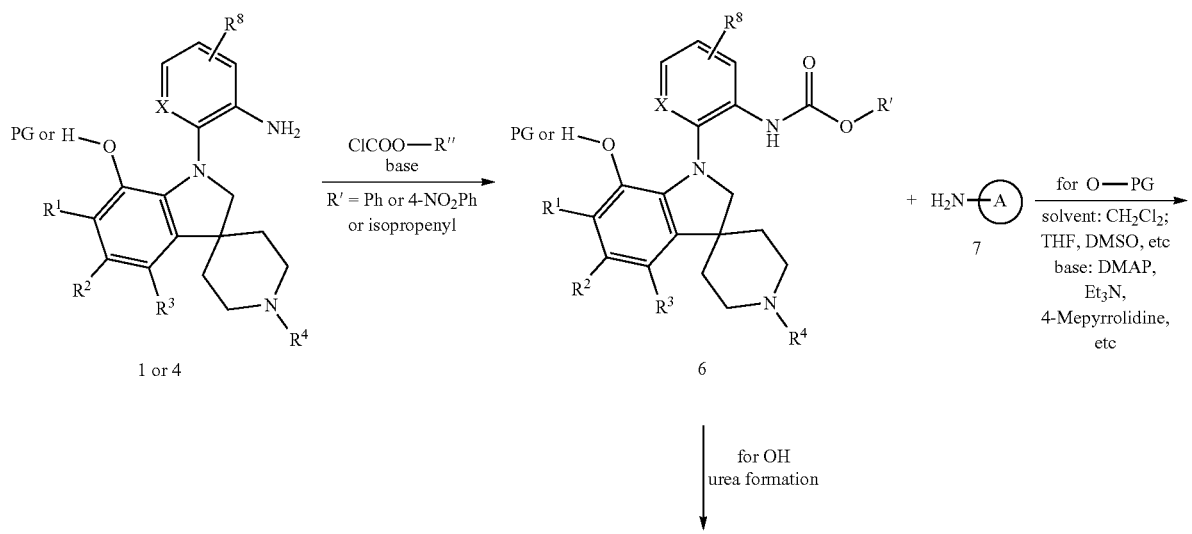

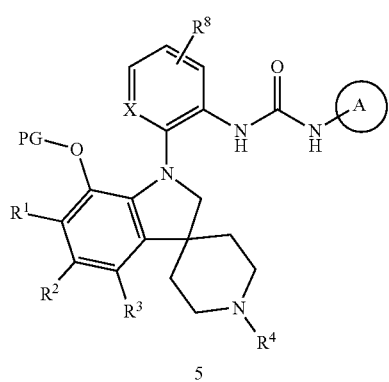

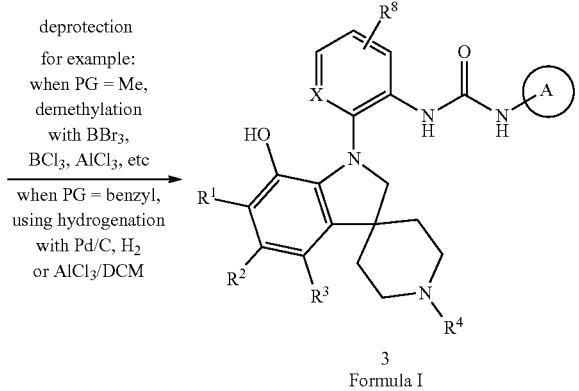

5

3
Formula I

Scheme 3 describes a preparation of compounds of the present invention with general formula I, the substituted ureas 3 from the key isocyanate intermediate 8. Substituted anilines and amino-substituted heteroaromatics 7 are commercially available or can readily be prepared from commercially available materials by methods known to one skilled in the art of organic synthesis. Reaction of the isocyanate 8 with aniline 7 typically occurs at temperatures between 20° C. and 80° C. in a variety of solvents such as tetrahydrofuran, dichloromethane, dichloroethane or dioxane. The key isocyanate intermediate 8 can be prepared via treatment of the aniline 4, prepared according to Schemes 6 to 12, with a phosgene equivalent in an organic solvent such as dichloromethane, dichloroethane or toluene, to produce the corresponding isocyanate. Phosgene equivalents include diphosgene, triphosgene, carbonyl diimidazole, trichloromethyl chloroformate and disuccinimidyl carbonate.

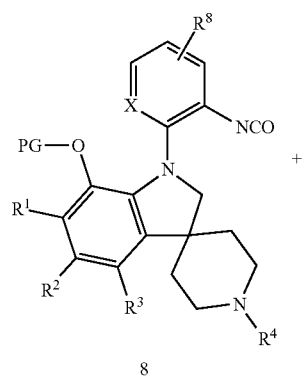

8 solvent: $CH_2Cl_2$,
THF, dioxanes
with or without
base, such as
$K_2CO_3$, $Et_3N$, DMAP

7

Scheme 3

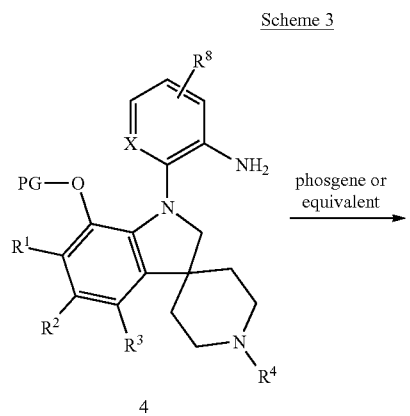

4

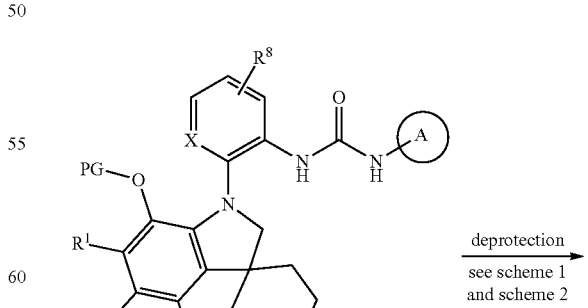

5

-continued

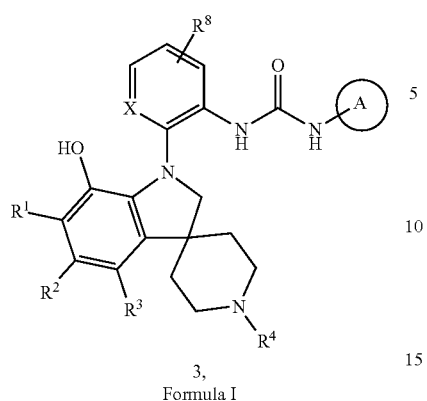

3,
Formula I

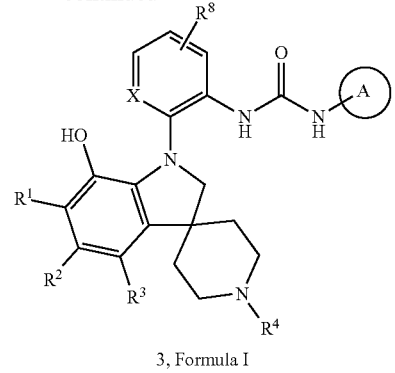

3, Formula I

Alternatively, Scheme 4 depicts a preparation of the compound of the present invention with general formula I, the substituted urea 3, via Curtius rearrangement of the carboxylic acid 9 using diphenylphosphoryl azide (DPPA) in the presence of aniline intermediate 1 or 4 while heating in toluene. Aryl/heteroaryl/alkyl carboxylic acids 9 are commercially available or can readily be prepared from commercially available materials by methods known to one skilled in the art of organic synthesis.

Scheme 5 exemplifies some of the carbocyclic or heterocyclic A ring intermediates in $NH_2$-A (compound 7) or COOH-A (compound 9) that can be used to prepare compounds of the present invention. Ring A is optionally substituted. These intermediates are either commercially available or can be prepared using methods known to those skilled in the art of organic synthesis.

Scheme 4

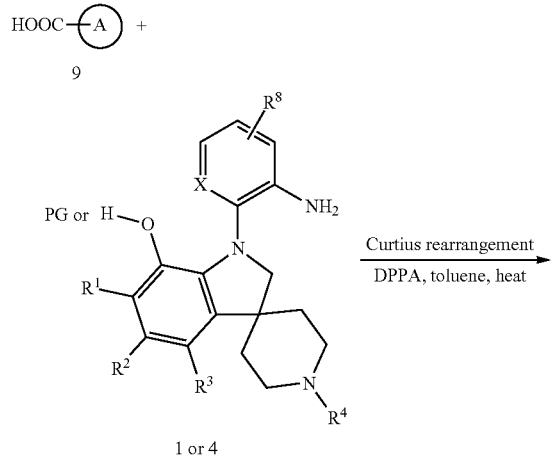

Scheme 5

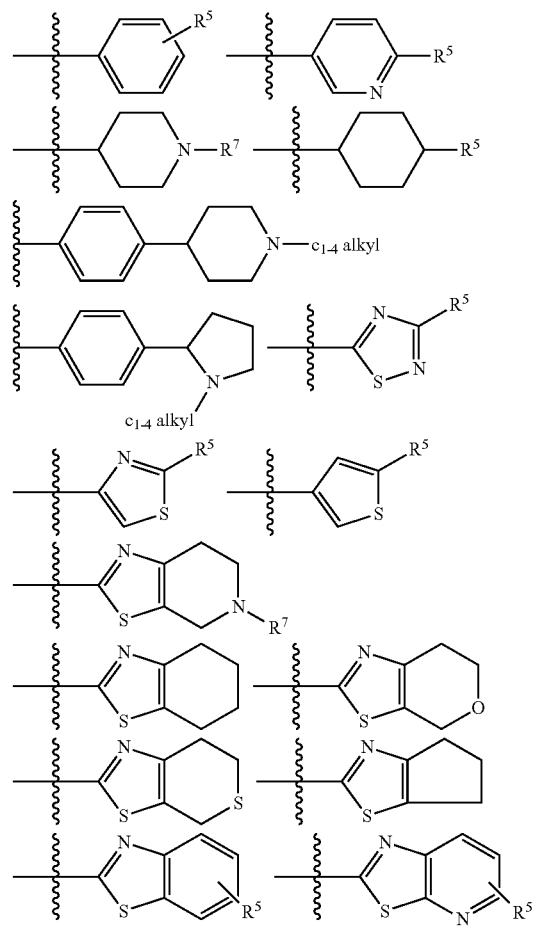

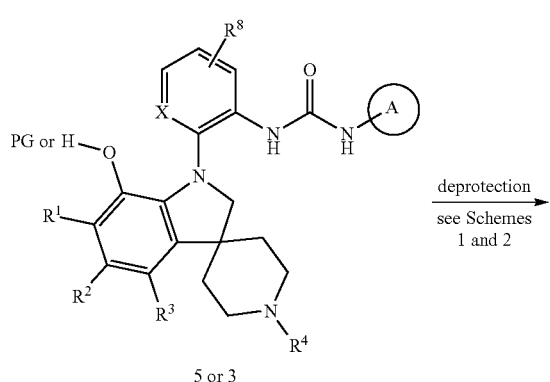

5 or 3

Scheme 6 outlines one possible preparation of aniline intermediates 4, which proceeds by aromatic nucleophilic substitution followed by reduction. Nitro phenyl derivatives or nitro pyridinyl derivatives 10, substituted in the ortho position with a halogen (such as chlorine, or fluorine), are commercially available or can readily be prepared by one skilled in the art of organic synthesis. They can be reacted with NH-containing cyclics 11 as nucleophiles to provide the corresponding compounds 12. Typical reaction conditions involve the reaction of a nucleophile and a halonitro aryl/heteroaryl derivative either in organic solvent such as THF, DMF, toluene, dioxane or n-butanol, or under neat condition, in the presence of a base such as potassium carbonate, cesium carbonate, triethylamine, tert-butoxide, or DIEA. The reaction temperature is usually between room temperature and reflux condition. Reaction conditions can be chosen based on the nucleophilicity of 11 and/or halogen difference. Microwave irradiation and/or heating at higher temperature can also be used to accelerate the rate of reaction. Following aromatic nucleophilic substitution, the resulting nitro derivative 12 can be reduced to the corresponding aniline. Typical conditions include hydrogenation in the presence of a metal catalyst such as palladium or platinum. Other conditions include treatment with reducing agents such as SnCl$_2$ or Zinc or iron powder with ammonium chloride.

Scheme 6

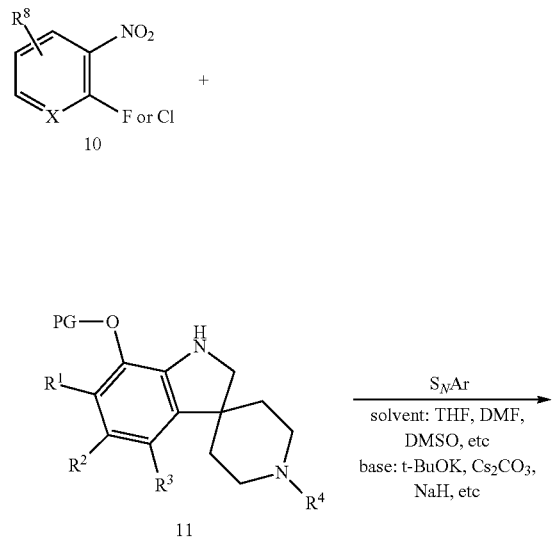

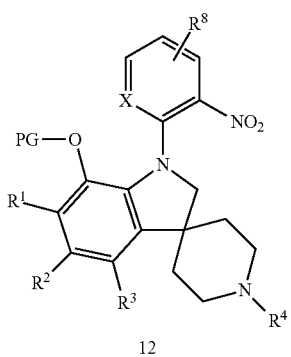

On the other hand, the aniline intermediate 4 can be synthesized via Cu or Pd chemistry (for a review paper, see, Ley, S. V. et al., *Angew. Chem. Int. Ed.*, 42:5400-5449 (2003)) between a 1,2-substituted aryl/heteroaryl halide 13 and a Nil-containing cyclic 11 followed by deprotection functional transformation of intermediate 14 as exemplified in Scheme 7. Microwave irradiation can also be used to accelerate the rate of reaction in the coupling step when using the Pd or Cu chemistry. For example, the ester 15 can coupled with the amine 11 via the Chan-Lam chemistry in the presence of Cu catalyst Cu(OAc)$_2$ and a base such as Et$_3$N or Py in CH$_2$Cl$_2$ (For a recent review, see Qiao, J. X. et al., *Synthesis*, 829-856 (2011)) to form intermediate 16, which can be hydrolyzed, followed by Curtius rearrangement to afford the protected amine 17. Removal of the protecting group in 17 can give the desired aniline intermediate 4, On the other hand, coupling of the bromo nitro compound 18 with the amine 11 via Buchwald-Hartwig amination in the presence of a palladium (0) catalyst such as tris(dibenzylideneacetone)dipalladium(0) (Pd$_2$(dba)$_3$) or a palladium (II) catalyst such as palladium acetate (Pd(OAc)$_2$)) with a phosphine ligand such as BINAP or Xantphos and a base such as Cs$_2$CO$_3$ or t-BuONa, can afford the nitro intermediate 19. Reduction of the nitro group in 19 with a variety of reducing reagent such as Zn, Fe, Pd/C—H$_2$, SnCl$_2$, Na$_2$S$_2$O$_4$, can afford the desired aniline intermediate 4.

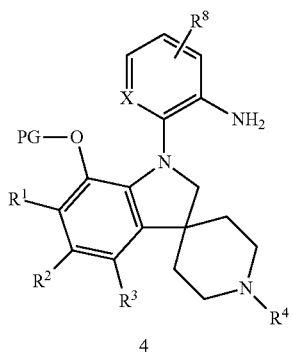

Scheme 7

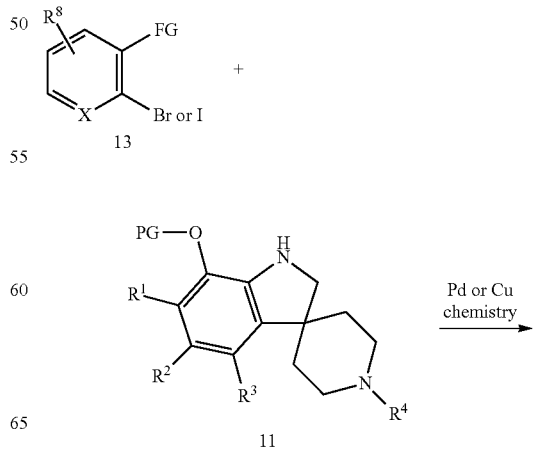

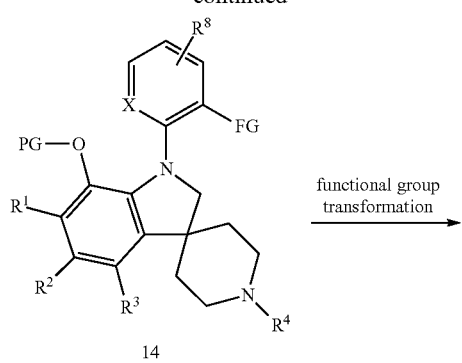
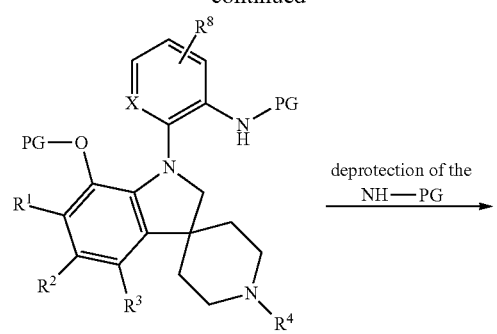
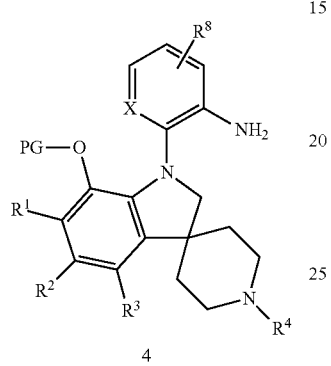
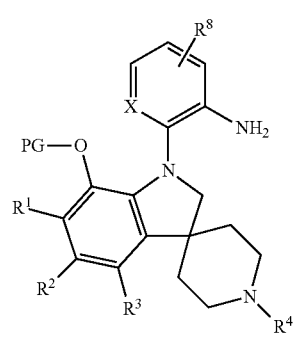
For Example:
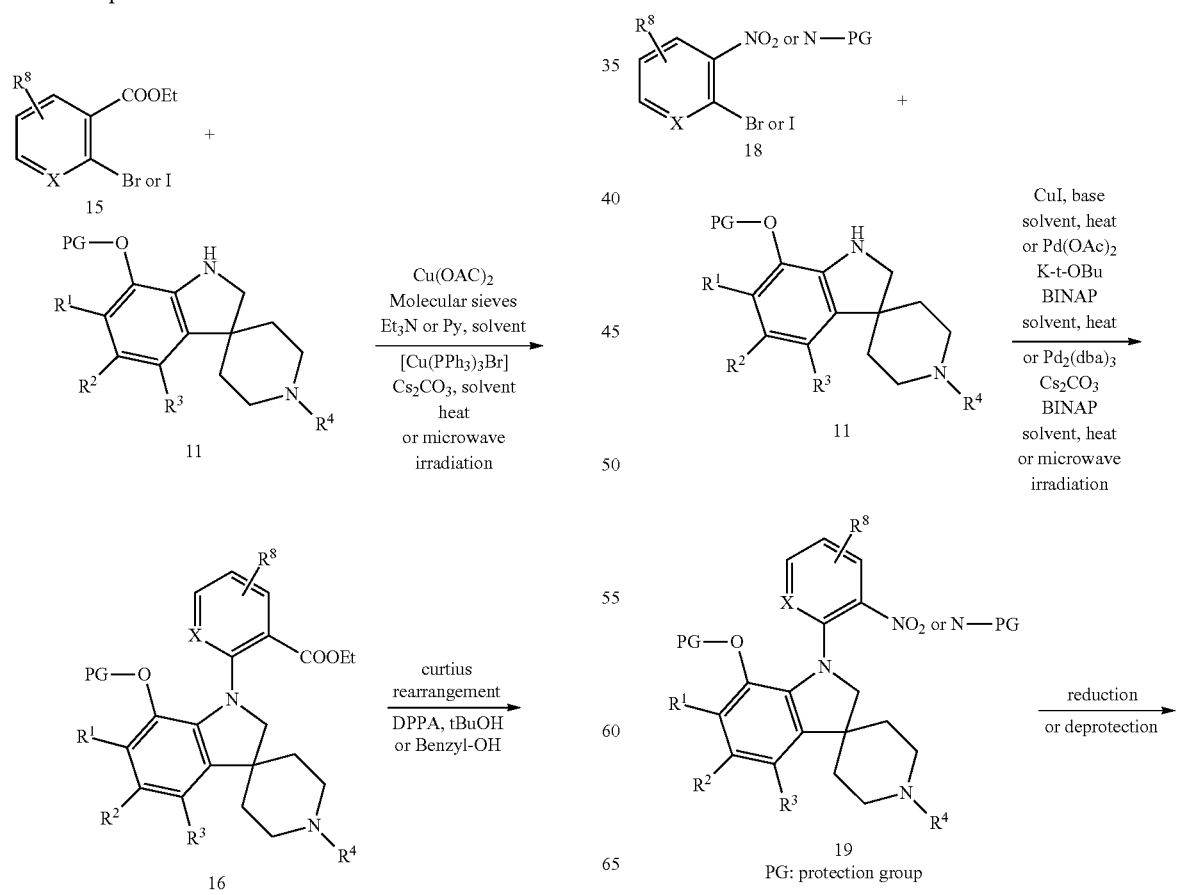
PG: protection group

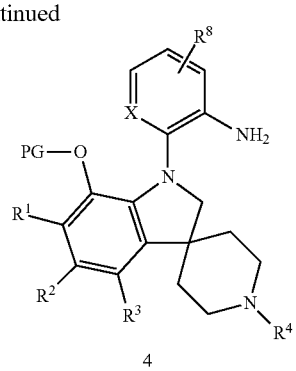

4

Compounds of the present invention wherein the amine intermediate 11 is a substituted spiropiperidinyl indoline derivative or a substituted spiropyrrolidinyl indoline derivative can be prepared by using the methods shown in Schemes 8 to 12 and by using methods known to those skilled in the art of organic synthesis.

Scheme 8 illustrates the preparation of the indoline derivative 11 via Fischer indole synthesis followed by reduction of the indolenine intermediate. Substituted phenyl hydrazines 20 are commercially available or can readily be prepared from commercially available materials by methods known to one skilled in the art of organic synthesis. Thus, Fischer indole reaction of the substituted phenyl hydrazine 20 and the aldehyde 21 under acidic conditions (e.g., $H_2SO_4$, HCl, HOAc, TFA, MsOH, $ZnCl_2$) at reaction temperature from 0° C. to refluxing in solvent such as $CH_2Cl_2$, toluene, EtOH, HOAc, 1,4-dioxane, can yield the indolenine intermediate 23, followed by reduction of 23 with reducing agent such as $NaBH_4$, $NaCNBH_3$, or $LiBH_4$ in MeOH at −78° C. to room temperature or refluxing to afford the desired indoline 11.

Scheme 8

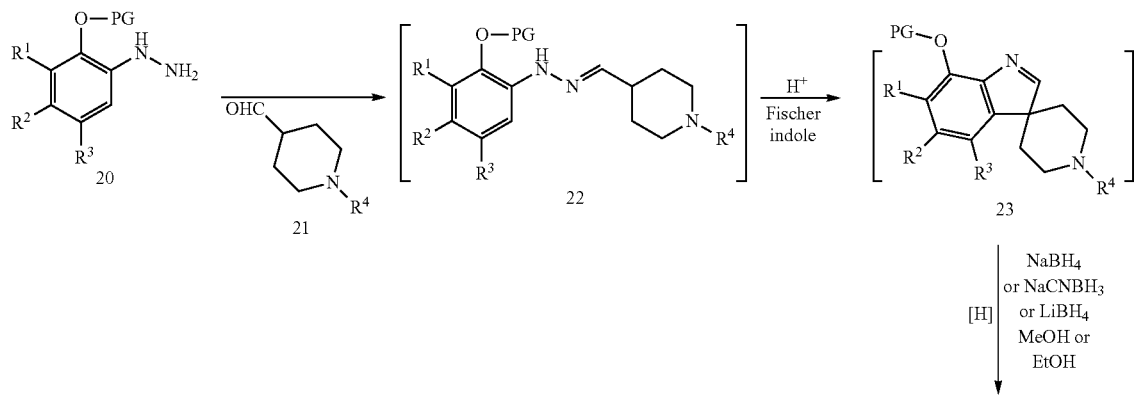

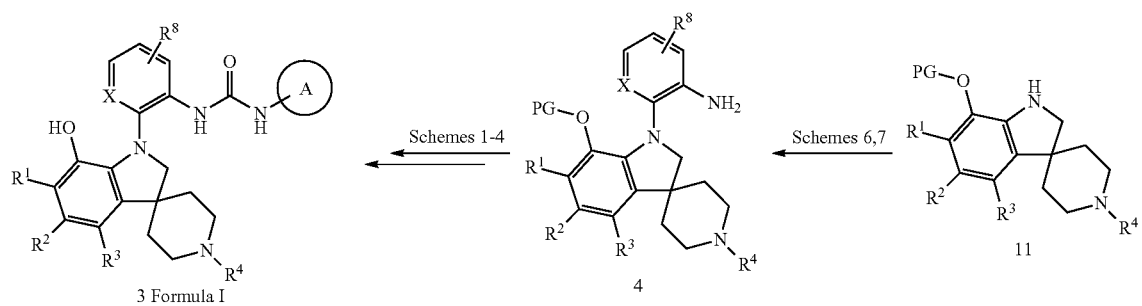

Alternatively, the indolinyl derivative 11 in the present invention can be synthesized via the reduction of indol-2-ones 24 using reducing agents such as LiAlH$_4$, BH$_3$ (Scheme 9). The indol-2-one intermediates 24 are either commercially available or can be prepared using methods known to those skilled in the art of organic synthesis. For example, sequential alkylation of intermediate 25 followed by reduction of the nitro group in 26 and subsequent intermolecular cyclization can afford the desired indol-2-one 24.

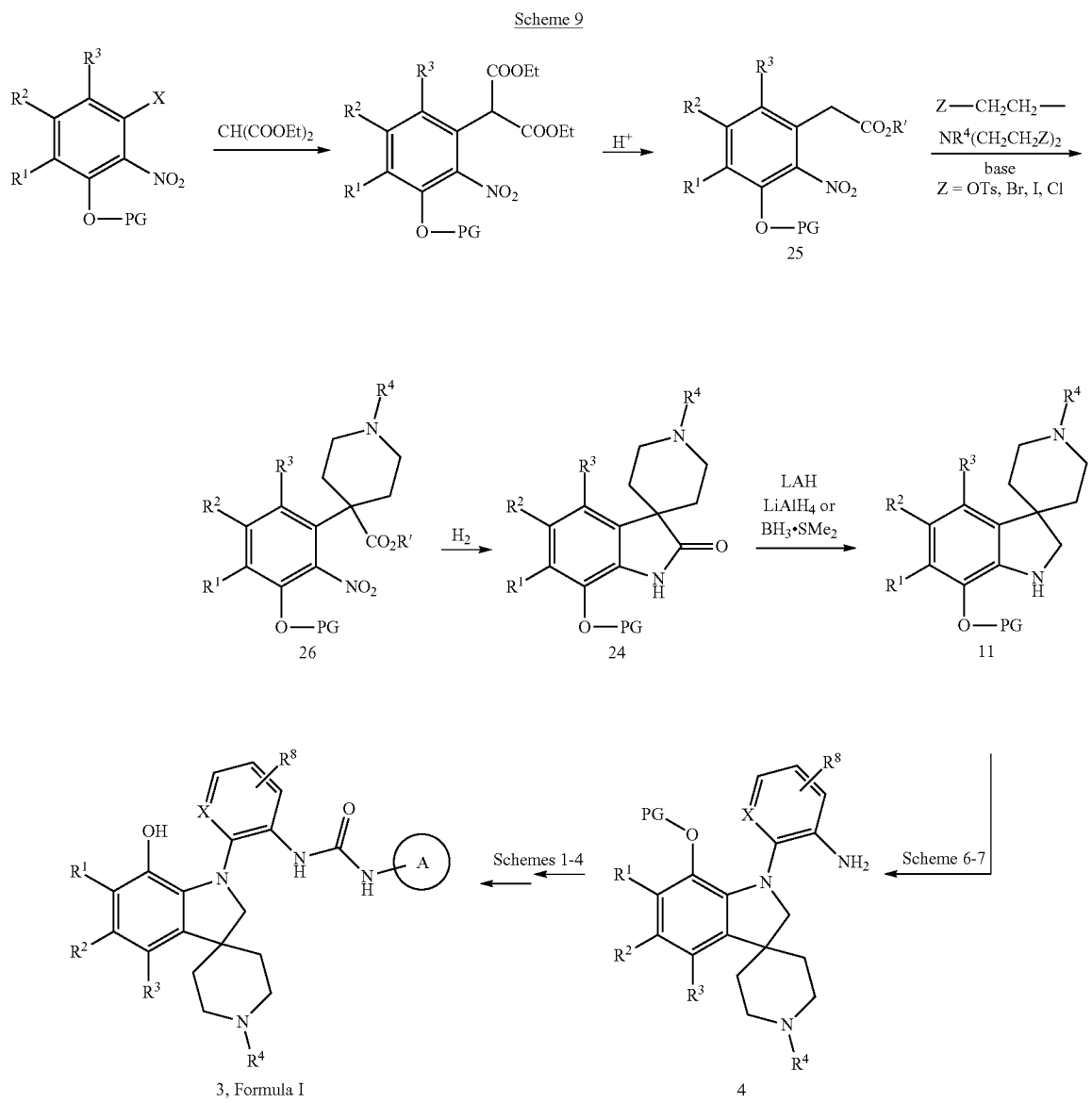

Scheme 9

Alternatively, in Scheme 10, the indol-2-one intermediate 24 can be prepared from the reduction of the indol-2,3-dione 27 followed by sequential alkylation. On the other hand, the indol-2-one 24 can be prepared from the Cl, Br, or I intermediate 28 via either intramolecular Heck reaction of in the presence of a palladium catalyst (such as Pd$_2$(dba)$_3$, Pd(OAc)$_2$), a phosphine ligand (such as BINAP, PCy$_3$, P(t-Bu)$_3$), a base (such as NaO-t-Bu), in solvent (such as 1,4-dioxane, toluene) or via a radical cyclization process with Bu$_3$SnH, AIBN in DMF or toluene under normal heating or microwave irradiation.

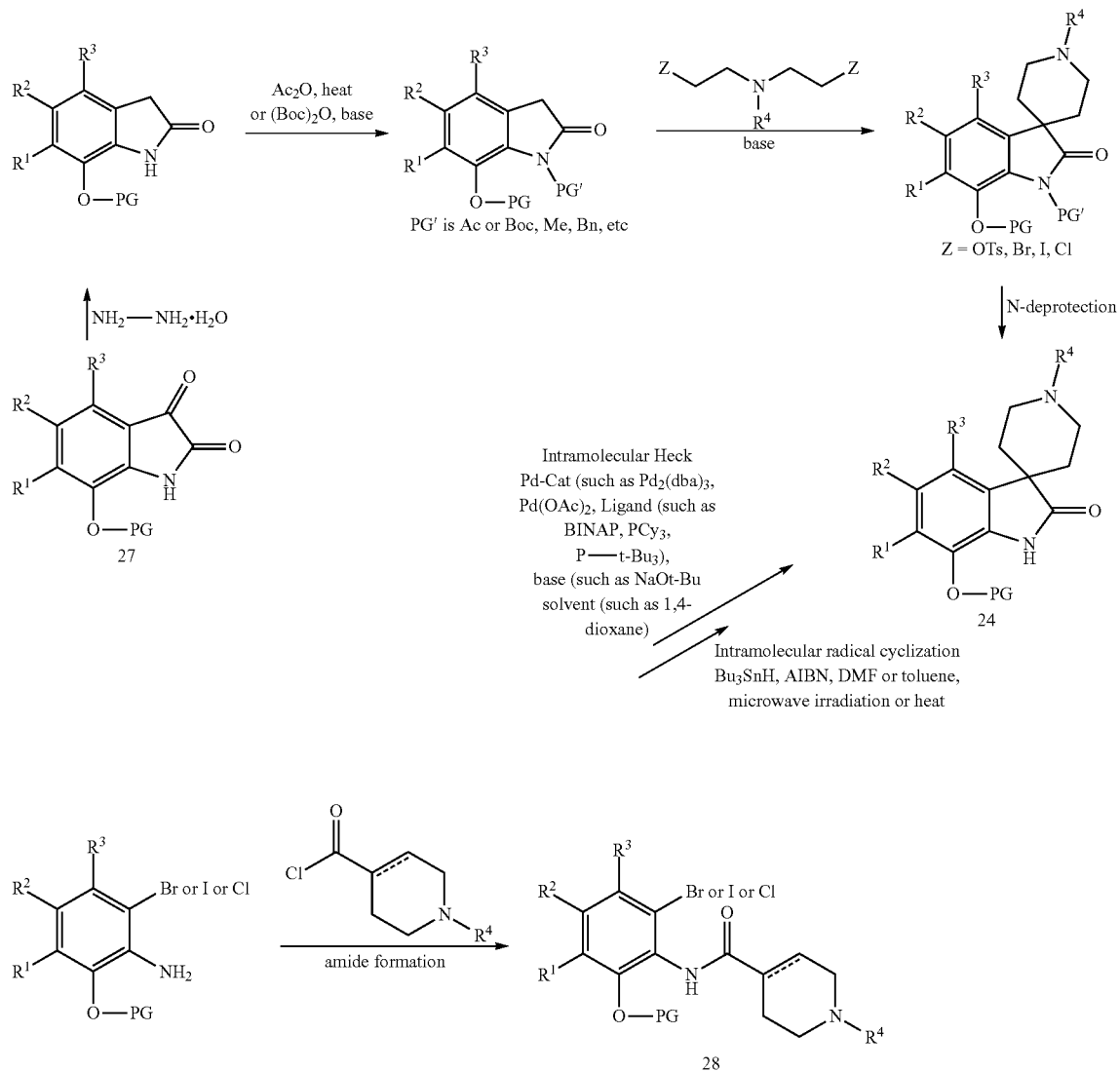

Scheme 10

Scheme 11 indicates that the indoline intermediate 11 can also be prepared via alkylation of the nitrile intermediate 29 followed by reductive cyclization of the resulting piperidinyl derivative 30. The nitrile intermediate 29 can be prepared from displacement either the bromide, or tosylate 31 with nitrile anion. Intermediate 30 can also be obtained by reaction of a tertiary alcohol 32 in the presence of a Lewis acid (such as $ZnI_2$) and TMSCN (Schwarz, O., et al., *Tetrahedron Lett.*, 1009 (2002)). The alcohol 32 can be prepared via ortho lithiation of the fluoride 33, then trapping with the ketone 34.

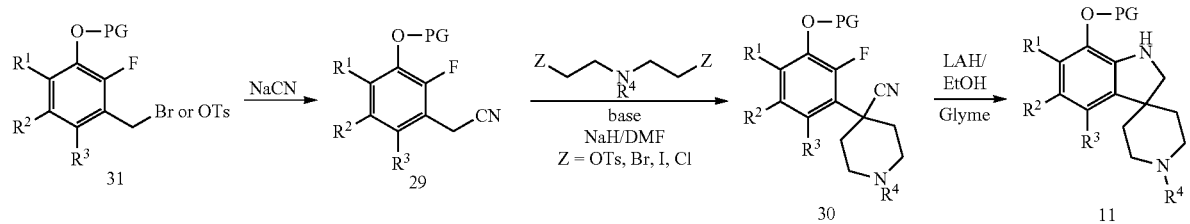

Scheme 11

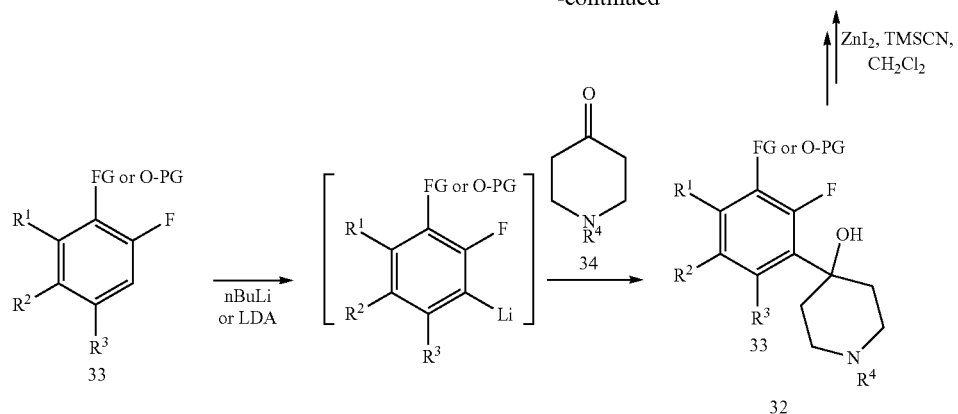

Scheme 12 illustrates the 7-OH indoline intermediate 34 in the present invention can be prepared via a variety of methods known to the skill of art of organic synthesis. For example, 7-OH indolines can be prepared via thallation of N-formylindolines 35 or N-acetylindolines (Yamada, *Chemical & Pharmaceutical Bulletin*, 788 (2006)) or via acid hydrolysis of the amide lactone 36 (Ishiyama, K., et al., *Tetrahedron Lett.*, 1021 (2005)), or via benzylic hydroperoxide rearrangement of intermediate 37 (Boger, *J. Org. Chem.*, 5436 (1986)).

Scheme 12

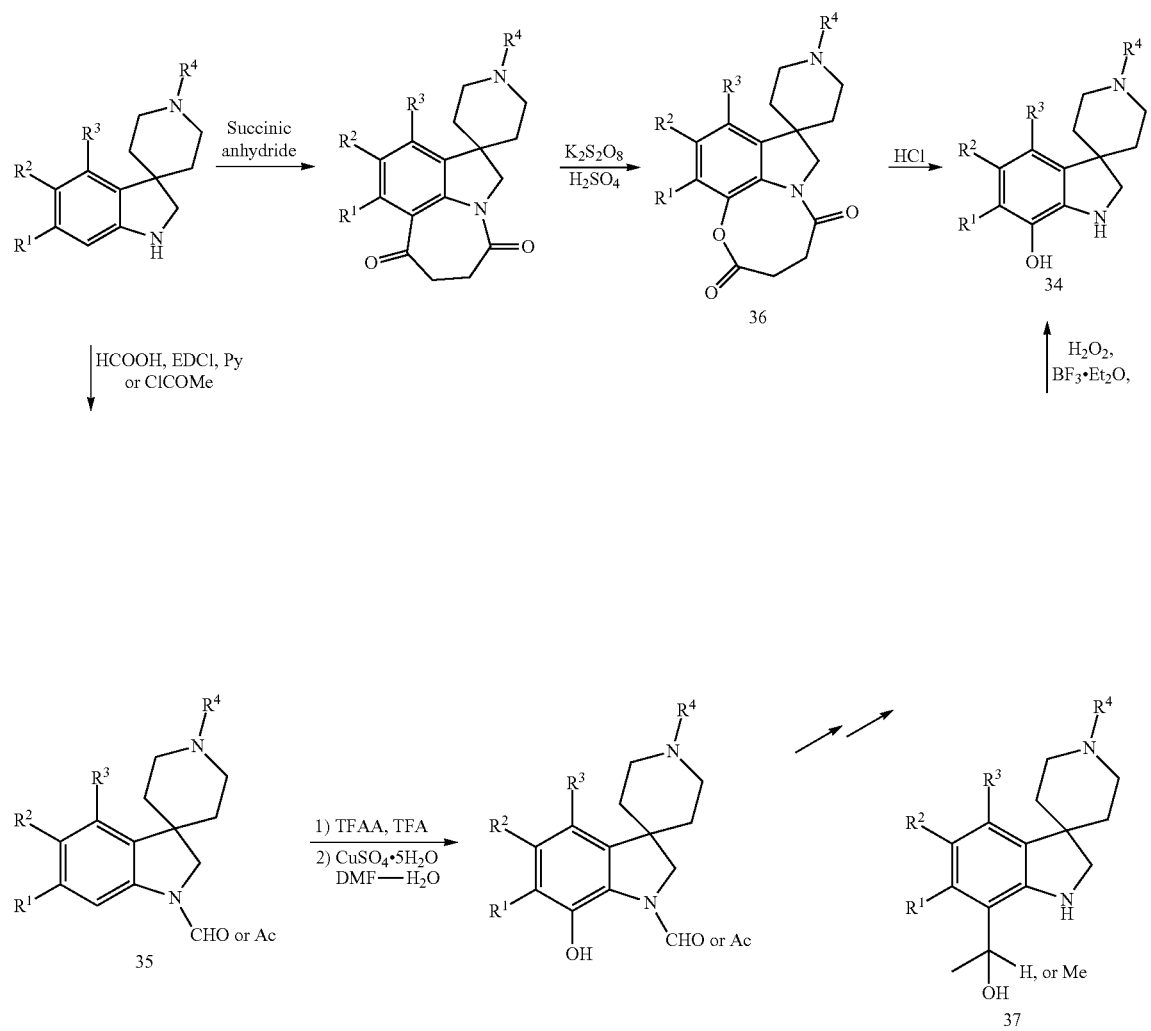

Scheme 13
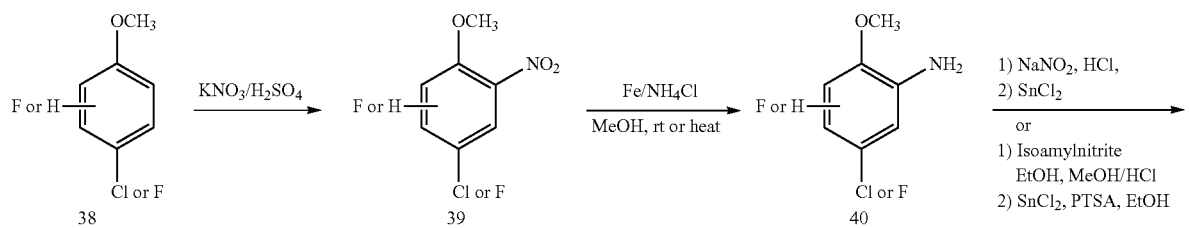
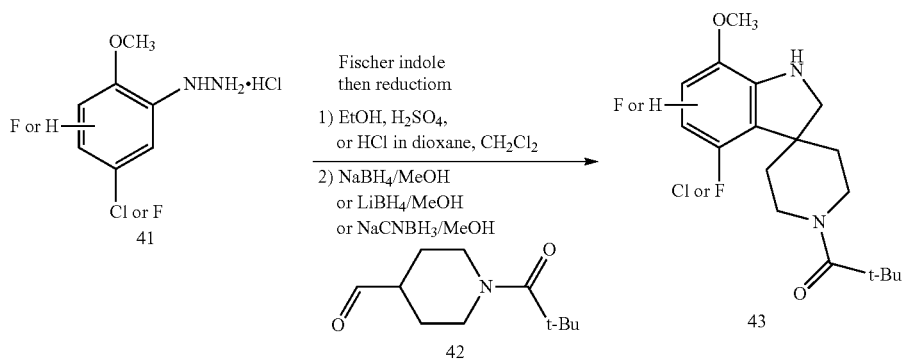
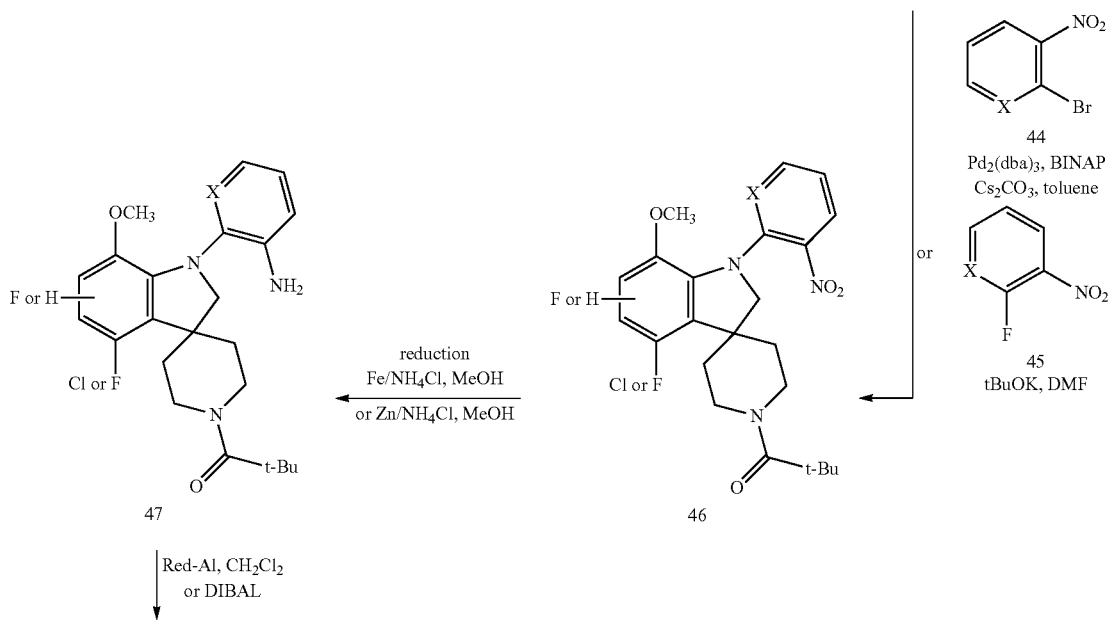

-continued

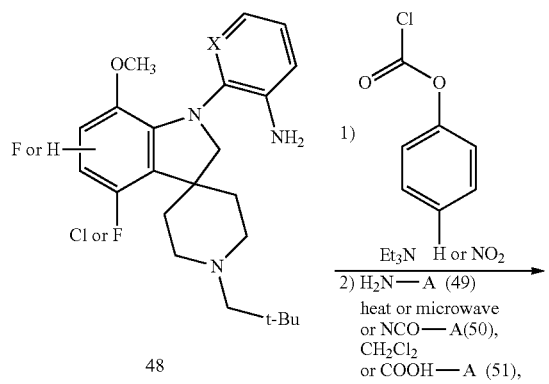

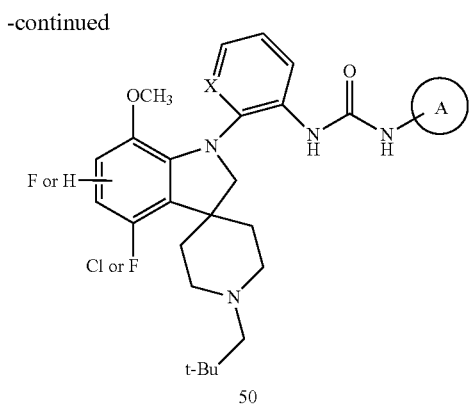

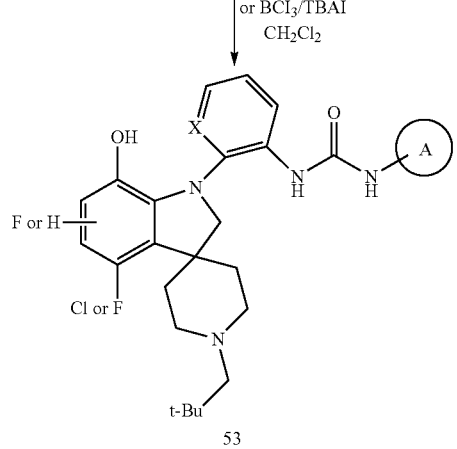

Scheme 13 illustrates the synthesis of compounds in the present invention wherein, $R^4$ is a halogen group, such as Cl, or F. Nitration of the methoxy intermediate 38 followed by reduction of the nitro group in 39 afforded the aniline 40. Diazotization of 40 followed by reduction formed the hydrazine 41. Hydrazone formation of 41 with the aldehyde 42, followed by cyclic imine formation under Fischer indole condition and subsequently reducing the imine afforded the pivaloyl protected spiropiperidinyl indoline intermediate 43. Pd-catalyzed cross-coupling of 43 with 44 under Buchwald-Hartwig condition or $S_NAr$ displacement of 45 with 43 yielded the N-aryl derivative 46. Reduction of the $NO_2$ group of 46 followed by reduction of the pivaloyl group in 47 to the neopentyl group led to the aniline intermediate 48. Urea formation of 48 with either the aniline 49 or the isocyanate 50 or the acid 51 using methods shown in Schemes 1 to 4 afforded 52. Demethylation of 52 with either $AlCl_3$ under microwave irradiation or $BCl_3$/TBAI at −78° C. to room temperature yielded the desired compound 53 of the present of the invention.

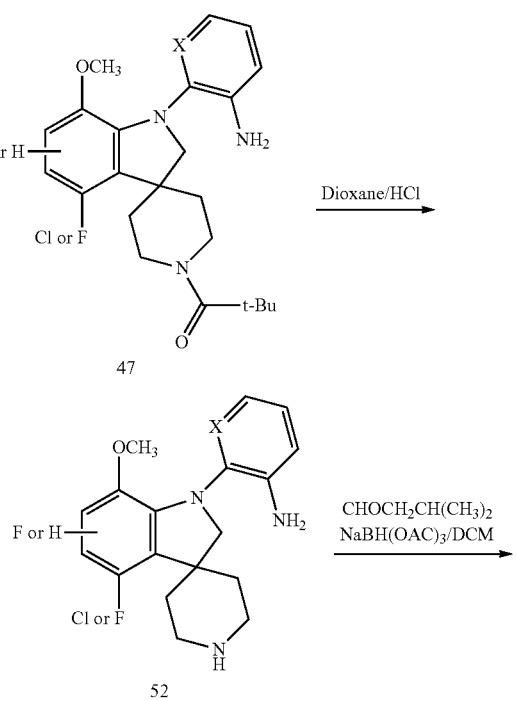

Scheme 14

-continued

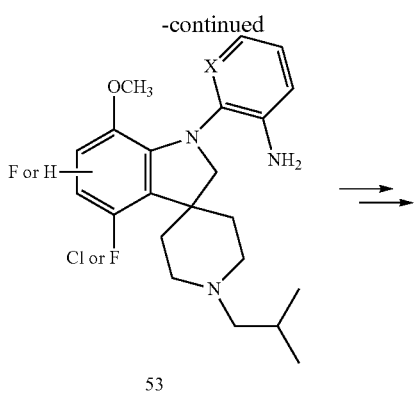

53

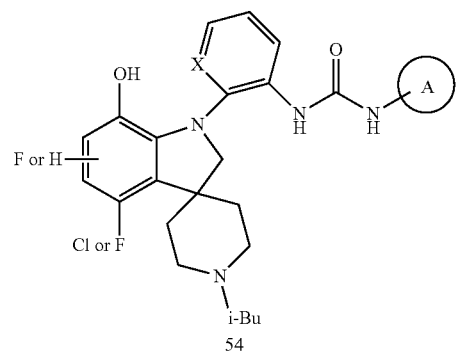

54

On the other hand, Scheme 14 shows that hydrolysis of the pivaloyl group in 47 followed by reductive amination of the resulting unsubstituted piperidine 54 can afford the isobutyl derivative 55, which can be transformed to the desired compound 56 of the present invention using procedures similar to those for compound 53.

The synthesis of compound 57 in the present invention wherein R is a trifluoromethyl group is essentially similar to those procedures illustrated in Scheme 13. Subsequently, the trifluoromethyl group can be hydrolyzed in aqueous NaOH in the presence of variety of nucleophiles such as NH—R, SH—R, OH—R, to form carboxylic acid or esters (58), nitriles (59), and monocyclic or bicyclic heterocycles (60) such as benzoxazoles, benzimidazoles, benzithiazoles (Scheme 15).

Scheme 15

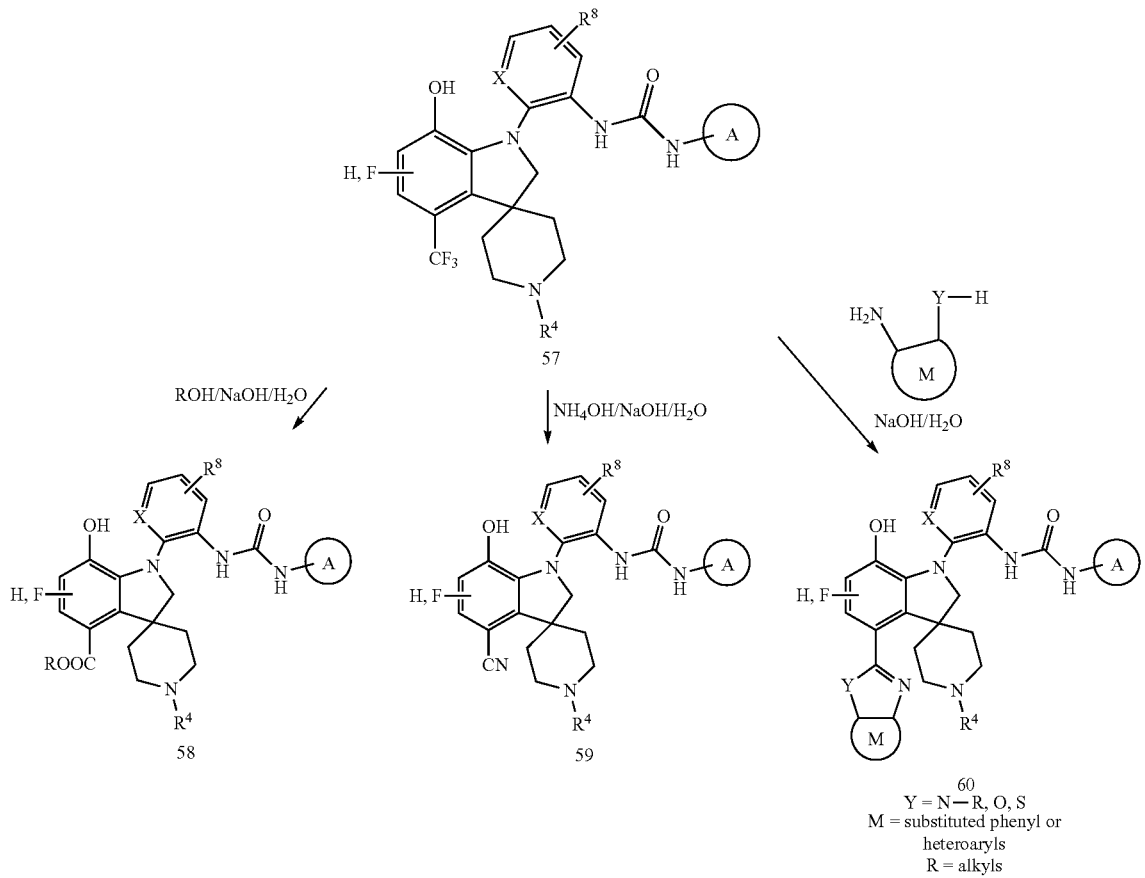

X = CH or N

The synthesis of compounds 61 in the present invention wherein, $R^3$ is a bromo group is essentially similar to those procedures illustrated in Scheme 14. Scheme 16 illustrates compounds of the present invention with a variety heteroaryl or aryl or alkyl type of $R^3$ substituents can be obtained from the bromo derivative 61 by using methods known to one skilled in the art of organic synthesis. For instance, the bromo group can be transferred to other groups such as aryl, heteroaryl, alkyl groups via palladium chemistry such as Suzuki coupling (Suzuki, *Pure Appl. Chem.*, 63:419-422 (1991). Miyaura et al., *Chemistry Reviews*, 95:2457-2483 (1995)), Heck reaction (Heck, *Comprehensive Organic synthesis*, Vol. 4, Pergamon Press, Oxford (1990), Hiyama cross-coupling reaction (Hiyama, *Metal Catalyzed Cross-coupling Reactions*, Ch. 10, p. 421, Wiley-VCH, Weinhein (1998)), and Negishi cross-coupling reaction (Negishi, *Acc. Chem. Res.*, 15340 (1982)), or via organocopper chemistry such as Ullman coupling (Hassan et al., *Chemical Reviews*, 102:1359-1469 (2002)).

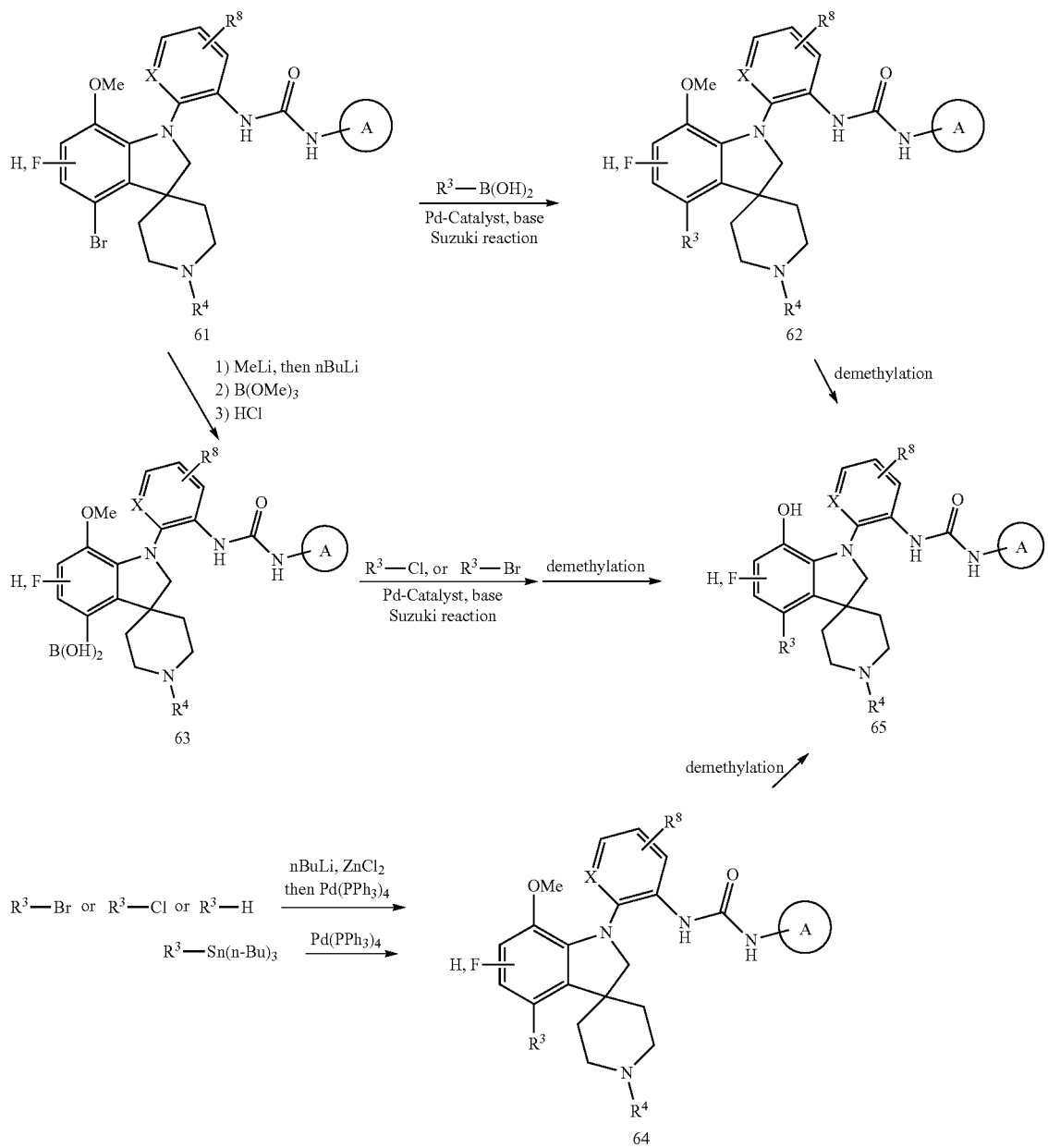

Scheme 16

$R^3$ = heteroaryl, aryl, alkyl, alkenyl, alkynyl, etc.

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running Discovery VP software using Method A: PHENOMENEX®

Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm). Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a VARIAN® ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running Discovery VP software, coupled with a Waters ZQ mass spectrometer running MassLynx version 3.5 software using:

Method A: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: Luna C-18 5μ (4.5×30 mm). Flow rate was 4 ml/min. and UV detection was set to 220 nm. The LC column was maintained at room temperature.

Method B: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: L XTERRA® C-8 (4.5×30 mm). Flow rate was 4 ml/min. and UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5u C18 (4.5×50 mm). Flow rate was 4 ml/min. and UV detection was set to 220 nm. The LC column was maintained at room temperature.

Method D: A linear gradient using solvent A (10% methanol, 90% water, 0.1% of TFA) and solvent B (90% methanol, 10% water, 0.1% of TFA); 0-100% of solvent B over 2 min and then 100% of solvent B over 2 min. Column: PHENOMENEX® Luna 5u C18 (4.5×30 mm). Flow rate was 4 ml/min. and UV detection was set to 220 nm. The LC column was maintained at room temperature.

Method E: A linear gradient using solvent A (10% acetonitrile, 90% water, 10 mM $NH_4OAc$) and solvent B (90% acetonitrile, 10% water, 10 mM $NH_4OAc$); 0-100% of solvent B over 4 min and then 100% of solvent B over 1 min. Column: PHENOMENEX® Luna 5u C18 (4.5×50 mm). Flow rate was 4 ml/min. and UV detection was set to 220 nm. The LC column was maintained at room temperature.

Method F: A linear gradient using solvent A (10% acetonitrile, 90% water, 0.1% TFA) and solvent B (90% acetonitrile, 10% water, 0.1% TFA); 0-100% of solvent B over 4 min and then 100% of solvent B over 1 min. Column: PHENOMENEX® Luna 5u C18 (4.6×30 mm). Flow rate was 4 ml/min. and UV detection was set to 220 nm. The LC column was maintained at room temperature.

Method G: A linear gradient using solvent A (10% acetonitrile, 90% water, 0.05% TFA) and solvent B (90% acetonitrile, 10% water, 0.05% TFA); 0-100% of solvent B over 8 min and then 100% of solvent B over 2 min. Column: ZORBAX® C18 (4.6×75 mm). Flow rate was 2.5 ml/min. and UV detection was set to 220 nm. The LC column was maintained at room temperature.

Method H: A linear gradient using solvent A (10% acetonitrile, 90% water, 0.05% TFA) and solvent B (90% acetonitrile, 10% water, 0.05% TFA); 0-100% of solvent B over 10 min. Column: Sunfire C18 (4.5×150 mm). Flow rate was 1.0 ml/min. and UV detection was set to 220 nm. The LC column was maintained at room temperature.

Method I: A linear gradient using solvent A (10% acetonitrile, 90% water, 10 mM $NH_4OAc$) and solvent B (90% acetonitrile, 10% water, 10 mM $NH_4OAc$); 0-100% of solvent B over 2 min and then 100% of solvent B over 1 min. Column: PHENOMENEX® Luna 5u C18 (4.5×30 mm). Flow rate was 4 ml/min. and UV detection was set to 220 nm. The LC column was maintained at room temperature.

Method J: A linear gradient using solvent A (100% water, 10 mM $NH_4OAc$) and solvent B (100% acetonitrile); 10-80% of solvent B over 6 min, 80-95% of solvent B over 2 min, 95% of solvent B over 2 min, then 95-10% of solvent B over 2 min. Column: Atlantis dC18 5 μM (4.5×50 mm). Flow rate was 0.8 ml/min. and UV detection was set to 220 nm. The LC column was maintained at room temperature.

Method K: A linear gradient using solvent A (10% MeOH, 90% water, 0.1% TFA) and solvent B (90% MeOH, 10% water, 0.1% TFA); 0-100% of solvent B over 2 min, 100-0% of solvent B over 1 min. Column: CHROMOLITH® SpeedROD C18 (4.6×30 mm). Flow rate was 5 ml/min. and UV detection was set to 220 nm. The LC column was maintained at room temperature.

Method L: A linear gradient using solvent A (100% water, 0.05% of TFA) and solvent B (100% acetonitrile, 0.05% of TFA); 2-98% of solvent B over 1 min and then 98% of solvent B over 30 sec. Column: BEH C-18 (2.1×50 mm). Flow rate was 0.8 mL/min. and UV detection was set to 220 nm. The LC column was maintained at room temperature.

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. and UV detection was set to 220 nm. The LC column was maintained at room temperature.

Method C: A linear gradient using solvent A (0.1% DEA in $H_2O$, pH adjusted to 8.5 with dil. OPA) and solvent B (acetonitrile); 10-100% of solvent B over 12 min and then 100% of solvent B over 6 min. Column: Sunfire C18 3.5 um (4.6×150 mm). Flow rate was 1 ml/min. and UV detection was set to 220 nm. The LC column was maintained at room temperature.

Method D: A linear gradient using solvent A (0.1% DEA in $H_2O$, pH adjusted to 8.5 with dil. OPA) and solvent B (acetonitrile); 10-100% of solvent B over 12 min and then 100% of solvent B over 6 min. Column: Xbridge Phenyl 3.5 um (4.6×150 mm). Flow rate was 1 ml/min. and UV detection was set to 220 nm. The LC column was maintained at room temperature.

IV. Biology

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for $P2Y_1$ antagonists have been recently reviewed (Burnstock, G. et al., *J. Pharm. Exp. Ther.*, 295:862-869 (2000)) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

It is also desirable and preferable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-platelet agent, e.g., a P2Y1 antagonist. Exemplary subjects include human beings of any age with risk factors for platelet associated disorders. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

P2Y$_1$ Assays

Binding Assay A

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology*, John Wiley and Sons, NY, N.Y. (1995)). The essential coding sequences were subcloned into pCDNA 3.1 (Invitrogen) to produce a P2Y$_1$ expression construct. This construct was then transfected into the human embryonic kidney cell line HEK-293 and stable transfectants selected in GENETICIN® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at −70° C. until used.

Binding reactions were performed in WGA FLASHPLATE®s (PerkinElmer Life Sciences, Cat # SMP105A) in a volume of 200 μL containing ~45 fmol of P2Y$_1$ receptor (5 μg of total protein), 0.5 nM [$^{33}$P] 2MeS-ADP (PerkinElmer; 2,000 Ci/mmol), and various concentrations of the test compound (usually between 50 μM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

Binding Assay B—Scintillation Proximity Assay (SPA) for P2Y$_1$ Binding

A SPA membrane binding assay was used to identify inhibitors of [$^{33}$P] 2MeS-ADP binding to cloned human P2Y$_1$ receptors (The P2Y$_1$ receptor membranes were provided by Biology and the cloning of the receptor and P2Y$_1$ receptor membrane preparation is same as described by Biology). Binding reactions were performed in 384-well OptiPlates (PerkinElmer Life Sciences, Cat #6007299) in a volume of 50 μL containing ~15 fmol of P2Y$_1$ receptor (1.7 μg of total protein), 0.3 nM [$^{33}$P] 2MeS-ADP (PerkinElmer; 2,000 Ci/mmol), various concentrations of the test compound (usually between 10 μM and 160 pM) in Buffer B containing 1% DMSO in assay buffer (15 mM, HEPES, 145 mM potassium chloride, 5 mM sodium Chloride, 5 mM EDTA, 0.1 mM MgCl$_2$, pH 7.4) and 100 μg of SPA bead (WGA polystyrene Image beads, #RPNQ 0260V, Amersham). Reactions were allowed to proceed to completion at room temperature for 1 hour followed by centrifugation of the plate for 5 min. About 40 μL of the aqueous solution was aspirated. Plates were sealed and the [$^{33}$P] 2MeS-ADP bound to the P2Y$_1$ receptor membranes that were bound to the SPA bead were determined in a Gen 4 LEADSEEKER$^{SM}$ (Amersham) Image Reader. Dose-response curves (IC$_{50}$) were fit by non-linear regression (Toolset an in house data processing program) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 14 nM.

ADP Induced Platelet Aggregation Assay

The ability of P2Y$_1$ antagonists covered in the present invention to inhibit platelet aggregation induced by 10 μM ADP was tested using human platelet rich plasma (PRP) as described in *Platelet Protocols: Research and Clinical Laboratory Procedures* (White, M. M. et al., Academic Press (1999)). Human blood was collected in 30 μM (final concentration in blood) argatroban (GSK) as the anticoagulant at a ratio of 1 ml per 9 ml of blood. The PRP was isolated by centrifugation at 170 g for 12 minutes. The platelet poor plasma (PPP) was used as the blank for optical aggregometry. Compounds of the present invention in DMSO solution was preincubated with 250 μl PRP at 37° C. for 1 minute with stirring speed of 1000 rpm. Aggregation was initiated by addition of 2.5 μl of 1 mM ADP (Chrono-log, Havertown, Pa.) for a final ADP concentration of 10 μM. Platelet aggregation was monitored using Optical Aggregometer (Chrono-log, Havertown, Pa.) and the area under the curve (AUC) at 5 minute was measured. IC$_{50}$ was calculated using vehicle control as 0% inhibition.

The effectiveness of compounds of the present invention as antithrombotic agents and can be determined using relevant in vivo thrombosis models, including in vivo rat FeCl$_2$-induced carotid artery thrombosis, in vivo rabbit electrically-induced carotid artery thrombosis, and in vivo rabbit arterio-venous shunt thrombosis models. The potential of compounds of the present invention to have an undesirable bleeding liability can be determined using relevant in vivo rat models of cuticle and mesenteric bleeding time or in vivo rabbit cuticle bleeding model. An ideal compound from the present invention will demonstrate strong antithrombotic activity at doses that minimize the bleeding liability.

In Vivo FeCl$_2$-Induced Carotid Artery Thrombosis (FeAT) Model

The FeAT model described by Schumacher et al. (*J. Pharmacol. Exp. Ther.*, 322:9369-377 (2007)) can be used in this study. SPRAGUE DAWLEY® rats (350 to 450 g) are anesthetized with Na-pentobarbital (50 mg/kg i.p.) and the trachea is intubated with polyethylene-205 tubing to ensure airway patency. Temperature is maintained with a warming table and heat lamp. A polyethylene-50 catheter is inserted into the left carotid artery to obtain blood samples for measuring ex vivo platelet aggregation responses to ADP and measuring drug concentration. The right carotid artery is exposed and fitted with transit time doppler probe attached to a T206 flowmeter (Transonic Systems Inc., Ithaca, N.Y.). A piece of parafilm "M" (American National Can, Greenwich, Conn.) is inserted under the vessel and, following baseline flow measurements, a 2 mm by 5 mm strip of filter paper saturated with a 50% solution of FeCl$_2$ is placed on top of the artery for 10 min. The carotid artery is dissected free 60 min after filter paper application and opened lengthwise to expose the thrombus, which is removed, blotted dry and weighed on an AE50 balance (Mettler, Toledo, Ind.). Carotid blood flow is monitored continuously on a TA4000 physiologic recorder (Gould, Cleveland, Ohio). Integrated blood flow is determined as an area under the curve and normalized as percent of baseline (0 min) flow over 60 min to provide a measure of average blood flow over the duration of thrombus formation.

In Vivo Rabbit Electrically-induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The ED$_{50}$ (dose that increased average carotid blood flow over 90 min to 50% of the control) of compounds are estimated by a nonlinear least square regression program using the Hill sigmoid E equation (DeltaGraph; SPSS Inc., Chicago, Ill.).

In Vivo Rabbit Arterio-venous (AV) Shunt Thrombosis Model

The rabbit AV shunt model, described by Wong et al. (Wong, P. C. et al., *J. Pharmacol. Exp. Ther.*, 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID$_{50}$ values (dose which produces 50% inhibition of thrombus formation) are estimated by a nonlinear least square regression program using the Hill sigmoid E equation (DeltaGraph; SPSS Inc., Chicago, Ill.).

In Vivo Rat Cuticle Bleeding Time (CBT) and Mesenteric Bleeding Time (MBT) Model The CBT and MBT models described by Schumacher et al. (*J. Pharmacol. Exp. Ther.*, 322:1-9 (2007)) can be used in this study. SPRAGUE DAWLEY® rats (350 to 450 g) are anesthetized with Na-pentobarbital (50 mg/kg i.p.) and the trachea is intubated with polyethylene-205 tubing to ensure airway patency. Temperature is maintained with a warming table and heat lamp. A polyethylene-50 catheter is inserted into the left carotid artery to obtain blood samples for measuring ex vivo platelet aggregation responses to ADP.

For the MBT the abdomen is opened via a midline incision and the small intestine is exteriorized. The jejunum is exposed, held in place with clamps and superfused with Ringer's solution maintained at 37° C. Small arteries that branch perpendicular to the mesenteric artery and course over the surface of the jejunum are observed through an SZH10 stereomicroscope (Olympus Corp., Lake Success, N.Y.). These vessels are punctured with a 30-gauge hypodermic needle, and the time in sec from puncturing until bleeding stopped and remained stopped for 30 sec is recorded. The maximum bleeding time recorded is 10 min and 3 to 5 replicate bleed times are determined.

For the CBT toenails are cut with a single edged razor blade at the location where the quick meets the nail. The cuticle is immediately superfused with Ringer's solution maintained at 37° C., and the time until bleeding stopped and remained stopped for 30 sec is recorded. The maximum bleeding time recorded is 15 min. Three replicate bleeding times are determined on the hind paw.

In Vivo Rabbit Cuticle Bleeding Time Model

The rabbit cuticle bleeding time model, described by Wong et al. (Wong, P. C. et al., *J. Pharmacol. Exp. Ther.*, 303:993-1000 (2002)), can be used in this study. Male rabbits were anesthetized with ketamine (50 mg/kg+50 mg/kg/h IM) and xylazine (10 mg/kg+10 mg/kg/h IM), These anesthetics are supplemented as needed, and their hind paws were shaved. A standard cut was made at the apex of the cuticle with a razor blade, Blood was allowed to flow freely by keeping the bleeding site in contact with 37° C. warm Lactated Ringer's solution. Bleeding time was defined as the time after transection when bleeding was ceased. It was measured by averaging the bleeding time of three nail cuticles in the control period and at 60 min of the treatment period. Compound or vehicle was infused i.v. 1 h before the cuticle bleeding and continuously during the bleeding time measurement period.

Comparator Compounds

The following comparator compounds and their preparations are disclosed in U.S. Patent Publication No. 2005/0261244 A1:

Suggested Comparators:

| Comparator No. Example No. in US 2005/0261244 A1 | Structure |
|---|---|
| Comparator 1 Example 51 (US 2005/0261244 A1) | *(structure shown: spiroindoline-piperidine with N-isopropyl, phenyl-urea-phenyl-OCF₃)* |
| Comparator 2 Example 53 (US 2005/0261244 A1) | *(structure shown: spiroindoline-piperidine with N-isobutyl, phenyl-urea-phenyl-OCF₃)* |
| Comparator 3 Example 71 (US 2005/0261244 A1) | *(structure shown: spiroindoline-piperidine with N-isopropyl, pyridinyl-urea-phenyl-OCF₃)* |

The following representative in vitro biological data was measured in a binding assay for the Comparator Compounds and the exemplified examples herein:

TABLE 1

| Example No. | P2Y$_1$ K$_i$ (nM) using binding assay B | PA IC$_{50}$ (µM) @ 10 µM ADP |
|---|---|---|
| Comparator 1 | 300.4* | 29.2 |
| Comparator 2 | 20.2* | 8.8 |
| Comparator 3 | 5298* | NT |
| 1 | 10.3* | 1.7 |
| 2 | 9.0 | 0.6 |
| 3 | 8.9 | 0.1 |
| 4 | 9.9 | 0.4 |
| 5 | 8.3 | 0.4 |
| 6 | 4.4 | 0.9 |
| 7 | 4.0 | 0.6 |
| 8 | 5.7 | 1.1 |
| 9 | 10.5 | 0.9 |
| 10 | 4.5 | 0.1 |

TABLE 1-continued

| Example No. | P2Y$_1$ K$_i$ (nM) using binding assay B | PA IC$_{50}$ (μM) @ 10 μM ADP |
|---|---|---|
| 11 | 7.9 | 0.1 |
| 12 | 5.6 | 1.4 |
| 13 | 3.3* | 0.5 |
| 14 | 12.8 | 2.1 |
| 15 | 5.1 | 0.5 |
| 16 | 8.1 | 0.3 |
| 17 | 9.0 | 0.4 |
| 18 | 6.2 | 0.1 |
| 19 | 7.5 | 0.2 |
| 20 | 3.2 | 0.2 |
| 21 | 30.9 | 0.4 |
| 22 | 4.4 | 0.2 |
| 23 | 8.0 | 1.1 |
| 24 | 14.8 | 0.4 |
| 25 | 4.9 | 0.1 |
| 26 | 7.3 | 0.2 |
| 27 | 9.6 | 0.7 |
| 28 | 6.6 | 0.8 |
| 29 | 6.4 | 0.4 |
| 30 | 14.5 | 0.1 |
| 31 | 16.4 | 0.1 |
| 32 | 7.4 | 0.3 |
| 33 | 3.7* | 0.4 |
| 34 | 3.7* | 0.5 |
| 35 | 1.9* | 0.3 |
| 36 | 7.9 | 0.9 |
| 37 | 7.2 | 1.0 |
| 38 | 10.0 | 0.4 |
| 39 | 3.8 | 0.2 |
| 40 | 5.6 | 0.5 |
| 41 | 7.2 | 0.7 |
| 42 | 3.3* | 0.3 |
| 43 | 4.4* | 0.3 |
| 44 | 7.3 | 0.1 |
| 45 | 9.5 | 0.3 |
| 46 | 6.2 | 0.3 |
| 47 | 9.4 | 0.3 |
| 48 | 8.0 | 0.4 |
| 49 | 6.5 | 0.3 |
| 50 | 6.8 | 0.3 |
| 51 | 10.8 | 0.5 |
| 52 | 9.2 | 0.3 |
| 53 | 7.5 | 0.5 |
| 54 | 9.6 | 1.1 |
| 55 | 9.7 | 1.0 |
| 56 | 6.4 | 0.5 |
| 57 | 10.4 | 0.2 |
| 58 | 12.4 | 0.2 |
| 59 | 7.2 | 0.4 |
| 60 | 6.4 | 0.4 |
| 61 | 5.8 | 0.2 |
| 62 | 13.0 | 0.8 |
| 63 | 4.9 | 0.4 |
| 64 | 6.5 | 1.0 |
| 65 | 7.8 | 0.4 |
| 66 | 25.8 | 1.2 |
| 67 | 22.2 | 0.3 |
| 68 | NT | 0.7 |
| 69 | 21.4 | 0.8 |
| 70 | 29.4 | 1.0 |
| 71 | 11.1 | 0.3 |
| 72 | 22.4 | 0.2 |
| 73 | 17.9 | 0.5 |
| 74 | 10.3 | 0.2 |
| 75 | 7.5* | 0.4 |
| 76 | 9.1* | 0.7 |
| 77 | 8.7 | 0.3 |
| 78 | 7.9 | 0.7 |
| 79 | 9.0 | 0.7 |
| 80 | 14.4 | 0.9 |
| 81 | 5.0 | 0.6 |
| 82 | 24.8 | 1.0 |
| 83 | 5.7 | 0.2 |
| 84 | 11.8 | 0.5 |
| 85 | 3.7 | 0.4 |
| 86 | NT | 0.8 |
| 87 | NT | 0.9 |
| 88 | NT | 0.9 |
| 89 | 5.3 | 0.4 |
| 90 | 3.5 | 0.2 |
| 91 | 3.4 | 0.3 |
| 92 | 15.8 | 0.5 |
| 93 | 13.5 | 0.5 |
| 94 | 23.1 | 0.7 |
| 95 | 14.7 | 0.5 |
| 96 | 25.8 | 0.3 |
| 97 | 11.5 | 0.7 |
| 98 | 12.8 | 0.9 |
| 99 | 14.2 | 1.7 |
| 100 | 7.9 | 0.2 |
| 101 | 12.2 | 0.9 |
| 102 | 12.6 | 0.6 |
| 103 | 19.0 | 0.3 |
| 104 | 17.0 | 1.0 |
| 105 | 12.7 | 1.1 |
| 106 | 10.6 | 0.1 |
| 107 | 14.4 | 0.6 |
| 108 | 14.5 | 0.2 |
| 109 | 24.6 | 0.4 |
| 110 | 53.7 | 0.5 |
| 111 | 9.1 | 0.2 |
| 112 | 9.5 | 0.2 |
| 113 | 7.1 | 0.4 |
| 114 | 5.6 | 0.1 |
| 115 | 22.8 | 1.0 |
| 116 | 36.2 | 0.6 |
| 117 | 29.6 | 0.6 |
| 118 | 15.5 | 0.3 |
| 119 | 18.4 | 0.3 |
| 120 | 28.5 | 0.6 |
| 121 | 45.6 | 0.4 |
| 122 | 18.4 | 0.4 |
| 123 | 32.5 | 0.6 |
| 124 | 51.5 | 1.0 |
| 125 | 21.6 | 0.9 |
| 126 | 13.1 | 0.4 |
| 127 | NT | 0.5 |
| 128 | 8.0 | 0.2 |
| 129 | 8.7 | 0.7 |
| 130 | 16.8 | 0.6 |
| 131 | 22.5 | 1.0 |
| 132 | 12.4 | 0.7 |
| 133 | 1.2 | 0.3 |
| 134 | 136.7 | 0.4 |
| 135 | 21.7 | 0.6 |
| 136 | 73.4 | 0.5 |
| 137 | 44.7 | 0.4 |
| 138 | 24.6 | 0.2 |
| 139 | 103.9 | 0.4 |
| 140 | 52.4 | 0.6 |
| 141 | 33.9 | 0.9 |
| 142 | 9.6 | 0.5 |
| 143 | 24.0 | 0.9 |
| 144 | 13.0 | 0.7 |
| 145 | 18.4 | 0.6 |
| 146 | 11.2 | 0.6 |
| 147 | 14.8 | 0.5 |
| 148 | NT | 0.3 |
| 149 | 26.8 | 0.9 |
| 150 | 33.4 | 0.9 |
| 151 | NT | 0.3 |
| 152 | 10.2 | 0.2 |
| 153 | 11.5 | 0.4 |
| 154 | 38.8 | 0.4 |
| 155 | 22.5 | 0.1 |
| 156 | 20.2 | 0.2 |
| 157 | 12.3 | 0.2 |
| 158 | 15.4 | 0.3 |
| 159 | 281.1 | 0.1 |
| 160 | 199.3 | 0.1 |
| 161 | 41.1 | 0.2 |
| 162 | 65.5 | 0.5 |
| 163 | NT | 0.1 |
| 164 | 24.9 | 0.6 |

TABLE 1-continued

| Example No. | P2Y$_1$ K$_i$ (nM) using binding assay B | PA IC$_{50}$ (µM) @ 10 µM ADP |
|---|---|---|
| 165 | 56.2 | 0.3 |
| 166 | 6.8 | 0.1 |
| 167 | 3.3* | 0.5 |
| 168 | 8.6 | 0.3 |
| 169 | 11.5 | 0.2 |
| 170 | 6.5 | 0.5 |
| 171 | NT | 0.3 |
| 172 | 5.3 | 0.6 |
| 173 | 3.8 | 0.3 |
| 174 | 7.0 | 0.2 |
| 175 | 13.4 | 0.5 |
| 176 | 7.2 | 0.4 |
| 177 | NT | 0.7 |
| 178 | 12.2 | 0.9 |
| 179 | 12.6 | 0.6 |
| 180 | NT | 0.9 |

*Using binding assay A.
NT: Not tested.

The platelet aggregation assay measures the in vitro antiplatelet activity of a compound in platelet rich plasma. The assay is sensitive to plasma protein binding, and is believed to be a better predictor of actual in vivo activity. Surprisingly, it was discovered that the compounds of the present invention are unexpectedly significantly more active in the platelet aggregation assay than those exemplified in U.S. Patent Publication No. US 2005/0261244 A1.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., other anti-platelet agents or other pharmaceutically active material. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving $P2Y_1$ or anti-platelet activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1

1-Pivaloylpiperidine-4-carbaldehyde

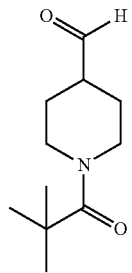

Intermediate 1A 1-(4-(Hydroxymethyl)piperidin-1-yl)-2,2-dimethylpropan-1-one: In a 500-ml round bottomed flask, to piperidin-4-yl methanol (20.0 g, 174 mmol) in dichloroethane (180 mL) was added triethylamine (24.2 mL, 174 mmol) followed by pivaloyl chloride (21.4 mL, 174 mmol). The mixture was stirred at 23° C. for 4 hours, then filtered and concentrated in vacuo. The filtrate was placed in EtOAc, washed with sat'd NH$_4$Cl (2×), water, brine, dried over Na$_2$SO$_4$, filtered and concentrated in vacuo to give Intermediate 1A (28 g, yield: 81%). $^1$H NMR (DMSO-d$_6$) δ ppm 4.47 (t, J=5.31 Hz, 1H), 4.25 (d, J=12.88 Hz, 2H), 3.23 (t, J=5.68 Hz, 2H), 2.71 (t, J=12.38 Hz, 2H), 1.56-1.68 (m, 3H), 1.16 (s, 9H), 0.96 (ddd, J=24.00, 12.25, 3.92 Hz, 2H); LCMS (ESI) m/z 200 (M+H)$^+$, RT=0.48 min (Method B).

Intermediate 1

A 1000-ml oven-dried flask capped with a rubber septum was evacuated and backfilled with argon. The flask was charged with oxalyl chloride (17.4 mL, 203 mmol) in DCM (320 mL). At −78° C., a solution of DMSO (28.9 mL, 406 mmol) in DCM (50 mL) was added dropwisely. After 30 min, Intermediate 1A (27.0 g, 135 mmol) in DCM (100 mL) was added dropwisely. After 30 min, triethylamine (75.5 mL, 542 mmol) was added, stirred for 30 min at −78° C. It was poured into water, extracted with DCM (3×). Combined organic layers were washed with water (3×300 mL), dried over Na$_2$SO$_4$, filtered and concentrated in vacuo to provide Intermediate 1 (24.2 g, yield: 91.0%). $^1$H NMR (DMSO-d$_6$) δ ppm 9.58 (s, 1H), 4.25 (d, J=10.36 Hz, 1H), 4.06 (ddd, J=13.52, 3.66, 3.54 Hz, 2H), 2.93-3.04 (m, 1H), 2.65-2.76 (m, 1H), 1.78-1.86 (m, 1H), 1.65 (d, J=12.38 Hz, 1H), 1.30-1.41 (m, 2H), 1.16 (s, 9H); LCMS (ESI) m/z 198 (M+H)$^+$, RT=0.518 min (Method B).

Alternatively, Intermediate 1 was prepared in a large-scale synthesis as following:

Intermediate 1B

Ethyl 1-pivaloylpiperidine-4-carboxylate: A solution of ethyl isonipecolate (375 g, 2.39 mol) in dry THF stirred at 0° C. under nitrogen atmosphere was added triethylamine (396 mL, 2.87 mol dropwise followed by the addition of pivaloyl chloride (312 mL, 2.51 mol). The mixture was allowed to attain rt under stirring overnight. On completion of the reaction, the solid mass obtained was filtered and the filtrate was concentrated to remove THF. The material was dissolved in ethyl acetate and washed with water, brine, dried over anhydrous sodium sulfate and concentrated under reduced pressure to give the crude Intermediate 1B (550 g). GC: 95.9% purity, RT=18.25 min (Column DB-624, 30×0.53 mm×3 um, Constant flow, flow rate=8.0 mL/min, Inlet temp.=150° C., Detector temp=250° C. Split ratio: 10:1, Oven temp.: Initial=50° C. for 2 min, Ramp: 15° C./min, Final=220° C. for 10 min). GCMS 241 (Mt); $^1$H NMR (400 MHz, CDCl$_3$) δ 1.21-1.26 (t, 3H, CH$_3$ of the ester group), 1.28 (s, 9H, 3× CH$_3$ of pivaloyl), 1.65-1.68 (m, 2H), 1.90 (m, 2H), 2.45-2.65 (m, 1H), 2.97 (m, 2H), 4.16-4.19 (q, 2H, OCH$_2$), 4.27-4.31 (d, 2H).

Intermediate 1A

Intermediate 1B (1153 g, 4.790 mol) was taken in a mixture of ethanol and dry THF (12 L, 1:1) and cooled to 0° C. Sodium borohydride (542.5 g, 14.35 mol) was added portionwise at 0° C. and then the reaction mixture was allowed to attain rt by stirring overnight. After the completion of reaction, water was added and ethanol and THF were concentrated under reduced pressure. The concentrated mass was dissolved in ethyl acetate and washed with water, brine, dried over anhydrous sodium sulfate and concentrated under reduced pressure to give Intermediate 1A (890 g, yield: 93.4%). GCMS: 199 (Mt); $^1$H NMR (300 MHz, CDCl$_3$) δ 1.28 (s, 9H, 3× CH$_3$ of pivaloyl), 1.76 (m, 4H), 1.80 (m, 1H), 2.05 (s, 1H, OH), 2.74-2.82 (t, 2H), 3.50 (d, 2H), 4.43-4.47 (d, 2H, CH$_2$OH).

Intermediate 1

The crude Intermediate 1A (890 g, 4.47 mol) obtained was dissolved in dichloromethane (9 L), and stirred at 0° C. under nitrogen atmosphere. Dess-Martin periodinane (1.90 kg, 4.47 mol) was added slowly and the reaction mixture was allowed to attain rt slowly and then stirred overnight. After completion of the reaction, the reaction mixture was basified to pH 11 with sodium carbonate. Water was added and the reaction mixture was filtered through CELITE®. The filtrate was concentrated and the mass obtained was dissolved in ethyl acetate, washed with sodium carbonate solution, brine, dried over anhydrous sodium sulfate and concentrated to give the crude Intermediate 1 (700 g).

Intermediate 2

1-(1-(2-Aminophenyl)-7-methoxyspiro[indoline-3,4'-piperidine]-1'-yl)-2,2-dimethylpropan-1-one

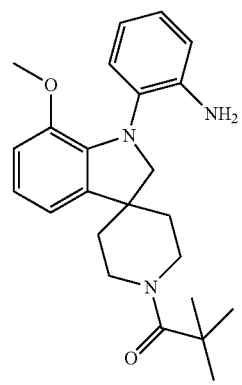 [SMILES: COc1cccc2c1N(c1ccccc1N)CC21CCN(C(=O)C(C)(C)C)CC1]

Intermediate 2A 1-(7-Methoxyspiro[indoline-3,4'-piperidine]-1'-yl)-2,2-dimethylpropan-1-one: In a 500-ml round bottomed flask, to Intermediate 1 (10 g, 51 mmol) in mixture of toluene (98 mL) and acetonitrile (2.4 mL) was added the (2-methoxyphenyl)hydrazine (7.35 g, 53 mmol) [Free base was prepared by dissolving the hydrazine HCl salt (10 g) in 15 mL of water. NaHCO$_3$ (4.81 g) was added carefully (exothermic) followed by the addition of 100 mL of diethyl ether. The layers were separated, and aqueous layer was extracted with 40 mL of diethyl ether. Combined organic layers were dried over Na$_2$SO$_4$, filtered and concentrated in vacuo to give 7.47 g of free base as a tan solid]. The mixture was stirred at 23° C. for 1 h. Trifluoroacetic acid (11.3 mL, 152 mmol) was added slowly, and the mixture was stirred at 23° C. for 4 h. The mixture was cooled to −20° C., and 7.3 mL of methanol was added. NaBH$_4$ (1.76 g, 46.6 mmol) was added carefully (exothermic). The mixture was poured into water/ethyl acetate, and the organic layer was separated and washed with saturated NaHCO$_3$, brine, dried over Na$_2$SO$_4$, filtered and concentrated in vacuo. Crude material was purified by flash chromatography eluting with 1-5% methanol in 99-95% dichloromethane to afford 8.75 g (yield: 57%) of Intermediate 2A. $^1$H NMR (DMSO-d$_6$) δ 7.00-7.07 (m, 1H), 6.90 (t, J=7.20 Hz, 2H), 4.24 (d, J=14.15 Hz, 2H), 3.82 (s, 3H), 3.57 (s, 2H), 2.97 (t, J=11.75 Hz, 2H), 1.60-1.72 (m, 4H), 1.21 (s, 9H). LCMS (ESI) m/z 303 (M+H)$^+$, RT=1.05 min (Method B).

Intermediate 2B 1-(7-Methoxy-1-(2-nitrophenyl)spiro[indoline-3,4'-piperidine]-1'-yl)-2,2-dimethylpropan-1-one: Toluene (100 mL, sparged with argon for 30 min) was added to a 350-ml sealable flask containing Intermediate 2A (6.41 g, 21.2 mmol), 1-bromo-2-nitrobenzene (8.56 g, 42.0 mmol), Pd$_2$ (dba)₃ (776 mg, 0.850 mmol), rac-BINAP (1.58 g, 2.54 mmol) and cesium carbonate (16.6 g, 50.9 mmol) under argon. The reaction was sealed and heated to 125° C. for 60 h. The reaction was cooled, filtered over CELITE®, and concentrated in vacuo. The crude material was purified directly by flash chromatography on BIOTAGE® using 20-35% ethyl acetate in hexanes to give Intermediate 2B (7.14 g, yield: 80%). ¹H NMR (400 MHz, DMSO-d₆) δ ppm 8.01 (dd, J=8.21, 1.39 Hz, 1H), 7.53-7.62 (m, 1H), 7.35 (d, J=8.34 Hz, 1H), 7.10 (t, J=7.71 Hz, 1H), 6.84-6.93 (m, 2H), 6.77-6.82 (m, 1H), 4.28 (d, J=12.63 Hz, 1H), 4.20 (d, J=14.15 Hz, 1H), 4.10 (s, 2H), 3.44 (s, 3H), 2.96-3.06 (m, 1H), 2.86-2.96 (m, 1H), 1.83-1.92 (m, 1H), 1.77 (d, J=12.13 Hz, 1H), 1.65 (d, J=12.63 Hz, 1H), 1.56 (td, J=13.07, 4.42 Hz, 1H), 1.20 (s, 9H). LCMS (ESI) m/z 424 (M+H)⁺, RT=1.857 min (Method B).

Intermediate 2

1-(1-(2-Aminophenyl)-7-methoxyspiro[indoline-3,4'-piperidine]-1'-yl)-2,2-dimethylpropan-1-one: In a 250-ml round bottomed flask, to Intermediate 2B (2.51 g, 5.90 mmol) in ethyl acetate (59 mL) was added the 10% Pd/C (500 mg). Air was removed and hydrogen atmosphere (balloon) was made (3 cycles). The reaction mixture was stirred for 3 h at 60° C., and then hydrogen balloon was removed. The mixture was filtered over CELITE®, and rinsed with 50 mL of ethyl acetate. The crude material was purified by flash chromatography (BIOTAGE®) eluting with 50-80% ethyl acetate in hexanes to provide Intermediate 2 (1.79 g, yield: 77%). ¹H NMR (400 MHz, DMSO-d₆) δ ppm 6.75-6.84 (m, 4H), 6.67 (dd, J=7.83, 1.26 Hz, 1H), 6.63 (dd, J=7.71, 1.14 Hz, 1H), 6.42 (td, J=7.39, 1.39 Hz, 1H), 4.82 (s, 2H), 4.26 (d, J=12.13 Hz, 1H), 4.19 (d, J=13.64 Hz, 1H), 4.05 (d, J=10.11 Hz, 1H), 3.45 (s, 3H), 3.16 (d, J=10.36 Hz, 1H), 2.90 (t, J=12.13 Hz, 1H), 2.81 (t, J=13.14 Hz, 1H), 1.74-1.79 (m, 1H), 1.71 (dd, 1H), 1.66 (dd, J=12.88, 4.04 Hz, 1H), 1.57 (d, J=13.14 Hz, 1H), 1.20 (s, 9H). LCMS (ESI) m/z 394 (M+H)⁺, RT=1.422 min (Method B).

Intermediate 3

1-(1-(2-Aminophenyl)-6-fluoro-7-methoxyspiro[indoline-3,4'-piperidine]-1'-yl)-2,2-dimethylpropan-1-one

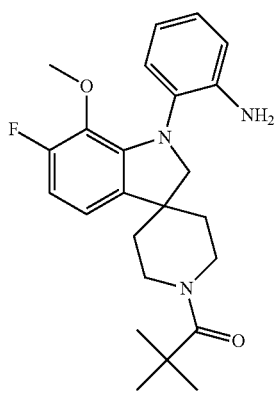 [SMILES: COc1c(F)ccc2c1N(c1ccccc1N)CC21CCN(C(=O)C(C)(C)C)CC1]

Intermediate 3 was prepared according to the procedures described in Intermediate 2 using (3-fluoro-2-methoxyphenyl)hydrazine as the starting material to afford 110 mg (yield: 15%) of Intermediate 3. LCMS (ESI) m/z 412 (M+H)⁺, RT=1.51 min (Method B).

Intermediate 4

1-(1-(2-Aminophenyl)-4-fluoro-7-hydroxyspiro[indoline-3,4'-piperidine]-1'-yl)-2,2-dimethylpropan-1-one

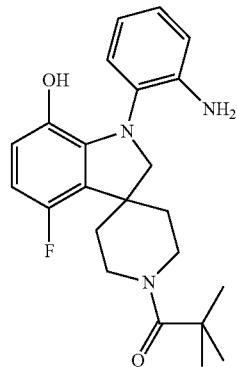 [SMILES: CC(C)(C)C(=O)N1CCC2(CC1)CN(c1ccccc1N)c1c(O)ccc(F)c12]

Intermediate 4A 2-(Benzyloxy)-5-fluoroaniline: Benzyl bromide (8.3 mL, 70 mmol) was added to a solution of potassium carbonate (8.80 g, 63.6 mmol) and 4-fluoro-2-nitrophenol (10.0 g, 63.6 mmol) in DMF (100 mL) and stirred at rt for 3 days. The reaction was diluted with water and EtOAc. The aqueous layer was extracted with EtOAc and then the combined organics were washed with sat'd NaHCO₃ solution, brine, and then dried over MgSO₄, filtered and evaporated to give crude ether product. This crude was taken up in ethanol (500 mL) and zinc (41.6 g, 636 mmol) and ammonium chloride (34.1 g, 636 mmol) were added and stirred at rt for 5 h. The reaction was diluted in EtOAc and filtered through CELITE® and then concentrated to give 12 g (yield: 88%) of Intermediate 4A. ¹H NMR (400 MHz, CDCl₃) δ ppm 3.87 (m, 2H), 5.03 (s, 2H), 6.36 (t, J=8.6 Hz, 1H), 6.45 (d, J=9.9 Hz, 1H), 6.75 (dd, J=5.0, 8.5 Hz, 1H), 7.35-7.45 (m, 5H); LCMS (ESI) m/z 218 (M+H)⁺, RT=1.74 min (Method A).

Intermediate 4B (2-(Benzyloxy)-5-fluorophenyl)hydrazine: A suspension of Intermediate 4A (12.2 g, 55.9 mmol) in 6M HCl (35 mL) was cooled to −10° C. with mechanical stirring and a solution of sodium nitrite (4.00 g, 58.7 mmol) in water (10 mL) was added slowly to keep the temperature below 0° C. After the addition, the reaction was stirred for an additional 20 min. at −10 to 0° C. A solution of tin(II) chloride (31.8 g, 168 mmol) in conc. HCl (50 mL) was added slowly resulting in precipitation. After 20 min, a gum resulted and the solution was decanted off and the gum was suspended in 10% NaOH solution. This suspension was extracted with ether (2×). The combined organics were dried over MgSO₄, filtered and evaporated to give Intermediate 4B which was used directly in the next step.

Intermediate 4C 1-(7-(Benzyloxy)-4-fluorospiro[indoline-3,4'-piperidine]-1'-yl)-2,2-dimethylpropan-1-one: TFA (6.40 mL, 86.6 mmol) was added to a solution of the TFA salt of Intermediate 4B (10.0 g, 28.9 mmol) and Intermediate 1 (5.70 g, 28.9 mmol) in toluene (36 mL) and acetonitrile (1.8 mL). The reaction was heated to 40° C. for 3 h. The reaction was cooled to rt and methanol (6 mL) was added. The reaction was cooled to −20° C. and sodium borohydride (1.10 g, 28.9 mmol) was added portion-wise. After the addition the reaction was allowed to warm to 0° C. for 30 min and then quenched with water and diluted with EtOAc. The organic layer was dried over MgSO₄, filtered and evaporated to give crude product. The crude was purified by flash chromatography using EtOAc/hexanes (30-100%) to give 3.02 g (yield: 26%) of Intermediate 4C as a brown solid. $^1$H NMR (400 MHz, CDCl₃) δ ppm 1.28 (s, 9H), 1.76 (m, 2H), 2.15 (m, 2H), 2.85 (m, 2H), 3.53 (s, 2H), 3.95 (br s, 1H), 4.38 (d, J=13.4 Hz, 2H), 4.97 (s, 2H), 6.27 (t, J=9.4 Hz, 1H), 6.61 (dd, J=4.0, 8.8 Hz, 1H), 7.29-7.40 (m, 5H). LCMS (ESI) m/z 397 (M+H)⁺, RT=1.85 min (Method A).

Intermediate 4D 1-(7-(Benzyloxy)-4-fluoro-1-(2-nitrophenyl)spiro[indoline-3,4'-piperidine]-1'-yl)-2,2-dimethylpropan-1-one: A solution of Intermediate 4C (3 g, 7.6 mmol) in toluene (75 mL, sparged with argon for 30 min) was added to a sealable flask containing 2-bromo-1-nitrobenzene (1.8 g, 9.1 mmol), Pd₂(dba)₃ (0.28 mg, 0.30 mmol), rac-BINAP (0.57 g, 0.90 mmol), and Cs₂CO₃ (3.0 g, 9.1 mmol). The vessel was sealed and heated to 120° C. for 2 days. The reaction mixture was cooled, filtered through CELITE®, rinsed with EtOAc and then the filtrate was concentrated. This crude was purified by flash chromatography using EtOAc/hexanes (30-50%) to give 3.12 g (80%) of Intermediate 4D as a red solid. LCMS (ESI) m/z 518 (M+H)⁺, RT=2.33 min (Method A). $^1$H NMR (400 MHz, CDCl₃) δ ppm 1.30 (s, 9H), 1.78 (dd, J=2.2, 13.5 Hz, 1H), 1.97 (dd, J=2.2, 13.6 Hz, 1H), 2.18 (td, J=4.5, 13.3 Hz, 1H), 2.33 (td, J=4.3, 13.1 Hz, 1H), 2.75 (t, 1H), 2.91 (t, 1H), 3.90 (d, J=9.9 Hz, 1H), 4.13 (d, J=9.6 Hz, 1H), 4.40 (d, 1H), 4.51 (d, 1H), 4.72 (s, 2H), 6.50 (t, J=9.1 Hz, 1H), 6.67 (dd, J=4.2, 9.0 Hz, 1H), 6.90 (m, 2H), 7.01 (t, J=7.1 Hz, 1H), 7.10-7.25 (m, 4H), 7.41 (m, 1H), 7.78 (dd, J=1.5, 8.3 Hz, 1H).

Intermediate 4

1-(1-(2-Aminophenyl)-4-fluoro-7-hydroxyspiro[indoline-3,4'-piperidine]-1'-yl)-2,2-dimethylpropan-1-one: Palladium on carbon (640 mg, 10% w/w, 0.60 mmol) was added to a solution of Intermediate 4D (3.12 g, 6.03 mmol) in ethanol (50 mL) and EtOAc (50 mL) and stirred under an atmosphere of hydrogen for 6 days. The reaction mixture was filtered through CELITE®, rinsed with EtOAc and then the filtrate was concentrated. This crude was purified by flash chromatography using EtOAc/hexanes (10-50%) to give 970 mg (yield: 40%) of Intermediate 4. LCMS (ESI) m/z 398 (M+H)⁺, RT=1.44 min (Method A).

Intermediate 5

1-(2-Aminophenyl)-4-fluoro-1'-neopentylspiro[indoline-3,4'-piperidin]-7-ol

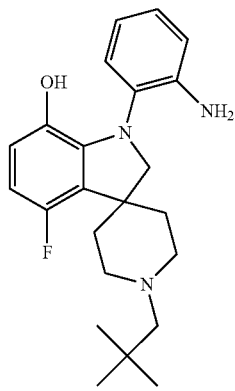 [SMILES: CC(C)(C)CN1CCC2(CC1)CN(c1ccccc1N)c1c(O)ccc(F)c12]

Lithium aluminum hydride (460 mg, 12.2 mmol) was added to a solution of Intermediate 4 (970 mg, 2.44 mmol) in THF (30 mL) at rt and stirred for 30 min. The reaction was diluted with dichloromethane (20 mL) and then quenched with sat'd Na₂SO₄ solution (1 mL). This mixture was stirred vigorously for 5 min. while aluminum salts precipitated and then filtered through CELITE® and concentrated to give 720 mg (77%) of Intermediate 5. LCMS (ESI) m/z 384 (M+H)⁺, RT=1.17 min (Method A).

Intermediate 6

Benzyl 1-(2-aminophenyl)-7-(benzyloxy)-4-cyanospiro[indoline-3,4'-piperidine]-1'-carboxylate

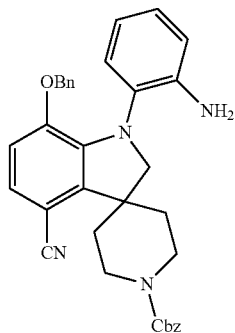 [SMILES: N#Cc1ccc(OCc2ccccc2)c2c1C1(CCN(C(=O)OCc3ccccc3)CC1)CN2c1ccccc1N]

Intermediate 6A

3-Amino-4-(benzyloxy)benzonitrile: Benzyl bromide (3.23 mL, 26.8 mmol) was added to a solution of potassium carbonate (3.4 g, 24 mmol) and 4-hydroxy-3-nitrobenzonitrile (4.0 g, 24 mmol) in DMF (50 mL) and stirred at rt for 16 h. The reaction was diluted with water and EtOAc. The aqueous layer was extracted with EtOAc and then the combined organics were washed with sat'd NaHCO₃ solution, brine, and then dried over MgSO₄, filtered and evaporated to give crude ether product. This crude was taken up in ethanol (200 mL) and zinc (15.9 g, 243 mmol) and ammonium chloride (13.0 g, 243 mmol) were added and stirred at rt for 24 hrs. The reaction was diluted in EtOAc and filtered through CELITE® and then concentrated to give Intermediate 6A which was taken directly on to the next step. LCMS (ESI) m/z 225 (M+H)$^+$, RT=1.77 min (Method A).

Intermediate 6B 4-(Benzyloxy)-3-hydrazinylbenzonitrile: Intermediate 6B was prepared (4.9 g, yield: 84%) following similar procedure as described in Intermediate 4B by replacing Intermediate 4A with Intermediate 6A (5.4 g, 24 mmol). LCMS (ESI) m/z 223 (M−NH$_3$+1)$^+$, RT=1.23 min (Method A).

Intermediate 6C

Benzyl 4-formylpiperidine-1-carboxylate: To oxalyl chloride (10.3 mL, 0.120 mol) in 150 mL of DCM and at −78° C., a solution of DMSO (17.1 mL, 0.241 mol) in DCM (25 mL) was added dropwisely. After 30 min, benzyl 4-(hydroxymethyl)-piperidine-1-carboxylate (20 g, 0.080 mol) in DCM (25 mL) was added dropwisely. After 30 min, Et$_3$N (44.7 mL, 0.321 mol) was added. The resulting solution was stirred for 30 min at −78° C. The reaction was diluted with water, extracted with DCM (3×). Combined organic layers were washed with water (3×500 mL), dried over Na$_2$SO$_4$, filtered and concentrated to give Intermediate 6C (18.5 g, 93.0%). MS (ESI) m/z 247 (M+H)$^+$.

Intermediate 6D

Benzyl 7-(benzyloxy)-4-cyanospiro[indoline-3,4'-piperidine]-1'-carboxylate: To Intermediate 6C (3.93 g, 15.9 mmol) in toluene/ACN (29 mL/0.72 mL) was added Intermediate 6B (3.99 g, 16.7 mmol) and the mixture was stirred at 23° C. for 3 hours. TFA (3.54 mL, 47.7 mmol) was added slowly and the mixture was stirred at 23° C. and stirred for 60 h. The reaction was heated at 80° C. for 3 h. After cooled to −20° C., methanol (5.2 mL) was added followed by careful addition of NaBH$_4$ (0.55 g, 15 mmol). The reaction was then poured into water/ethyl acetate. The organic layer was separated and washed with saturated NaHCO$_3$, brine, dried over Na$_2$SO$_4$, filtered and concentrated. The residue was purified by flash chromatography to give Intermediate 6D (4.68 g, 65.0%). MS (ESI) m/z 454.1 (M+H)$^+$.

Intermediate 6

Intermediate 6 was prepared following similar procedure as described in Intermediate 2B by replacing Intermediate 2A with Intermediate 6D. MS (ESI) m/z 575 (M+H)$^+$.

Intermediate 7

2-(4-Chloro-7-methoxy-1'-neopentylspiro[indoline-3,4'-piperidine]-1-yl)aniline

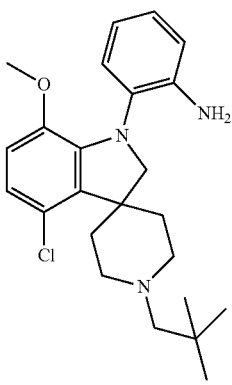 [SMILES: COc1ccc(Cl)c2c1N(c1ccccc1N)CC21CCN(CC(C)(C)C)CC1]

Intermediate 7A (5-Chloro-2-methoxyphenyl)hydrazine, HCl: To a solution of 5-chloro-2-methoxyaniline (11.0 g, 69.8 mmol) in 100 mL of 3N HCl was added sodium nitrite (5.3 g, 77 mmol) in 25 mL of H$_2$O dropwise (1 ml/min) at ice-salt bath temperature. The resulting mixture was stirred for 1 h after the addition was completed. To this solution was added tin(II) chloride dihydrate (14.5 mL, 174 mmol) in 40 mL of conc. HCl dropwise. After addition, the resulting mixture was stirred for 1 h at ice-salt bath temperature. The white solid from the mixture was filtered, and washed with cold brine (20 mL) and 2N HCl (20 mL). The filtrate was dried under reduced pressure to yield Intermediate 7A (18.4 g, 88.0 mmol, 126% yield), which contains SnCl$_2$ as well as more than 1.0 equiv. HCl as a co-salt.

Intermediate 7B 1-(4-Chloro-7-methoxyspiro[indoline-3,4'-piperidine]-1'-yl)-2,2-dimethylpropan-1-one: A solution of Intermediate 7A (4.0 g, 19 mmol) and 1-pivaloylpiperidine-4-carbaldehyde (3.2 g, 16 mmol) in CH$_2$Cl$_2$ (30 mL) and dioxane (15 mL) of 4N HCl was stirred for 1 h at 0° C. The solution was evaporated to provide a yellow solid, which was re-dissolved in MeOH (30 mL). The methanolic solution of the imine was cooled down to 0° C. and sodium cyanoborohydride (2.04 g, 32.4 mmol) was added by portions over 30 min. The resulting solution was stirred for 1 h at 0° C. Reaction was quenched by adding 10 mL of 1N HCl dropwise and the resulting solution was stirred at ambient temperature. Reaction mixture was then concentrated to provide a yellow solid, which was partitioned between 1N NaOH (20 mL) and dichloromethane (100 mL). Aqueous layer was further extracted with EtOAc (50 mL). The combined organic layers were dried over Na$_2$SO$_4$ and concentrated to yield an oily residue, which was purified by flash chromatography (silica gel, eluting with EtOAc/hexanes) to yield Intermediate 7B (1.70 g, 5.05 mmol, 31.1% yield) as a colorless solid. LCMS (ESI) m/z 337.3 (M+H)$^+$, RT=1.52 min (Method D).

Intermediate 7C 1-(4-Chloro-7-methoxy-1-(2-nitrophenyl)spiro[indoline-3,4'-piperidine]-1'-yl)-2,2-dimethylpropan-1-one: To a solution of Intermediate 7B (1.70 g, 5.05 mmol) in a degassed toluene (40 mL) was added 2-bromo-nitrobenzene (1.9 g, 9.5 mmol), $Cs_2CO_3$ (3.95 g, 12.1 mmol), BINAP (0.377 g, 0.606 mmol) and $Pd_2(dba)_3$ (0.185 g, 0.202 mmol), and the resulting mixture was stirred for 10 min at 25° C. with argon bubbling. The reaction mixture was sealed in microwave tube and stirred at 115° C. for 16 h. Reaction mixture was filtered and concentrated to yield a dark oily residue, which was purified by flash chromatography (silica gel, eluting with EtOAc/hexanes) to yield Intermediate 7C (1.8 g, 3.9 mmol, 78% yield) as a brown solid. LCMS (ESI) m/z 458.4 $(M+H)^+$, RT=2.05 min (Method D).

Intermediate 7D 1-(1-(2-Aminophenyl)-4-chloro-7-methoxyspiro[indoline-3,4'-piperidine]-1'-yl)-2,2-dimethylpropan-1-one: To a solution of Intermediate 7C (1.8 g, 3.93 mmol) in ethanol (40 mL) was added zinc (0.360 mL, 39.3 mmol) and ammonium chloride (1.38 mL, 39.3 mmol) and the resulting solution was stirred for 12 h at 25° C. The reaction mixture was filtered and organic solution was concentrated to give a light brown oily residue. The crude was partitioned in EtOAc (50 mL) and brine (20 mL). Aqueous layer was extracted with EtOAc (30 mL). The combined organic solution was dried over $Na_2SO_4$ and concentrated to provide Intermediate 7D (1.6 g, 3.7 mmol, 95% yield) as a light brown oil, which was subjected to the following reaction without further purification. LCMS (ESI) m/z 428.2 $(M+H)^+$, RT=1.71 min (Method D).

Intermediate 7

2-(4-Chloro-7-methoxy-1'-neopentylspiro[indoline-3,4'-piperidine]-1-yl)aniline: To a solution of Intermediate 7D (1.6 g, 3.7 mmol) in DCM (50 mL) was added RED-AL® (6.08 mL, 18.7 mmol) dropwise for 20 min and the resulting solution was stirred for 5 h at 25° C. Reaction was quenched by adding drops of aqueous $NaHCO_3$ into the reaction mixture. It was then diluted with DCM (50 mL) and washed with aqueous $NaHCO_3$ (30 mL). Organic layer was dried over $Na_2SO_4$ and concentrated in vacuo to yield Intermediate 7 (1.2 g, 2.9 mmol, 78% yield) as oil, which was subjected to the following reaction without further purification. LCMS (ESI) m/z 414.3 $(M+H)^+$, RT=1.30 min (Method D).

Alternatively, Intermediate 7 was prepared in a large-scale synthesis as following:

Intermediate 7A

To a solution of 2-methoxy-5-chloroaniline (100 g, 0.636 mol) in 6N HCl (600 mL) was added slowly an aqueous solution of sodium nitrite (52.7 g, 0.764 mol) maintaining the temperature between −5 to 0° C. The reaction mixture was then stirred for about 1 h maintaining the temperature below 0° C. A solution of stannous chloride (362 g, 1.90 mol) in conc. HCl was added slowly at −5 to 0° C. and stirring was continued for another 1.5 h after which the reaction mixture was brought to room temperature slowly. The white solid was then filtered, washed with 2N HCl to remove the stannous chloride, and then washed with diethyl ether and air-dried to give Intermediate 7A (120 g, yield: 90.0%). $^1$H NMR (400 MHz, DMSO-$d_6$) δ 3.82 (s, 3H, $OCH_3$), 6.95-7.00 (m, 2H), 7.135-7.139 (d, 1H), 10.28 (bs, 3H, NH and $NH_2$). $^{13}$C NMR (100 MHz, DMSO-$d_6$) δ 56.48, 112.61, 114.37, 121.59, 124.75, 135.95, 146.82.

Intermediate 7B-a 1-(4-Chloro-7-methoxyspiro[indole-3,4'-piperidine]-1'-yl)-2,2-dimethylpropan-1-one: To a solution of Intermediate 7A (130 g, 0.628 mol) in methanol (1.3 L) was added intermediate 1 (123 g, 0.628 mol) under nitrogen. The mixture was stirred at rt for 2.5 h. TLC showed the completion of the reaction after which the reaction mixture was cooled to 0° C. Conc. sulfuric acid (51.3 mL, 0.941 mol) was added slowly and the contents were stirred at rt overnight. The mixture was heated at 50° C. for 3 h. Methanol was evaporated under reduced pressure and the reaction mass was dissolved in ethyl acetate, washed with diluted NaOH, water and brine. The organic layer was dried over $Na_2SO_4$ and concentrated under reduced pressure. The crude mass was purified by flash chromatography using hexanes/ethyl acetate=20/80 to get the pure Intermediate 7B-a (85 g, yield: 41%). MS (ESI) m/z 335.1 $(M+H)^+$. $^1$H NMR (300 MHz, $CDCl_3$) δ 1.35 (s, 9H, $3×CH_3$ of pivaloyl), 1.45 (d, 2H), 2.75-2.83 (m, 2H), 3.19-3.22 (t, 2H), 4.68-4.71 (d, 2H), 6.87-6.89 (d, 1H), 7.18-7.20 (d, 1H), 8.68 (s, 1H).

Intermediate 7B

To a solution of Intermediate 7B-a (33 g, 98.6 mmol) in dry MeOH (330 mL) at 0° C. was added sodium borohydride portionwise (3.75 g, 98.6 mmol) under nitrogen atmosphere. The contents were stirred at rt overnight under nitrogen atmosphere. After completion of the reaction, the reaction mass was quenched with water at rt and then concentrated under reduced pressure to remove MeOH completely. The residue was then extracted into ethyl acetate, washed with water and brine. The organic layer was separated, dried over $Na_2SO_4$ and concentrated under reduced pressure to give the crude product. The pure Intermediate 7B was obtained by crystallization from ethyl acetate (28 g, yield: 85%). MS (ESI) m/z 337.1 $(M+H)^+$. $^1$H NMR (300 MHz, DMSO-$d_6$) δ 1.21 (s, 9H), 1.53-1.56 (d, 2H), 2.21-2.28 (m, 2H), 2.86 (t, 2H), 3.49-3.49 (d, 2H), 3.72 (s, 3H), 4.26-4.30 (d, 2H), 5.51 (bs, 1H), 6.48-6.48 (d, 1H), 6.67-6.69 (d, 1H). $^{13}$C NMR (100 MHz, DMSO-$d_6$) δ 28.53, 33.47, 38.57, 42.11, 47.52, 55.80, 56.22, 111.96, 118.39, 121.47, 130.44, 143.01, 144.02, 175.19.

Intermediate 7C

A suspension of Intermediate 7B (24 g, 71 mmol), 2-bromo nitrobenzene (21.6 g, 107 mmol), BINAP (8.88 g, 14.2 mmol), palladium acetate (1.6 g, 7.1 mmol), cesium carbonate (34.8 g, 107 mmol) in dry xylene (240 mL) was stirred under nitrogen atmosphere in a sealed tube at 130° C. for 16 h. The reaction mixture was filtered through CELITE®, washed thoroughly with MeOH and ethyl acetate, and concentrated under reduced pressure. The crude mass was purified by flash chromatography using hexanes/ethyl acetate=60:40 to give Intermediate 7C (23 g, yield: 72%). MS (ESI) m/z 458.2 $(M+H)^+$. $^1$H NMR (400 MHz, DMSO-$d_6$) δ 1.21 (s, 9H, 3× $CH_3$ of pivaloyl), 1.65-1.72 (t, 2H), 2.08-2.14 (m, 1H), 2.57-2.64 (dt, 1H), 2.81-2.87 (t, 1H), 2.94-2.30 (t, 1H), 3.40 (s, 3H, $OCH_3$), 4.15-4.18 (d, 1H), 4.24-4.35 (m, 3H), 6.8 (s, 2H), 7.18-7.22 (m, 1H), 7.43-7.46 (dd, 1H), 7.60-7.64 (m, 1H), 7.99-8.02 (dd, 1H).

Intermediate 7D

To a solution of Intermediate 7C (30 g, 66 mmol) in a 1:1 mixture of methanol and ethanol (600 mL) was added Raney nickel (6 g). The resulting mixture was stirred under hydrogen for 16 h. After the completion of reaction, the reaction mixture was filtered through CELITE® and washed with methanol. The filtrate was concentrated under reduced pressure to give the crude product which was purified by flash chromatography using hexanes/ethyl acetate=60:40 as the eluent to give Intermediate 7D (24 g, yield: 86%). MS (ESI) m/z 428.2 (M+H)$^+$. $^1$H NMR (400 MHz, DMSO-d$_6$) δ 1.19 (s, 9H), 1.53-1.57 (d, 1H), 1.71-1.75 (d, 1H), 2.25-2.33 (m, 2H), 2.72-2.86 (m, 2H), 3.19-3.27 (m, 2H), 3.41 (s, 3H), 4.21-4.33 (m, 2H), 4.90 (s, 2H), 6.40-6.45 (t, 1H), 6.65-6.68 (m, 2H), 6.70-6.86 (m, 4H).

Intermediate 7

To a solution of Intermediate 7D (160 g, 0.374 mol) in dichloromethane (3.2 L) was added RED-AL® (570 mL, 65.0%, 1.87 mol) dropwise with stirring under nitrogen atmosphere over a period of 1 h. The temperature was maintained below 40° C. during the addition. The reaction mixture was then stirred at rt for 4 h. The reaction was quenched with saturated sodium bicarbonate solution and extracted with dichloromethane. The organic layer was washed with water, brine, dried over Na$_2$SO$_4$, and concentrated under reduced pressure to give the crude product, which was purified by flash chromatography using hexanes/ethyl acetate=90/10 as the eluent to give the pure Intermediate 7 (121 g, yield: 78.0%). MS (ESI) m/z 414.2 (M+H)$^+$; Orthogonal HPLC purity: 96.4% (Method A), 96.1% (Method B); $^1$H NMR (400 MHz, DMSO-d$_6$) δ 0.84 (s, 9H, 3×CH$_3$ of neopentyl), 1.38-1.41 (d, 1H), 1.56-1.59 (d, 1H), 2.01 (s, 2H), 2.12-2.16 (t, 1H), 2.27-2.29 (t, 1H), 2.52-2.53 (d, 1H), 2.56-2.66 (m, 2H), 2.714-2.73 (d, 1H), 3.08-3.10 (d, 1H), 3.42 (s, 3H), 4.03-4.06 (d, 1H), 4.84 (s, 2H), 6.39-6.43 (t, 1H), 6.60-6.62 (d, 1H), 6.66-6.68 (d, 1H), 6.71-6.78 (m, 2H), 6.80-6.85 (t, 1H). $^{13}$C NMR (100 MHz, DMSO-d$_6$) δ 27.57, 32.80, 34.61, 45.50, 52.43, 55.67, 63.99, 69.37, 113.65, 114.72, 115.72, 121.29, 122.67, 125.18, 133.34, 134.65, 139.99, 143.21, 145.35.

Intermediate 8

1-(1-(2-Aminophenyl)-7-hydroxy-4-(trifluoromethyl)spiro[indoline-3,4'-piperidine]-1'-yl)-2,2-dimethylpropan-1-one

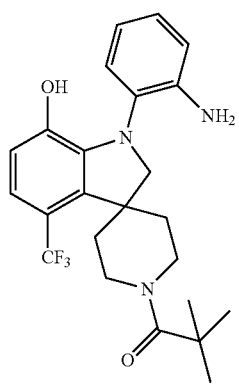 [SMILES: CC(C)(C)C(=O)N1CCC2(CC1)CN(c1ccccc1N)c1c(O)ccc(C(F)(F)F)c12]

Intermediate 8A (2-(Benzyloxy)-5-(trifluoromethyl)phenyl)hydrazine: Intermediate 8A was prepared (4.7 g, 16 mmol, 89% yield) following similar procedure described in Intermediate 4B by replacing Intermediate 4A with 2-(benzyloxy)-5-(trifluoromethyl)aniline (4.99 g, 18.7 mmol). LC-MS (ESI) m/z 266.2 (M+H)$^+$, RT=2.61 min (Method C).

Intermediate 8B 1-(7-(Benzyloxy)-4-(trifluoromethyl)spiro[indoline-3,4'-piperidine]-1'-yl)-2,2-dimethylpropan-1-one: Intermediate 8A (2.3 g, 8.2 mmol) was stirred in ethanol (15 mL) at room temperature under argon. Isobutyraldehyde (0.409 g, 5.67 mmol) was added and the reaction mixture was stirred for 30 min. LC-MS (ESI) m/z 337.3 (M+H)$^+$, RT=2.24 min (Method D). At 0° C., H$_2$SO$_4$ (0.944 mL, 17.7 mmol) was added to the above stirred mixture dropwise. The resulting mixture was stirred 50° C. under argon for 3 h. The mixture was stirred for additional 3 hours at 50° C. and then room temperature for 16 h. The mixture was cooled at −10° C., and MeOH (10 mL) was added, followed by addition of NaBH$_4$ (0.462 g, 12.2 mmol) portionwise. The mixture was stirred at −10° C. H$_2$O was added carefully to quench the reaction, followed by the addition of CH$_2$Cl$_2$. The organic layer was washed with H$_2$O, dried over MgSO$_4$, filtered and concentrated. The residue was dissolved in a small amount of CH$_2$Cl$_2$, and was purified on a silica gel column, eluting with 0-100% hexanes in EtOAc and the desired product eluted at 40-50% EtOAc to give Intermediate 8B (1.08 g, 2.42 mmol, 29.7% yield). LC-MS (ESI) m/z 447.4 (M+H)$^+$, RT=3.65 min (Method C).

Intermediate 8C 1-(7-(Benzyloxy)-1-(2-nitrophenyl)-4-(trifluoromethyl)spiro[indoline-3,4'-piperidine]-1'-yl)-2,2-dimethylpropan-1-one: Intermediate 8C was prepared (0.58 g, 1.0 mmol, 91% yield) following similar procedure as described in Intermediate 2B by replacing intermediate 2A with Intermediate 8B (0.50 g, 1.1 mmol). LC-MS (ESI) m/z 568.5 (M+H)$^+$, RT=4.13 min (Method C).

Intermediate 8

1-(1-(2-Aminophenyl)-7-hydroxy-4-(trifluoromethyl)spiro[indoline-3,4'-piperidine]-1'-yl)-2,2-dimethylpropan-1-one: To a solution of Intermediate 8C (510 mg, 0.899 mmol) in MeOH (20 mL) was added palladium on carbon (13 mg, 0.090 mmol). The reaction mixture was stirred at rt under H$_2$ for 4 h. Ammonium formate (56.7 mg, 0.180 mmol) was added and it was stirred for 2 h. The Pd catalyst was removed by filtration and the solvent was evaporated under reduced pressure. The residue was purified on silica gel cartridge (40 g) and the crude was eluted with hexanes and EtOAc, 0 to 100% gradient for 16 minutes to give Intermediate 8. LC-MS (ESI) m/z 448.4 (M+H)$^+$, RT=3.19 min (Method C).

Intermediate 9

1-(1-(3-Aminopyridin-2-yl)-7-hydroxy-4-(trifluoromethyl)spiro[indoline-3,4'-piperidine]-1'-yl)-2,2-dimethylpropan-1-one

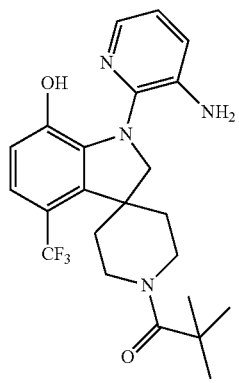 [SMILES: CC(C)(C)C(=O)N1CCC2(CC1)CN(c1ncccc1N)c1c(O)ccc(C(F)(F)F)c12]

Intermediate 9A 1-(7-(Benzyloxy)-1-(3-nitropyridin-2-yl)-4-(trifluoromethyl)spiro[indoline-3,4'-piperidine]-1'-yl)-2,2-dimethylpropan-1-one: Intermediate 9A was prepared following similar procedure described in intermediate 4D by replacing 2-bromo-1-nitrobenzene with 2-bromo-3-nitropyridine and by replacing Intermediate 4C with Intermediate 8B. LC-MS (ESI) m/z 569.5 (M+H)$^+$, RT=4.04 min (Method C).

Intermediate 9

1-(1-(3-Aminopyridin-2-yl)-7-hydroxy-4-(trifluoromethyl)spiro[indoline-3,4'-piperidine]-1'-yl)-2,2-dimethylpropan-1-one: To a solution of Intermediate 9A (100 mg, 0.176 mmol) in methanol was added palladium on carbon (1.9 mg, 0.018 mmol), followed by ammonium formate (2.2 mg, 0.035 mmol). The reaction mixture was stirred under H$_2$ for 30 minutes. The catalyst was removed by filtration. The solvent was evaporated under reduced pressure to afford Intermediate 9 (65 mg, 0.15 mmol, 82% yield). LC-MS (ESI) m/z 449.4 (M+H)$^+$, RT=2.60 min (Method C).

Intermediate 10

2-(7-Methoxy-1'-neopentyl-4-(trifluoromethyl)spiro[indoline-3,4'-piperidine]-1-yl)aniline

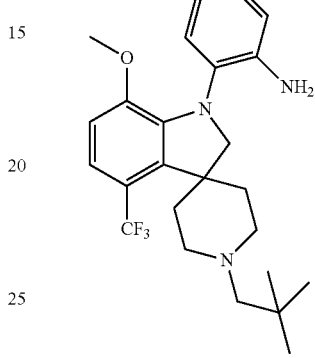

Intermediate 10 was prepared following similar procedures described in Intermediate 7 by replacing 2-methoxy-5-chloroaniline with 2-methoxy-5-trifluoromethylaniline. LCMS (ESI) m/z 448.5 (M+H)$^+$, RT=2.43 min (Method C).

Intermediate 11

1-(3-Aminopyridin-2-yl)-1'-neopentyl-4-(trifluoromethyl)spiro[indoline-3,4'-piperidin]-7-ol

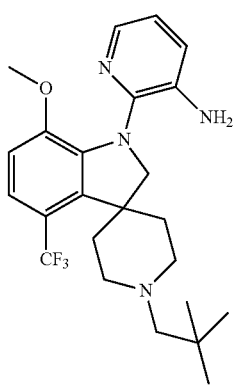 [SMILES: COc1ccc(C(F)(F)F)c2c1N(c1ncccc1N)CC21CCN(CC(C)(C)C)CC1]

Intermediate 11 was prepared following similar procedures described in Intermediate 10 by replacing 2-bromo nitrobenzene with 2-bromo-3-nitropyridine. LC-MS (ESI) m/z 449.4 (M+H)$^+$, RT=2.60 min (Method C).

Intermediate 12

2-(4,6-Difluoro-7-methoxy-1'-neopentylspiro[indoline-3,4'-piperidine]-1-yl)aniline

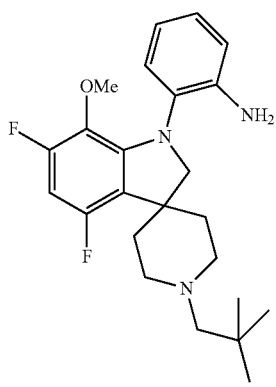 [SMILES: COc1c(F)cc(F)c2c1N(c1ccccc1N)CC21CCN(CC(C)(C)C)CC1]

Intermediate 12A 1-(3,5-Difluoro-2-methoxyphenyl)-2-(diphenylmethylene)hydrazine: Palladium (II) acetate (0.040 g, 0.18 mmol) and xantphos (0.104 g, 0.179 mmol) were stirred in toluene (1 mL) at room temperature for 2 min. 1-Bromo-3,5-difluoro-2-methoxybenzene (4.00 g, 17.9 mmol), (diphenylmethylene)hydrazine (3.52 g, 17.9 mmol) and sodium tert-butoxide (2.41 g, 25.1 mmol) were added followed by the addition of toluene (4 mL). The mixture was degassed twice and was stirred for 6 h at 100° C. under argon. After cooling, EtOAc and $H_2O$ were added. The organic layer was separated. The aqueous phase was extracted one more time with EtOAc. The combined EtOAc layers were washed with $H_2O$, then brine, dried over $MgSO_4$, filtered, and concentrated. The crude was dissolved in a small amount of $CH_2Cl_2$ and added to a silica gel column and was eluted with hexanes/EtOAc to give Intermediate 12A (6.0 g, 15 mmol, 84% yield). $^1$H NMR (400 MHz, $CDCl_3$) δ ppm 3.63 (br. s, 3H), 6.14-6.38 (m, 1H), 7.08-7.20 (m, 5H), 7.45-7.68 (m, 5H), 7.97 (s, 1H). $^{19}$F NMR (376.5 MHz, Acetone-$d_6$) δ ppm −115.46, −129.88.

Intermediate 12B (3,5-Difluoro-2-methoxyphenyl)hydrazine hydrochloride: Intermediate 12A (4.7 g, 14 mmol) was heated at 100° C. in ethanol (50 mL) and hydrochloric acid, 37% (50 mL) for 2 h. After cooling, the solvents were evaporated and the residue was extracted with $Et_2O$ (3×). The organic layers were concentrated. The residue was azeotroped with toluene (3×), and $Et_2O$ was added. The resulting precipitate was filtered to give Intermediate 12B (1.99 g, 9.45 mmol, 68.0% yield) as off-white solids. LC-MS (ESI) m/z 158.1 (M+H)$^+$, RT=0.85 min (Method D).

Intermediate 12C 1-(4,6-Difluoro-7-methoxyspiro[indoline-3,4'-piperidine]-1'-yl)-2,2-dimethylpropan-1-one: Intermediate 12B (600 mg, 3.45 mmol) was stirred in $CH_2Cl_2$ (40 mL) at 0° C. under argon. Intermediate 1 (612 mg, 3.10 mmol) was added followed by the addition of HCl (3.01 mL, 12.1 mmol) in dioxanes (4M solution). The reaction mixture was stirred for 2 h. The mixture was cooled at −10° C., and MeOH (20 mL) was added, followed by addition of $NaBH_4$ (272 mg, 7.19 mmol) portionwise. The mixture was stirred at −10° C. for 1 min. $H_2O$ was added carefully to quench the reaction, followed by the addition of $CH_2Cl_2$. The organic layer was washed with $H_2O$, dried over $MgSO_4$, filtered and concentrated. The residue was dissolved in a small amount of $CH_2Cl_2$, and was purified on a silica gel column eluting with 0-100% hexanes in EtOAc and the desired product eluted at 60% EtOAc to give Intermediate 12C (175 mg, 0.517 mmol, 15.0% yield). $^1$H NMR (400 MHz, $CDCl_3$) δ ppm 1.30 (m, 9H), 1.78 (d, J=12.6 Hz, 2H), 1.93-2.40 (m, 2H), 2.88 (t, J=12.9 Hz, 2H), 3.61 (s, 3H), 3.83 (s, 3H), 4.42 (d, J=13.7 Hz, 2H), 5.48-6.27 (m, 1H); LC-MS (ESI) m/z 339.4 (M+H)$^+$, RT=3.21 min (Method C).

Intermediate 12D 1-(4,6-Difluoro-7-methoxy-1-(2-nitrophenyl)spiro[indoline-3,4'-piperidine]-1'-yl)-2,2-dimethylpropan-1-one: Intermediate 12D was prepared following procedure described in Intermediate 2B (200 mg, 83.0% yield). $^1$H NMR (400 MHz, $CDCl_3$) δ ppm 1.30 (m, 9H), 1.55-2.01 (m, 2H), 2.09-2.39 (m, 2H), 2.59-3.01 (m, 2H), 3.34 (s, 3H), 3.77 (d, J=9.7 Hz, 1H), 4.04-4.17 (m, 1H), 4.46 (dd, J=21.8, 15.2 Hz, 2H), 6.20-6.47 (m, 1H), 7.21-7.37 (m, 2H), 7.51-7.59 (m, 1H), 8.01 (d, J=8.3 Hz, 1H); LC-MS (ESI) m/z 460.5 (M+H)$^+$, RT=2.03 min (Method D).

Intermediate 12E 1-(1-(2-Aminophenyl)-4,6-difluoro-7-methoxyspiro[indoline-3,4'-piperidine]-1'-yl)-2,2-dimethylpropan-1-one: Intermediate 12D (0.20 g, 0.44 mmol), ammonium chloride (0.233 g, 4.35 mmol), and zinc (0.20 g, 3.1 mmol) were stirred in methanol (20 mL) at room temperature for 1.5 h. The reaction mixture was filtered through CELITE® and rinsed with $CH_2Cl_2$. The organic layer was concentrated and the crude was added to a silica gel column (40 g) and was eluted with hexanes/EtOAc (eluted at 80-100% EtOAc in hexanes) to give pure Intermediate 12E (135 mg, 0.314 mmol, 72.2% yield). LC-MS (ESI) m/z 430.5 (M+H)$^+$, RT=1.68 min (Method D).

Intermediate 12

2-(4,6-Difluoro-7-methoxy-1'-neopentylspiro[indoline-3,4'-piperidine]-1-yl)aniline: Intermediate 12 was prepared following similar procedures described in Intermediate 7 by replacing Intermediate 7D with Intermediate 12E. LC-MS (ESI) m/z 416.2 (M+H)$^+$, RT=1.30 min (Method D).

Intermediate 13

1-(1-(2-Aminophenyl)-7-(benzyloxy)-4,5-difluorospiro[indoline-3,4'-piperidine]-1'-yl)-2,2-dimethylpropan-1-one

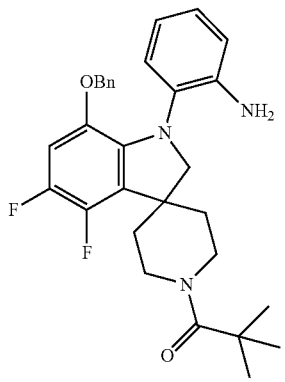 [SMILES: CC(C)(C)C(=O)N1CCC2(CC1)CN(c1ccccc1N)c1c(OCc3ccccc3)cc(F)c(F)c12]

Intermediate 13A

Aniline 2-(benzyloxy)-4,5-difluoroaniline: 4,5-Difluoro-2-nitrophenol (2.82 g, 10.6 mmol), zinc dust (6.95 g, 106 mmol), and ammonium chloride (5.69 g, 106 mmol) were stirred in ethanol (150 mL) at room temperature for 16 h. The reaction mixture was filtered through CELITE® and concentrated. The residue was dissolved in $CH_2Cl_2$ and washed with $H_2O$ and brine, dried over $MgSO_4$, filtered and concentrated to dryness to give essentially pure Intermediate 13A (2.33 g, 9.91 mmol, 93.0% yield) as tan solids. LC-MS (ESI) m/z 236.2 (M+H)$^+$, RT=2.35 min (Method C).

Intermediate 13B (2-(Benzyloxy)-4,5-difluorophenyl)hydrazine: Intermediate 13A (2.3 g, 9.8 mmol) was suspended in 6M HCl (10 mL). The mixture was stirred at 0° C. A solution of sodium nitrite (0.89 g, 13 mmol) in water (1.1 mL) was added dropwise. The mixture was stirred at 0° C. for 2 h. To this stirred mixture was added a cold solution of tin(II) chloride dihydrate (6.62 g, 29.3 mmol) in hydrochloric acid (37%, 10 mL). The resulting suspension was stirred for 30 min, and water (40 mL) was added and stirred for another 30 min. $CH_2Cl_2$ was added followed by the addition of 3N NaOH (150 mL). The organic layer was washed with $H_2O$, brine, dried over $MgSO_4$, filtered, and concentrated to give light yellow solids of Intermediate 13B (1.56 g, 6.23 mmol, 63.8% yield). LC-MS (ESI) m/z 234.2 (M–$NH_3$+1)$^+$, RT=2.43 min (Method C).

Intermediate 13C 1-(7-(Benzyloxy)-4,5-difluorospiro[indoline-3,4'-piperidine]-1'-yl)-2,2-dimethylpropan-1-one: Intermediate 13B (450 mg, 1.80 mmol) was stirred in ethanol (5 mL) at rt under argon. Intermediate 1 (355 mg, 1.80 mmol) was added and the reaction mixture was stirred for 1 h. LC-MS (ESI) m/z 430.4 (M+H)$^+$, RT=2.05 min (Method D). At 0° C., $H_2SO_4$ (0.288 mL, 5.39 mmol) was added to the above stirred mixture dropwise. The resulting mixture was stirred rt for 16 h and then cooled at −10° C., and MeOH (5 mL) was added, followed by addition of $NaBH_4$ (272 mg, 7.19 mmol) portionwise. The mixture was stirred at −10° C. till LC-MS showed the completion of the reduction. $H_2O$ was added carefully to quench the reaction, followed by the addition of $CH_2Cl_2$. The organic layer was washed with $H_2O$, dried over $MgSO_4$, filtered and concentrated. The residue was dissolved in a small amount of $CH_2Cl_2$, and was purified on a silica gel column, eluting with 0-100% hexanes in EtOAc and the desired product eluted at 50% EtOAc to give Intermediate 13C (160 mg, 0.386 mmol, 21.5% yield). $^1$H NMR (400 MHz, CDCl$_3$) δ ppm 1.15-1.36 (m, 9H), 1.70 (d, J=13.2 Hz, 2H), 1.95-2.24 (m, 2H), 2.78 (t, J=12.9 Hz, 2H), 3.45 (s, 2H), 4.32 (d, J=13.7 Hz, 2H), 4.86 (s, 2H), 6.47 (dd, J=11.8, 6.3 Hz, 1H), 6.94-7.49 (m, 5H); LC-MS (ESI) m/z 415.4 (M+H)$^+$, RT=1.82 min (Method D).

Intermediate 13D 1-(7-(Benzyloxy)-4,5-difluoro-1-(2-nitrophenyl)spiro[indoline-3,4'-piperidine]-1'-yl)-2,2-dimethylpropan-1-one: Intermediate 13D was prepared as red solids following similar procedure described in Intermediate 2B by replacing Intermediate 2A with Intermediate 13C (59.5% yield). $^1$H NMR (400 MHz, CDCl$_3$) δ ppm 1.26-1.32 (m, 9H), 1.64-1.80 (m, 1H), 1.91-2.05 (m, 1H), 2.05-2.21 (m, 1H), 2.22-2.39 (m, 1H), 2.74 (t, J=13.2 Hz, 1H), 2.88 (t, J=12.9 Hz, 1H), 3.90 (d, J=9.9 Hz, 1H), 3.99-4.18 (m, 1H), 4.45 (dd, J=34.6, 13.7 Hz, 2H), 4.70 (s, 2H), 6.59 (dd, J=11.8, 6.3 Hz, 1H), 6.89 (d, J=6.0 Hz, 2H), 7.00 (t, J=8.0 Hz, 1H), 7.07-7.27 (m, 4H), 7.40 (t, J=7.7 Hz, 1H), 7.77 (d, J=8.2 Hz, 1H); LC-MS (ESI) m/z 536.2 (M+H)$^+$, RT=3.82 min (Method C).

Intermediate 13

1-(1-(2-Aminophenyl)-7-(benzyloxy)-4,5-difluoro spiro[indoline-3,4'-piperidine]-1'-yl)-2,2-dimethylpropan-1-one: Intermediate 13 was prepared as yellowish powder following a similar procedure described for Intermediate 12E by replacing Intermediate 12D with Intermediate 13D (91% yield). LC-MS (ESI) m/z 506.5 (M+H)$^+$, RT=3.58 min (Method C).

Intermediate 14

1-(1-(2-Aminophenyl)-7-(benzyloxy)-4,5-difluorospiro[indoline-3,4'-piperidine]-1'-yl)-2,2-dimethylpropan-1-one

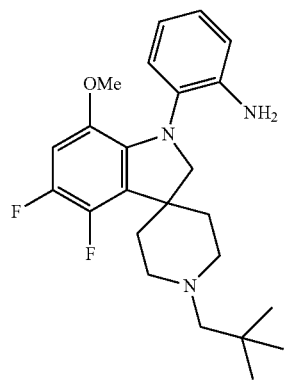 [SMILES: COc1cc(F)c(F)c2c1N(c1ccccc1N)CC21CCN(CC(C)(C)C)CC1]

Intermediate 14A 1-(1-(2-Aminophenyl)-4,5-difluoro-7-methoxyspiro[indoline-3,4'-piperidine]-1'-yl)-2,2-dimethylpropan-1-one: Intermediate 14A was prepared following similar procedures as described in Intermediate 13 by replacing 3,4-difluorophenol with 1,2-difluoro-4-methoxybenzene. LC-MS (ESI) m/z 430.2 (M+H)$^+$, RT=1.76 min (Method D).

Intermediate 14

1-(1-(2-Aminophenyl)-7-(benzyloxy)-4,5-difluorospiro[indoline-3,4'-piperidine]-1'-yl)-2,2-dimethylpropan-1-one: Intermediate 14 was prepared following the similar procedure described in Intermediate 7 by replacing Intermediate 7D with Intermediate 14A. LC-MS (ESI) m/z 416.2 (M+H)$^+$, RT=1.26 min (Method D).

Intermediate 15

2-(4-Chloro-5-fluoro-7-methoxy-1'-neopentylspiro[indoline-3,4'-piperidine]-1-yl)aniline

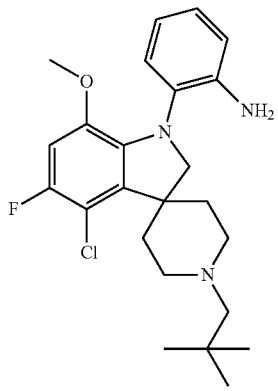

Intermediate 15A

1-Chloro-2-fluoro-4-methoxy-5-nitrobenzene: To 1-chloro-2-fluoro-4-methoxybenzene (5.00 g, 31.2 mmol) in conc. H$_2$SO$_4$ (30 mL) at −10° C. to 0° C., potassium nitrate (3.47 g, 34.4 mmol) was added portionwise to the reaction mixture. The reaction was stirred at 0° C. for 2 h. The reaction was quenched with iced water and filtered. The obtained solids were recrystallized with hexanes to give Intermediate 15A (4.8 g, 75%).

Intermediate 15B

5-Chloro-4-fluoro-2-methoxyaniline: To Intermediate 15A (2.0 g, 9.8 mmol) in MeOH (50 mL) was added a solution of saturated NH$_4$Cl solution (10 mL). The reaction mixture was stirred at 60° C. then added iron powder (3.8 g, 69 mmol) portionwise. The reaction mixture was stirred at 70° C. for 16 h. The reaction mixture was filtered through CELITE®, washed with DCM and concentrated. The crude was purified by flash chromatography eluting with EtOAc/hexanes (8:2) to give Intermediate 15B (1.5 g, 88%). LCMS (ESI) m/z 176.0 (M+H)$^+$, RT=0.65 min (Method D).

Intermediate 15C (5-Chloro-4-fluoro-2-methoxyphenyl)hydrazine hydrochloride: To Intermediate 15B (2.00 g, 11.4 mmol) was added 10N HCl (6 mL). After cooled to −20° C., sodium nitrite (0.87 g, 13 mmol) in water was added dropwise. The reaction was stirred for 45 min at −20° C. SnCl$_2$ (6.5 g, 34 mmol) in 10N HCl (10-15 mL) was added dropwise at −20° C. The reaction was left for stirring for 2 h. The precipitate solids were filtered and washed with conc. HCl (2×) to remove tin impurities, and then recrystallized with hexanes to give Intermediate 15C (1.8 g, 70%). LCMS (ESI) m/z 190.0 (M+H)$^+$, RT=0.75 min (Method D).

Intermediate 15D 1-(4-Chloro-5-fluoro-7-methoxyspiro[indoline-3,4'-piperidine]-1'-yl)-2,2-dimethylpropan-1-one: To Intermediate 15C (1.0 g, 4.4 mmol) in EtOH (15 mL) was added 1-pivaloylpiperidine-4-carbaldehyde (950 mg, 4.80 mmol). The reaction was stirred at room temperature for 10 min. The reaction was cooled to 0° C. and conc. H$_2$SO$_4$ (1.5 mL, 26 mmol) was added dropwise. The reaction was stirred at room temperature for 16 h. The reaction was cooled to 0° C. and MeOH (20 mL) was added followed by the addition of NaBH$_4$ (0.501 g, 13.2 mmol) portionwise. After 30 min at room temperature, the reaction was quenched with water, extracted with EtOAc, washed with saturated NaHCO$_3$ and brine, and purified by flash chromatography (Hex:EtOAc=6:4) to give Intermediate 15D (0.35 g, 22%). LCMS (ESI) m/z 355.2 (M+H)$^+$, RT=1.53 min (Method D).

Intermediate 15E 1-(4-Chloro-5-fluoro-7-methoxy-1-(2-nitrophenyl)spiro[indoline-3,4'-piperidine]-1'-yl)-2,2-dimethylpropan-1-one: To Intermediate 15D (1.2 g, 3.3 mmol) in toluene (25 mL) was added 1-bromo-2-nitrobenzene (1.1 g, 5.0 mmol), BINAP (123 mg, 0.198 mmol), Pd$_2$(dba)$_3$ (121 mg, 0.132 mmol) and cesium carbonate (1.6 g, 5.0 mmol). The reaction mixture was heated at 100° C. under nitrogen for overnight. The reaction mixture was filtered through CELITE®, concentrated and purified by flash chromatography to give Intermediate 15E (1.0 g, 62%). LCMS (ESI) m/z 476.2 (M+H)$^+$, RT=2.14 min (Method D).

Intermediate 15F 1-(1-(2-Aminophenyl)-4-chloro-5-fluoro-7-methoxyspiro[indoline-3,4'-piperidine]-1'-yl)-2,2-dimethylpropan-1-one: To Intermediate 15E (1.5 g, 3.1 mmol) in MeOH (25 mL) was added a solution of saturated NH$_4$Cl (10 mL) in water at 50° C. and iron powder (1.4 g, 25 mmol) portionwise. The reaction mixture was heated at 70° C. for 5 h. The reaction mixture was filtered through CELITE®, concentrated, and extracted with EtOAc. The organic layer was washed with brine, dried over Na$_2$SO$_4$, and concentrated to give Intermediate 15F (1.1 g, 78%). LCMS (ESI) m/z 446.2 (M+H)$^+$, RT=2.00 min (Method F).

Intermediate 15

2-(4-Chloro-5-fluoro-7-methoxy-1'-neopentylspiro[indoline-3,4'-piperidine]-1-yl)aniline: To Intermediate 15F (0.70 g, 1.6 mmol) in DCM (20 mL) was added RED-AL® (2.4 g, 13 mmol) dropwise at 0° C. The reaction was stirred at room temperature for 16 h. The reaction was quenched by saturated NaHCO₃ solution. The organic layer was dried over Na₂SO₄, concentrated and purified by flash chromatography (Hex: EtOAc=7:3) to give Intermediate 15 (0.48 g, 71%). LCMS (ESI) m/z 432.2 (M+H)⁺, RT=1.35 min (Method D).

Intermediate 16

2-(4-Chloro-6-fluoro-7-methoxy-1'-neopentylspiro [indoline-3,4'-piperidine]-1-yl)aniline

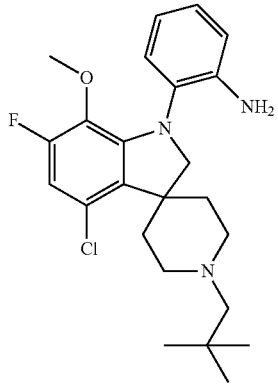 [SMILES: COc1c(F)cc(Cl)c2c1N(c1ccccc1N)CC21CCN(CC(C)(C)C)CC1]

Intermediate 16 was prepared following similar procedures as described in Intermediate 15 by replacing 1-chloro-2-fluoro-4-methoxybenzene with 4-chloro-2-fluoro-1-methoxybenzene. LCMS (ESI) m/z 432.2/434.2 (M+H)⁺, RT=1.43 min (Method D).

Intermediate 17

2-(1'-Isobutyl-7-methoxy-4-(trifluoromethyl)spiro [indoline-3,4'-piperidine]-1-yl)aniline

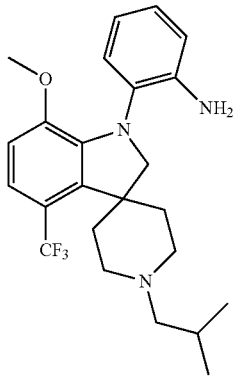 [SMILES: COc1ccc(C(F)(F)F)c2c1N(c1ccccc1N)CC21CCN(CC(C)C)CC1]

Intermediate 17A

Benzyl 7-methoxy-1-(2-nitrophenyl)-4-(trifluoromethyl) spiro-[indoline-3,4'-piperidine]-1'-carboxylate: Intermediate 17A was prepared following similar procedures described in Intermediates 2A, 2B, and 2C by replacing Intermediate 1 with benzyl 4-formylpiperidine-1-carboxylate. LCMS (ESI) m/z 542.5 (M+H)⁺, RT=2.15 min (Method D).

Intermediate 17B

7-Methoxy-1-(2-nitrophenyl)-4-(trifluoromethyl)spiro [indoline-3,4'-piperidine]: To a solution of Intermediate 17A (0.90 g, 1.7 mmol) in DCM (4 mL) was cooled to 0° C. and added iodotrimethylsilane (0.679 mL, 4.99 mmol). The reaction mixture was stirred at rt for 30 min. It was quenched with ice and filtered, and then washed with DCM. The filtrate was further extracted with EtOAc. The organic layer was dried over Na₂SO₄ and evaporated under reduced pressure. The crude product was dissolved in a small amount of DCM and charged to a 12 g silica gel cartridge which was eluted with a 9 minutes gradient from 0 to 100% EtOAc in hexane to give Intermediate 17B (780 mg, 1.92 mmol, 115% yield). LCMS (ESI) m/z 408.4 (M+H)⁺, RT=1.47 min (Method D).

Intermediate 17C

1'-Isobutyl-7-methoxy-1-(2-nitrophenyl)-4-(trifluoromethyl)spiro[indoline-3,4'-piperidine]: To a solution of Intermediate 17B (680 mg, 1.67 mmol) and sodium triacetoxyborohydride (531 mg, 2.50 mmol) in MeOH (5.00 mL) was added isobutyraldehyde (0.183 mL, 2.00 mmol) and acetic acid (9.56 µL, 0.167 mmol). The reaction mixture was stirred at rt for 4 h and then quenched with ice and concentrated in vacuo. The crude product was partitioned between saturated NaHCO₃ and EtOAc. The organic solvent was evaporated under reduced pressure to give Intermediate 17C (400 mg, 0.863 mmol, 51.7% yield). LCMS (ESI) m/z 464.5 (M+H)⁺, RT=1.51 min (Method D).

Intermediate 17

2-(1'-Isobutyl-7-methoxy-4-(trifluoromethyl)spiro[indoline-3,4'-piperidine]-1-yl)aniline: To a solution of Intermediate 17C (400 mg, 0.863 mmol) in MeOH was added ammonium chloride (231 mg, 4.32 mmol) and zinc (282 mg, 4.32 mmol). The reaction mixture was stirred at rt for 1 h. Filtered and the solvent was removed under reduced pressure. The desired product was then triturated in EtOAc to give Intermediate 17 (260 mg, 69.5% yield). LCMS (ESI) m/z 434.4 (M+H)⁺, RT=1.33 min (Method D).

Intermediate 18

2-(4-Chloro-1'-isobutyl-7-methoxyspiro[indoline-3, 4'-piperidine]-1-yl)aniline

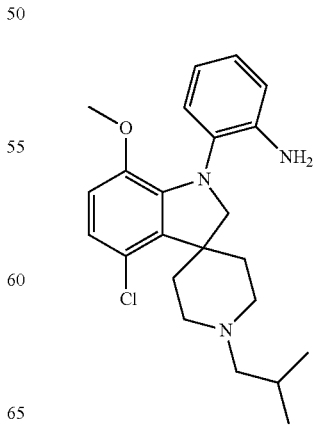

Intermediate 18A

Benzyl 4-chloro-7-methoxyspiro[indoline-3,4'-piperidine]-1'-carboxylate: Intermediate 18A (2.10 g, 5.43 mmol, 37.8% yield) was prepared following the same procedure as described in Intermediate 17A. LCMS (ESI) m/z 387.4 (M+H)$^+$, RT=1.71 min (Method D).

Intermediate 18B

Benzyl 4-chloro-7-methoxy-1-(2-nitrophenyl)spiro[indoline-3,4'-piperidine]-1'-carboxylate: Intermediate 18B was prepared (1.50 g, 2.95 mmol, 61.8% yield) following similar procedure as described in Intermediate 17B by replacing 17A with 18A (1.85 g, 4.78 mmol). LCMS (ESI) m/z 508.4 (M+H)$^+$, RT=2.09 min (Method D).

Intermediate 18C

4-Chloro-7-methoxy-1-(2-nitrophenyl)spiro[indoline-3,4'-piperidine]: Intermediate 18C (48 mg, 0.13 mmol, 65% yield) was prepared following similar procedure as described in Intermediate 17C by replacing 17B with 18B (100 mg, 0.197 mmol). LCMS (ESI) m/z 374.3 (M+H)$^+$, RT=1.42 min (Method D).

Intermediate 18D

4-Chloro-1'-isobutyl-7-methoxy-1-(2-nitrophenyl)spiro[indoline-3,4'-piperidine]: Intermediate 18D (460 mg, 1.07 mmol, 80.0% yield) was prepared following similar procedure as described in Intermediate 17D by replacing 17C with 18C (500 mg, 1.34 mmol). LCMS (ESI) m/z 430.4 (M+H)$^+$, RT=2.65 min (Method C).

Intermediate 18

2-(4-Chloro-1'-isobutyl-7-methoxyspiro[indoline-3,4'-piperidine]-1-yl)aniline: Intermediate 18 (348 mg, 0.870 mmol, 87.0% yield) was prepared following similar procedure as described in Intermediate 17 by replacing 17D with 18D (430 mg, 1.00 mmol). LCMS (ESI) m/z 344.4 (M+H)$^+$, RT=2.14 min (Method C).

Intermediate 19

2-(4-Chloro-7-methoxy-1'-neopentylspiro[indoline-3,4'-piperidine]-1-yl)pyridin-3-amine

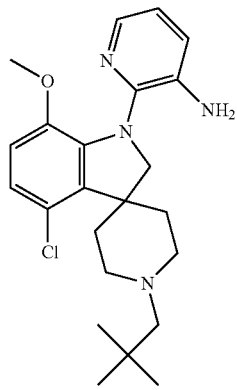 [SMILES: COc1ccc(Cl)c2c1N(c1ncccc1N)CC21CCN(CC(C)(C)C)CC1]

Intermediate 19 was prepared following similar procedures as described in Intermediate 7C by replacing 2-bromo-1-nitrobenzene with 2-bromo-3-nitropyridine. $^1$H NMR (400 MHz, MeOD) δ ppm 1.12 (s, 9H), 1.95 (m 2H), 2.87-3.30 (m, 10H), 3.47 (s, 3H), 6.77-6.85 (m, 2H), 7.02 (dd, J=7.70, 4.95 Hz, 1H), 7.19 (d, J=8.25 Hz, 1H), 7.55 (d, J=4.95 Hz, 1H). LCMS (ESI) m/z 415.1 (M+H)$^+$, RT=1.61 min (Method C).

Intermediate 20

1-(2-Aminophenyl)-N,N-diethyl-7-methoxy-1'-neopentylspiro[indoline-3,4'-piperidine]-4-sulfonamide

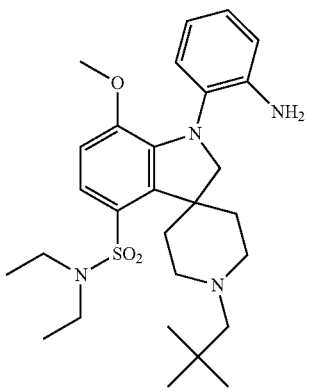 [SMILES: CCN(CC)S(=O)(=O)c1ccc(OC)c2c1C1(CCN(CC(C)(C)C)CC1)CN2c1ccccc1N]

Intermediate 20A

N,N-Diethyl-3-hydrazinyl-4-methoxybenzenesulfonamide: Intermediate 20A (1.64 g, 4.20 mmol, 70.0% yield) was prepared following the same procedure as Intermediate 7A by replacing 2-methoxy-5-chloroaniline with 3-amino-N,N-diethyl-4-methoxybenzenesulfonamide (1.55 g, 6.00 mmol). The crude was used for subsequent steps without further purification. LCMS (ESI) m/z 274.4 (M+H)$^+$, RT=0.94 min (Method D).

Intermediate 20B

N,N-Diethyl-7-methoxy-1'-pivaloylspiro[indoline-3,4'-piperidine]-4-sulfonamide: Intermediate 20B (891.6 mg, 1.426 mmol, 23.77% yield) was prepared following the same procedure as Intermediate 7B by replacing Intermediate 7A with Intermediate 20A (1.64 g, 6.00 mmol). The crude was used for subsequent steps without further purification. LCMS (ESI) m/z 438.5 (M+H)$^+$, RT=2.66 min (Method C).

Intermediate 20C

N,N-Diethyl-7-methoxy-1-(2-nitrophenyl)-1'-pivaloyl-spiro[indoline-3,4'-piperidine]-4-sulfonamide: Intermediate 20C (752 mg, 1.30 mmol, 64.7% yield) was prepared as orange solid following the same procedure as Intermediate 7C by replacing Intermediate 7B with Intermediate 20B (885 mg, 2.02 mmol). The crude was used for subsequent steps without further purification. LCMS (ESI) m/z 559.5 (M+H)$^+$, RT=1.52 min (Method D).

Intermediate 20D 1-(2-Aminophenyl)-N,N-diethyl-7-methoxy-1'-pivaloyl-spiro[indoline-3,4'-piperidine]-4-sulfonamide: Intermediate 20D (595 mg, 1.10 mmol, 82.0% yield) was prepared as light tan solid following the same procedure as intermediate 7D by replacing Intermediate 7C with Intermediate 20C (746 mg, 1.34 mmol). The crude was used for subsequent steps without further purification. LCMS (ESI) m/z 529.6 (M+H)+, RT=2.98 min (Method C).

Intermediate 20

1-(2-Aminophenyl)-N,N-diethyl-7-methoxy-1'-neopentylspiro[indoline-3,4'-piperidine]-4-sulfonamide: Intermediate 20 (466 mg, 0.905 mmol, 81.0% yield) was prepared as an off white solid following the same procedure as Intermediate 7 by replacing Intermediate 7D with Intermediate 20D (591 mg, 1.12 mmol). The crude was used for subsequent steps without further purification. LCMS (ESI) m/z 515.6 (M+H)+, RT=1.38 min (Method D).

Intermediate 21

1-(2-Aminophenyl)-7-methoxy-N, N-dimethyl-1'-neopentylspiro[indoline-3,4'-piperidine]-4-sulfonamide

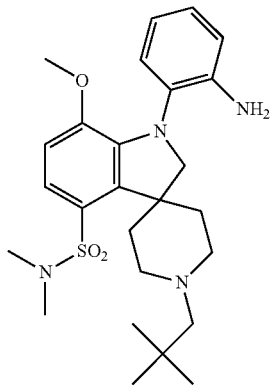 [SMILES: COc1ccc(S(=O)(=O)N(C)C)c2c1N(c1ccccc1N)CC21CCN(CC(C)(C)C)CC1]

Intermediate 21A

4-Methoxy-3-nitrobenzene-1-sulfonyl chloride: To 4-methoxybenzene-1-sulfonyl chloride (20.7 g, 100 mmol) in conc. sulfuric acid (70 mL, 1.3 mol) at 0° C. was carefully added dropwise conc. nitric acid (4.5 mL, 71 mmol) while maintaining an internal temperature of about 5° C. Upon completion of the addition, the reaction was carefully poured over ice which contained 100 mL of ether. Phases were separated and aqueous phases were extracted with ether (4×). The combined organics were dried over Na2SO4, filtered, and evaporated to give 13.68 g of crude Intermediate 21A as a yellow viscous oil, which was used for subsequent steps without further purification. LCMS (ESI) m/z 251.4 (M+H)+, RT=0.78 min (Method D).

Intermediate 21B

4-Methoxy-N,N-dimethyl-3-nitrobenzenesulfonamide: To a mixture of Intermediate 21A (4.58 g, 18.2 mmol) and 4-methoxybenzene-1-sulfonyl chloride (2.307 g, 11.17 mmol) in THF (anhydrous) (100 mL) was added pyridine (2.62 mL, 32.4 mmol) then dimethylamine (2.0M in THF) (14.7 mL, 29.4 mmol). The reaction mixture was stirred under nitrogen at ambient for 16 h. Reaction was diluted with water and extracted with EtOAc (4×). The combined extracts were washed with water and brine, dried, and evaporated. Residue was purified to give Intermediate 21B (1.79 g, 6.88 mmol, 37.8% yield) as straw colored solid. LCMS (ESI) m/z 261.2 (M+H)+, RT=1.16 min (Method D).

Intermediate 21C

3-Amino-4-methoxy-N,N-dimethylbenzenesulfonamide: To Intermediate 21B (1.79 g, 6.88 mmol) in ethanol (absolute) (30 mL) under nitrogen was added Pd—C (10%, 0.732 g, 0.688 mmol). A balloon atmosphere of hydrogen was introduced and the reaction was stirred at ambient temperature for 16 h. Reaction mixture was filtered through CELITE® with the aid of MeOH and solvents were evaporated to give Intermediate 21C (1.5 g, 6.4 mmol, 93% yield) as dark colored solid. LCMS (ESI) m/z 231.2 (M+H)+, RT=0.70 min (Method D).

Intermediate 21D

7-Methoxy-N,N-dimethyl-1'-pivaloylspiro[indoline-3,4'-piperidine]-4-sulfonamide: To Intermediate 21C (920 mg, 4.00 mmol) was added hydrogen chloride (4M in dioxane) (7.99 mL, 32.0 mmol) and EtOH (absolute) (20 mL). After cooled to 0° C., isoamyl nitrite (0.672 mL, 4.79 mmol) was added dropwise and stirring was continued at 0° C. for 1 h. The resulting solution was added dropwise to a solution of tin(II) chloride dihydrate (1893 mg, 8.390 mmol) in EtOH (absolute) (10 mL) which had been pre-cooled to 0° C. and stirred for 1 h at 0° C. then evaporated to give a dark yellow oil. The oil was cooled to 0° C. and taken up in pyridine (16.16 mL, 200.0 mmol) and added 1-pivaloylpiperidine-4-carbaldehyde (828 mg, 4.19 mmol). The reaction was stirred for 30 min at 0° C. then stored in the refrigerator at 5° C. for overnight. The reaction slurry was evaporated to a light yellow semi-solid which was diluted with EtOH (25 mL). After cooled to 0° C., conc. H2SO4 (4.0 mL, 75 mmol) was added dropwise. The reaction was stirred for 30 min at 0° C., allowed to warm to ambient, then heated to 45° C. for 1 h then allowed to stir at ambient temperature for 3 days. The reaction slurry was cooled to 0° C. and sodium borohydride (2.27 g, 60.0 mmol) was added portionwise and stirred for 30 min at 0° C. then warmed to ambient temperature. The reaction mixture was filtered through CELITE® with the aid of MeOH and added to saturated NaHCO3 which contained EtOAc. The aqueous phase was adjusted to pH >7 with additional NaHCO3 solid. The aqueous phases were extracted with EtOAc (3×). Combined organics were washed with water then brine, dried over Na2SO4, filtered and evaporated. Residue was purified by flash chromatography to give Intermediate 21D (279 mg, 0.681 mmol, 17.1% yield) isolated as faint yellow colored oil. LCMS (ESI) m/z 410.3 (M+H)+, RT=1.23 min (Method D).

Intermediate 21

1-(2-Aminophenyl)-7-methoxy-N,N-dimethyl-1'-neopentylspiro[indoline-3,4'-piperidine]-4-sulfonamide: Intermediate 21 was prepared as a yellow glassine solid following the similar procedures as described in Intermediate 20C to Intermediate 20 by replacing Intermediate 20B with 21D. LCMS (ESI) m/z 387.2 (M+H)+, RT=1.99 min (Method C).

Intermediate 22

5-Chlorothiazolo[5,4-b]pyridin-2-amine

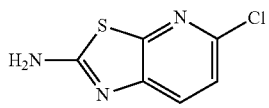 [SMILES: Nc1nc2ccc(Cl)nc2s1]

To a solution of 2,6-dichloro-3-nitropyridine (100 g, 0.518 mol) in acetic acid (1 L) was added iron powder (86.49 g, 1.555 mol) portion wise. The resulting reaction mixture was stirred at room temperature for 6 h. The completion of the reaction was confirmed by checking TLC system (PE/EA=8:2). The reaction mass was concentrated under high vacuum. The crude was dissolved in water (1 L) and EtOAc (2 L). While stirring, the pH of the aqueous solution was adjusted to 6.5 using powder $Na_2CO_3$. The mixture was filtered through CELITE® and the organic layer was separated, dried and concentrated to give 2,4-dichloroaniline (80 g, 95%) as a white solid. $^1$H NMR (400 MHz, DMSO-$d_6$) δ ppm 7.14-7.2 (2H, m); 5.78 (2H, s).

A solution of 2,4-dichloroaniline (50 g, 0.307 mol) and potassium thiocyanate (90 g, 0.921 mol) in ethanol (750 mL) and conc. hydrochloric acid (37%, 1 L) was stirred at 100° C. for 40-45 h. The completion of the reaction was confirmed by checking TLC system (PE/EA=7.5/2.5). The reaction mixture was cooled down to room temperature and concentrated to provide a brown solid, which was partitioned in dichloromethane (250 mL) and aqueous 1N NaOH (150 mL). The solid was filtered and dried to provide Intermediate 22 (32 g, 56% yield) as a light yellow solid. $^1$H NMR (400 MHz, DMSO-$d_6$) δ ppm 7.94 (s, 2H), 7.63 (d, J=8.4 Hz, 1H), 7.27 (d, J=8.4 Hz, 1H). $^{13}$C NMR (100 MHz, DMSO-$d_6$) δ ppm 166.55, 154.87, 146.69, 141.46, 126.64, 121.62.

Intermediate 23

5-Fluorothiazolo[5,4-b]pyridin-2-amine

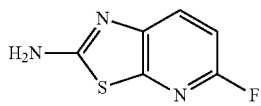

To a solution of 6-fluoropyridin-3-amine (1.0 g, 8.9 mmol) in acetic acid (29 mL) was added potassium thiocyanate (2.77 mL, 53.5 mmol). At 0° C., bromine (0.483 mL, 9.37 mmol) was added dropwise. The mixture was stirred at room temperature for 4 h and concentrated. The residue was taken up in dichloromethane and 1N NaOH, extracted with dichloromethane (3×). The combined red organic layers were washed with 1N NaOH, dried over $MgSO_4$, concentrated, and purified by flash chromatography (silica gel, eluting with EtOAc/Hexanes) to give Intermediate 23 (933 mg, 5.51 mmol, 61.8% yield). LCMS (ESI) m/z 170.1 (M+H)+, RT=0.85 min (Method D). $^1$H NMR (400 MHz, DMSO-$d_6$) δ ppm 7.42-8.18 (m, 3H), 6.85-7.20 (m, 1H).

Intermediate 24

5-Methoxythiazolo[5,4-b]pyridin-2-amine

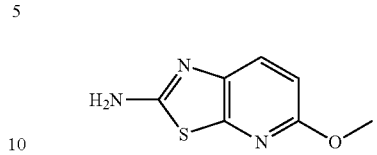

To a solution of 6-methoxypyridin-3-amine (1.24 g, 10.0 mmol) in acetic acid (33 mL) was added potassium thiocyanate (3.10 mL, 60.0 mmol). At 0° C., bromine (0.541 mL, 10.5 mmol) was added dropwise. The mixture was stirred at room temperature for 4 h and concentrated. The residue was taken up in dichloromethane and 1N NaOH, extracted with dichloromethane (3×). The combined organic layers were washed with 1N NaOH, dried over $MgSO_4$, concentrated, and purified by flash chromatography (silica gel, eluting with EtOAc/Hexanes) to give Intermediate 24 (1.5 g, 8.3 mmol, 83% yield). LCMS (ESI) m/z 182.1 (M+H)+, RT=0.88 min (Method D). $^1$H NMR (400 MHz, DMSO-$d_6$) δ ppm 7.59 (d, J=8.8 Hz, 1H), 7.41 (s, 2H), 6.67 (d, J=8.3 Hz, 1H), 3.81 (s, 3H).

Example 1

1-(2-(7-Hydroxy-1'-neopentylspiro[indoline-3,4'-piperidine]-1-yl)phenyl)-3-(4-(trifluoromethoxy)phenyl)urea

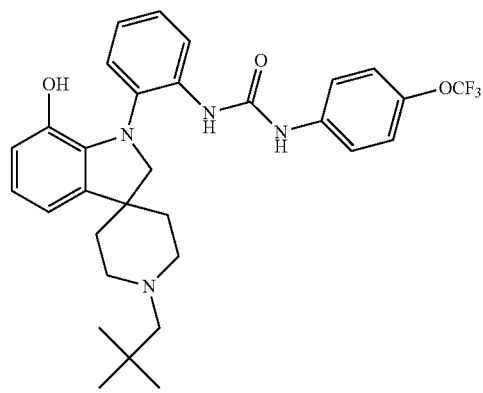 [SMILES: CC(C)(C)CN1CCC2(CC1)CN(c1ccccc1NC(=O)Nc1ccc(OC(F)(F)F)cc1)c1c(O)cccc12]

Example 1A 1-(2-(7-Methoxy-1'-pivaloylspiro[indoline-3,4'-piperidine]-1-yl)phenyl)-3-(4-(trifluoromethoxy)phenyl)urea: In a 100-ml round bottomed flask, to Intermediate 2 (1.55 g, 3.93 mmol) in THF (19 mL) was added 1-isocyanato-4-(trifluoromethoxy)benzene (594 µL, 3.93 mmol). The mixture was stirred for 2 h at 23° C., and then was concentrated in vacuo. The crude material was purified by flash chromatography (BIOTAGE®) eluting with 30-50% ethyl acetate: 70-50% hexanes to afford 2.17 g (yield: 92%) of Example 1A. $^1$H NMR (400 MHz, DMSO-$d_6$) δ ppm 9.54 (s, 1H), 8.42 (s, 1H), 8.08-8.14 (m, J=7.58 Hz, 1H), 7.52-7.57 (m, 2H), 7.28 (d, J=8.34 Hz, 2H), 7.07 (ddd, J=8.34, 6.19, 2.65 Hz, 1H), 6.85-6.90 (m, 4H), 6.81-6.84 (m, 1H), 4.26 (d, J=13.64 Hz, 1H), 4.16 (d, J=12.13 Hz, 1H), 4.08 (d, J=10.61 Hz, 1H), 3.48 (s, 3H), 3.27 (d, J=10.61 Hz, 1H), 2.81-2.92 (m, 2H), 1.80-1.87 (m, 1H), 1.68-1.79 (m, 2H), 1.58-1.65 (m, 1H), 1.18 (s, 9H). LCMS (ESI) m/z 597 (M+H)$^+$, RT=2.143 min (Method B).

Example 1B 1-(2-(7-Hydroxy-1'-pivaloylspiro[indoline-3,4'-piperidine]-1-yl)phenyl)-3-(4-(trifluoromethoxy)phenyl)urea: To Example 1A (2.1 g, 3.52 mmol) in DCM (35 mL) at −20° C., was added 1M BBr$_3$ solution in DCM (8.8 mL, 8.8 mmol) dropwisely. The mixture was allowed to reach 0° C. and stirred for 3 h. At 0° C., BBr$_3$ solution in DCM (8.8 mL, 8.8 mmol) was added, and then the reaction temperature was allowed to reach 23° C. The mixture was stirred for 2 h, and then neutralized with NH$_4$OH. The resulting mixture was stirred for 15 min and layers were separated. The organic layer was poured into 1N HCl, and extracted with DCM (2×). The combined organic layers were washed with water, dried over Na$_2$SO$_4$, filtered and concentrated in vacuo. The crude material was purified to give 1.294 g (yield: 63%) of Example 1B. $^1$H NMR (400 MHz, DMSO-d$_6$) δ ppm 9.58 (s, 1H), 8.98 (s, 1H), 8.43 (s, 1H), 8.11 (d, J=8.08 Hz, 1H), 7.52-7.58 (m, 2H), 7.28 (d, J=8.34 Hz, 2H), 7.05 (ddd, J=8.27, 4.42, 4.23 Hz, 1H), 6.86 (d, J=3.79 Hz, 2H), 6.68-6.77 (m, 2H), 6.61 (dd, J=7.33, 1.52 Hz, 1H), 4.26 (d, J=13.89 Hz, 1H), 4.15 (d, J=13.14 Hz, 1H), 4.07 (d, J=10.61 Hz, 1H), 3.23 (d, J=10.61 Hz, 1H), 2.80-2.91 (m, 2H), 1.79-1.86 (m, 1H), 1.68-1.74 (m, 2H), 1.54-1.63 (m, 1H), 1.18 (s, 9H). LCMS (ESI) m/z 583 (M+H)$^+$, RT=2.02 min (Method B).

Example 1

1-(2-(7-Hydroxy-1'-neopentylspiro[indoline-3,4'-piperidine]-1-yl)phenyl)-3-(4-(trifluoromethoxy)phenyl)urea: In a 100-ml flask, to Example 1B (1.29 g, 2.21 mmol) in THF (11 mL) was added LiAlH$_4$ (151 mg, 3.99 mmol) at 23° C. The mixture was stirred at 23° C. for 6 h, and 100 mg of LiAlH$_4$ was added. The mixture was stirred for additional 16 h at 23° C. It was poured into Rochelle's salt solution, stirred for 16 h and filtered over CELITE®. It was extracted with ethyl acetate (3×), washed with Rochelle's salt solution, water, brine, dried over Na$_2$SO$_4$, filtered and concentrated in vacuo. The crude material was purified by flash chromatography (BIOTAGE®) eluting with 20-35% ethyl acetate: 80-65% hexanes to afford 1.05 g (83%) of Example 1 as an off-white solid. $^1$H NMR (400 MHz, DMSO-d$_6$) δ ppm 9.56 (s, 1H), 8.96 (s, 1H), 8.37 (s, 1H), 8.05 (d, J=8.34 Hz, 1H), 7.55 (d, J=9.09 Hz, 2H), 7.28 (d, J=8.84 Hz, 2H), 7.03 (td, J=7.52, 1.64 Hz, 1H), 6.80-6.88 (m, 2H), 6.71-6.79 (m, 2H), 6.60 (d, J=7.07 Hz, 1H), 3.96 (d, J=10.36 Hz, 1H), 3.08 (d, J=10.36 Hz, 1H), 2.71 (d, J=10.61 Hz, 1H), 2.61 (d, J=10.61 Hz, 1H), 2.19 (t, J=12.51 Hz, 1H), 2.12 (t, J=12.00 Hz, 1H), 1.86-1.95 (m, J=11.87 Hz, 1H), 1.79-1.86 (m, 1H), 1.71 (d, J=11.62 Hz, 1H), 1.46 (d, J=12.38 Hz, 1H), 0.82 (s, 9H). LCMS (ESI) m/z 569.0 (M+H)$^+$, purity=99.07%, RT=5.43 min (Method G). HRMS calc for C$_{31}$H$_{36}$N$_4$O$_3$F$_3$=569.2734. found=569.2730.

Example 2

1-(4-tert-Butylphenyl)-3-(2-(6-fluoro-7-hydroxy-1'-neopentylspiro[indoline-3,4'-piperidine]-1-yl)phenyl)urea

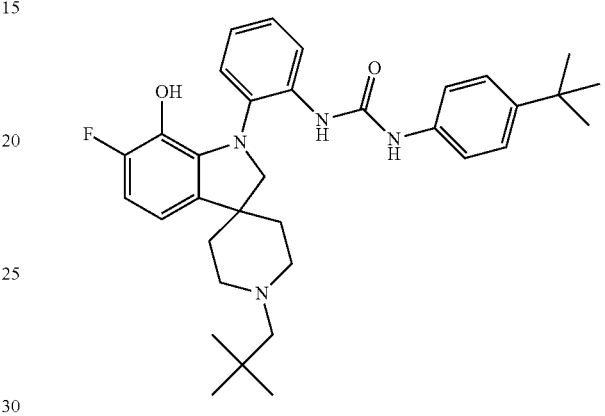

Example 2A 1-(1-(2-Aminophenyl)-6-fluoro-7-hydroxyspiro[indoline-3,4'-piperidine]-1'-yl)-2,2-dimethylpropan-1-one: Example 2A was prepared according to the procedures described for Example 1B using Intermediate 3 as the starting material to afford 33 mg (yield: 31%) of Example 2A. LCMS (ESI) m/z 398 (M+H)$^+$, RT=1.36 min (Method B).

Example 2

1-(4-tert-Butylphenyl)-3-(2-(6-fluoro-7-hydroxy-1'-neopentylspiro-[indoline-3,4'-piperidine]-1-yl)phenyl)urea: The title compound Example 2 (20 mg, yield: 41%) was prepared according to the procedures described in Example 1 using Example 2A and 1-isocyanato-4-(tert-butyl)benzene as starting materials. $^1$H NMR (400 MHz, DMSO-d$_6$) δ ppm 9.29 (s, 1H), 9.15 (s, 1H), 8.39 (s, 1H), 8.25-8.36 (m, 1H), 8.18 (d, J=7.83 Hz, 1H), 7.33-7.40 (m, 2H), 7.28 (d, J=8.59 Hz, 2H), 7.10 (t, J=7.58 Hz, 1H), 6.93 (s, 1H), 6.82-6.92 (m, 1H), 6.69-6.80 (m, 1H), 6.61 (dd, J=7.71, 4.17 Hz, 1H), 4.11 (d, J=10.61 Hz, 1H), 3.27 (s, 2H), 3.12 (s, 2H), 2.88-2.99 (m, 2H), 2.27-2.39 (m, 2H), 2.23 (d, J=13.90 Hz, 1H), 2.01 (d, J=14.65 Hz, 1H), 1.76 (d, J=12.38 Hz, 1H), 1.25 (s, 9H), 1.03 (s, 9H). LCMS (ESI) m/z 559.0 (M+H)$^+$, RT=9.23 min (Method H).

Example 3

1-(6-Fluorobenzo[d]thiazol-2-yl)-3-(2-(7-hydroxy-1'-neopentyl-4-(trifluoromethyl)spiro[indoline-3,4'-piperidine]-1-yl)phenyl)urea

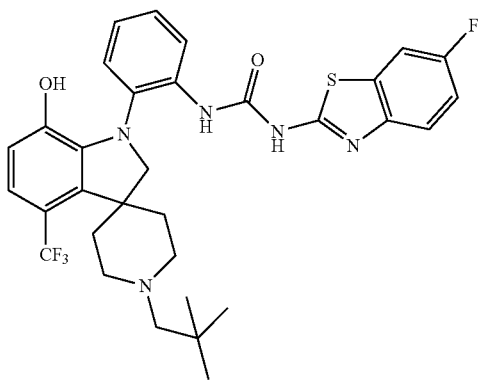 [SMILES: CC(C)(C)CN1CCC2(CC1)CN(c1ccccc1NC(=O)Nc1nc3ccc(F)cc3s1)c1c(O)ccc(C(F)(F)F)c12]

Example 3A 1-(6-Fluorobenzo[d]thiazol-2-yl)-3-(2-(7-methoxy-1'-neopentyl-4-(trifluoromethyl)spiro[indoline-3,4'-piperidine]-1-yl)phenyl)urea: To a solution of Intermediate 10 in DCM (9 mL) was added Na₂CO₃ (320 mg, 3.02 mmol), followed by addition of 4-nitrophenyl chloroformate (446 mg, 2.21 mmol). The reaction mixture was stirred at rt for 1 h. The crude carbamate was used directly after aqueous work up. To a solution of 4-nitrophenyl 2-(7-methoxy-1'-neopentyl-4-(trifluoromethyl)spiro[indoline-3,4'-piperidine]-1-yl)phenylcarbamate (150 mg, 0.245 mmol) in DCM (2.5 mL) was added DMAP (9.0 mg, 0.073 mmol) and 2-amino-6-fluorobenzothiazole (61 mg, 0.37 mmol, 1.5 equiv). The reaction mixture was irradiated at 85° C. under microwave condition for 15 minutes. Solvent was evaporated under reduced pressure. The crude product was dissolved in a small amount of CH₂Cl₂ and charged to a 12 g silica gel cartridge which was eluted with a gradient of 0 to 100% EtOAc in hexanes, followed by a 15 minutes gradient of 0 to 10% MeOH in CH₂Cl₂ to afford the desired Example 3A (100 mg, 0.156 mmol, 63.6% yield). LCMS (ESI) m/z 642.6 (M+H)⁺, RT=3.50 min (Method C).

Example 3

1-(6-Fluorobenzo[d]thiazol-2-yl)-3-(2-(7-hydroxy-1'-neopentyl-4-(trifluoromethyl)spiro[indoline-3,4'-piperidine]-1-yl)phenyl)urea: To a solution of Example 3A (100 mg, 0.156 mmol) in DCM (1.5 mL) was added TBAI (403 mg, 1.09 mmol). The reaction mixture was cooled to −50° C. and added BCl₃ (1.247 mL, 1.247 mmol). The reaction mixture was stirred at rt for 16 h and was quenched with ice. The organic layer was dried over Na₂SO₄ and evaporated under reduced pressure. The crude product was purified on preparative HPLC to afford Example 3 (59 mg, 0.094 mmol, 61% yield). ¹H NMR (400 MHz, MeOD) δ ppm 1.08 (s, 9H) 1.69-2.14 (m, 2H), 2.32-2.61 (m, 1H), 2.62-2.88 (m, 1H), 2.97 (s, 2H), 3.04-3.15 (m, 1H), 3.21 (m, 1H), 3.45-3.62 (m, 3H), 4.10-4.20 (m, 1H), 6.72-6.81 (m, 1H), 7.01-7.13 (m, 3H), 7.17-7.28 (m, 3H), 7.59 (dd, J=8.35, 2.64 Hz, 1H), 8.07-8.17 (m, 1H). LCMS (ESI) m/z 628.6 (M+H)⁺, RT=3.22 min (Method C).

Example 4

1-(2-(4-Chloro-7-hydroxy-1'-isobutylspiro[indoline-3,4'-piperidine]-1-yl)phenyl)-3-(6-fluorobenzo[d]thiazol-2-yl)urea

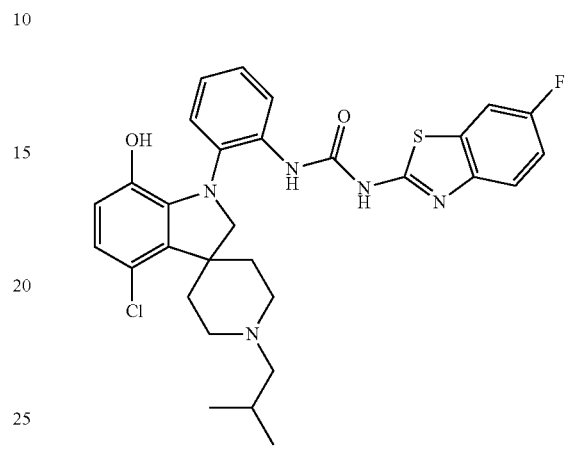

Example 4A 1-(2-(4-Chloro-1'-isobutyl-7-methoxyspiro[indoline-3,4'-piperidine]-1-yl)phenyl)-3-(6-fluorobenzo[d]thiazol-2-yl)urea: Example 4A (23 mg, 0.039 mmol, 52% yield) was prepared following similar procedures described in Example 3A by replacing Intermediate 10 with Intermediate 18 (30 mg, 0.075 mmol). LCMS (ESI) m/z 594.5 (M+H)⁺, RT=1.86 min (Method D).

Example 4

1-(2-(4-Chloro-7-hydroxy-1'-isobutylspiro[indoline-3,4'-piperidine]-1-yl)phenyl)-3-(6-fluorobenzo[d]thiazol-2-yl)urea: To a solution of Example 4A (30 mg, 0.050 mmol) in DCM (1 mL) was added tetrabutylammonium iodide (149 mg, 0.404 mmol), followed by addition of boron trichloride (0.454 mL, 0.454 mmol). The reaction mixture was stirred at an ambiguous temperature for 16 h. The reaction was quenched with MeOH and evaporated the solvents. The crude product was purified on preparative HPLC using a 10 minutes gradient from 0 to 100% B to afford Example 4 (6.0 mg, 10 μmol, 20% yield) as a yellowish powder. ¹H NMR (400 MHz, MeOD) δ ppm 1.00 (d, J=6.59 Hz, 6H), 1.04 (d, J=6.15 Hz, 2H), 1.27-1.35 (m, 1H), 2.80-2.97 (m, 4H), 3.02-3.13 (m, 1H), 3.34 (s, 1H), 3.49 (d, J=10.55 Hz, 3H), 4.16 (d, J=10.55 Hz, 1H), 6.62 (d, J=8.35 Hz, 1H), 6.75 (d, J=8.79 Hz, 1H), 7.01-7.13 (m, 3H), 7.17-7.25 (m, 1H), 7.59 (dd, J=8.57, 2.86 Hz, 2H), 8.10 (d, J=7.47 Hz, 1H). LCMS (ESI) m/z 580.5 (M+H)⁺, RT=1.65 min (Method D).

Examples 5 to 76 were prepared according the procedures described in Examples 1 and 2 by using the appropriate amine Intermediates and the appropriate isocyanates.

| Example | Name | Structure | [M + H]+ | $t_R$ (min) | LC/MS Method |
|---|---|---|---|---|---|
| 5 | 1-(4-tert-Butylphenyl)-3-(2-(7-hydroxy-1'-neopentylspiro[indoline-3,4'-piperidine]-1-yl)phenyl)urea | 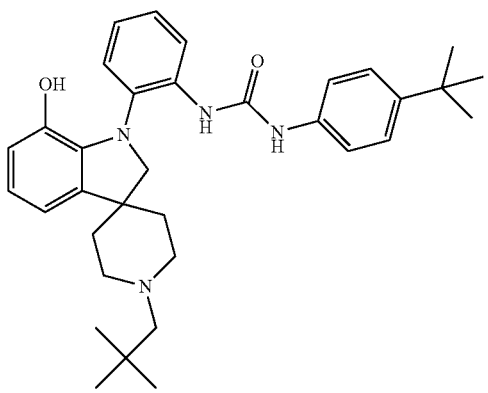 [SMILES: CC(C)(C)CN1CCC2(CC1)CN(c1ccccc1NC(=O)Nc1ccc(C(C)(C)C)cc1)c1c(O)cccc12] | 541.0 | 6.75 | G |
| 6 | 1-(2-(4-Fluoro-7-hydroxy-1'-neopentylspiro[indoline-3,4'-piperidine]-1-yl)phenyl)-3-(4-(trifluoromethoxy)phenyl)urea | 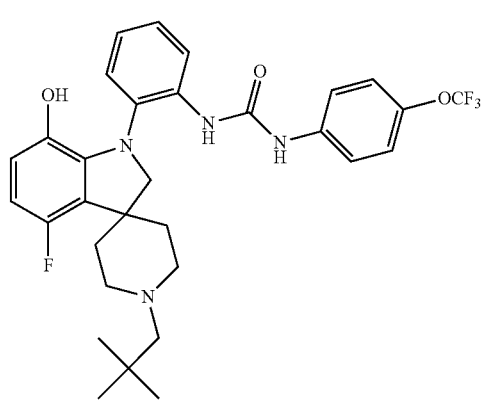 [SMILES: CC(C)(C)CN1CCC2(CC1)CN(c1ccccc1NC(=O)Nc1ccc(OC(F)(F)F)cc1)c1c(O)ccc(F)c12] | 587 | 1.72 | A |
| 7 | 1-(4-tert-Butylphenyl)-3-(2-(4-fluoro-7-hydroxy-1'-neopentylspiro[indoline-3,4'-piperidine]-1-yl)phenyl)urea | 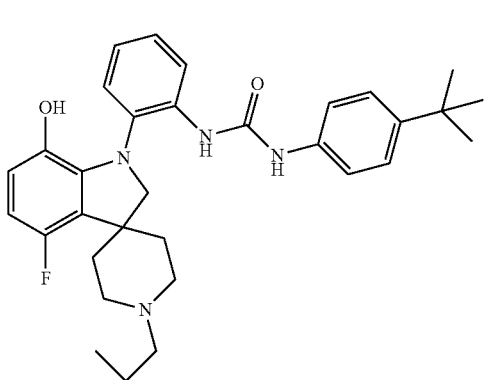 | 559 | 1.75 | A |
| 8 | 1-(2-(4-Cyano-7-hydroxy-1'-neopentylspiro[indoline-3,4'-piperidine]-1-yl)phenyl)-3-(4-(trifluoromethoxy)phenyl)urea | 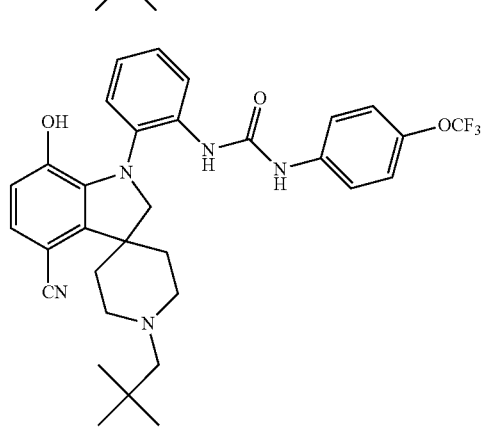 | 594 | 1.71 | A |

-continued

| Example | Name | Structure | [M + H]+ | $t_R$ (min) | LC/MS Method |
|---|---|---|---|---|---|
| 9 | 1-(4-tert-Butylphenyl)-3-(2-(4,5-difluoro-7-hydroxy-1'-neopentylspiro[indoline-3,4'-piperidine]-1-yl)phenyl)urea | 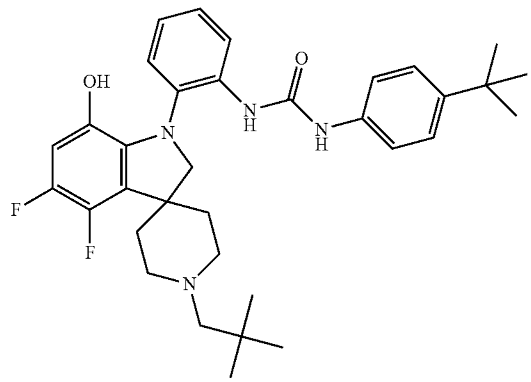 [SMILES: CC(C)(C)CN1CCC2(CC1)CN(c1ccccc1NC(=O)Nc1ccc(C(C)(C)C)cc1)c1c(O)cc(F)c(F)c12] | 577.6 | 1.81 | D |
| 10 | 1-(2-(7-Hydroxy-1'-neopentyl-4-(trifluoromethyl)spiro[indoline-3,4'-piperidine]-1-yl)phenyl)-3-(4-(trifluoromethoxy)phenyl)urea | 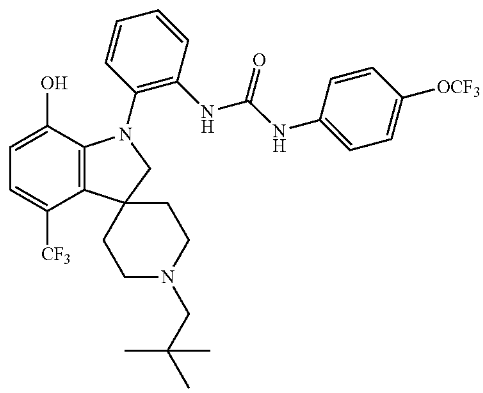 [SMILES: CC(C)(C)CN1CCC2(CC1)CN(c1ccccc1NC(=O)Nc1ccc(OC(F)(F)F)cc1)c1c(O)ccc(C(F)(F)F)c12] | 637.5 | 4.01 | C |
| 11 | 1-(4-tert-Butylphenyl)-3-(2-(7-hydroxy-1'-neopentyl-4-(trifluoromethyl)spiro[indoline-3,4'-piperidine]-1-yl)phenyl)urea | 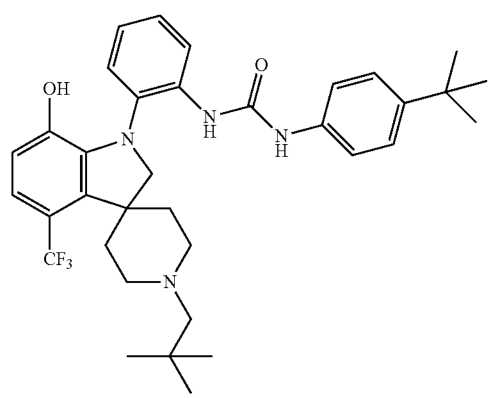 [SMILES: CC(C)(C)CN1CCC2(CC1)CN(c1ccccc1NC(=O)Nc1ccc(C(C)(C)C)cc1)c1c(O)ccc(C(F)(F)F)c12] | 609.6 | 1.61 | D |
| 12 | 1-(2-(7-Hydroxy-1'-neopentyl-4-(trifluoromethyl)spiro[indoline-3,4'-piperidine]-1-yl)pyridin-3-yl)-3-(4-(trifluoromethoxy)phenyl)urea | 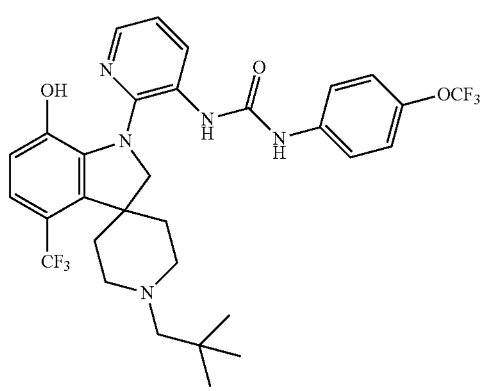 [SMILES: CC(C)(C)CN1CCC2(CC1)CN(c1ncccc1NC(=O)Nc1ccc(OC(F)(F)F)cc1)c1c(O)ccc(C(F)(F)F)c12] | 638.6 | 2.59 | C |

-continued

| Example | Name | Structure | [M + H]+ | t_R (min) | LC/MS Method |
|---|---|---|---|---|---|
| 13 | 1-(4-tert-Butylphenyl)-3-(2-(7-hydroxy-1'-neopentyl-4-(trifluoromethyl)spiro[indoline-3,4'-piperidine]-1-yl)pyridin-3-yl)urea | 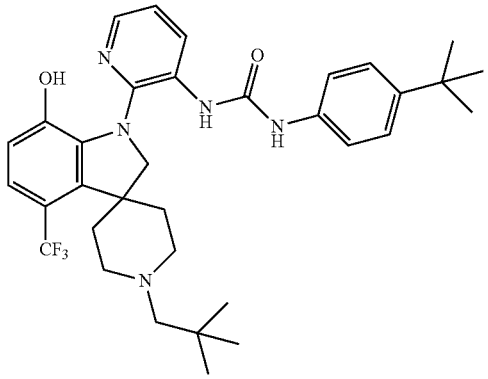 [SMILES: CC(C)(C)CN1CCC2(CC1)CN(c1ncccc1NC(=O)Nc1ccc(C(C)(C)C)cc1)c1c(O)ccc(C(F)(F)F)c12] | 610.7 | 3.74 | C |
| 14 | 1-(2-(6-Fluoro-7-hydroxy-1'-neopentylspiro[indoline-3,4'-piperidine]-1-yl)phenyl)-3-(4-(trifluoromethoxy)phenyl)urea | 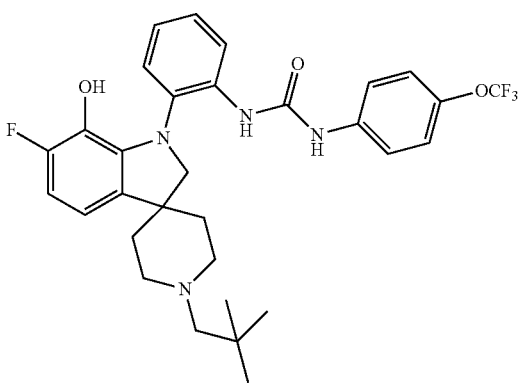 [SMILES: CC(C)(C)CN1CCC2(CC1)CN(c1ccccc1NC(=O)Nc1ccc(OC(F)(F)F)cc1)c1c2ccc(F)c1O] | 587.5 | 3.08 | C |
| 15 | 1-(3,4-Difluorophenyl)-3-(2-(7-hydroxy-1'-neopentyl-4-(trifluoromethyl)spiro[indoline-3,4'-piperidine]-1-yl)phenyl)urea | 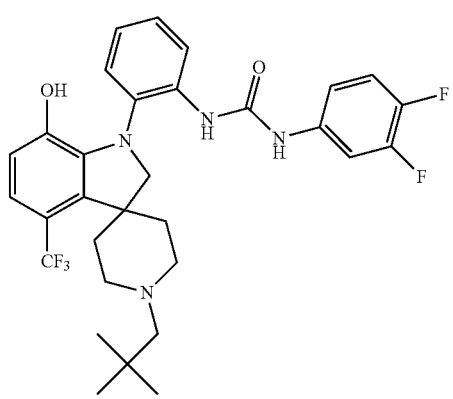 [SMILES: CC(C)(C)CN1CCC2(CC1)CN(c1ccccc1NC(=O)Nc1ccc(F)c(F)c1)c1c(O)ccc(C(F)(F)F)c12] | 589.6 | 1.62 | D |
| 16 | 1-(3-(Ethylthio)-1,2,4-thiadiazol-5-yl)-3-(2-(7-hydroxy-1'-neopentyl-4-(trifluoromethyl)spiro[indoline-3,4'-piperidine]-1-yl)phenyl)urea | 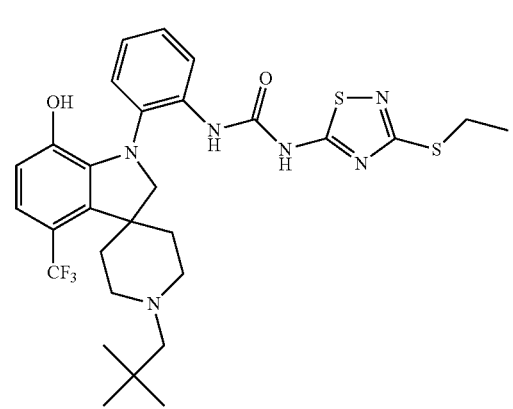 [SMILES: CCSc1nsc(NC(=O)Nc2ccccc2N2CC3(CCN(CC(C)(C)C)CC3)c3c(C(F)(F)F)ccc(O)c32)n1] | 621.6 | 3.09 | C |

| Example | Name | Structure | [M + H]+ | $t_R$ (min) | LC/MS Method |
|---|---|---|---|---|---|
| 17 | 1-(4-(Difluoromethoxy)phenyl)-3-(2-(7-hydroxy-1'-neopentyl-4-(trifluoromethyl)spiro[indoline-3,4'-piperidine]-1-yl)phenyl)urea | 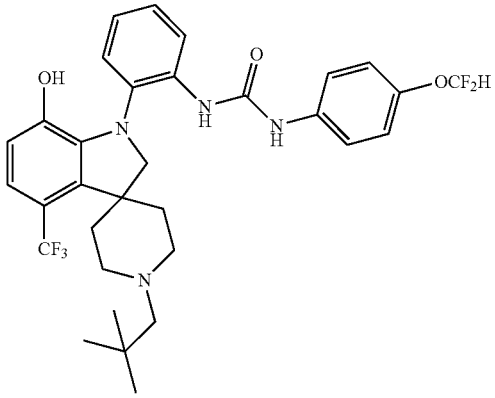 | 619.7 | 2.90 | C |
| 18 | 1-(2-Chlorothiazol-4-yl)-3-(2-(7-hydroxy-1'-neopentyl-4-(trifluoromethyl)spiro[indoline-3,4'-piperidine]-1-yl)phenyl)urea | 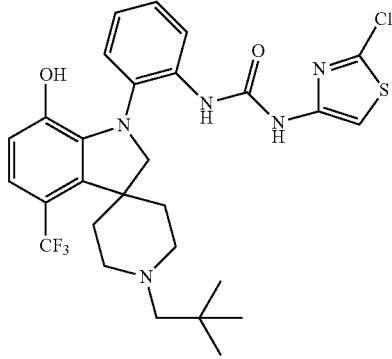 [SMILES: CC(C)(C)CN1CCC2(CC1)CN(c1ccccc1NC(=O)Nc1csc(Cl)n1)c1c(O)ccc(C(F)(F)F)c12] | 594.5 | 2.85 | C |
| 19 | 1-(2-(7-Hydroxy-1'-neopentyl-4-(trifluoromethyl)spiro[indoline-3,4'-piperidine]-1-yl)phenyl)-3-(3-isopropyl-1,2,4-thiadiazol-5-yl)urea | 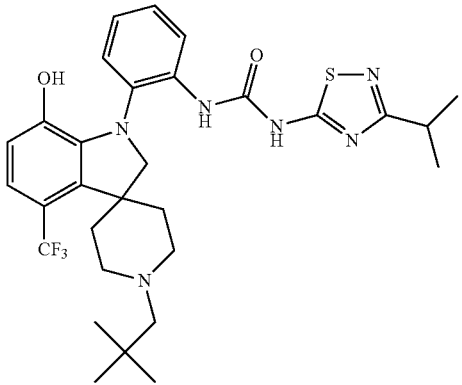 [SMILES: CC(C)c1nsc(NC(=O)Nc2ccccc2N2CC3(CCN(CC(C)(C)C)CC3)c3c(C(F)(F)F)ccc(O)c32)n1] | 603.6 | 1.57 | D |
| 20 | 1-(2,4-Difluorophenyl)-3-(2-(7-hydroxy-1'-neopentyl-4-(trifluoromethyl)spiro[indoline-3,4'-piperidine]-1-yl)phenyl)urea | 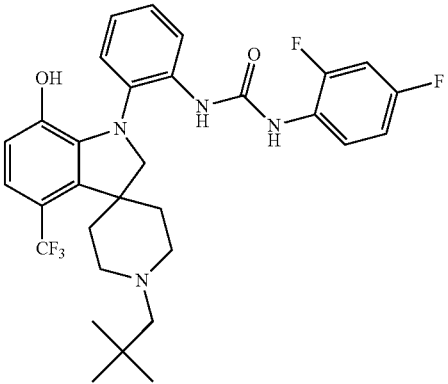 [SMILES: CC(C)(C)CN1CCC2(CC1)CN(c1ccccc1NC(=O)Nc1ccc(F)cc1F)c1c(O)ccc(C(F)(F)F)c12] | 589.6 | 1.65 | D |

-continued

| Example | Name | Structure | [M + H]⁺ | $t_R$ (min) | LC/MS Method |
|---|---|---|---|---|---|
| 21 | 1-(6-Chlorobenzo[d]thiazol-2-yl)-3-(2-(7-hydroxy-1'-neopentyl-4-(trifluoromethyl)spiro[indoline-3,4'-piperidine]-1-yl)phenyl)urea | 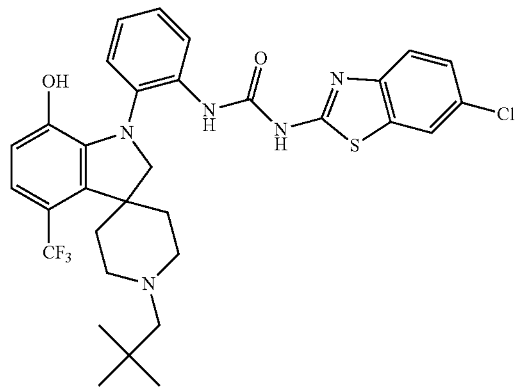 [SMILES: CC(C)(C)CN1CCC2(CC1)CN(c1ccccc1NC(=O)Nc1nc3ccc(Cl)cc3s1)c1c(O)ccc(C(F)(F)F)c12] | 644.6 | 1.84 | D |
| 22 | 1-(2-(7-Hydorxy-1'-neopentyl-4-(trifluoromethyl)spiro[indoline-3,4'-piperidine]-1-yl)phenyl)-3-(4-(trifluoromethyl)phenyl)urea | 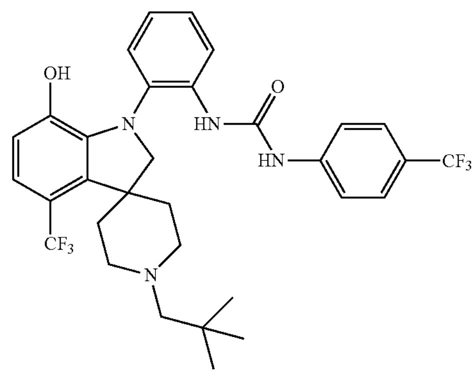 [SMILES: CC(C)(C)CN1CCC2(CC1)CN(c1ccccc1NC(=O)Nc1ccc(C(F)(F)F)cc1)c1c(O)ccc(C(F)(F)F)c12] | 621.6 | 2.62 | C |
| 23 | 1-(2-(7-Hydroxy-1'-neopentyl-4-(trifluoromethyl)spiro[indoline-3,4'-piperidine]-1-yl)phenyl)-3-(6-(trifluoromethyl)pyridin-3-yl)urea | 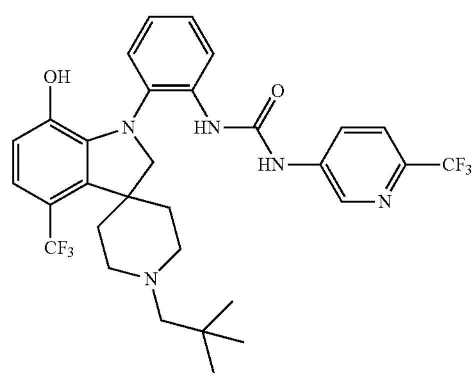 [SMILES: CC(C)(C)CN1CCC2(CC1)CN(c1ccccc1NC(=O)Nc1ccc(C(F)(F)F)nc1)c1c(O)ccc(C(F)(F)F)c12] | 622.6 | 3.03 | C |
| 24 | 1-(2-(7-Hydroxy-1'-neopentyl-4-(trifluoromethyl)spiro[indoline-3,4'-piperidine]-1-yl)phenyl)-3-(1-neopentylpiperidin-4-yl)urea | 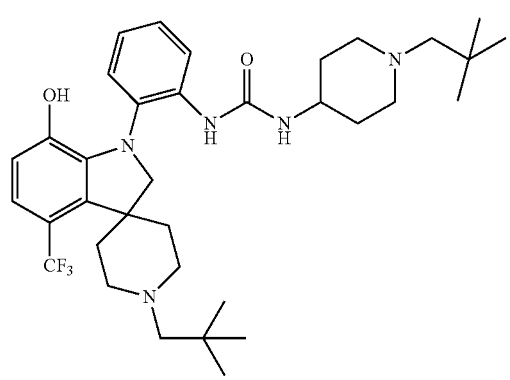 [SMILES: CC(C)(C)CN1CCC(NC(=O)Nc2ccccc2N2CC3(CCN(CC(C)(C)C)CC3)c3c(C(F)(F)F)ccc(O)c32)CC1] | 630.7 | 2.60 | C |

-continued

| Example | Name | Structure | [M + H]⁺ | t_R (min) | LC/MS Method |
|---|---|---|---|---|---|
| 25 | 1-(2-(7-Hydroxy-1'-neopentyl-4-(trifluoromethyl)spiro[indoline-3,4'-piperidine]-1-yl)phenyl)-3-(2-methylthiazol-4-yl)urea | 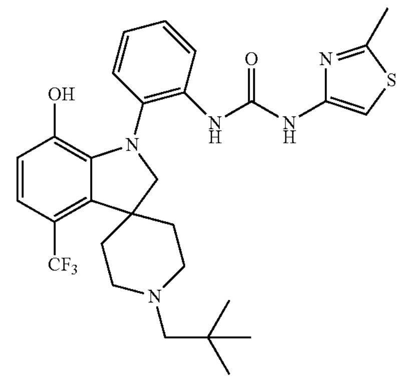 [SMILES: Cc1nc(NC(=O)Nc2ccccc2N2CC3(CCN(CC(C)(C)C)CC3)c3c(C(F)(F)F)ccc(O)c32)cs1] | 574.6 | 2.82 | C |
| 26 | 1-(5-Chlorothiophen-3-yl)-3-(2-(7-hydroxy-1'-neopentyl-4-(trifluoromethyl)spiro[indoline-3,4'-piperidine]-1-yl)phenyl)urea | 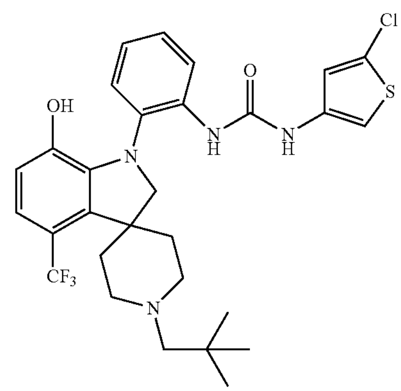 [SMILES: CC(C)(C)CN1CCC2(CC1)CN(c1ccccc1NC(=O)Nc1csc(Cl)c1)c1c(O)ccc(C(F)(F)F)c12] | 593.5 | 3.10 | C |
| 27 | 1-(4-tert-Butylcyclohexyl)-3-(2-(7-hydroxy-1'-neopentyl-4-(trifluoromethyl)spiro[indoline-3,4'-piperidine]-1-yl)phenyl)urea | 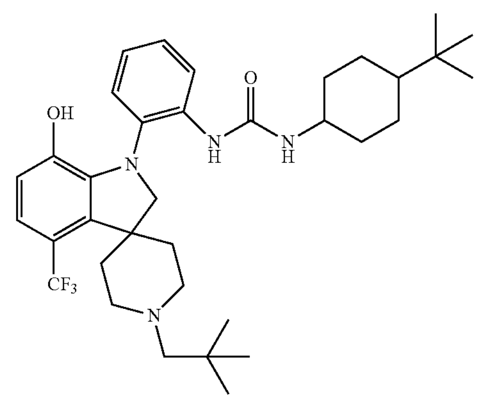 [SMILES: CC(C)(C)CN1CCC2(CC1)CN(c1ccccc1NC(=O)NC1CCC(C(C)(C)C)CC1)c1c(O)ccc(C(F)(F)F)c12] | 615.7 | 1.87 | C |
| 28 | 1-(2-(7-Hydroxy-1'-neopentyl-4-(trifluoromethyl)spiro[indoline-3,4'-piperidine]-1-yl)phenyl)-3-(2-isopropylthiazol-4-yl)urea | 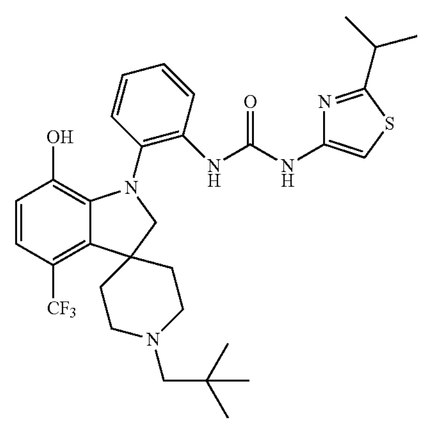 [SMILES: CC(C)c1nc(NC(=O)Nc2ccccc2N2CC3(CCN(CC(C)(C)C)CC3)c3c(C(F)(F)F)ccc(O)c32)cs1] | 602.5 | 3.00 | C |

-continued

| Example | Name | Structure | [M + H]+ | t_R (min) | LC/MS Method |
|---|---|---|---|---|---|
| 29 | 1-(2-(7-Hydroxy-1'-neopentyl-4-(trifluoromethyl)spiro[indoline-3,4'-piperidine]-1-yl)phenyl)-3-(thiazol-2-yl)urea | 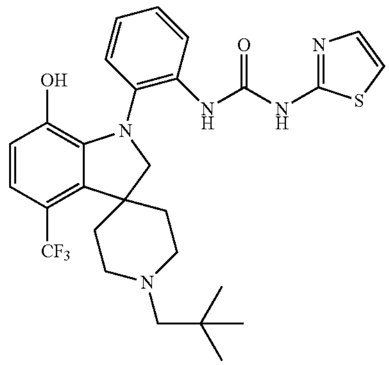 [SMILES: CC(C)(C)CN1CCC2(CC1)CN(c1ccccc1NC(=O)Nc1nccs1)c1c(O)ccc(C(F)(F)F)c12] | 560.1 | 2.63 | C |
| 30 | 1-(6-Chlorobenzo[d]thiazol-2-yl)-3-(2-(7-hydroxy-1'-isobutyl-4-(trifluoromethyl)spiro[indoline-3,4'-piperidine]-1-yl)phenyl)urea | 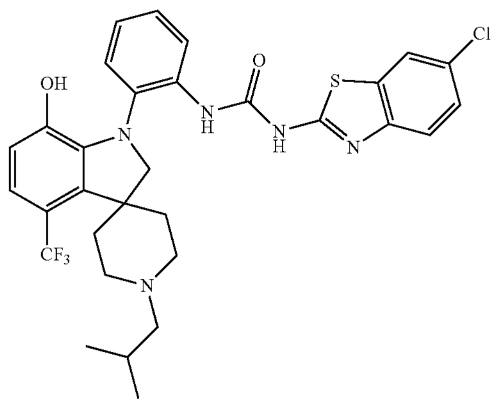 | 630.4 | 1.74 | D |
| 31 | 1-(6-Fluorobenzo[d]thiazol-2-yl)-3-(2-(7-hydroxy-1'-isobutyl-4-(trifluoromethyl)spiro[indoline-3,4'-piperidine]-1-yl)phenyl)urea | 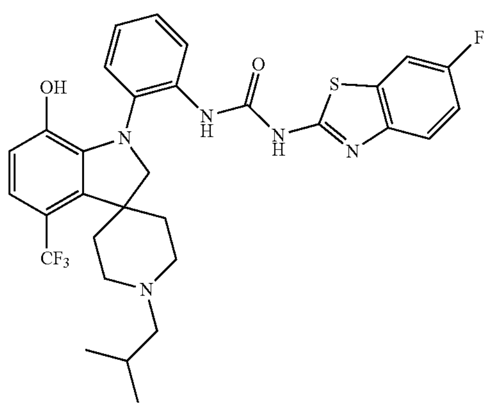 [SMILES: CC(C)CN1CCC2(CC1)CN(c1ccccc1NC(=O)Nc1nc3ccc(F)cc3s1)c1c(O)ccc(C(F)(F)F)c12] | 614.5 | 1.68 | D |
| 32 | 1-(2-(4-Fluoro-7-hydroxy-1'-neopentylspiro[indoline-3,4'-piperidine]-1-yl)phenyl)-3-(6-fluorobenzo[d]thiazol-2-yl)urea | 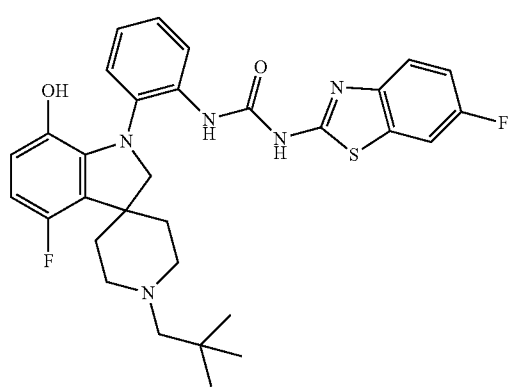 [SMILES: CC(C)(C)CN1CCC2(CC1)CN(c1ccccc1NC(=O)Nc1nc3ccc(F)cc3s1)c1c(O)ccc(F)c12] | 578.2 | 1.63 | D |

| Example | Name | Structure | [M + H]+ | tR (min) | LC/MS Method |
|---|---|---|---|---|---|
| 33 | 1-(2-(7-Hydroxy-4-fluoro-1'-neopentylspiro[indoline-3,4'-piperidine]-1-yl)phenyl)-3-(6-chlorobenzo[d]thiazol-2-yl)urea | 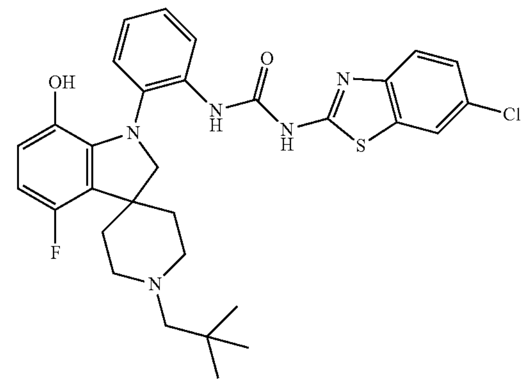 [SMILES: CC(C)(C)CN1CCC2(CC1)CN(c1ccccc1NC(=O)Nc1nc3ccc(Cl)cc3s1)c1c(O)ccc(F)c12] | 594.2 | 1.73 | D |
| 34 | 1-(2-(7-Hydroxy-4-fluoro-1'-neopentylspiro[indoline-3,4'-piperidine]-1-yl)phenyl)-3-(6-methylbenzo[d]thiazol-2-yl)urea | 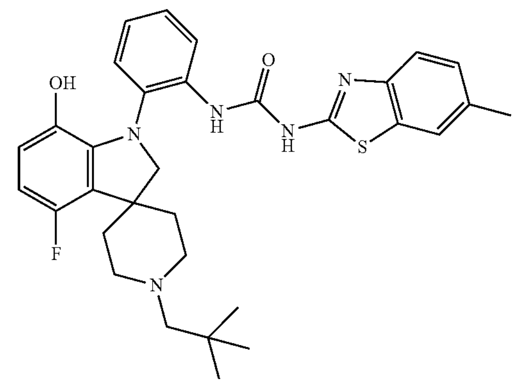 [SMILES: Cc1ccc2nc(NC(=O)Nc3ccccc3N3CC4(CCN(CC(C)(C)C)CC4)c4c(F)ccc(O)c43)sc2c1] | 574.1 | 1.68 | D |
| 35 | 1-(2-(4-Fluoro-7-hydroxy-1'-neopentylspiro[indoline-3,4'-piperidine]-1-yl)phenyl)-3-(3-isopropyl-1,2,4-thiadiazol-5-yl)urea | 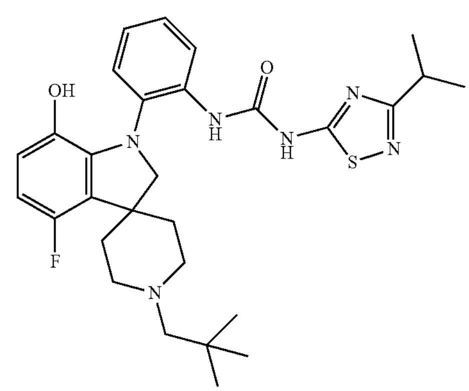 [SMILES: CC(C)c1nsc(NC(=O)Nc2ccccc2N2CC3(CCN(CC(C)(C)C)CC3)c3c(F)ccc(O)c32)n1] | 553.5 | 1.51 | D |
| 36 | 1-(2-(4-Fluoro-7-hydroxy-1'-neopentylspiro[indoline-3,4'-piperidine]-1-yl)phenyl)-3-(6-methoxybenzo[d]thiazol-2-yl)urea | 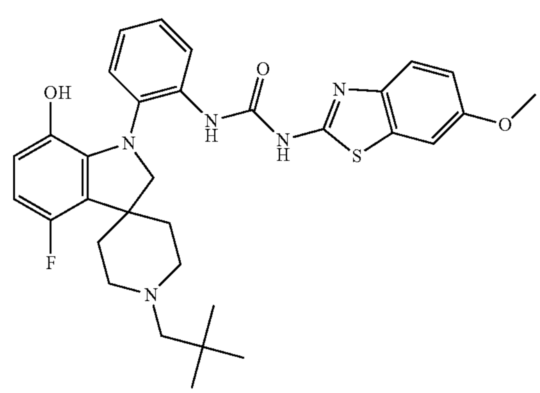 [SMILES: COc1ccc2nc(NC(=O)Nc3ccccc3N3CC4(CCN(CC(C)(C)C)CC4)c4c(F)ccc(O)c43)sc2c1] | 590.2 | 0.84 | D |

-continued

| Example | Name | Structure | [M + H]+ | $t_R$ (min) | LC/MS Method |
|---|---|---|---|---|---|
| 37 | 1-(2-(4-Fluoro-7-hydroxy-1'-neopentylspiro[indoline-3,4'-piperidine]-1-yl)phenyl)-3-(4-(trifluoromethyl)phenyl)urea | 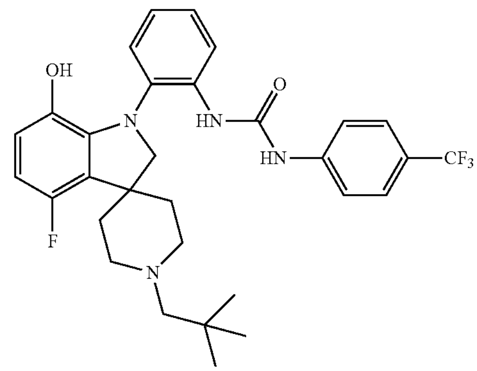 [SMILES: CC(C)(C)CN1CCC2(CC1)CN(c1ccccc1NC(=O)Nc1ccc(C(F)(F)F)cc1)c1c(O)ccc(F)c12] | 571.3 | 4.01 | D |
| 38 | 1-(2-(4-Chloro-7-hydroxy-1'-neopentylspiro[indoline-3,4'-piperidine]-1-yl)phenyl)-3-(6-chlorobenzo[d]thiazol-2-yl)urea | 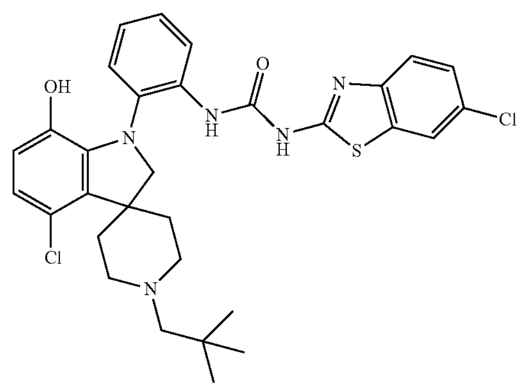 [SMILES: CC(C)(C)CN1CCC2(CC1)CN(c1ccccc1NC(=O)Nc1nc3ccc(Cl)cc3s1)c1c(O)ccc(Cl)c12] | 610.1 | 1.75 | D |
| 39 | 1-(2-(4-Chloro-7-hydroxy-1'-neopentylspiro[indoline-3,4'-piperidine]-1-yl)phenyl)-3-(6-fluorobenzo[d]thiazol-2-yl)urea | 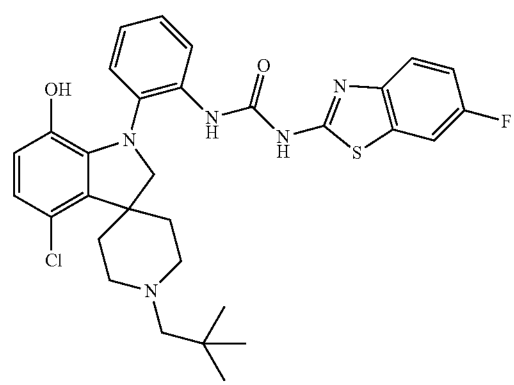 [SMILES: CC(C)(C)CN1CCC2(CC1)CN(c1ccccc1NC(=O)Nc1nc3ccc(F)cc3s1)c1c(O)ccc(Cl)c12] | 594.2 | 1.67 | D |
| 40 | 1-(2-(4-Chloro-7-hydroxy-1'-neopentylspiro[indoline-3,4'-piperidine]-1-yl)phenyl)-3-(6-methylbenzo[d]thiazol-2-yl)urea | 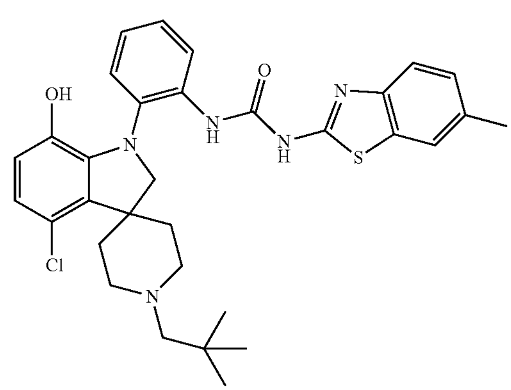 [SMILES: Cc1ccc2nc(NC(=O)Nc3ccccc3N3CC4(CCN(CC(C)(C)C)CC4)c4c(Cl)ccc(O)c43)sc2c1] | 590.4 | 1.62 | D |

-continued

| Example | Name | Structure | [M + H]+ | t_R (min) | LC/MS Method |
|---|---|---|---|---|---|
| 41 | Methyl 2-(3-(2-(4-Chloro-7-hydroxy-1'-neopentylspiro[indoline-3,4'-piperidine]-1-yl)phenyl)ureido)benzo[d]thiazole-6-carboxylate | 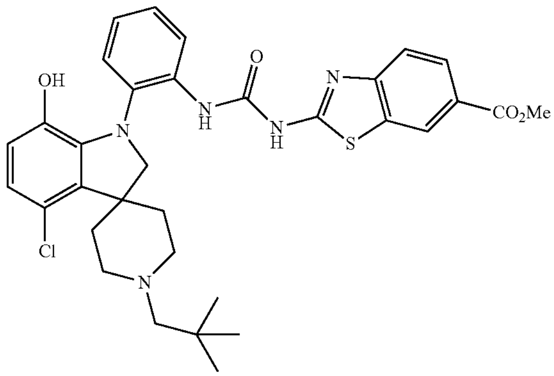 [SMILES: COC(=O)c1ccc2nc(NC(=O)Nc3ccccc3N3CC4(CCN(CC(C)(C)C)CC4)c4c(Cl)ccc(O)c43)sc2c1] | 633.9 | 1.72 | D |
| 42 | 1-(2-(4-Chloro-7-hydroxy-1'-neopentylspiro[indoline-3,4'-piperidine]-1-yl)phenyl)-3-(3-methyl-1,2,4-thiadiazol-5-yl)urea | 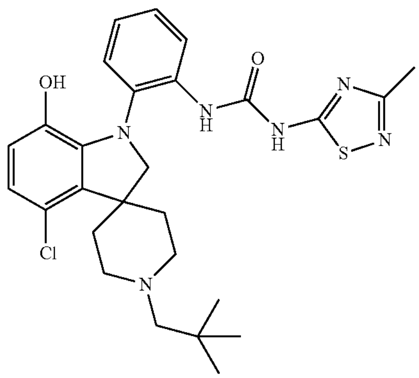 [SMILES: Cc1nsc(NC(=O)Nc2ccccc2N2CC3(CCN(CC(C)(C)C)CC3)c3c(Cl)ccc(O)c32)n1] | 541.1 | 1.47 | D |
| 43 | 1-(2-(4-Chloro-7-hydroxy-1'-neopentylspiro[indoline-3,4'-piperidine]-1-yl)phenyl)-3-(3-isopropyl-1,2,4-thiadiazol-5-yl)urea | 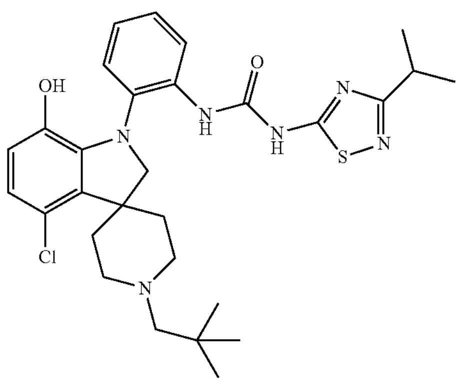 [SMILES: CC(C)c1nsc(NC(=O)Nc2ccccc2N2CC3(CCN(CC(C)(C)C)CC3)c3c(Cl)ccc(O)c32)n1] | 569.2 | 1.58 | D |
| 44 | 1-(2-(4-Chloro-7-hydroxy-1'-neopentylspiro[indoline-3,4'-piperidine]-1-yl)phenyl)-3-(3-(ethylthio)-1,2,4-thiadiazol-5-yl)urea | 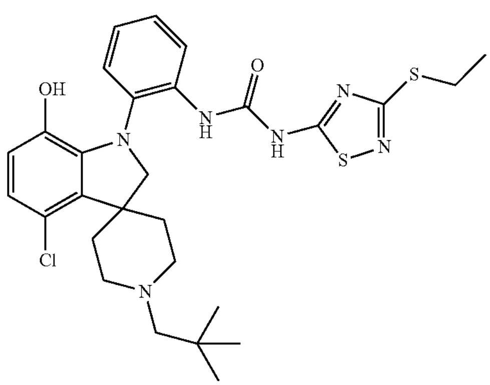 [SMILES: CCSc1nsc(NC(=O)Nc2ccccc2N2CC3(CCN(CC(C)(C)C)CC3)c3c(Cl)ccc(O)c32)n1] | 587.1 | 1.67 | D |

-continued

| Example | Name | Structure | [M + H]+ | t_R (min) | LC/MS Method |
|---|---|---|---|---|---|
| 45 | 1-(2-(4-Chloro-7-hydroxy-1'-neopentylspiro[indoline-3,4'-piperidine]-1-yl)phenyl)-3-(4,5,6,7-tetrahydrobenzo[d]thiazol-2-yl)urea, TFA | 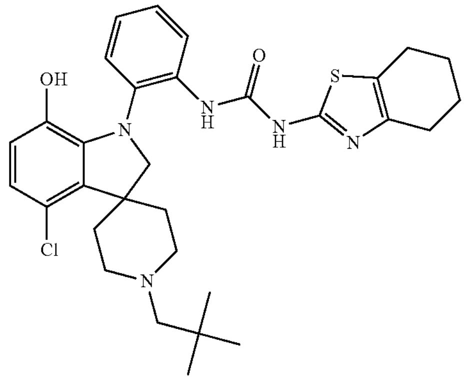 [SMILES: CC(C)(C)CN1CCC2(CC1)CN(c1ccccc1NC(=O)Nc1nc3c(s1)CCCC3)c1c(O)ccc(Cl)c12] | 580.3 | 1.48 | D |
| 46 | 1-(2-(4-Chloro-7-hydroxy-1'-neopentylspiro[indoline-3,4'-piperidine]-1-yl)phenyl)-3-(5,6-dihydro-4H-cyclopenta[d]thiazol-2-yl)urea, TFA | 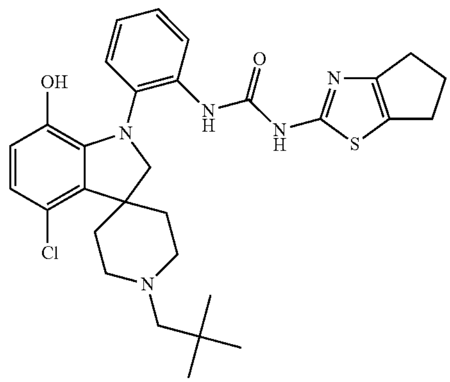 [SMILES: CC(C)(C)CN1CCC2(CC1)CN(c1ccccc1NC(=O)Nc1nc3c(s1)CCC3)c1c(O)ccc(Cl)c12] | 566.3 | 1.52 | D |
| 47 | 1-(2-(4-Chloro-7-hydroxy-1'-neopentylspiro[indoline-3,4'-piperidine]-1-yl)phenyl)-3-(6-methoxybenzo[d]thiazol-2-yl)urea, TFA | 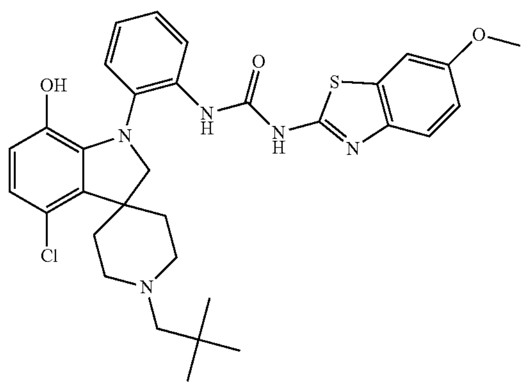 [SMILES: COc1ccc2nc(NC(=O)Nc3ccccc3N3CC4(CCN(CC(C)(C)C)CC4)c4c(Cl)ccc(O)c43)sc2c1] | 606.3 | 1.56 | D |
| 48 | 1-(2-(4-Chloro-7-hydroxy-1'-neopentylspiro[indoline-3,4'-piperidine]-1-yl)phenyl)-3-(6,7-dihydro-4H-pyrano[4,3-d]thiazol-2-yl)urea, TFA | 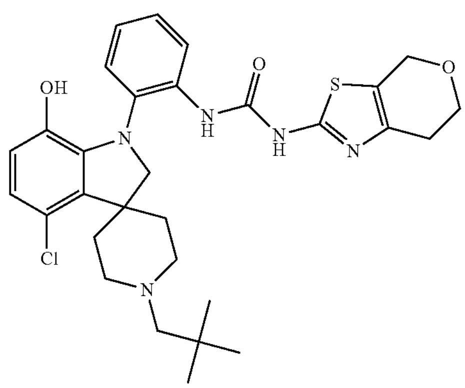 [SMILES: CC(C)(C)CN1CCC2(CC1)CN(c1ccccc1NC(=O)Nc1nc3c(s1)COCC3)c1c(O)ccc(Cl)c12] | 582.2 | 1.37 | D |

-continued

| Example | Name | Structure | [M + H]+ | t_R (min) | LC/MS Method |
|---|---|---|---|---|---|
| 49 | 1-(2-(4-Chloro-7-hydroxy-1'-neopentylspiro[indoline-3,4'-piperidine]-1-yl)phenyl)-3-(6,7-dihydro-4H-thiopyrano[4,3-d]thiazol-2-yl)urea, TFA | 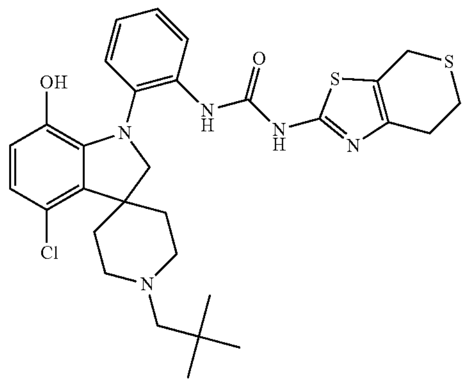 [SMILES: CC(C)(C)CN1CCC2(CC1)CN(c1ccccc1NC(=O)Nc1nc3c(s1)CSCC3)c1c(O)ccc(Cl)c12] | 598.2 | 1.51 | D |
| 50 | 1-(2-(4-Chloro-7-hydroxy-1'-neopentylspiro[indoline-3,4'-piperidine]-1-yl)phenyl)-3-(3-methoxy-1,2,4-thiadiazol-5-yl)urea, TFA | 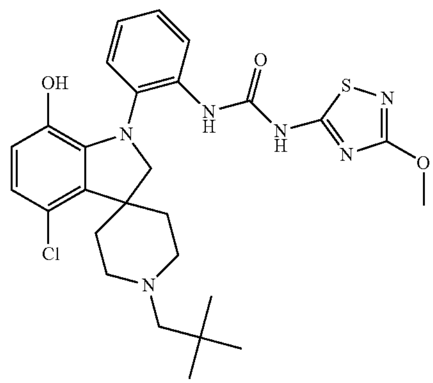 [SMILES: COc1nsc(NC(=O)Nc2ccccc2N2CC3(CCN(CC(C)(C)C)CC3)c3c(Cl)ccc(O)c32)n1] | 557.3 | 1.41 | D |
| 51 | 1-(2-(4-Chloro-7-hydroxy-1'-neopentylspiro[indoline-3,4'-piperidine]-1-yl)phenyl)-3-(6-nitrobenzo[d]thiazol-2-yl)urea, TFA | 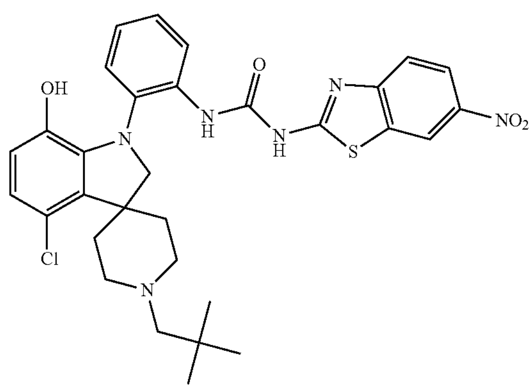 [SMILES: CC(C)(C)CN1CCC2(CC1)CN(c1ccccc1NC(=O)Nc1nc3ccc([N+](=O)[O-])cc3s1)c1c(O)ccc(Cl)c12] | 621.2 | 1.72 | D |
| 52 | 1-(2-(4-Chloro-7-hydroxy-1'-neopentylspiro[indoline-3,4'-piperidine]-1-yl)phenyl)-3-(6-(trifluoromethoxy)benzo[d]thiazol-2-yl)urea, TFA | 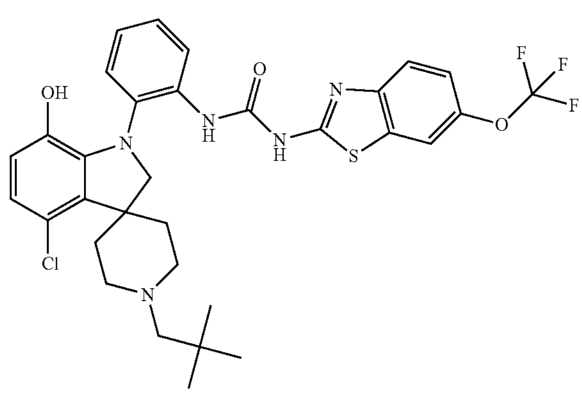 [SMILES: CC(C)(C)CN1CCC2(CC1)CN(c1ccccc1NC(=O)Nc1nc3ccc(OC(F)(F)F)cc3s1)c1c(O)ccc(Cl)c12] | 660.2 | 1.83 | D |

| Example | Name | Structure | [M + H]+ | t_R (min) | LC/MS Method |
|---|---|---|---|---|---|
| 53 | 1-(Benzo[d]thiazol-2-yl)-3-(2-(4-chloro-7-hydroxy-1'-neopentylspiro[indoline-3,4'-piperidine]-1-yl)phenyl)urea, TFA | 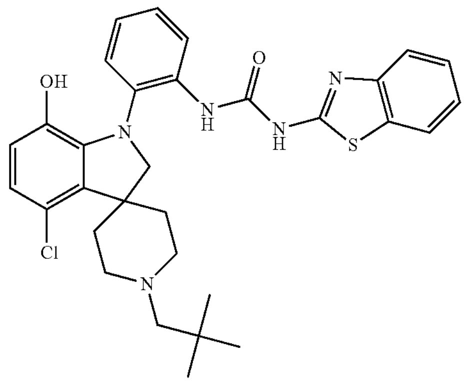 [SMILES: CC(C)(C)CN1CCC2(CC1)CN(c1ccccc1NC(=O)Nc1nc3ccccc3s1)c1c(O)ccc(Cl)c12] | 576.1 | 1.62 | D |
| 54 | 1-(2-(4-Chloro-7-hydroxy-1'-neopentylspiro[indoline-3,4'-piperidine]-1-yl)phenyl)-3-(2,4-difluorophenyl)urea | 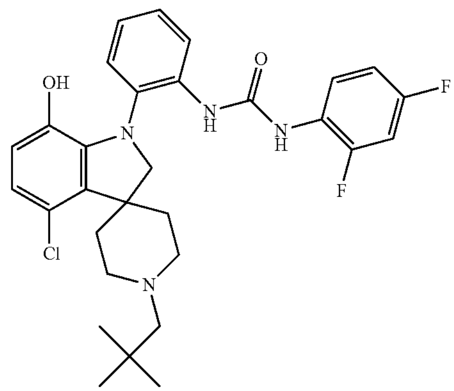 [SMILES: CC(C)(C)CN1CCC2(CC1)CN(c1ccccc1NC(=O)Nc1ccc(F)cc1F)c1c(O)ccc(Cl)c12] | 555.6 | 2.77 | C |
| 55 | 1-(4-tert-Butylphenyl)-3-(2-(4-chloro-7-hydroxy-1'-neopentylspiro[indoline-3,4'-piperidine]-1-yl)phenyl)urea | 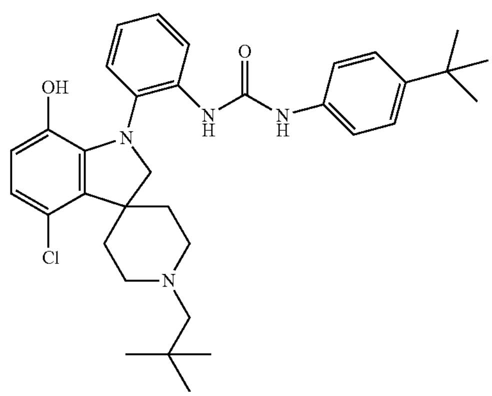 [SMILES: CC(C)(C)CN1CCC2(CC1)CN(c1ccccc1NC(=O)Nc1ccc(C(C)(C)C)cc1)c1c(O)ccc(Cl)c12] | 575.5 | 3.22 | C |
| 56 | 1-(2-(4-Chloro-7-hydroxy-1'-neopentylspiro[indoline-3,4'-piperidine]-1-yl)phenyl)-3-(3-fluoro-4-methylphenyl)urea | 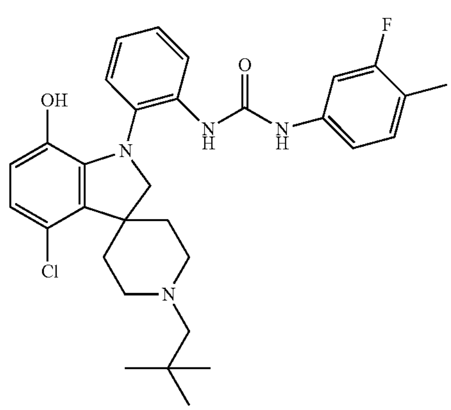 [SMILES: Cc1ccc(NC(=O)Nc2ccccc2N2CC3(CCN(CC(C)(C)C)CC3)c3c(Cl)ccc(O)c32)cc1F] | 551.4 | 2.92 | C |

-continued

| Example | Name | Structure | [M + H]+ | $t_R$ (min) | LC/MS Method |
|---|---|---|---|---|---|
| 57 | 1-(2-(4-Chloro-7-hydroxy-1'-neopentylspiro[indoline-3,4'-piperidine]-1-yl)phenyl)-3-(4-(1-isobutylpyrrolidin-2-yl)phenyl)urea | 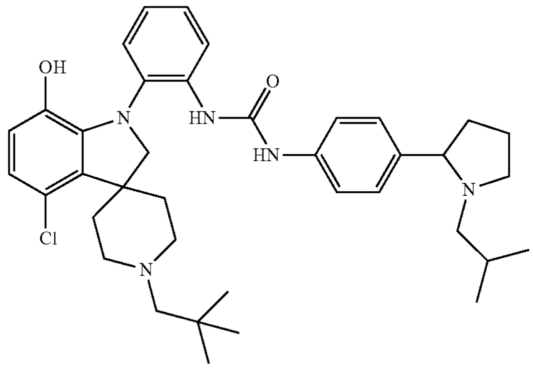 [SMILES: CC(C)CN1CCCC1c1ccc(NC(=O)Nc2ccccc2N2CC3(CCN(CC(C)(C)C)CC3)c3c(Cl)ccc(O)c32)cc1] | 644.5 | 2.48 | C |
| 58 | 1-(2-(4-Chloro-7-hydroxy-1'-neopentylspiro[indoline-3,4'-piperidine]-1-yl)phenyl)-3-(4-(1-neopentylpyrrolidin-2-yl)phenyl)urea | 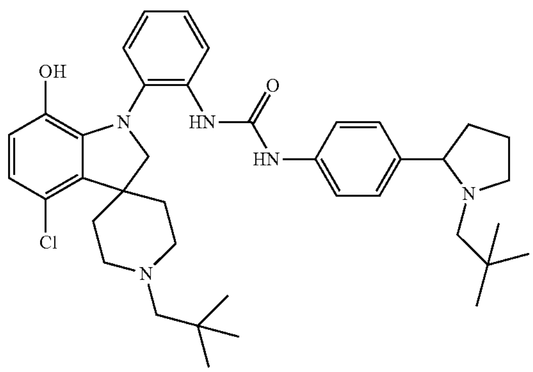 [SMILES: CC(C)(C)CN1CCC2(CC1)CN(c1ccccc1NC(=O)Nc1ccc(C3CCCN3CC(C)(C)C)cc1)c1c(O)ccc(Cl)c12] | 658.5 | 2.55 | C |
| 59 | 1-(2-(4-Chloro-7-hydroxy-1'-neopentylspiro[indoline-3,4'-piperidine]-1-yl)phenyl)-3-(4-(trifluoromethoxy)phenyl)urea | 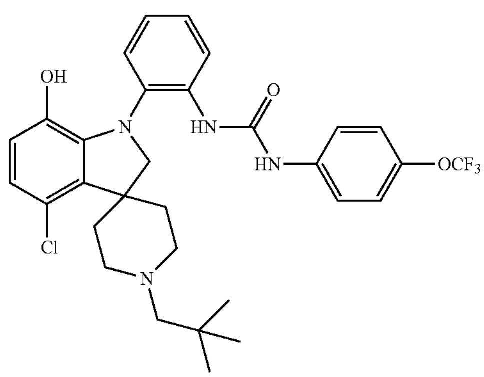 [SMILES: CC(C)(C)CN1CCC2(CC1)CN(c1ccccc1NC(=O)Nc1ccc(OC(F)(F)F)cc1)c1c(O)ccc(Cl)c12] | 603.5 | 3.19 | C |
| 60 | 1-(2-(4-Chloro-7-hydroxy-1'-neopentylspiro[indoline-3,4'-piperidin]-1-yl)phenyl)-3-(4-(trifluoromethyl)phenyl)urea | 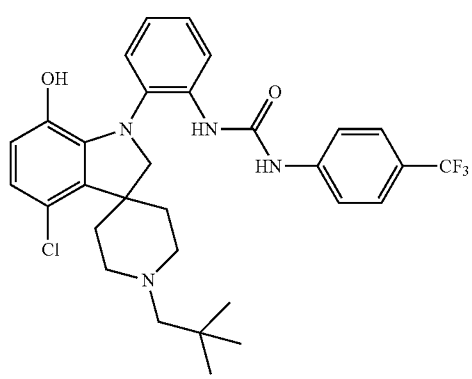 | 587.6 | 3.16 | C |

-continued

| Example | Name | Structure | [M + H]⁺ | t_R (min) | LC/MS Method |
|---|---|---|---|---|---|
| 61 | 1-(2-(4-Chloro-7-hydroxy-1'-neopentylspiro[indoline-3,4'-piperidin]-1-yl)phenyl)-3-(2-chlorothiazol-4-yl)urea | 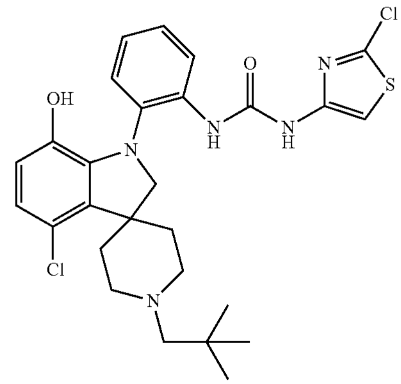 [SMILES: CC(C)(C)CN1CCC2(CC1)CN(c1ccccc1NC(=O)Nc1csc(Cl)n1)c1c(O)ccc(Cl)c12] | 560.4 | 2.70 | C |
| 62 | 1-(2-(4-Chloro-7-hydroxy-1'-neopentylspiro[indoline-3,4'-piperidine]-1-yl)phenyl)-3-(2-isopropylthiazol-4-yl)urea | 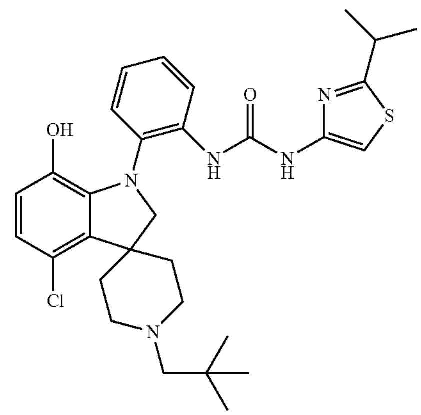 [SMILES: CC(C)c1nc(NC(=O)Nc2ccccc2N2CC3(CCN(CC(C)(C)C)CC3)c3c(Cl)ccc(O)c32)cs1] | 568.6 | 2.85 | C |
| 63 | 1-(2-(4-Chloro-7-hydroxy-1'-neopentylspiro[indoline-3,4'-piperidine]-1-yl)phenyl)-3-(2-(trifluoromethyl)thiazol-4-yl)urea | 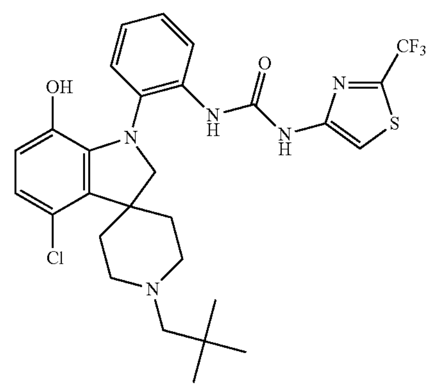 [SMILES: CC(C)(C)CN1CCC2(CC1)CN(c1ccccc1NC(=O)Nc1csc(C(F)(F)F)n1)c1c(O)ccc(Cl)c12] | 594.0 | 2.94 | C |
| 64 | 1-(2-(4-Chloro-7-hydroxy-1'-isobutylspiro[indoline-3,4'-piperidine]-1-yl)phenyl)-3-(4-(trifluoromethyl)phenyl)urea | 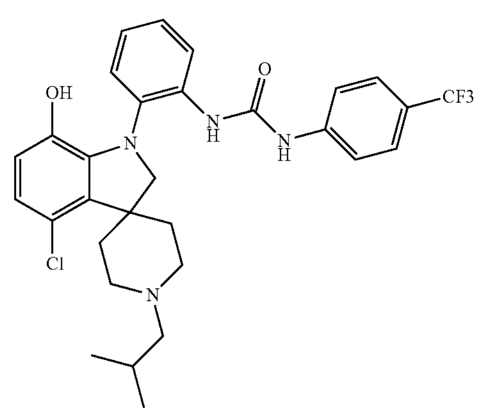 [SMILES: CC(C)CN1CCC2(CC1)CN(c1ccccc1NC(=O)Nc1ccc(C(F)(F)F)cc1)c1c(O)ccc(Cl)c12] | 573.5 | 1.66 | D |

| Example | Name | Structure | [M + H]⁺ | $t_R$ (min) | LC/MS Method |
|---|---|---|---|---|---|
| 65 | 1-(2-(4-Chloro-7-hydroxy-1'-isobutylspiro[indoline-3,4'-piperidine]-1-yl)phenyl)-3-(6-chlorobenzo[d]thiazol-2-yl)urea | 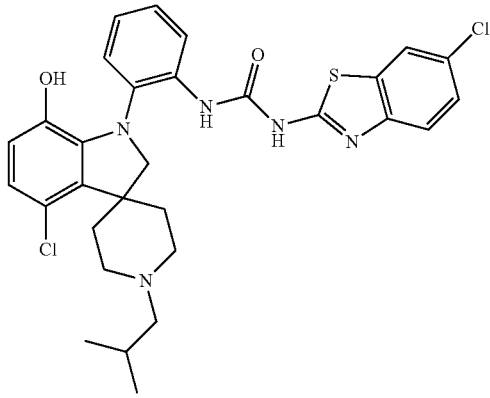 [SMILES: CC(C)CN1CCC2(CC1)CN(c1ccccc1NC(=O)Nc1nc3ccc(Cl)cc3s1)c1c(O)ccc(Cl)c12] | 596.3 | 1.77 | D |
| 66 | 1-(2-(4-Chloro-7-hydroxy-1'-neopentylspiro[indoline-3,4'-piperidine]-1-yl)pyridin-3-yl)-3-(6-fluorobenzo[d]thiazol-2-yl)urea | 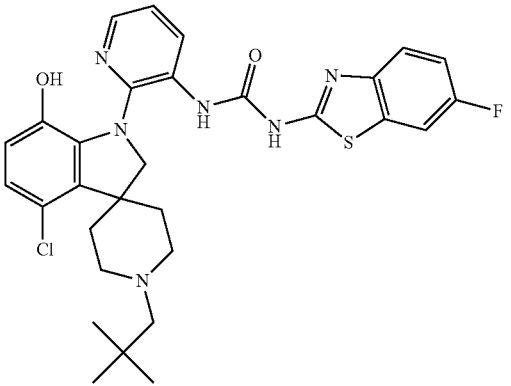 [SMILES: CC(C)(C)CN1CCC2(CC1)CN(c1ncccc1NC(=O)Nc1nc3ccc(F)cc3s1)c1c(O)ccc(Cl)c12] | 595.0 | 2.71 | C |
| 67 | 1-(2-(4-Chloro-7-hydroxy-1'-neopentylspiro[indoline-3,4'-piperidine]-1-yl)-4-fluorophenyl)-3-(6-fluorobenzo[d]thiazol-2-yl)urea | 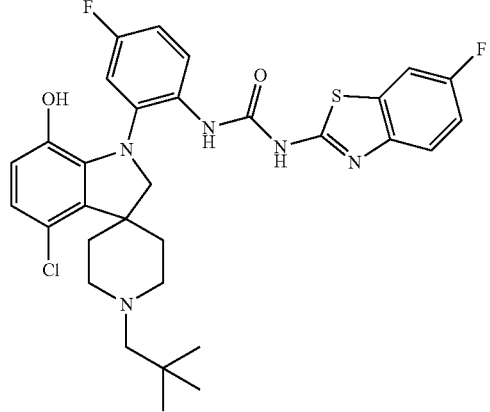 [SMILES: CC(C)(C)CN1CCC2(CC1)CN(c1cc(F)ccc1NC(=O)Nc1nc3ccc(F)cc3s1)c1c(O)ccc(Cl)c12] | 612.6 | 3.07 | C |

| Example | Name | Structure | [M + H]+ | t_R (min) | LC/MS Method |
|---|---|---|---|---|---|
| 68 | 1-(2-(4-Chloro-7-hydroxy-1'-neopentylspiro[indoline-3,4'-piperidine]-1-yl)-5-fluorophenyl)-3-(6-fluorobenzo[d]thiazol-2-yl)urea | 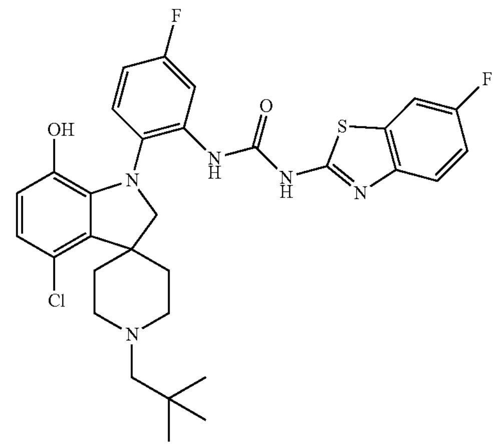 [SMILES: CC(C)(C)CN1CCC2(CC1)CN(c1ccc(F)cc1NC(=O)Nc1nc3ccc(F)cc3s1)c1c(O)ccc(Cl)c12] | 612.6 | 3.19 | C |
| 69 | 1-(2-(4-Chloro-7-hydroxy-1'-neopentylspiro[indoline-3,4'-piperidine]-1-yl)-5-cyanophenyl)-3-(4-(trifluoromethoxy)phenyl)urea | 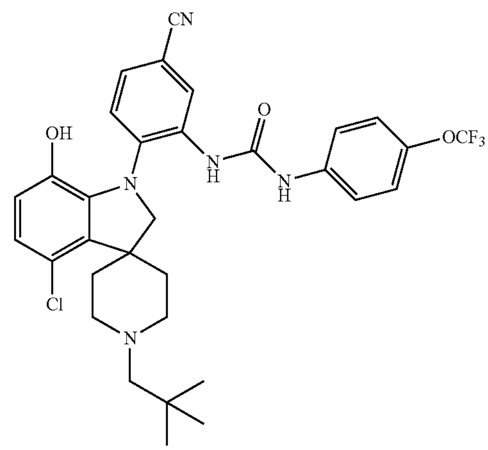 [SMILES: CC(C)(C)CN1CCC2(CC1)CN(c1ccc(C#N)cc1NC(=O)Nc1ccc(OC(F)(F)F)cc1)c1c(O)ccc(Cl)c12] | 628.6 | 3.10 | C |
| 70 | 1-(2-(4-Chloro-7-hydroxy-1'-neopentylspiro[indoline-3,4'-piperidine]-1-yl)-5-cyanophenyl)-3-(6-fluorobenzo[d]thiazol-2-yl)urea | 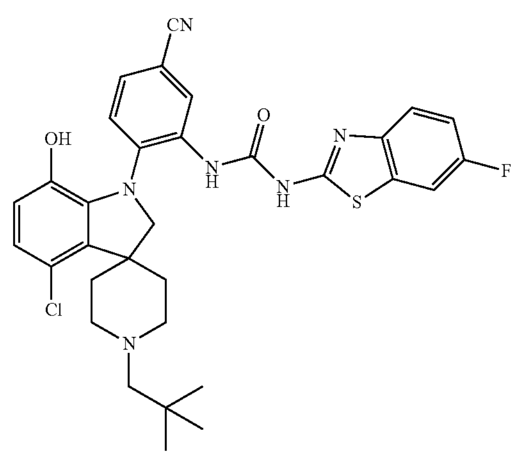 [SMILES: CC(C)(C)CN1CCC2(CC1)CN(c1ccc(C#N)cc1NC(=O)Nc1nc3ccc(F)cc3s1)c1c(O)ccc(Cl)c12] | 619.3 | 3.10 | C |

-continued

| Example | Name | Structure | [M + H]⁺ | $t_R$ (min) | LC/MS Method |
|---|---|---|---|---|---|
| 71 | 1-(2-(4-Chloro-7-hydroxy-1'-neopentylspiro[indoline-3,4'-piperidine]-1-yl)phenyl)-3-(5-(2,2,2-trifluoroethyl)-4,5,6,7-tetrahydrothiazolo[5,4-c]pyridin-2-yl)urea | 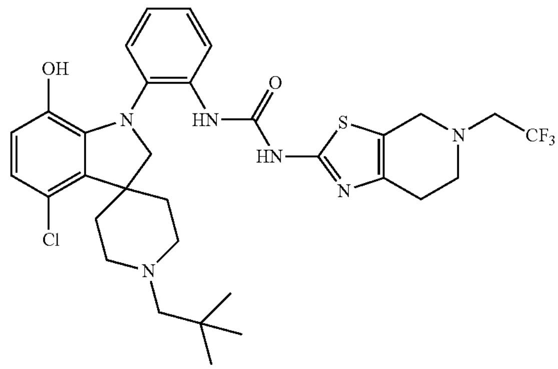 [SMILES: CC(C)(C)CN1CCC2(CC1)CN(c1ccccc1NC(=O)Nc1nc3c(s1)CN(CC(F)(F)F)CC3)c1c(O)ccc(Cl)c12] | 663.1 | 2.90 | C |
| 72 | 1-(2-(4-Chloro-7-hydroxy-1'-neopentylspiro[indoline-3,4'-piperidine]-1-yl)phenyl)-3-(5-(2,2,2-trifluoroacetyl)-4,5,6,7-tetrahydrothiazolo[5,4-c]pyridin-2-yl)urea | 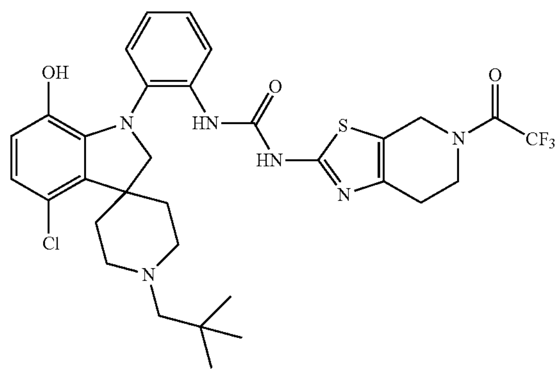 [SMILES: CC(C)(C)CN1CCC2(CC1)CN(c1ccccc1NC(=O)Nc1nc3c(s1)CN(C(=O)C(F)(F)F)CC3)c1c(O)ccc(Cl)c12] | 677.4 | 1.59 | D |
| 73 | 1-(2-(4-Chloro-7-hydroxy-1'-neopentylspiro[indoline-3,4'-piperidine]-1-yl)phenyl)-3-(5-isobutyryl-4,5,6,7-tetrahydrothiazolo[5,4-c]pyriidn-2-yl)urea | 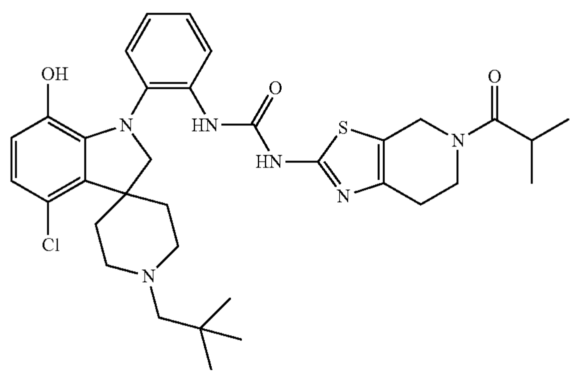 [SMILES: CC(C)C(=O)N1CCc2nc(NC(=O)Nc3ccccc3N3CC4(CCN(CC(C)(C)C)CC4)c4c(Cl)ccc(O)c43)sc2C1] | 651.5 | 1.52 | D |
| 74 | 1-(2-(4-Chloro-7-hydroxy-1'-neopentylspiro[indoline-3,4'-piperidine]-1-yl)phenyl)-3-(5-isobutyl-4,5,6,7-tetrahydrothiazolo[5,4-c]pyridin-2-yl)urea | 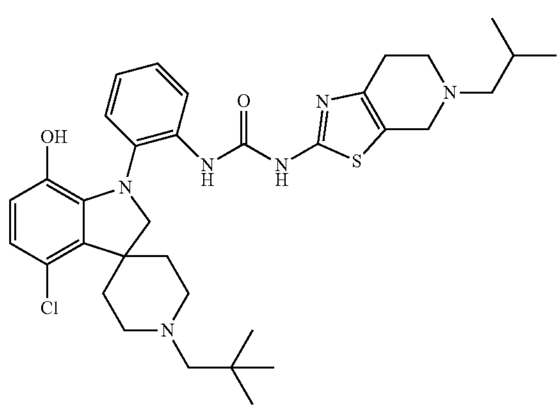 [SMILES: CC(C)CN1CCc2nc(NC(=O)Nc3ccccc3N3CC4(CCN(CC(C)(C)C)CC4)c4c(Cl)ccc(O)c43)sc2C1] | 637.7 | 2.26 | C |

| Example | Name | Structure | [M + H]+ | $t_R$ (min) | LC/MS Method |
|---|---|---|---|---|---|
| 75 | 1-(6-Chlorobenzo[d]thiazol-2-yl)-3-(2-(7-hydroxy-1'-neopentylspiro[indoline-3,4'-piperidine]-1-yl)phenyl)urea | 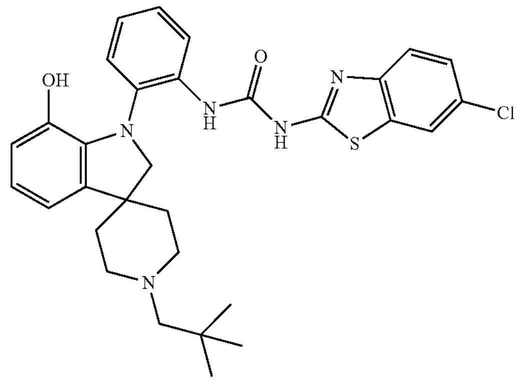 [SMILES: CC(C)(C)CN1CCC2(CC1)CN(c1ccccc1NC(=O)Nc1nc3ccc(Cl)cc3s1)c1c(O)cccc12] | 576.0 | 1.79 | D |
| 76 | 1-(2-(5-Fluoro-7-hydroxy-1'-neopentylspiro[indoline-3,4'-piperidine]-1-yl)phenyl)-3-(4-(trifluoromethoxy)phenyl)urea | 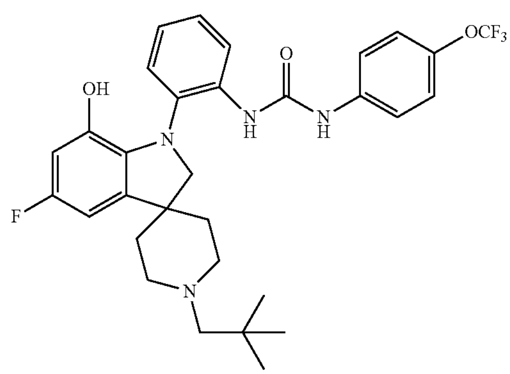 [SMILES: CC(C)(C)CN1CCC2(CC1)CN(c1ccccc1NC(=O)Nc1ccc(OC(F)(F)F)cc1)c1c(O)cc(F)cc12] | 585.4 | 3.65 | C |

Example 77

Methyl 1-(2-(3-(6-fluorobenzo[d]thiazol-2-yl)ureido)phenyl)-7-hydroxy-1'-neopentylspiro[indoline-3,4'-piperidine]-4-carboxylate

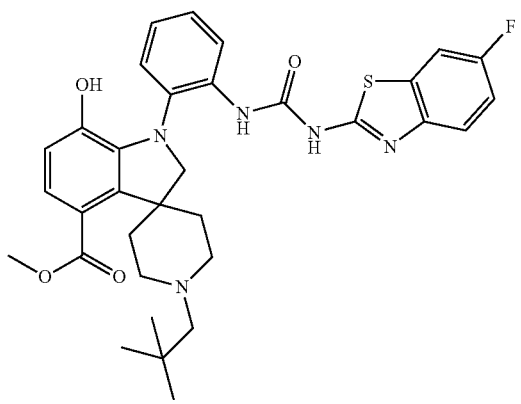 [SMILES: COC(=O)c1ccc(O)c2c1C1(CCN(CC(C)(C)C)CC1)CN2c1ccccc1NC(=O)Nc1nc2ccc(F)cc2s1]

To a solution of 1-(2-(7-hydroxy-1'-neopentyl-4-(trifluoromethyl)spiro[indoline-3,4'-piperidine]-1-yl)phenyl)-3-(4-(trifluoromethoxy)phenyl)urea (Example 3, 10 mg, 0.016 mmol) in MeOH (200 µl) was added sodium hydroxide (200 µL, 0.200 mmol). The reaction mixture was stirred at rt for 16 h. The organic solvent was evaporated under reduced pressure and was purified via preparative HPLC to give Example 77 (8.0 mg, 0.013 mmol, 81% yield). $^1$H NMR (400 MHz, MeOD) δ ppm 1.11, 1.13 (2×s, 9H), 1.68-1.96 (m, 2H), 2.98 (s, 1H), 3.10 (m, 2H), 3.16-3.24 (m, 3H), 3.42 (m, 1H), 3.51-3.59 (m, 2H), 3.88-3.93 (m, 3H), 4.16 (dd, J=10.33, 5.05 Hz, 1H), 6.71 (d, J=8.35 Hz, 1H), 6.99-7.11 (m, 3H), 7.16-7.23 (m, 1H), 7.25-7.36 (m, 1H), 7.47-7.57 (m, 1H), 7.60 (d, J=1.76 Hz, 1H), 8.04-8.15 (m, 1H). LCMS (ESI) m/z 618.6 (M+H)+, RT=1.68 min (Method D).

Examples 78 and 79 were prepared following similar procedure as described in Example 77.

Example 78

Methyl 1-(2-(3-(2,4-difluorophenyl)ureido)phenyl)-7-hydroxy-1'-neopentylspiro[indoline-3,4'-piperidine]-4-carboxylate

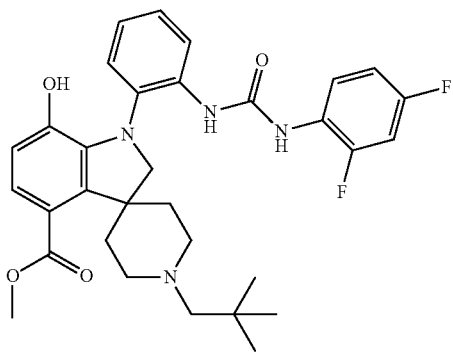 [SMILES: COC(=O)c1ccc(O)c2c1C1(CCN(CC(C)(C)C)CC1)CN2c1ccccc1NC(=O)Nc1ccc(F)cc1F]

LCMS (ESI) m/z 579.6 (M+H)$^+$, RT=1.62 min (Method D).

Example 79

Methyl 7-hydroxy-1'-neopentyl-1-(2-(3-(4-(trifluoromethoxy)phenyl)ureido)phenyl)-spiro[indoline-3,4'-piperidine]-4-carboxylate

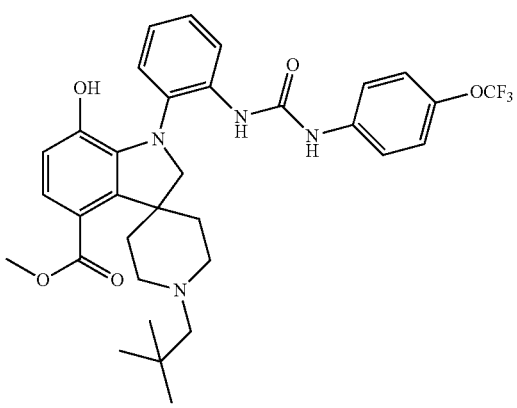 [SMILES: COC(=O)c1ccc(O)c2c1C1(CCN(CC(C)(C)C)CC1)CN2c1ccccc1NC(=O)Nc1ccc(OC(F)(F)F)cc1]

LCMS (ESI) m/z 627.5 (M+H)$^+$, RT=1.79 min (Method D).

Example 80

1-(6-Chlorobenzo[d]thiazol-2-yl)-3-(2-(4-cyano-7-hydroxy-1'-isobutylspiro[indoline-3,4'-piperidine]-1-yl)phenyl)urea

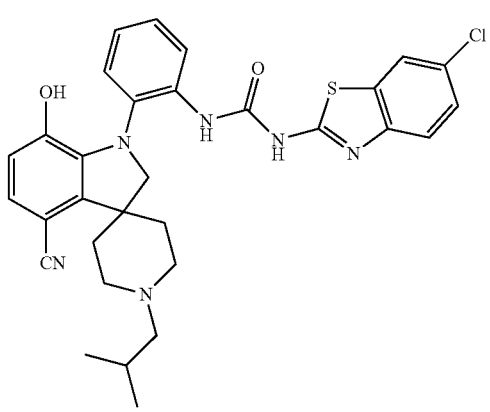 [SMILES: CC(C)CN1CCC2(CC1)CN(c1ccccc1NC(=O)Nc1nc3ccc(Cl)cc3s1)c1c(O)ccc(C#N)c12]

To 1-(6-chlorobenzo[d]thiazol-2-yl)-3-(2-(7-hydroxy-1'-isobutyl-4-(trifluoromethyl)spiro[indoline-3,4'-piperidine]-1-yl)phenyl)urea (Example 30, 6.0 mg, 9.5 μmol) was added sodium hydroxide (95 μL, 0.095 mmol) and ammonium hydroxide (27.5 μL, 0.190 mmol). The reaction mixture was stirred at 40° C. for 18 h. The crude product was purified using a 10 minutes gradient from 0 to 100% B and pump to dryness to give the title compound Example 80 (3.5 mg, 6.0 μmol, 63% yield). $^1$H NMR (400 MHz, MeOD) δ ppm 1.01 (d, J=6.60 Hz, 6H), 2.12 (t, J=14.02 Hz, 3H), 2.54-2.67 (m, 1H), 2.86 (m, 1H), 2.92 (d, J=7.15 Hz, 2H), 3.01 (t, J=12.09 Hz, 1H), 3.08-3.17 (m, 1H), 3.56 (d, J=10.44 Hz, 3H), 4.20 (d, J=10.44 Hz, 1H), 6.75 (d, J=8.24 Hz, 1H), 7.03-7.14 (m, 3H), 7.16-7.26 (m, 2H), 7.30 (m, 1H), 7.59 (dd, J=8.52, 2.47 Hz, 1H), 8.10 (d, J=7.15 Hz, 1H). LCMS (ESI) m/z 587.4 (M+H)$^+$, RT=1.69 min (Method D).

Examples 81 to 88 were prepared following similar procedure as described in Example 81.

| Example | Name | Structure | [M + H]+ | $t_R$ (min) | LC/MS Method |
|---|---|---|---|---|---|
| 81 | 1-(2-(4-Cyano-7-hydroxy-1'-neopentylspiro[indoline-3,4'-piperidine]-l-yl)phenyl)-3-(6-fluorobenzo[d]thiazol-2-yl)urea, trifluoroacetic acid salt | 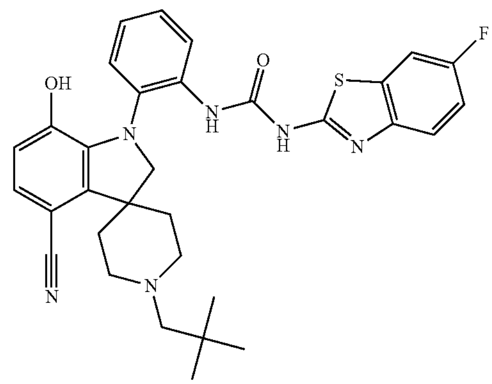 [SMILES: CC(C)(C)CN1CCC2(CC1)CN(c1ccccc1NC(=O)Nc1nc3ccc(F)cc3s1)c1c(O)ccc(C#N)c12] | 585.5 | 1.61 | D |
| 82 | 1-(4-tert-Butylphenyl)-3-(2-(4-cyano-7-hydroxy-1'-neopentylspiro[indoline-3,4'-piperidine]-l-yl)phenyl)urea, trifluoroacetic acid salt | 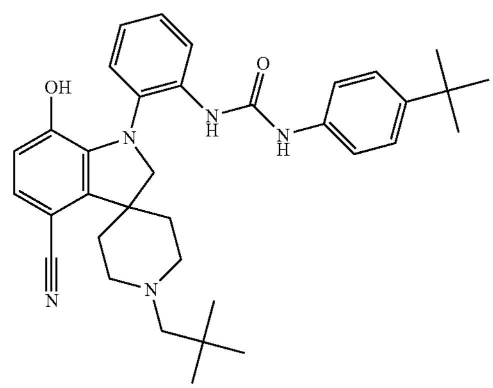 [SMILES: CC(C)(C)CN1CCC2(CC1)CN(c1ccccc1NC(=O)Nc1ccc(C(C)(C)C)cc1)c1c(O)ccc(C#N)c12] | 566.7 | 1.76 | D |
| 83 | 1-(6-Chlorobenzo[d]thiazol-2-yl)-3-(2-(4-cyano-7-hydroxy-1'-neopentylspiro[indoline-3,4'-piperidine]-l-yl)phenyl)urea, trifluoroacetic acid salt | 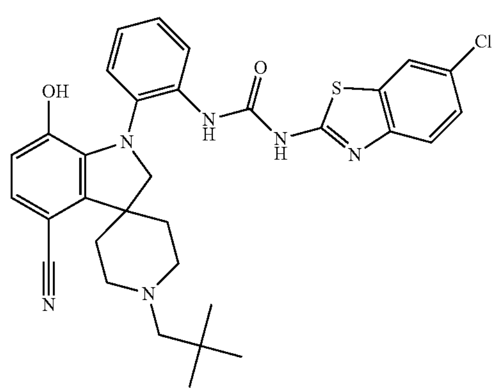 [SMILES: CC(C)(C)CN1CCC2(CC1)CN(c1ccccc1NC(=O)Nc1nc3ccc(Cl)cc3s1)c1c(O)ccc(C#N)c12] | 601.5/603.5 | 1.72 | D |
| 84 | 1-(2-(4-Cyano-7-hydroxy-1'-neopentylspiro[indoline-3,4'-piperidine]-l-yl)phenyl)-3-(6-methylbenzo[d]thiazol-2-yl)urea, trifluoroacetic acid salt | 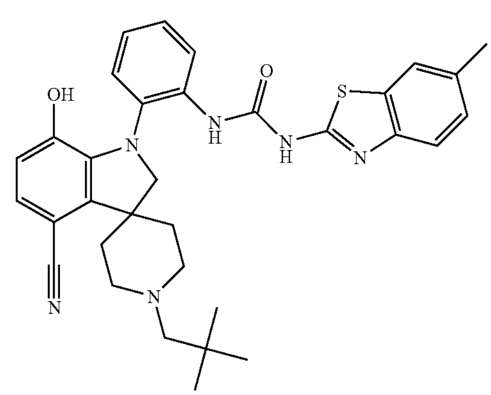 [SMILES: Cc1ccc2nc(NC(=O)Nc3ccccc3N3CC4(CCN(CC(C)(C)C)CC4)c4c(C#N)ccc(O)c43)sc2c1] | 581.6 | 1.64 | D |

-continued

| Example | Name | Structure | [M + H]⁺ | $t_R$ (min) | LC/MS Method |
|---|---|---|---|---|---|
| 85 | 1-(2-Chlorothiazol-4-yl)-3-(2-(4-cyano-7-hydroxy-1'-neopentylspiro[indoline-3,4'-piperidine]-1-yl)phenyl)urea | 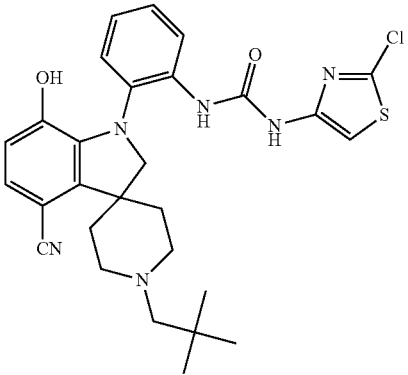 [SMILES: CC(C)(C)CN1CCC2(CC1)CN(c1ccccc1NC(=O)Nc1csc(Cl)n1)c1c(O)ccc(C#N)c12] | 551.1 | 2.50 | C |
| 86 | 1-(2-(4-Cyano-7-hydroxy-1'-neopentylspiro[indoline-3,4'-piperidin]-1-yl)phenyl)-3-(6-methoxybenzo[d]thiazol-2-yl)urea | 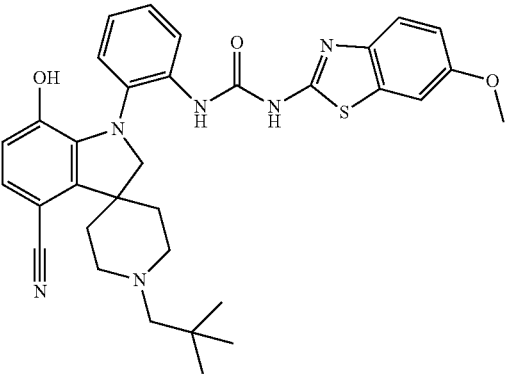 [SMILES: COc1ccc2nc(NC(=O)Nc3ccccc3N3CC4(CCN(CC(C)(C)C)CC4)c4c(C#N)ccc(O)c43)sc2c1] | 597.5 | 1.52 | D |
| 87 | 1-(2-(4-Cyano-7-hydroxy-1'-neopentylspiro[indoline-3,4'-piperidin]-1-yl)phenyl)-3-(5-fluorothiazolo[5,4-b]pyridin-2-yl)urea | 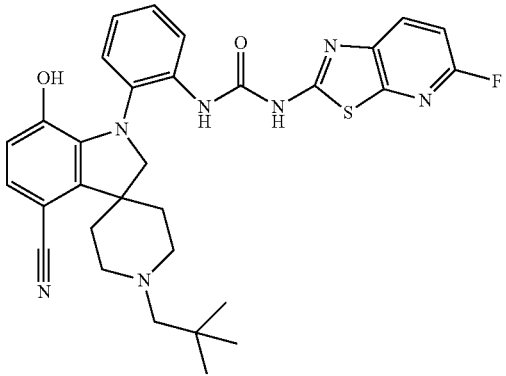 [SMILES: CC(C)(C)CN1CCC2(CC1)CN(c1ccccc1NC(=O)Nc1nc3ccc(F)nc3s1)c1c(O)ccc(C#N)c12] | 586.5 | 1.48 | D |
| 88 | 1-(2-(4-Cyano-7-hydroxy-1'-neopentylspiro[indoline-3,4'-piperidin]-1-yl)phenyl)-3-(3-isopropyl-1,2,4-thiadiazol-5-yl)urea | 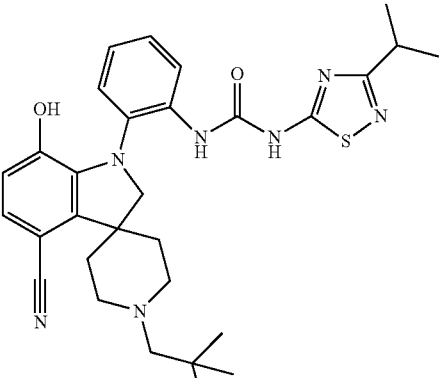 | 560.5 | 1.48 | D |

Example 89

7-Hydroxy-N,N-dimethyl-1'-neopentyl-1-(2-(3-(4-(trifluoromethoxy)phenyl)ureido)phenyl)spiro[indoline-3,4'-piperidine]-4-sulfonamide

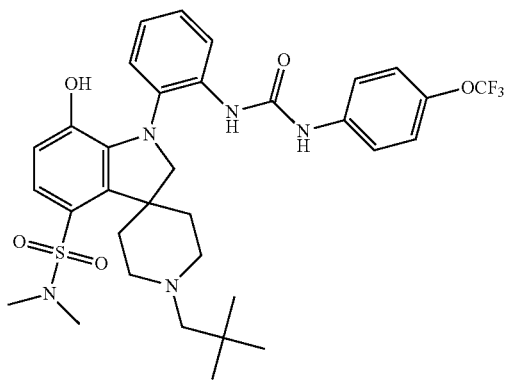 [SMILES: CN(C)S(=O)(=O)c1ccc(O)c2c1C1(CCN(CC(C)(C)C)CC1)CN2c1ccccc1NC(=O)Nc1ccc(OC(F)(F)F)cc1]

The title compound Example 89 was prepared following similar procedures as described in Example 3 by replacing intermediate 10 with Intermediate 21. LCMS (ESI) m/z 676.4 (M+H)$^+$, RT=1.65 min (Method D). $^1$H NMR (400 MHz, MeOD) δ ppm 7.50 (d, J=8.79 Hz, 2H), 7.19 (s, 1H), 7.15 (dt, J=8.35, 4.17 Hz, 3H), 7.09 (d, J=8.35 Hz, 1H), 6.99 (t, J=4.39 Hz, 2H), 6.74-6.78 (m, 1H), 4.10-4.17 (m, 1H), 3.52-3.59 (m, 2H), 3.32-3.49 (m, 2H), 3.03-3.26 (m, 2H), 2.98 (s, 1H), 2.96 (2H, s), 2.92-3.00 (m, 6H), 1.73-2.06 (m, 2H), 1.11 (d, 9H).

Examples 90 to 92 were prepared following similar procedures as described in Example 90.

| Example | Name | Structure | [M + H]$^+$ | $t_R$ (min) | LC/MS Method |
|---|---|---|---|---|---|
| 90 | 1-(2-(3-(4-tert-Butylphenyl)ureido)phenyl)-N,N-diethyl-7-hydroxy-1'-neopentylspiro[indoline-3,4'-piperidine]-4-sulfonamide, trifluoroacetic acid salt | 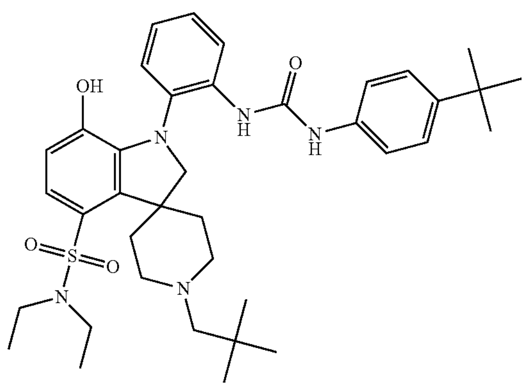 [SMILES: CCN(CC)S(=O)(=O)c1ccc(O)c2c1C1(CCN(CC(C)(C)C)CC1)CN2c1ccccc1NC(=O)Nc1ccc(C(C)(C)C)cc1] | 676.8 | 1.79 | D |
| 91 | N,N-Diethyl-7-hydroxy-1'-neopentyl-1-(2-(3-(4-(trifluoromethoxy)phenyl)ureido)phenyl)spiro[indoline-3,4'-piperidine]-4-sulfonamide trifluoroacetic acid salt | 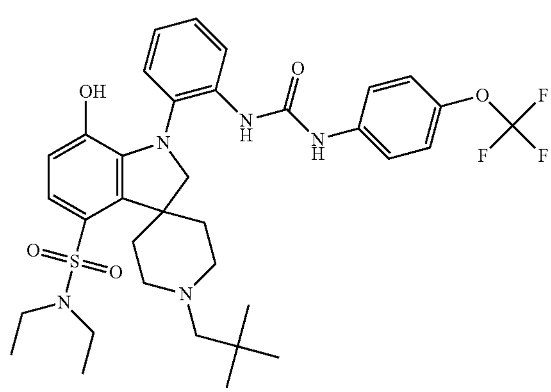 [SMILES: CCN(CC)S(=O)(=O)c1ccc(O)c2c1C1(CCN(CC(C)(C)C)CC1)CN2c1ccccc1NC(=O)Nc1ccc(OC(F)(F)F)cc1] | 704.8 | 1.75 | D |

-continued

| Example | Name | Structure | [M + H]⁺ | t_R (min) | LC/MS Method |
|---|---|---|---|---|---|
| 92 | 1-(2-(3-(6-Chlorobenzo[d]thiazol-2-yl)ureido)phenyl)-N,N-diethyl-7-hydroxy-1'-neopentylspiro[indoline-3,4'-piperidine]-4-sulfonamide | 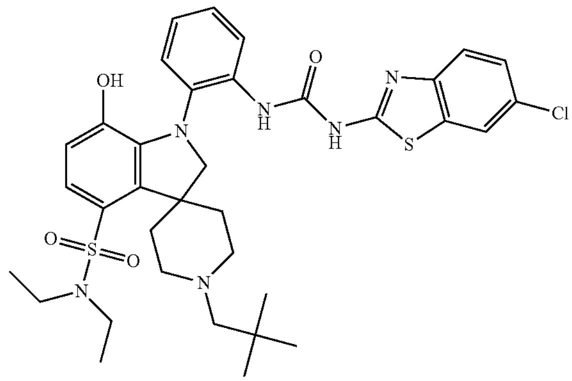 [SMILES: CCN(CC)S(=O)(=O)c1ccc(O)c2c1C1(CCN(CC(C)(C)C)CC1)CN2c1ccccc1NC(=O)Nc1nc2ccc(Cl)cc2s1] | 711.5 | 1.77 | D |

Examples 93 to 108 were prepared following similar procedures described in Examples 1-6 by using appropriate amines.

| Example | Name | Structure | [M + H]⁺ | t_R (min) | LC/MS Method |
|---|---|---|---|---|---|
| 93 | 1-(2-(4-Chloro-5-fluoro-7-hydroxy-1'-neopentylspiro[indoline-3,4'-piperidine]-1-yl)phenyl)-3-(6-fluorobenzo[d]thiazol-2-yl)urea | 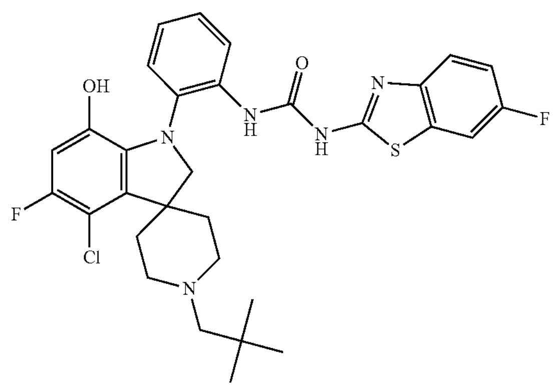 [SMILES: CC(C)(C)CN1CCC2(CC1)CN(c1ccccc1NC(=O)Nc1nc3ccc(F)cc3s1)c1c(O)cc(F)c(Cl)c12] | 612.2/614.2 | 1.69 | D |
| 94 | 1-(2-(4-Chloro-5-fluoro-7-hydroxy-1'-neopentylspiro[indoline-3,4'-piperidine]-1-yl)phenyl)-3-(6-chlorobenzo[d]thiazol-2-yl)urea | 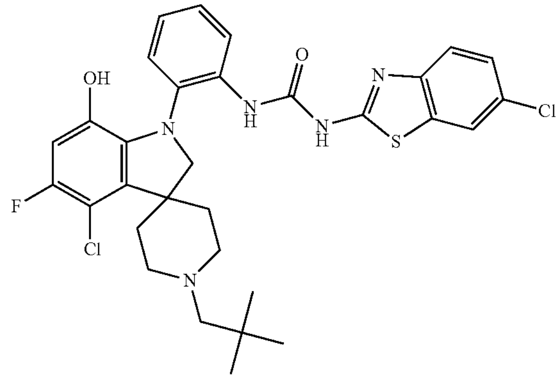 | 629.2 | 10.6 | J |

-continued

| Example | Name | Structure | [M + H]⁺ | $t_R$ (min) | LC/MS Method |
|---|---|---|---|---|---|
| 95 | 1-(2-(4,5-Difluoro-7-hydroxy-1'-neopentylspiro[indoline-3,4'-piperidine]-1-yl)phenyl)-3-(6-fluorobenzo[d]thiazol-2-yl)urea | 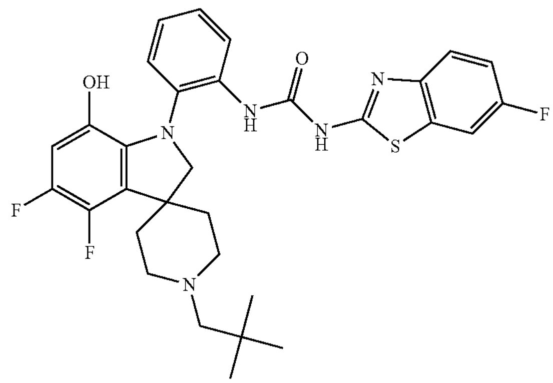 [SMILES: CC(C)(C)CN1CCC2(CC1)CN(c1ccccc1NC(=O)Nc1nc3ccc(F)cc3s1)c1c(O)cc(F)c(F)c12] | 596.1 | 9.94 | J |
| 96 | 1-(6-Chlorobenzo[d]thiazol-2-yl)-3-(2-(4,5-difluoro-7-hydroxy-1'-neopentylspiro[indoline-3,4'-piperidine]-1-yl)phenyl)urea | 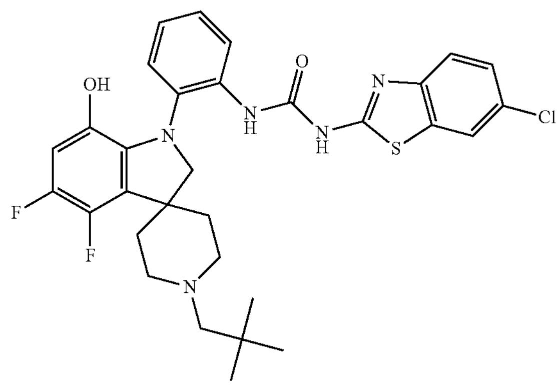 [SMILES: CC(C)(C)CN1CCC2(CC1)CN(c1ccccc1NC(=O)Nc1nc3ccc(Cl)cc3s1)c1c(O)cc(F)c(F)c12] | 612.0 | 3.24 | C |
| 97 | 1-(2-(4-Chloro-5-fluoro-7-hydroxy-1'-neopentylspiro[indoline-3,4'-piperidine]-1-yl)phenyl)-3-(6-methylbenzo[d]thiazol-2-yl)urea | 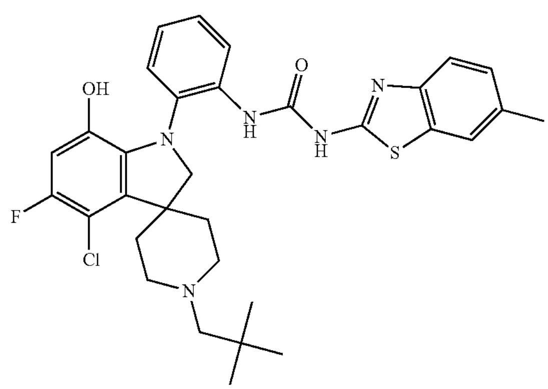 [SMILES: Cc1ccc2nc(NC(=O)Nc3ccccc3N3CC4(CCN(CC(C)(C)C)CC4)c4c(Cl)c(F)cc(O)c43)sc2c1] | 608.2 | 10.2 | J |
| 98 | 1-(2-(4-Chloro-6-fluoro-7-hydroxy-1'-neopentylspiro[indoline-3,4'-piperidine]-1-yl)phenyl)-3-(6-chlorobenzo[d]thiazol-2-yl)urea | 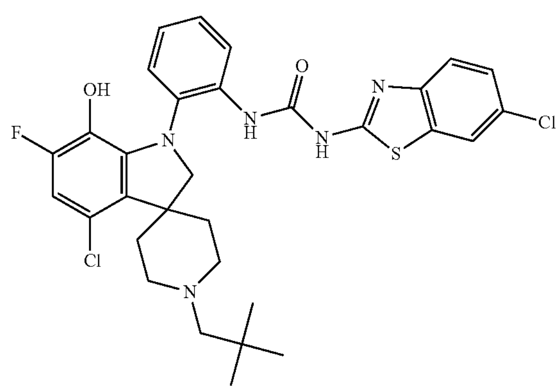 [SMILES: CC(C)(C)CN1CCC2(CC1)CN(c1ccccc1NC(=O)Nc1nc3ccc(Cl)cc3s1)c1c(O)c(F)cc(Cl)c12] | 628.1/630.2 | 14.4 | C |

-continued

| Example | Name | Structure | [M + H]+ | t_R (min) | LC/MS Method |
|---|---|---|---|---|---|
| 99 | 1-(2-(4,6-Difluoro-7-hydroxy-1'-neopentylspiro[indoline-3,4'-piperidine]-1-yl)phenyl)-3-(4-(1-isobutylpyrrolidin-2-yl)phenyl)urea | 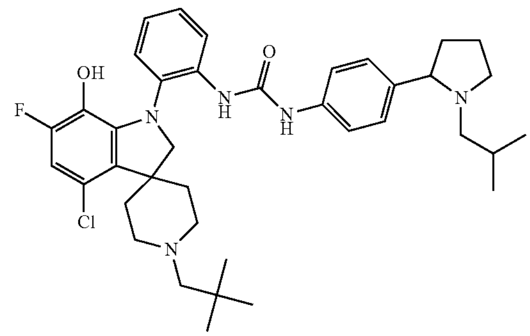 [SMILES: CC(C)CN1CCCC1c1ccc(NC(=O)Nc2ccccc2N2CC3(CCN(CC(C)(C)C)CC3)c3c(Cl)cc(F)c(O)c32)cc1] | 646.4 | 1.33 | D |
| 100 | 1-(2-(4-Chloro-6-fluoro-7-hydroxy-1'-neopentylspiro[indoline-3,4'-piperidine]-1-yl)phenyl)-3-(6-fluorobenzo[d]thiazol-2-yl)urea | 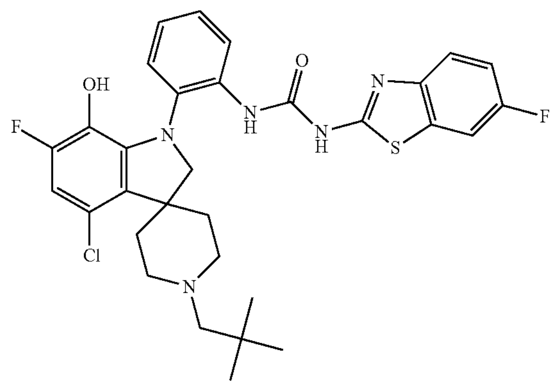 [SMILES: CC(C)(C)CN1CCC2(CC1)CN(c1ccccc1NC(=O)Nc1nc3ccc(F)cc3s1)c1c(O)c(F)cc(Cl)c12] | 612.0/614.0 | 8.19<br>9.94 | A<br>B |
| 101 | 1-(2-(4-Chloro-5-fluoro-7-hydroxy-1'-neopentylspiro[indoline-3,4'-piperidin]-1-yl)phenyl)-3-(5-chlorothiazolo[5,4-b]pyridin-2-yl)urea | 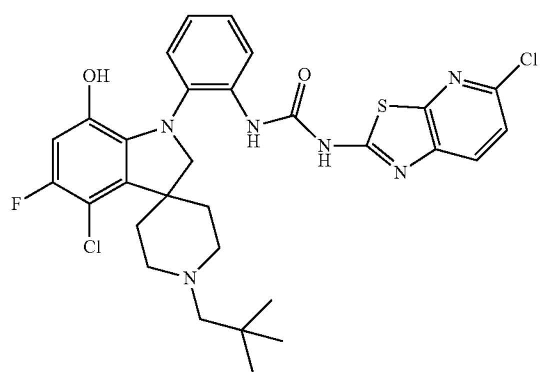 [SMILES: CC(C)(C)CN1CCC2(CC1)CN(c1ccccc1NC(=O)Nc1nc3ccc(Cl)nc3s1)c1c(O)cc(F)c(Cl)c12] | 629.3 | 1.62 | D |
| 102 | 1-(2-(4-Chloro-5-fluoro-7-hydroxy-1'-neopentylspiro[indoline-3,4'-piperidin]-1-yl)phenyl)-3-(5-fluorothiazolo[5,4-b]pyridin-2-yl)urea | 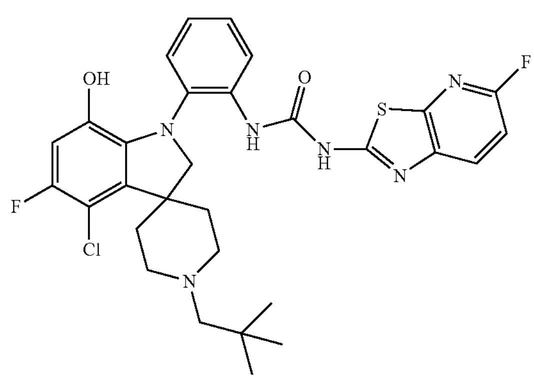 [SMILES: CC(C)(C)CN1CCC2(CC1)CN(c1ccccc1NC(=O)Nc1nc3ccc(F)nc3s1)c1c(O)cc(F)c(Cl)c12] | 613.3 | 2.93 | C |

| Example | Name | Structure | [M + H]⁺ | $t_R$ (min) | LC/MS Method |
|---|---|---|---|---|---|
| 103 | 1-(2-(4-Chloro-5-fluoro-7-hydroxy-1'-neopentylspiro[indoline-3,4'-piperidin]-1-yl)phenyl)-3-(2-chlorothiazol-4-yl)urea | 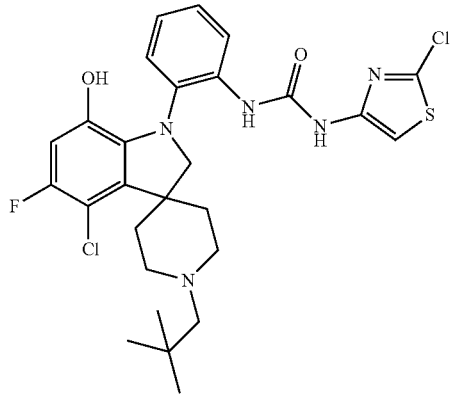 [SMILES: CC(C)(C)CN1CCC2(CC1)CN(c1ccccc1NC(=O)Nc1csc(Cl)n1)c1c(O)cc(F)c(Cl)c12] | 579.0 | 2.80 | C |
| 104 | 1-(2-(4,5-Difluoro-7-hydroxy-1'-neopentylspiro[indoline-3,4'-piperidine]-1-yl)phenyl)-3-(4-(1-isobutylpyrrolidin-2-yl)phenyl)urea | 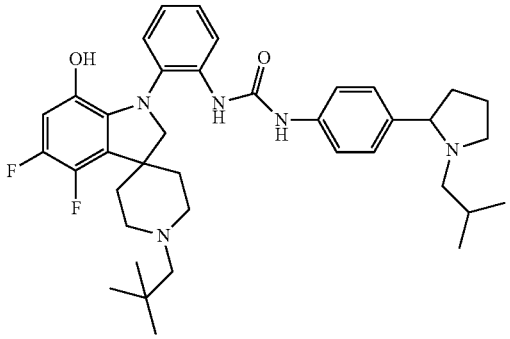 [SMILES: CC(C)CN1CCCC1c1ccc(NC(=O)Nc2ccccc2N2CC3(CCN(CC(C)(C)C)CC3)c3c(F)c(F)cc(O)c32)cc1] | 646.4 | 1.35 | K |
| 105 | 1-(2-(4-Chloro-5-fluoro-7-hydroxy-1'-neopentylspiro[indoline-3,4'-piperidine]-1-yl)phenyl)-3-(4-(1-isobutylpiperidin-4-yl)phenyl)urea | 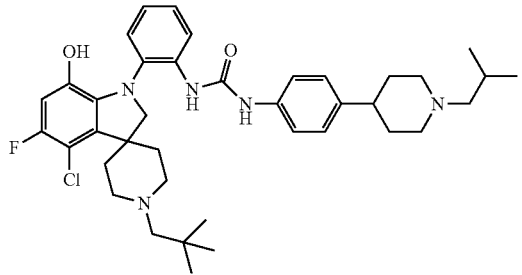 [SMILES: CC(C)CN1CCC(c2ccc(NC(=O)Nc3ccccc3N3CC4(CCN(CC(C)(C)C)CC4)c4c(Cl)c(F)cc(O)c43)cc2)CC1] | 676.4 | 1.42 | K |
| 106 | 1-(2-(7-Hydroxy-1'-isobutyl-4-(trifluoromethyl)spiro[indoline-3,4'-piperidine]-1-yl)phenyl)-3-(4-(trifluoromethoxy)phenyl)urea | 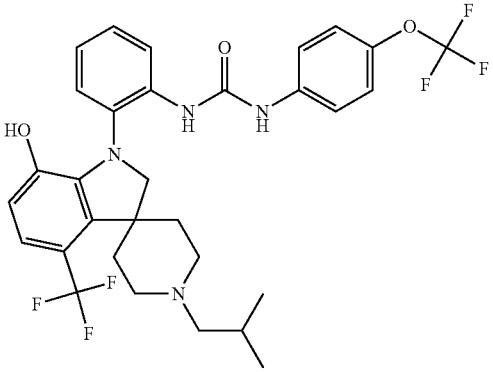 [SMILES: CC(C)CN1CCC2(CC1)CN(c1ccccc1NC(=O)Nc1ccc(OC(F)(F)F)cc1)c1c(O)ccc(C(F)(F)F)c12] | 623.0 | 1.69 | D |

-continued

| Example | Name | Structure | [M + H]⁺ | $t_R$ (min) | LC/MS Method |
|---|---|---|---|---|---|
| 107 | 1-(2-(7-Hydroxy-1'-isopropyl-4-(trifluoromethyl)spiro[indoline-3,4'-piperidine]-1-yl)phenyl)-3-(4-(trifluoromethoxy)phenyl)urea | 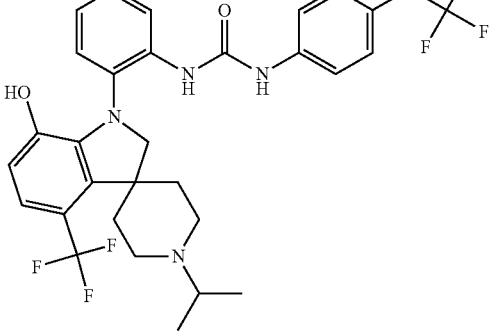 | 609.0 | 1.64 | D |
| 108 | 1-(2-(7-Hydroxy-1'-neopentyl-4-(trifluoromethyl)spiro[indoline-3,4'-piperidin]-1-yl)phenyl)-3-(6-methoxybenzo[d]thiazol-2-yl)urea | 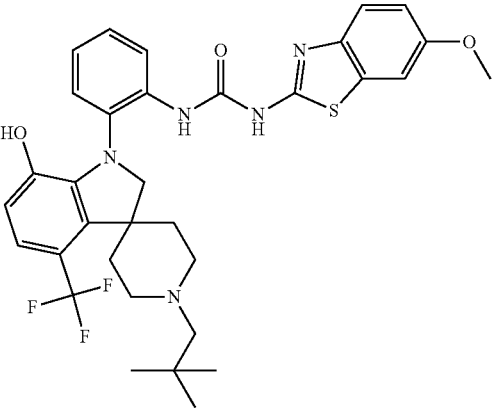 [SMILES: COc1ccc2nc(NC(=O)Nc3ccccc3N3CC4(CCN(CC(C)(C)C)CC4)c4c(C(F)(F)F)ccc(O)c43)sc2c1] | 640.3 | 2.98 | C |

Example 109

1-(5-Chlorothiazolo[5,4-b]pyridin-2-yl)-3-(2-(7-hydroxy-1'-neopentyl-4-(5-(trifluoromethyl)benzo[d]thiazol-2-yl)spiro[indoline-3,4'-piperidin]-1-yl)phenyl)urea

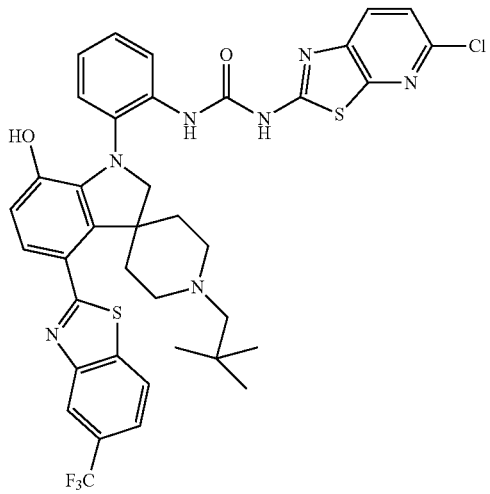 [SMILES: CC(C)(C)CN1CCC2(CC1)CN(c1ccccc1NC(=O)Nc1nc3ccc(Cl)nc3s1)c1c(O)ccc(-c3nc4cc(C(F)(F)F)ccc4s3)c12]

To a solution of 1-(5-chlorothiazolo[5,4-b]pyridin-2-yl)-3-(2-(7-hydroxy-1'-neopentyl-4-(trifluoromethyl)spiro[indoline-3,4'-piperidine]-1-yl)phenyl)urea (50 mg, 0.078 mmol) and 2-amino-4-(trifluoromethyl)benzenethiol (44.9 mg, 0.233 mmol) was added 1N sodium hydroxide (1550 µL, 1.550 mmol), and was stirred at 50° C. for 3 days. The reaction mixture was adjusted to neutral by addition of 1N HCl. EtOAc was added, and the organic layer was separated, concentrated, and purified on Prep HPLC using a 10 minutes gradient from 0 to 100% B (Column: PHENOMENEX® Axia Luna 100×20 mm 5u (10 min gradient). Solvent A: 10% ACN-90% H₂O-0.1% TFA; Solvent B: 90% ACN-10% H₂O-0.1% TFA) to give Example 109 (11 mg, 0.011 mmol, 14% yield). LC-MS ESI m/z 613 [M+H]⁺, RT=3.13 min (Method C). ¹H NMR (400 MHz, MeOD) δ 8.15-8.02 (m, 1H), 7.70 (d, J=7.1 Hz, 1H), 7.40 (d, J=8.6 Hz, 1H), 7.27-7.17 (m, 2H), 7.15-7.05 (m, 2H), 6.84-6.72 (m, 1H), 4.21-4.12 (m, 1H), 3.60 (d, J=10.6 Hz, 3H), 3.26 (d, J=17.4 Hz, 2H), 3.01 (s, 2H), 2.87-2.76 (m, 1H), 2.64-2.55 (m, 1H), 2.12 (d, J=15.4 Hz, 1H), 2.02 (d, J=16.4 Hz, 1H), 1.17-1.10 (m, 9H).

Examples 110 to 151 were prepared according the procedure described in Example 110 by using the appropriately substituted 2-amino-benzenethiols.

| Example | Name | Structure | [M + H]+ | $t_R$ (min) | LC/MS Method |
|---|---|---|---|---|---|
| 110 | 1-(2-(4-(5-Chlorobenzo[d]thiazol-2-yl)-7-hydroxy-1'-neopentylspiro[indoline-3,4'-piperidin]-1-yl)phenyl)-3-(5-chlorothiazolo[5,4-b]pyridin-2-yl)urea | 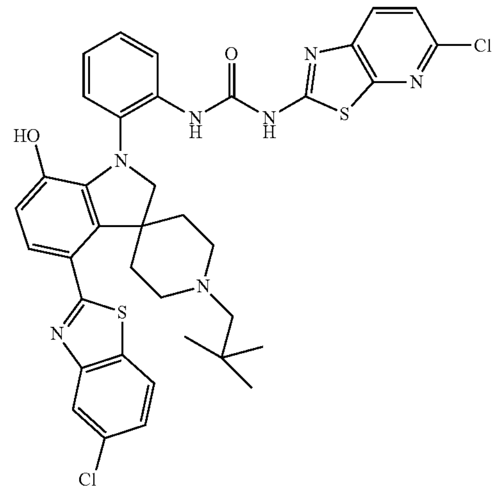 [SMILES: CC(C)(C)CN1CCC2(CC1)CN(c1ccccc1NC(=O)Nc1nc3ccc(Cl)nc3s1)c1c(O)ccc(-c3nc4cc(Cl)ccc4s3)c12] | 745.0 | 3.52 | C |
| 111 | 1-(2-(4-(5-Chlorobenzo[d]thiazol-2-yl)-7-hydroxy-1'-neopentylspiro[indoline-3,4'-piperidine]-1-yl)phenyl)-3-(2-chlorothiazol-4-yl)urea | 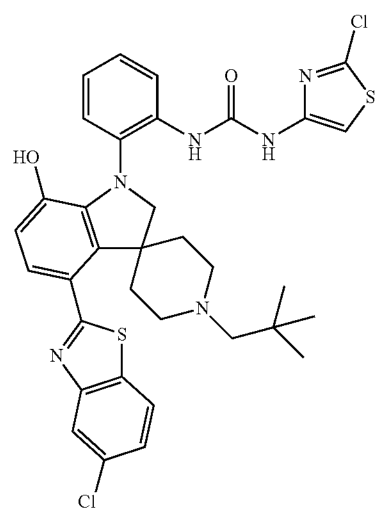 [SMILES: CC(C)(C)CN1CCC2(CC1)CN(c1ccccc1NC(=O)Nc1csc(Cl)n1)c1c(O)ccc(-c3nc4cc(Cl)ccc4s3)c12] | 694.0 | 3.45 | C |
| 112 | 1-(2-Chlorothiazol-4-yl)-3-(2-(4-(5-fluorobenzo[d]thiazol-2-yl)-7-hydroxy-1'-neopentylspiro[indoline-3,4'-piperidin]-1-yl)phenyl)urea | 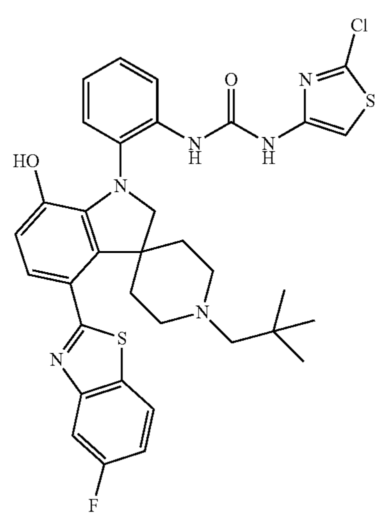 | 677.0 | 3.29 | D |

| Example | Name | Structure | [M + H]+ | t_R (min) | LC/MS Method |
|---|---|---|---|---|---|
| 113 | 1-(2-(4-(6-Chlorobenzo[d]thiazol-2-yl)-7-hydroxy-1'-neopentylspiro[indoline-3,4'-piperidin]-1-yl)phenyl)-3-(2-chlorothiazol-4-yl)urea | 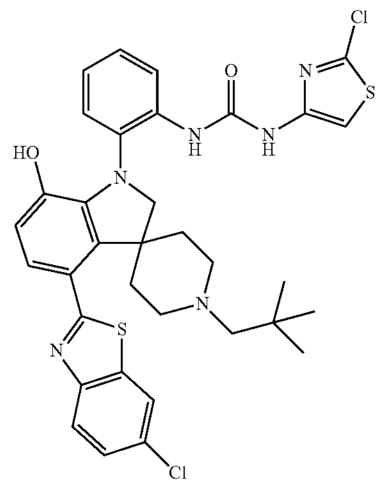 [SMILES: CC(C)(C)CN1CCC2(CC1)CN(c1ccccc1NC(=O)Nc1csc(Cl)n1)c1c(O)ccc(-c3nc4ccc(Cl)cc4s3)c12] | 692.9 | 2.47 | C |
| 114 | 1-(2-Chlorothiazol-4-yl)-3-(2-(4-(6-fluorobenzo[d]thiazol-2-yl)-7-hydroxy-1'-neopentylspiro[indoline-3,4'-piperidin]-1-yl)phenyl)urea | 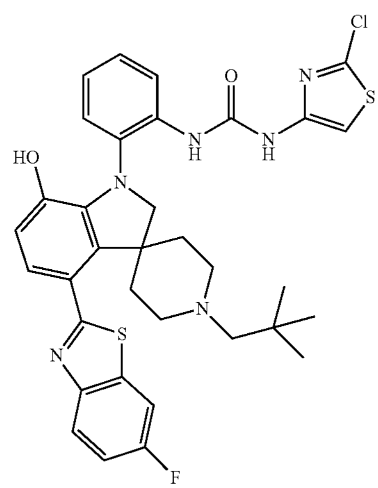 [SMILES: CC(C)(C)CN1CCC2(CC1)CN(c1ccccc1NC(=O)Nc1csc(Cl)n1)c1c(O)ccc(-c3nc4ccc(F)cc4s3)c12] | 677.0 | 1.74 | D |
| 115 | 1-(2-(4-(4-Chlorobenzo[d]thiazol-2-yl)-7-hydroxy-1'-neopentylspiro[indoline-3,4'-piperidin]-1-yl)phenyl)-3-(4-(trifluoromethoxy)phenyl)urea | 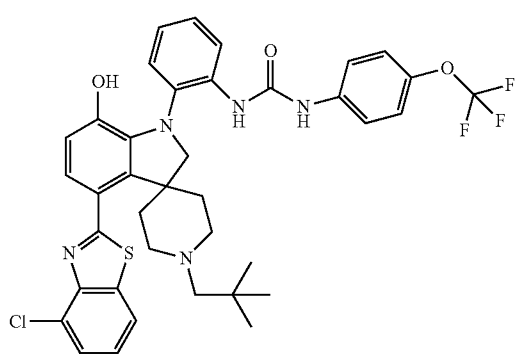 [SMILES: CC(C)(C)CN1CCC2(CC1)CN(c1ccccc1NC(=O)Nc1ccc(OC(F)(F)F)cc1)c1c(O)ccc(-c3nc4c(Cl)cccc4s3)c12] | 736.0 | 1.88 | D |

| Example | Name | Structure | [M + H]+ | tR (min) | LC/MS Method |
|---|---|---|---|---|---|
| 116 | 1-(2-(4-(4-Chlorobenzo[d]thiazol-2-yl)-7-hydroxy-1'-neopentylspiro[indoline-3,4'-piperidin]-1-yl)phenyl)-3-(6-fluorobenzo[b]thiazol-2-yl)urea | 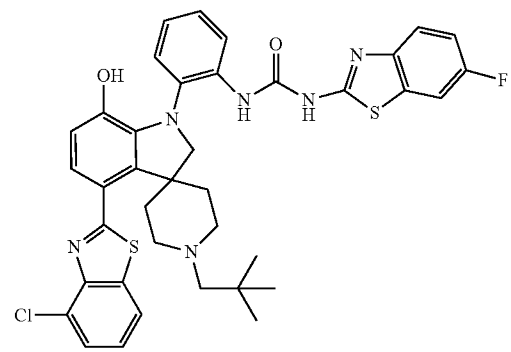 [SMILES: CC(C)(C)CN1CCC2(CC1)CN(c1ccccc1NC(=O)Nc1nc3ccc(F)cc3s1)c1c(O)ccc(-c3nc4c(Cl)cccc4s3)c12] | 726.9 | 1.83 | D |
| 117 | 1-(2-(4-(4-Chlorobenzo[d]thiazol-2-yl)-7-hydroxy-1'-neopentylspiro[indoline-3,4'-piperidin]-1-yl)phenyl)-3-(5-chlorothiazolo[5,4-b]pyridin-2-yl)urea | 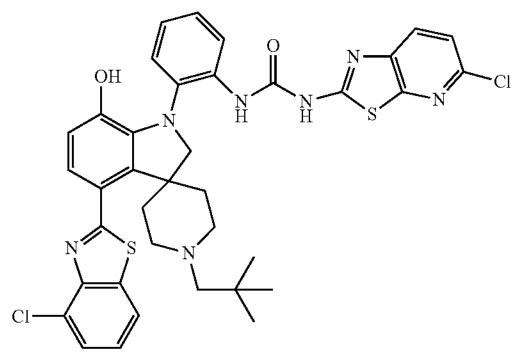 [SMILES: CC(C)(C)CN1CCC2(CC1)CN(c1ccccc1NC(=O)Nc1nc3ccc(Cl)nc3s1)c1c(O)ccc(-c3nc4c(Cl)cccc4s3)c12] | 743.9 | 1.82 | D |
| 118 | 1-(2-(4-(4-Chlorobenzo[d]thiazol-2-yl)-7-hydroxy-1'-neopentylspiro[indoline-3,4'-piperidin]-1-yl)phenyl)-3-(2-chlorothiazol-4-yl)urea | 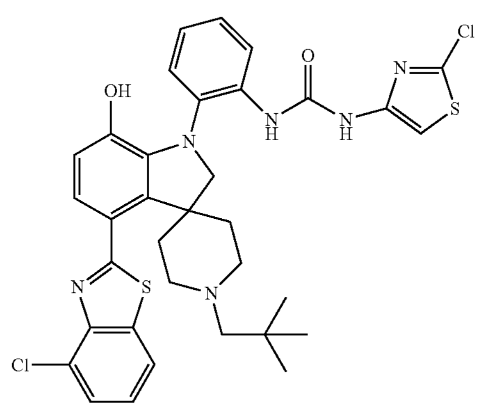 [SMILES: CC(C)(C)CN1CCC2(CC1)CN(c1ccccc1NC(=O)Nc1csc(Cl)n1)c1c(O)ccc(-c3nc4c(Cl)cccc4s3)c12] | 692.9 | 3.30 | C |
| 119 | 1-(2-(4-(6-Bromobenzo[d]thiazol-2-yl)-7-hydroxy-1'-neopentylspiro[indoline-3,4'-piperidin]-1-yl)phenyl)-3-(2-chlorothiazol-4-yl)urea | 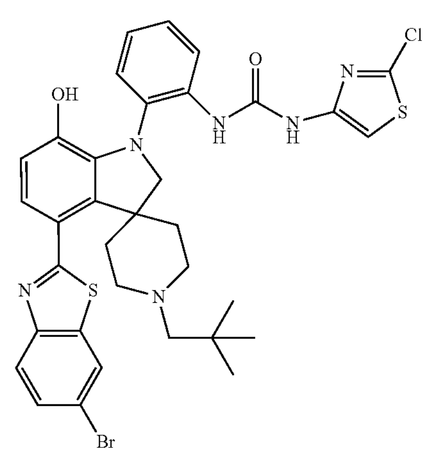 [SMILES: CC(C)(C)CN1CCC2(CC1)CN(c1ccccc1NC(=O)Nc1csc(Cl)n1)c1c(O)ccc(-c3nc4ccc(Br)cc4s3)c12] | 736.9 | 1.84 | D |

-continued

| Example | Name | Structure | [M + H]⁺ | $t_R$ (min) | LC/MS Method |
|---|---|---|---|---|---|
| 120 | 1-(2-(4-(5-Chlorobenzo[d]thiazol-2-yl)-7-hydroxy-1'-neopentylspiro[indoline-3,4'-piperidin]-1-yl)phenyl)-3-(2-(trifluoromethyl)thiazol-4-yl)urea | 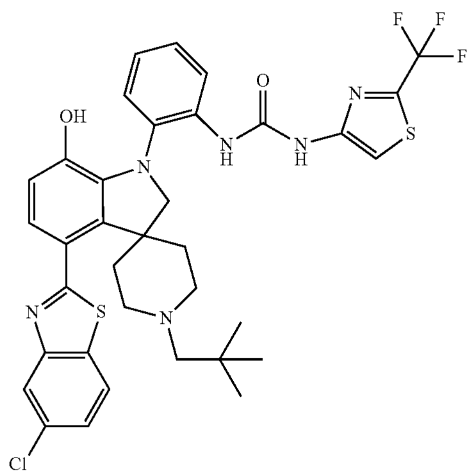 [SMILES: CC(C)(C)CN1CCC2(CC1)CN(c1ccccc1NC(=O)Nc1csc(C(F)(F)F)n1)c1c(O)ccc(-c3nc4cc(Cl)ccc4s3)c12] | 727.0 | 1.86 | D |
| 121 | 1-(2-(4-(6-Bromobenzo[d]thiazol-2-yl)-7-hydroxy-1'-neopentylspiro[indoline-3,4'-piperidin]-1-yl)phenyl)-3-(4-(trifluoromethoxy)phenyl)urea | 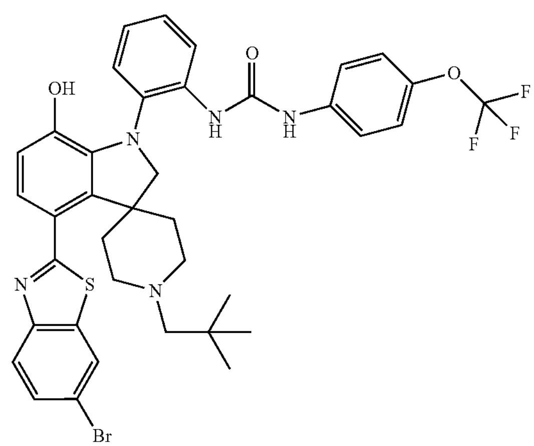 [SMILES: CC(C)(C)CN1CCC2(CC1)CN(c1ccccc1NC(=O)Nc1ccc(OC(F)(F)F)cc1)c1c(O)ccc(-c3nc4ccc(Br)cc4s3)c12] | 780.3 | 3.63 | C |
| 122 | 1-(2-(4-(7-Chlorobenzo[d]thiazol-2-yl)-7-hydroxy-1'-neopentylspiro[indoline-3,4'-piperidin]-1-yl)phenyl)-3-(2-chlorothiazol-4-yl)urea | 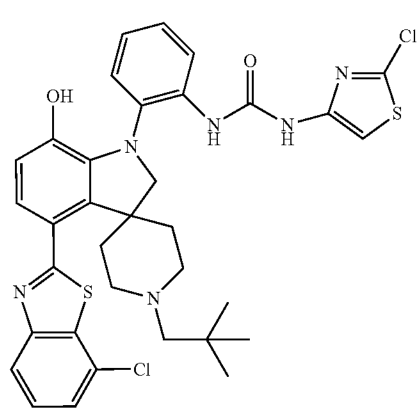 [SMILES: CC(C)(C)CN1CCC2(CC1)CN(c1ccccc1NC(=O)Nc1csc(Cl)n1)c1c(O)ccc(-c3nc4cccc(Cl)c4s3)c12] | 691.2 | 1.00 | L |

| Example | Name | Structure | [M + H]⁺ | $t_R$ (min) | LC/MS Method |
|---|---|---|---|---|---|
| 123 | 1-(2-(4-(7-Chlorobenzo[d]thiazol-2-yl)-7-hydroxy-1'-neopentylspiro[indoline-3,4'-piperidin]-1-yl)phenyl)-3-(4-(trifluoromethoxy)phenyl)urea | 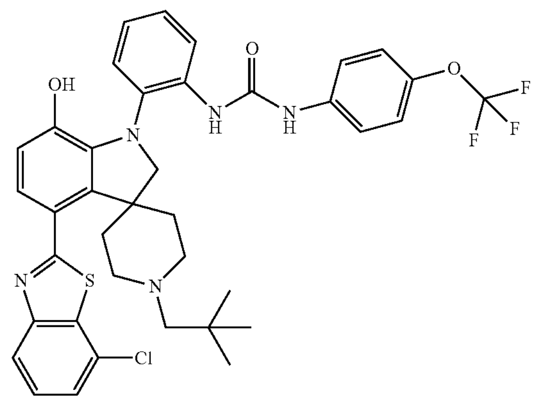 [SMILES: CC(C)(C)CN1CCC2(CC1)CN(c1ccccc1NC(=O)Nc1ccc(OC(F)(F)F)cc1)c1c(O)ccc(-c3nc4cccc(Cl)c4s3)c12] | 736.2 | 1.05 | L |
| 124 | 1-(6-Chlorobenzo[d]thiazol-2-yl)-3-(2-(4-(7-chlorobenzo[d]thiazol-2-yl)-7-hydroxy-1'-neopentylspiro[indoline-3,4'-piperidin]-1-yl)phenyl)urea | 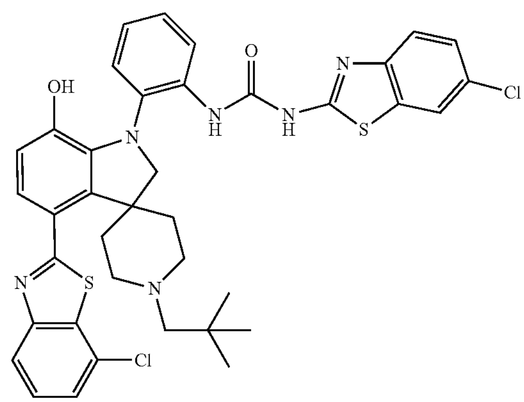 [SMILES: CC(C)(C)CN1CCC2(CC1)CN(c1ccccc1NC(=O)Nc1nc3ccc(Cl)cc3s1)c1c(O)ccc(-c3nc4cccc(Cl)c4s3)c12] | 743.2 | 1.05 | L |
| 125 | 1-(2-(4-(6-Chlorobenzo[d]thiazol-2-yl)-7-hydroxy-1'-neopentylspiro[indoline-3,4'-piperidin]-1-yl)phenyl)-3-(5-chlorothiazolo[5,4-b]pyridin-2-yl)urea | 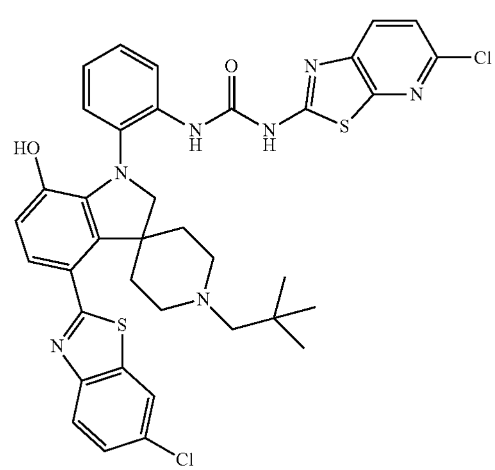 [SMILES: CC(C)(C)CN1CCC2(CC1)CN(c1ccccc1NC(=O)Nc1nc3ccc(Cl)nc3s1)c1c(O)ccc(-c3nc4ccc(Cl)cc4s3)c12] | 743.9 | 1.90 | D |

| Example | Name | Structure | [M + H]⁺ | $t_R$ (min) | LC/MS Method |
|---|---|---|---|---|---|
| 126 | 1-(5-Chlorothiazolo[5,4-b]pyridin-2-yl)-3-(2-(4-(5-fluorobenzo[d]thiazol-2-yl)-7-hydroxy-1'-neopentylspiro[indoline-3,4'-piperidin]-1-yl)phenyl)urea | 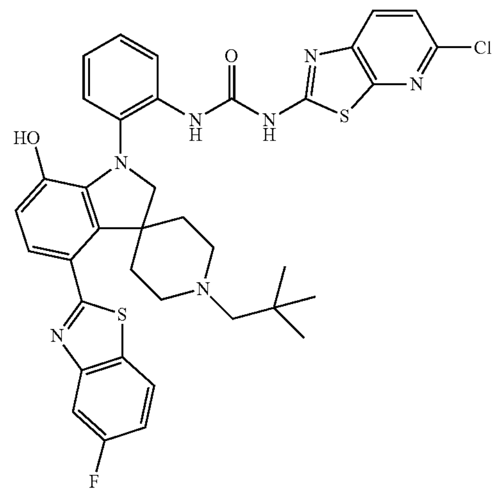 [SMILES: CC(C)(C)CN1CCC2(CC1)CN(c1ccccc1NC(=O)Nc1nc3ccc(Cl)nc3s1)c1c(O)ccc(-c3nc4cc(F)ccc4s3)c12] | 727.9 | 1.83 | D |
| 127 | 1-(6-Chlorobenzo[d]thiazol-2-yl)-3-(2-(4-(5-fluorobenzo[d]thiazol-2-yl)-7-hydroxy-1'-neopentylspiro[indoline-3,4'-piperidin]-1-yl)phenyl)urea | 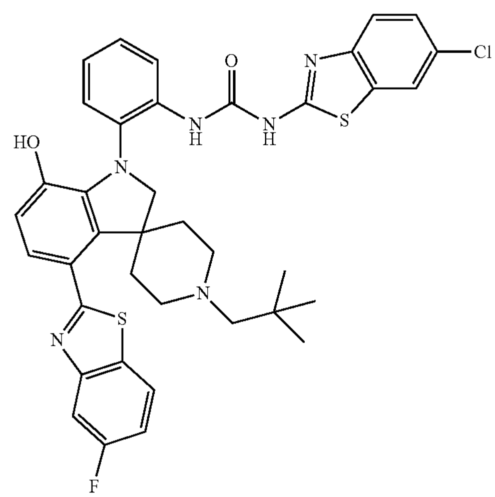 [SMILES: CC(C)(C)CN1CCC2(CC1)CN(c1ccccc1NC(=O)Nc1nc3ccc(Cl)cc3s1)c1c(O)ccc(-c3nc4cc(F)ccc4s3)c12] | 727.3 | 3.47 | C |
| 128 | 1-(2-Chlorothiazol-4-yl)-3-(2-(7-hydroxy-4-(6-methoxybenzo[d]thiazol-2-yl)-1'-neopentylspiro[indoline-3,4'-piperidin]-1-yl)phenyl)urea | 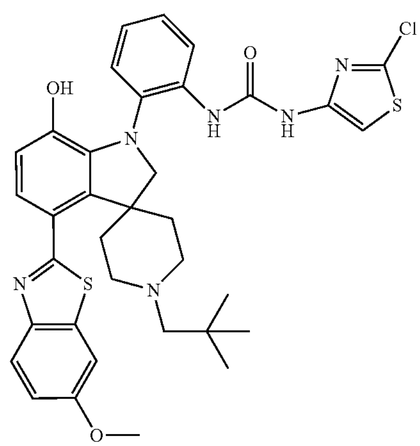 [SMILES: COc1ccc2nc(-c3ccc(O)c4c3C3(CCN(CC(C)(C)C)CC3)CN4c3ccccc3NC(=O)Nc3csc(Cl)n3)sc2c1] | 688.9 | 1.68 | D |

| Example | Name | Structure | [M + H]+ | t_R (min) | LC/MS Method |
|---|---|---|---|---|---|
| 129 | 1-(2-(7-Hydroxy-4-(6-methoxybenzo[d]thiazol-2-yl)-1'-neopentylspiro[indoline-3,4'-piperidin]-1-yl)phenyl)-3-(2-(trifluoromethyl)thiazol-4-yl)urea | 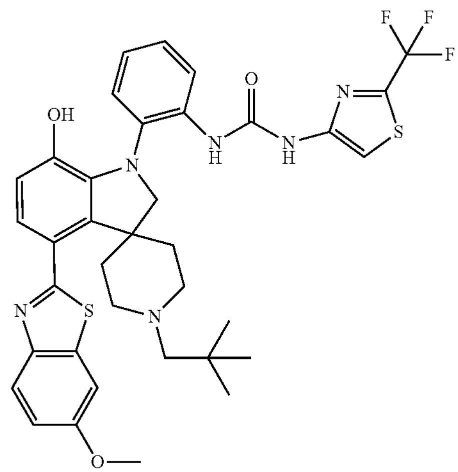 [SMILES: COc1ccc2nc(-c3ccc(O)c4c3C3(CCN(CC(C)(C)C)CC3)CN4c3ccccc3NC(=O)Nc3csc(C(F)(F)F)n3)sc2c1] | 723.3 | 0.98 | L |
| 130 | 1-(2-(7-Hydroxy-4-(6-methoxybenzo[d]thiazol-2-yl)-1'-neopentylspiro[indoline-3,4'-piperidin]-1-yl)phenyl)-3-(4-(trifluoromethoxy)phenyl)urea | 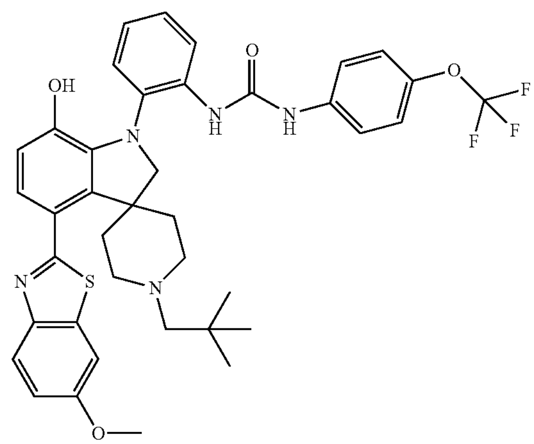 [SMILES: COc1ccc2nc(-c3ccc(O)c4c3C3(CCN(CC(C)(C)C)CC3)CN4c3ccccc3NC(=O)Nc3ccc(OC(F)(F)F)cc3)sc2c1] | 732.4 | 1.00 | L |
| 131 | 1-(6-Chlorobenzo[d]thiazol-2-yl)-3-(2-(7-hydroxy-4-(6-methoxybenzo[d]thiazol-2-yl)-1'-neopentylspiro[indoline-3,4'-piperidin]-1-yl)phenyl)urea | 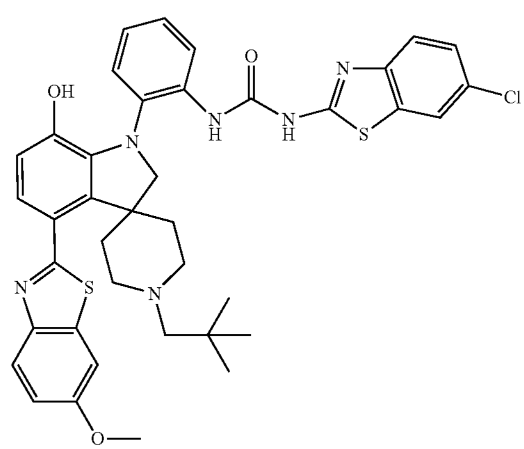 [SMILES: COc1ccc2nc(-c3ccc(O)c4c3C3(CCN(CC(C)(C)C)CC3)CN4c3ccccc3NC(=O)Nc3nc4ccc(Cl)cc4s3)sc2c1] | 739.3 | 1.00 | L |

-continued

| Example | Name | Structure | [M + H]⁺ | $t_R$ (min) | LC/MS Method |
|---|---|---|---|---|---|
| 132 | 1-(2-(4-(6-Fluorobenzo[d]thiazol-2-yl)-7-hydroxy-1'-neopentylspiro[indoline-3,4'-piperidin]-1-yl)phenyl)-3-(2-(trifluoromethyl)thiazol-4-yl)urea | 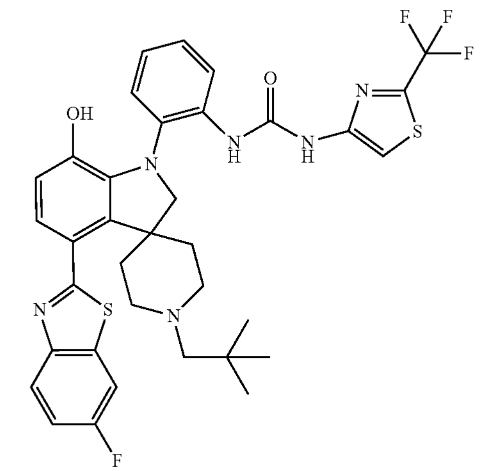 [SMILES: CC(C)(C)CN1CCC2(CC1)CN(c1ccccc1NC(=O)Nc1csc(C(F)(F)F)n1)c1c(O)ccc(-c3nc4ccc(F)cc4s3)c12] | 710.9 | 1.53 | D |
| 133 | 1-(2-(4-(5-Chlorobenzo[d]thiazol-2-yl)-7-hydroxy-1'-neopentylspiro[indoline-3,4'-piperidin]-1-yl)phenyl)-3-(6-fluorobenzo[d]thiazol-2-yl)urea | 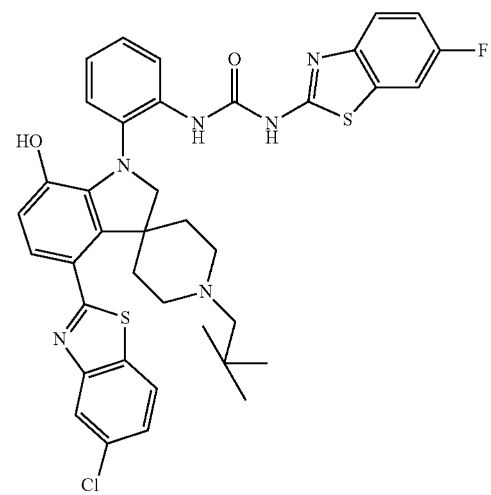 | 728.0 | 1.87 | D |
| 134 | 1-(2-(4-(5-Chlorobenzo[d]thiazol-2-yl)-7-hydroxy-1'-neopentylspiro[indoline-3,4'-piperidin]-1-yl)phenyl)-3-(4-(trifluoromethoxy)phenyl)urea | 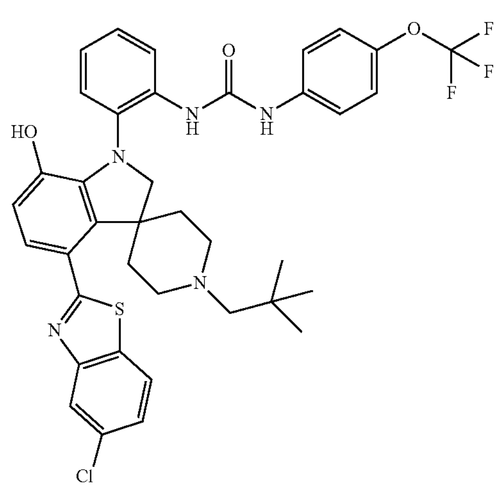 [SMILES: CC(C)(C)CN1CCC2(CC1)CN(c1ccccc1NC(=O)Nc1ccc(OC(F)(F)F)cc1)c1c(O)ccc(-c3nc4cc(Cl)ccc4s3)c12] | 737.0 | 1.91 | D |

-continued

| Example | Name | Structure | [M + H]+ | t_R (min) | LC/MS Method |
|---|---|---|---|---|---|
| 135 | 1-(2-(4-(5-Fluorobenzo[d]thiazol-2-yl)-7-hydroxy-1'-neopentylspiro[indoline-3,4'-piperidin]-1-yl)phenyl)-3-(4-(trifluoromethoxy)phenyl)urea | 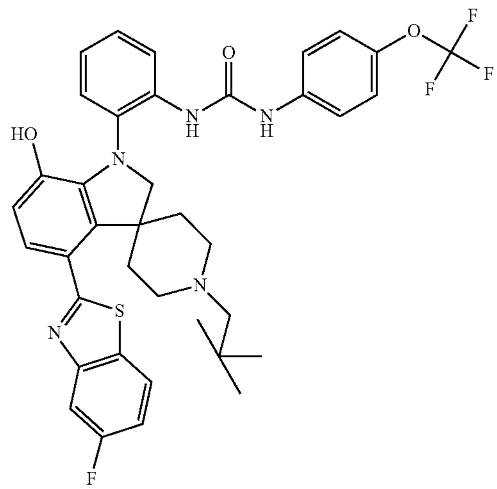 [SMILES: CC(C)(C)CN1CCC2(CC1)CN(c1ccccc1NC(=O)Nc1ccc(OC(F)(F)F)cc1)c1c(O)ccc(-c3nc4cc(F)ccc4s3)c12] | 720.0 | 2.86 | C |
| 136 | 1-(2-(4-(6-Chlorobenzo[d]thiazol-2-yl)-7-hydroxy-1'-neopentylspiro[indoline-3,4'-piperidin]-1-yl)phenyl)-3-(4-(trifluoromethoxy)phenyl)urea | 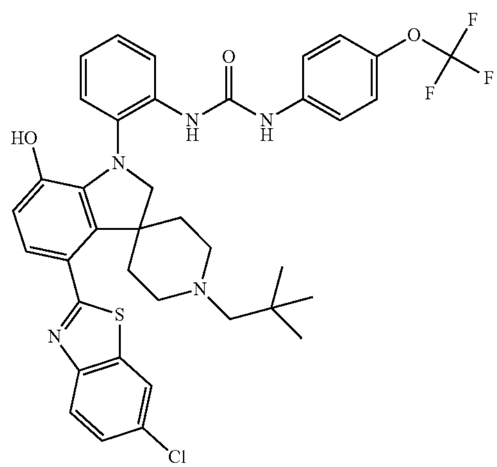 [SMILES: CC(C)(C)CN1CCC2(CC1)CN(c1ccccc1NC(=O)Nc1ccc(OC(F)(F)F)cc1)c1c(O)ccc(-c3nc4ccc(Cl)cc4s3)c12] | 737.0 | 1.92 | D |
| 137 | 1-(2-(4-(5-Chlorobenzo[d]thiazol-2-yl)-5-fluoro-7-hydroxy-1'-neopentylspiro[indoline-3,4'-piperidin]-1-yl)phenyl)-3-(4-(trifluoromethoxy)phenyl)urea | 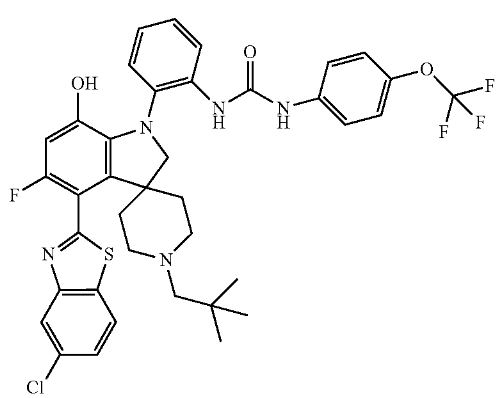 [SMILES: CC(C)(C)CN1CCC2(CC1)CN(c1ccccc1NC(=O)Nc1ccc(OC(F)(F)F)cc1)c1c(O)cc(F)c(-c3nc4cc(Cl)ccc4s3)c12] | 754.5 | 1.50 | D |

| Example | Name | Structure | [M + H]+ | $t_R$ (min) | LC/MS Method |
|---|---|---|---|---|---|
| 138 | 1-(6-Cluorobenzo[d]thiazol-2-yl)-3-(2-(4-(5-fluorobenzo[d]thiazol-2-yl)-7-hydroxy-1'-neopentylspiro[indoline-3,4'-piperidin]-1-yl)phenyl)urea | 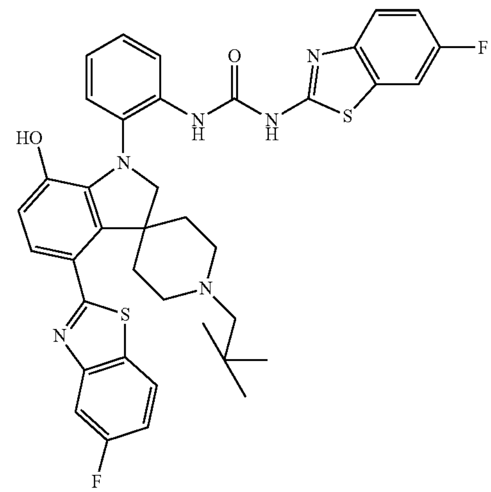 [SMILES: CC(C)(C)CN1CCC2(CC1)CN(c1ccccc1NC(=O)Nc1nc3ccc(F)cc3s1)c1c(O)ccc(-c3nc4cc(F)ccc4s3)c12] | 711.0 | 1.77 | D |
| 139 | 1-(2-(4-(6-Chlorobenzo[d]thiazol-2-yl)-7-hydroxy-1'-neopentylspiro[indoline-3,4'-piperidin]-1-yl)phenyl)-3-(6-fluorobenzo[d]thiazol-2-yl)urea | 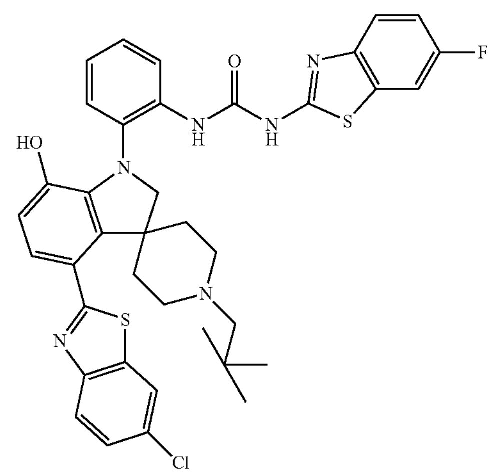 [SMILES: CC(C)(C)CN1CCC2(CC1)CN(c1ccccc1NC(=O)Nc1nc3ccc(F)cc3s1)c1c(O)ccc(-c3nc4ccc(Cl)cc4s3)c12] | 728.0 | 1.86 | D |
| 140 | 1-(2-(4-(5-Chlorobenzo[d]thiazol-2-yl)-5-fluoro-7-hydroxy-1'-neopentylspiro[indoline-3,4'-piperidin]-1-yl)phenyl)-3-(6-fluorobenzo[d]thiazol-2-yl)urea | 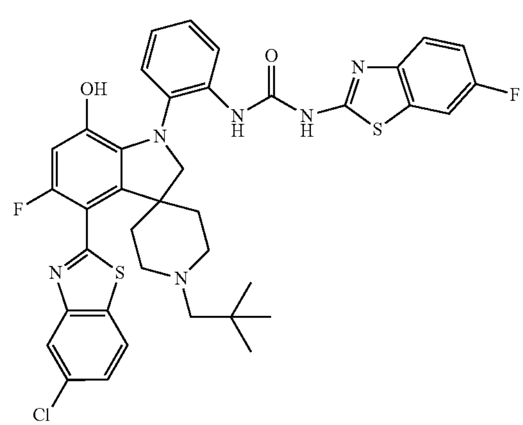 [SMILES: CC(C)(C)CN1CCC2(CC1)CN(c1ccccc1NC(=O)Nc1nc3ccc(F)cc3s1)c1c(O)cc(F)c(-c3nc4cc(Cl)ccc4s3)c12] | 744.9 | 1.83 | D |

| Example | Name | Structure | [M + H]⁺ | $t_R$ (min) | LC/MS Method |
|---|---|---|---|---|---|
| 141 | 1-(6-Chlorobenzo[d]thiazol-2-yl)-3-(2-(4-(5-chlorobenzo[d]thiazol-2-yl)-5-fluoro-7-hydroxy-1'-neopentylspiro[indoline-3,4'-piperidin]-1-yl)phenyl)urea | 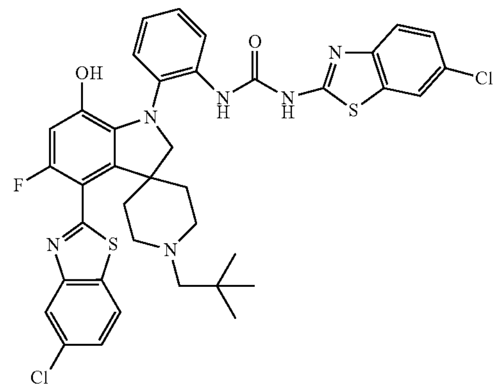 [SMILES: CC(C)(C)CN1CCC2(CC1)CN(c1ccccc1NC(=O)Nc1nc3ccc(Cl)cc3s1)c1c(O)cc(F)c(-c3nc4cc(Cl)ccc4s3)c12] | 761.3 | 3.64 | C |
| 142 | 1-(2-(4-(5-Chlorobenzo[d]thiazol-2-yl)-7-hydroxy-1'-isobutylspiro[indoline-3,4'-piperidine]-1-yl)phenyl)-3-(4-(trifluoromethoxy)phenyl)urea | 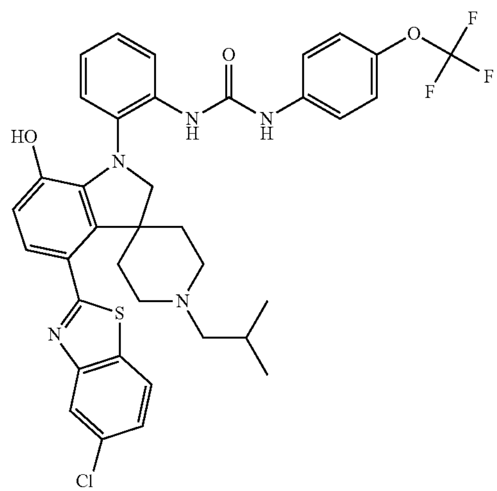 [SMILES: CC(C)CN1CCC2(CC1)CN(c1ccccc1NC(=O)Nc1ccc(OC(F)(F)F)cc1)c1c(O)ccc(-c3nc4cc(Cl)ccc4s3)c12] | 723.0 | 1.87 | D |
| 143 | 1-(2-(4-(5-Chlorobenzo[d]thiazol-2-yl)-7-hydroxy-1'-isopropylspiro[indoline-3,4'-piperidine]-1-yl)phenyl)-3-(4(trifluoromethoxy)phenyl)urea | 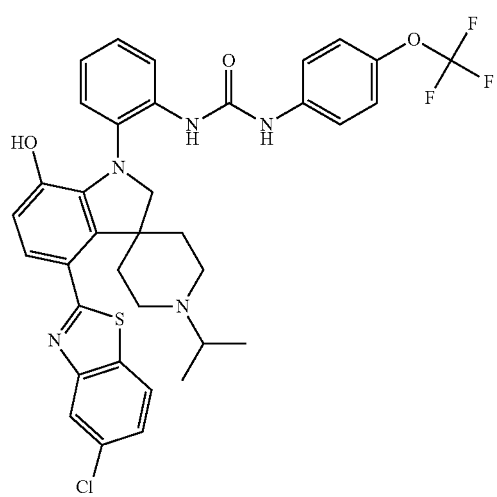 [SMILES: CC(C)N1CCC2(CC1)CN(c1ccccc1NC(=O)Nc1ccc(OC(F)(F)F)cc1)c1c(O)ccc(-c3nc4cc(Cl)ccc4s3)c12] | 709.0 | 1.81 | D |

| Example | Name | Structure | [M + H]⁺ | $t_R$ (min) | LC/MS Method |
|---|---|---|---|---|---|
| 144 | 1-(5-Chlorothiazolo[5,4-b]pyridin-2-yl)-3-(2-(4-(6-fluorobenzo[d]thiazol-2-yl)-7-hydroxy-1'-neopentylspiro[indoline-3,4'-piperidin]-1-yl)phenyl)urea | 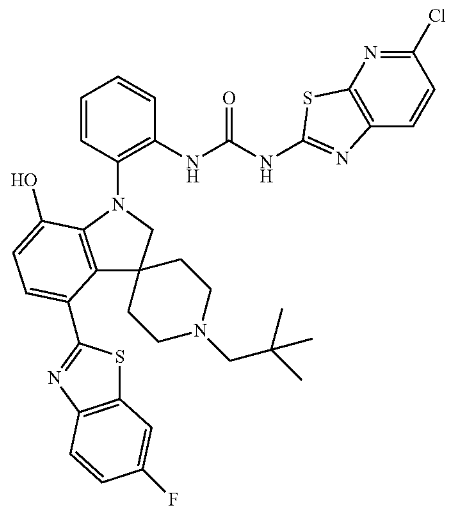 [SMILES: CC(C)(C)CN1CCC2(CC1)CN(c1ccccc1NC(=O)Nc1nc3ccc(Cl)nc3s1)c1c(O)ccc(-c3nc4ccc(F)cc4s3)c12] | 728.4 | 2.52 | F |
| 145 | 1-(6-Chlorobenzo[d]thiazol-2-yl)-3-(2-(4-(6-fluorobenzo[d]thiazol-2-yl)-7-hydroxy-1'-neopentylspiro[indoline-3,4'-piperidin]-1-yl)phenyl)urea | 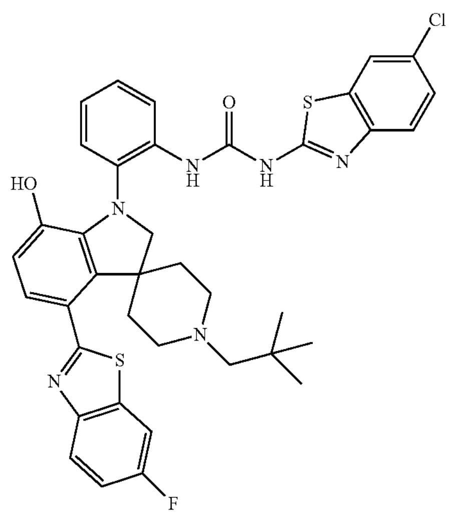 | 727.3 | 3.53 | C |
| 146 | 1-(2-(4-(5-Fluorobenzo[d]thiazol-2-yl)-7-hydroxy-1'-neopentylspiro[indoline-3,4'-piperidin]-1-yl)phenyl)-3-(6-methoxybenzo[d]thiazol-2-yl)urea | 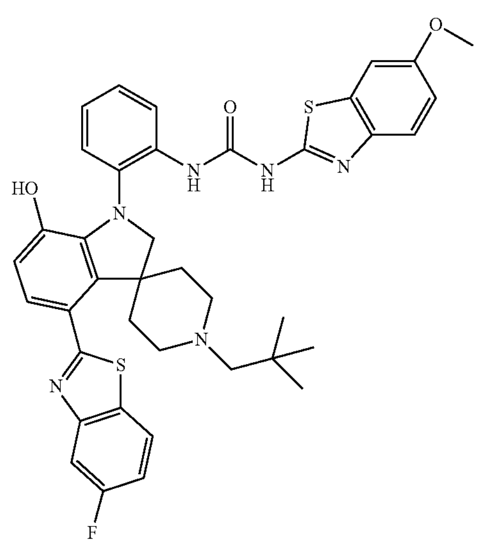 | 722.9 | 1.79 | D |

-continued

| Example | Name | Structure | [M + H]⁺ | $t_R$ (min) | LC/MS Method |
|---|---|---|---|---|---|
| 147 | 1-(2-(5-Fluoro-4-(6-fluorobenzo[d]thiazol-2-yl)-7-hydroxy-1'-neopentylspiro[indoline-3,4'-piperidin]-1-yl)phenyl)-3-(4-(trifluoromethoxy)phenyl)urea | 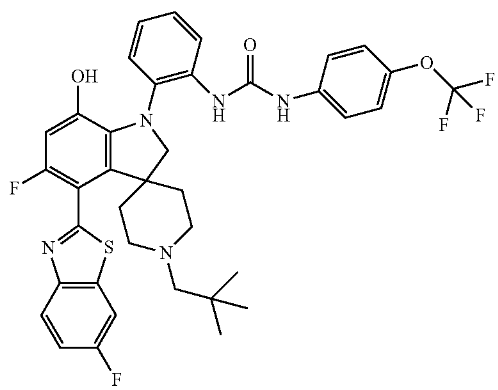 [SMILES: CC(C)(C)CN1CCC2(CC1)CN(c1ccccc1NC(=O)Nc1ccc(OC(F)(F)F)cc1)c1c(O)cc(F)c(-c3nc4ccc(F)cc4s3)c12] | 738.4 | 3.42 | C |
| 148 | 1-(6-Fluorobenzo[d]thiazol-2-yl)-3-(2-(4-(6-fluorobenzo[d]thiazol-2-yl)-7-hydroxy-1'-neopentylspiro[indoline-3,4'-piperidin]-1-yl)phenyl)urea | 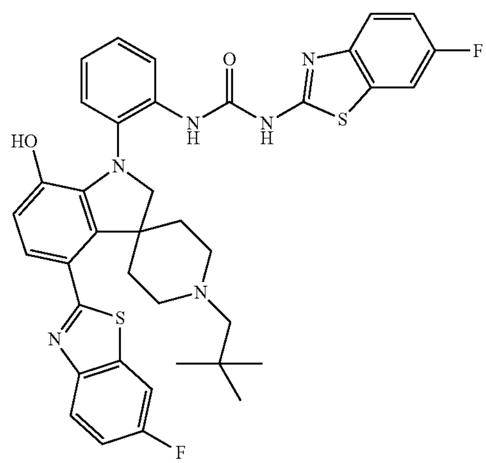 [SMILES: CC(C)(C)CN1CCC2(CC1)CN(c1ccccc1NC(=O)Nc1nc3ccc(F)cc3s1)c1c(O)ccc(-c3nc4ccc(F)cc4s3)c12] | 711.0 | 3.38 | C |
| 149 | 1-(6-Chlorobenzo[d]thiazol-2-yl)-3-(2-(4-(5-chlorobenzo[d]thiazol-2-yl)-7-hydroxy-1'-neopentylspiro[indoline-3,4'-piperidin]-1-yl)phenyl)urea | 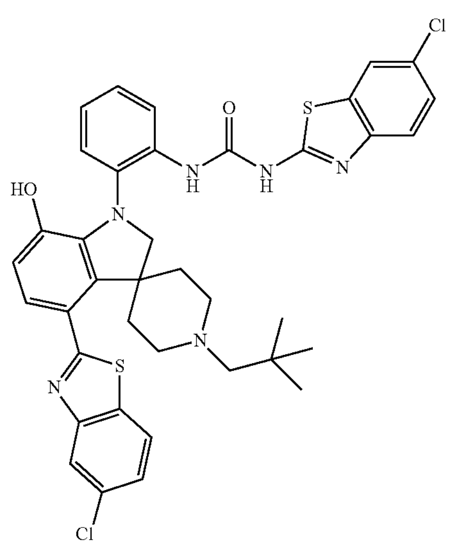 [SMILES: CC(C)(C)CN1CCC2(CC1)CN(c1ccccc1NC(=O)Nc1nc3ccc(Cl)cc3s1)c1c(O)ccc(-c3nc4cc(Cl)ccc4s3)c12] | 742.8 | 2.02 | D |

| Example | Name | Structure | [M + H]+ | $t_R$ (min) | LC/MS Method |
|---|---|---|---|---|---|
| 150 | 1-(2-(4-(5-Chlorobenzo[d]thiazol-2-yl)-7-hydroxy-1'-neopentylspiro[indoline-3,4'-piperidin]-1-yl)phenyl)-3-(6-methoxybenzo[d]thiazol-2-yl)urea | 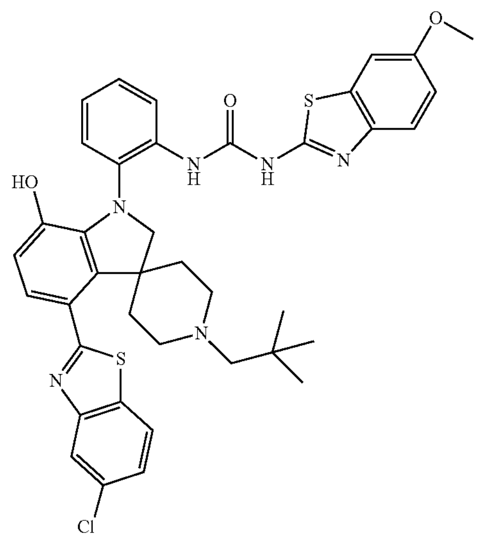 [SMILES: COc1ccc2nc(NC(=O)Nc3ccccc3N3CC4(CCN(CC(C)(C)C)CC4)c4c(-c5nc6cc(Cl)ccc6s5)ccc(O)c43)sc2c1] | 739.2 | 3.52 | C |
| 151 | 1-(2-(5-Fluoro-4-(6-fluorobenzo[d]thiazol-2-yl)-7-hydroxy-1'-neopentylspiro[indoline-3,4'-piperidin]-1-yl)phenyl)-3-(4-(trifluoromethoxy)phenyl)urea | 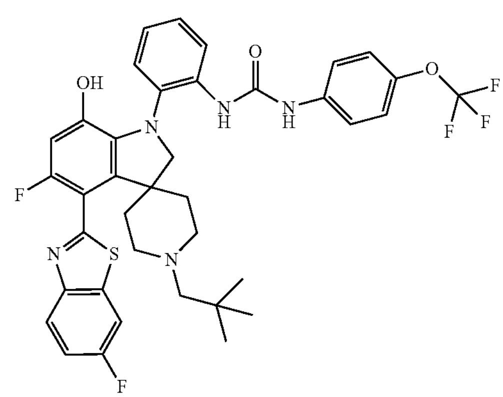 [SMILES: CC(C)(C)CN1CCC2(CC1)CN(c1ccccc1NC(=O)Nc1ccc(OC(F)(F)F)cc1)c1c(O)cc(F)c(-c3nc4ccc(F)cc4s3)c12] | 738.4 | 3.42 | C |

Example 152

1-(5-Chlorothiazolo[5,4-b]pyridin-2-yl)-3-(2-5-fluoro-4-(4-fluorophenyl)-7-hydroxy-1'-neopentyl-spiro[indoline-3,4'-piperidin]-1-yl)phenyl)urea

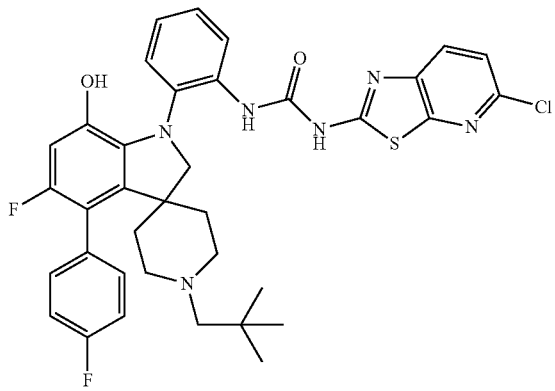 [SMILES: CC(C)(C)CN1CCC2(CC1)CN(c1ccccc1NC(=O)Nc1nc3ccc(Cl)nc3s1)c1c(O)cc(F)c(-c3ccc(F)cc3)c12]

Example 152A 1-(5-Fluoro-4-(4-fluorophenyl)-7-methoxy-1-(2-nitrophenyl)spiro[indoline-3,4'-piperidin]-1'-yl)-2,2-dimethylpropan-1-one: 1-(4-Bromo-5-fluoro-7-methoxy-1-(2-nitrophenyl)spiro[indoline-3,4'-piperidine]-1'-yl)-2,2-dimethylpropan-1-one (1.93 g, 3.71 mmol), 4-fluorophenylboronic acid (0.623 g, 4.45 mmol) were dissolved in DME (37.1 mL), and sodium carbonate (9.27 mL, 9.27 mmol) was added, degassed, followed by the addition of tetrakis(triphenylphosphine)palladium (0) (0.429 g, 0.371 mmol). The reaction was sealed and heated at 100° C. for 2 days, then cooled down to rt. The reaction mixture was partitioned between water and ether (2×), washed with brine, dried over MgSO$_4$, concentrated and purified by flash chromatography, eluting with EtOAc/hexanes to give Example 152A (1.6 g, 81%) as a red foam. LCMS (ESI) m/z 536.3 (M+H)$^+$, RT=4.15 min (Method C).

Example 152B 1-(1-(2-Aminophenyl)-5-fluoro-4-(4-fluorophenyl)-7-methoxyspiro[indoline-3,4'-piperidin]-1'-yl)-2,2-dimethylpropan-1-one: Example 152A (2.29 g, 4.28 mmol) in EtOAc (21.38 mL) and MeOH (21.38 mL) was added ammonium chloride (4.57 g, 86.0 mmol) and zinc (5.59 g, 86.0 mmol). The reaction was stirred at rt for 1 hr. The reaction mixture was filtered off solid, rinsed with EtOAc, concentrated, purified by flash chromatography, eluting with EtOAc/hexanes to give Example 152B (1.44 g, 67%) as a white solid. LCMS (ESI) m/z 506.3 (M+H)$^+$, RT=3.62 min (Method C).

Example 152C 2-(5-Fluoro-4-(4-fluorophenyl)-7-methoxy-1'-neopentyl-spiro[indoline-3,4'-piperidin]-1-yl)aniline: To a solution Example 152B (1.44 g, 2.85 mmol) in DCM (28.5 mL) was added RED-AL® (4.34 mL, 14.2 mmol) dropwise for 20 min. After addition, the reaction turned cloudy and was stirred at rt for 16 h. The reaction was quenched by adding drops of aq. NaHCO$_3$. The reaction mixture was then diluted with DCM and washed with aq. NaHCO$_3$. Aqueous layer was extracted again with DCM and the combined organic layers were dried over MgSO$_4$, concentrated and purified by flash chromatography, eluting with EtOAc/hexanes to give Example 152C (0.86 g, 61%) as a white foam. LCMS (ESI) m/z 492.4 (M+H)$^+$, RT=2.96 min (Method C).

Example 152D 1-(5-Chlorothiazolo[5,4-b]pyridin-2-yl)-3-(2-(5-fluoro-4-(4-fluorophenyl)-7-methoxy-1'-neopentylspiro[indoline-3,4'-piperidin]-1-yl)phenyl)urea: To a solution of Example 152C (858 mg, 1.75 mmol) and potassium carbonate (482 mg, 3.49 mmol) in DCE (15 ml) was added 4-nitrophenyl carbonochloridate (387 mg, 1.92 mmol) portionwise and the solution was stirred for 1 h at rt. 5-Chlorothiazolo[5,4-b]pyridin-2-amine (486 mg, 2.62 mmol) and DMAP (213 mg, 1.75 mmol) were added and the mixture was stirred at 75° C. for 4.5 h. The reaction was diluted with DCM and washed with 1N NaOH (30 ml×2) and brine consecutively. The organic layer was dried over MgSO$_4$, concentrated, and purified by flash chromatography (eluting with EtOAc/hexanes) to give Example 152D (0.98 g, 80%) as a pale yellow solid. LCMS (ESI) m/z 703.4 (M+H)$^+$, RT=3.78 min (Method C).

Example 152E

To a solution of Example 152D (1.27 g, 1.81 mmol) in CH$_2$Cl$_2$ (36.1 mL) was added tetrabutylammonium iodide (4.00 g, 10.8 mmol). The reaction was cooled down to −78° C., degassed several times with vacuum/argon and trichloroborane (9.03 mL, 9.03 mmol) was added dropwise. The reaction was slowly warmed to rt for 16 h. MeOH and H$_2$O were added and stirred for 30 min. The mixture was concentrated and the residue was diluted with DCM, washed with sat. NaHCO$_3$, NH$_4$Cl, brine, dried over MgSO$_4$, filtered, concentrated, and purified by flash chromatography (eluting with EtOAc/hexanes/1% triethylamine) to give Example 152E (0.74 g, 50%) as a brownish solid. LCMS (ESI) m/z 689.4 (M+H)$^+$, RT=3.48 min (Method C).

Example 152

MSA Salt

Example 152E (52 g, 75 mmol) was dissolved EtOAc (1900 mL)/EtOH (750 mL) and the solution was obtained. Methanesulfonic acid (5.14 mL, 79 mmol) in EtOAc (250 mL) was added to the solution. The reaction mixture was stirred for 5 min. The solvent was removed to 250 g, and the mixture was stirred at rt for 1 hr. The solid was collected and washed with EtOH. The salt was dried under vacuum to give solid 51.9 g (84%) of Example 152.MSA as off white solid. $^1$H NMR (500 MHz, DMSO-d$_6$) δ ppm 11.75 (s, 1H) 11.81 (s, 1H) 9.66 (s, 1H) 9.13 (br. s., 1H) 8.75 (br. s., 1H) 8.15 (dd, J=8.20, 1.26 Hz, 1H) 8.04 (d, J=8.51 Hz, 1H) 7.50 (J=8.51, 1H) 7.50-7.24 (m, 4H) 7.20 (J=8.20, 1H) 7.17 (dd, J=7.88, 1.58 Hz, 1H) 7.06 (m, 1H) 6.56 (J=10.7, 1H) 4.06 (d, J=10.09 Hz, 1H) 3.27 (d, J=10.40 Hz, 1H) 2.93-3.22 (m, 4H) 2.39 (dd, J=13.24, 3.78 Hz, 1H) 2.21 (dd, J=13.08, 3.63 Hz, 1H) 1.61-2.11 (m, 4H) 0.90 (s, 9H).

Examples 153 to 165 were prepared according the procedure described in Example 152 by using the appropriately substituted phenylboronic acids.

| Example | Name | Structure | [M + H]+ | tR (min) | LC/MS Method |
|---|---|---|---|---|---|
| 153 | 1-(2-(6-Fluoro-4-(4-fluorophenyl)-7-hydroxy-1'-neopentylspiro[indoline-3,4'-piperidin]-1-yl)phenyl)-3-(4-(trifluoromethoxy)phenyl)urea | 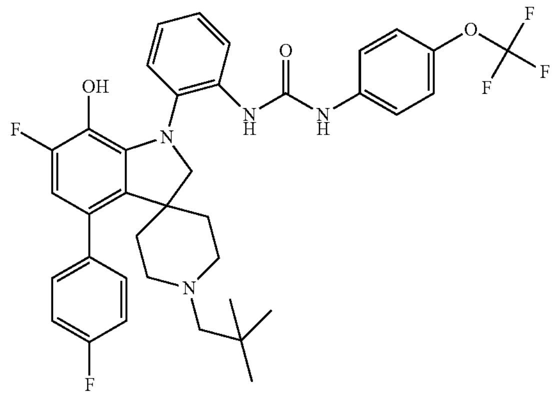 [SMILES: CC(C)(C)CN1CCC2(CC1)CN(c1ccccc1NC(=O)Nc1ccc(OC(F)(F)F)cc1)c1c(O)c(F)cc(-c3ccc(F)cc3)c12] | 681.5 | 3.39 | C |
| 154 | 1-(2-(6-Fluoro-7-hydroxy-1'-neopentyl-4-(4-(trifluoromethyl)phenyl)spiro[indoline-3,4'-piperidine]-1-yl)phenyl)-3-(4-(trifluoromethoxy)phenyl)urea | 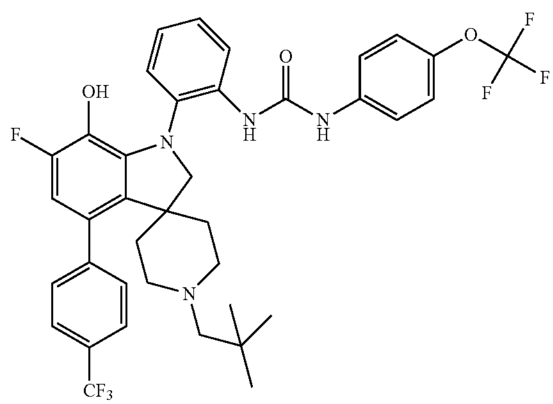 [SMILES: CC(C)(C)CN1CCC2(CC1)CN(c1ccccc1NC(=O)Nc1ccc(OC(F)(F)F)cc1)c1c(O)c(F)cc(-c3ccc(C(F)(F)F)cc3)c12] | 731.5 | 3.52 | C |
| 155 | 1-(2-(5-Fluoro-4-(4-fluorophenyl)-7-hydroxy-1'-neopentylspiro[indoline-3,4'-piperidin]-1-yl)phenyl)-3-(4-(trifluoromethoxy)phenyl)urea | 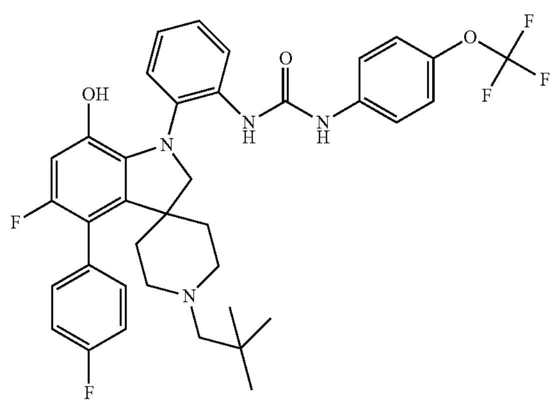 [SMILES: CC(C)(C)CN1CCC2(CC1)CN(c1ccccc1NC(=O)Nc1ccc(OC(F)(F)F)cc1)c1c(O)cc(F)c(-c3ccc(F)cc3)c12] | 681.5 | 3.12 | C |
| 156 | 1-(2-(4-(4-Chlorophenyl)-6-fluoro-7-hydroxy-1'-neopentylspiro[indoline-3,4'-piperidin]-1-yl)phenyl)-3-(4-(trifluoromethoxy)phenyl)urea | 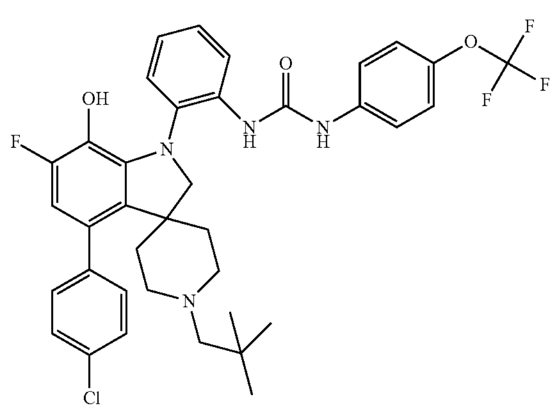 | 697.5 | 3.33 | C |

| Example | Name | Structure | [M + H]+ | tR (min) | LC/MS Method |
|---|---|---|---|---|---|
| 157 | 1-(2-(4-(4-Chlorophenyl)-5-fluoro-7-hydroxy-1'-neopentylspiro[indoline-3,4'-piperidin]-1-yl)phenyl)-3-(4-(trifluoromethoxy)phenyl)urea | 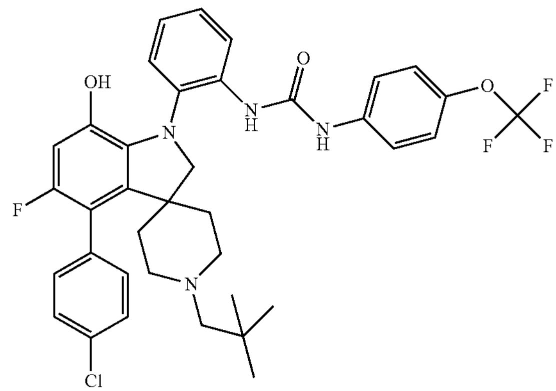 [SMILES: CC(C)(C)CN1CCC2(CC1)CN(c1ccccc1NC(=O)Nc1ccc(OC(F)(F)F)cc1)c1c(O)cc(F)c(-c3ccc(Cl)cc3)c12] | 697.5 | 3.36 | C |
| 158 | 1-(2-(4-(4-Chlorophenyl)-5-fluoro-7-hydroxy-1'-neopentylspiro[indoline-3,4'-piperidin]-1-yl)phenyl)-3-(2-(trifluoromethyl)thiazol-4-yl)urea | 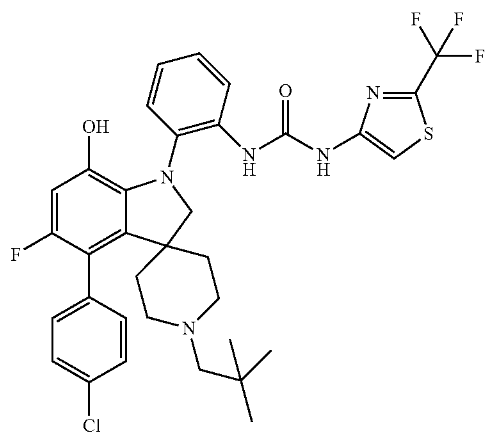 [SMILES: CC(C)(C)CN1CCC2(CC1)CN(c1ccccc1NC(=O)Nc1csc(C(F)(F)F)n1)c1c(O)cc(F)c(-c3ccc(Cl)cc3)c12] | 688.0 | 3.31 | C |
| 159 | 1-(2-(5-Fluoro-7-hydroxy-1'-neopentyl-4-(6-(trifluoromethyl)pyridin-3-yl)spiro[indoline-3,4'-piperidin]-1-yl)phenyl)-3-(2-(trifluoromethyl)thiazol-4-yl)urea | 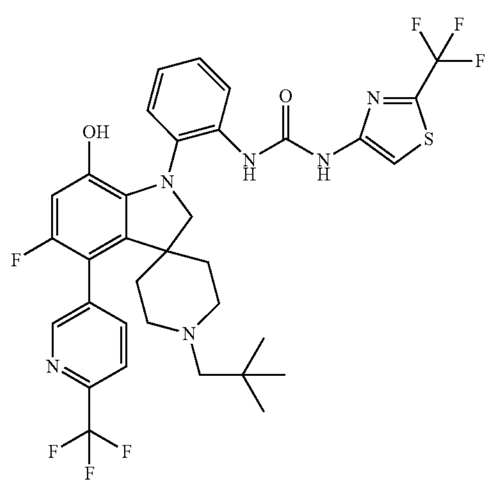 [SMILES: CC(C)(C)CN1CCC2(CC1)CN(c1ccccc1NC(=O)Nc1csc(C(F)(F)F)n1)c1c(O)cc(F)c(-c3ccc(C(F)(F)F)nc3)c12] | 723.5 | 0.97 | L |

| Example | Name | Structure | [M + H]+ | t_R (min) | LC/MS Method |
|---|---|---|---|---|---|
| 160 | 1-(2-(5-Fluoro-7-hydroxy-1'-neopentyl-4-(6-(trifluoromethyl)pyridin-3-yl)spiro[indoline-3,4'-piperidin]-1-yl)phenyl)-3-(4-(trifluoromethoxy)phenyl)urea | 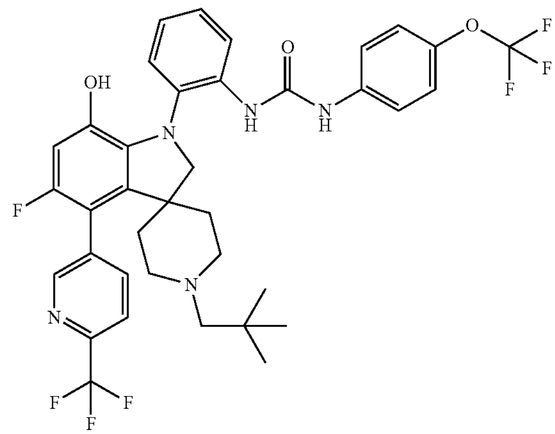 [SMILES: CC(C)(C)CN1CCC2(CC1)CN(c1ccccc1NC(=O)Nc1ccc(OC(F)(F)F)cc1)c1c(O)cc(F)c(-c3ccc(C(F)(F)F)nc3)c12] | 732.6 | 1.00 | L |
| 161 | 1-(2-(5-Fluoro-7-hydroxy-1'-neopentyl-4-(6-(trifluoromethyl)pyridin-3-yl)spiro[indoline-3,4'-piperidin]-1-yl)phenyl)-3-(6-fluorobenzo[d]thiazol-2-yl)urea | 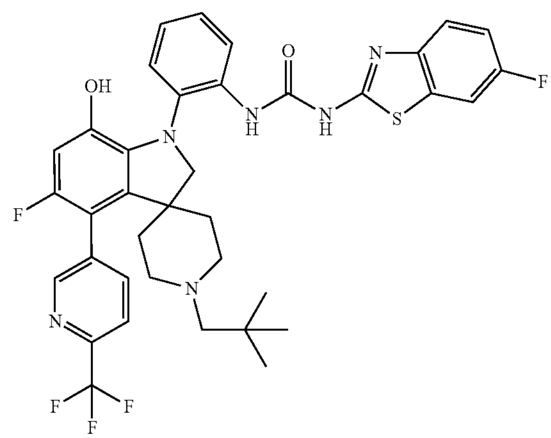 [SMILES: CC(C)(C)CN1CCC2(CC1)CN(c1ccccc1NC(=O)Nc1nc3ccc(F)cc3s1)c1c(O)cc(F)c(-c3ccc(C(F)(F)F)nc3)c12] | 723.1 | 1.70 | D |
| 162 | 1-(6-Chlorobenzo[d]thiazol-2-yl)-3-(2-(5-fluoro-7-hydroxy-1'-neopentyl-4-(6-(trifluoromethyl)pyridin-3-yl)spiro[indoline-3,4'-piperidin]-1-yl)phenyl)urea | 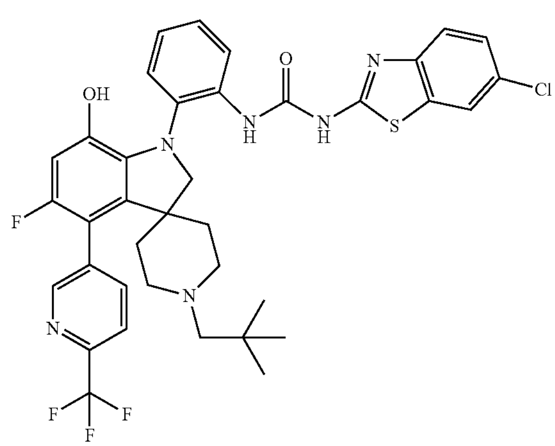 [SMILES: CC(C)(C)CN1CCC2(CC1)CN(c1ccccc1NC(=O)Nc1nc3ccc(Cl)cc3s1)c1c(O)cc(F)c(-c3ccc(C(F)(F)F)nc3)c12] | 739.0 | 1.80 | D |

| Example | Name | Structure | [M + H]⁺ | $t_R$ (min) | LC/MS Method |
|---|---|---|---|---|---|
| 163 | 1-(2-(4-(4-Chlorophenyl)-5-fluoro-7-hydroxy-1'-neopentylspiro[indoline-3,4'-piperidin]-1-yl)phenyl)-3-(2-chlorothiazol-4-yl)urea | 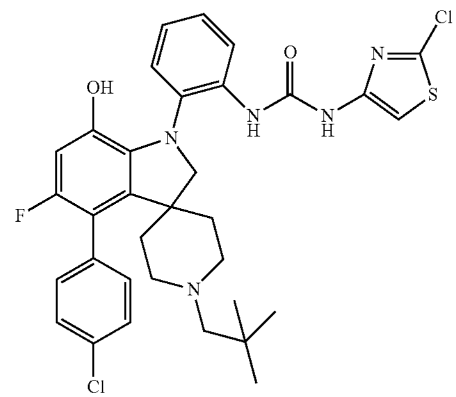 [SMILES: CC(C)(C)CN1CCC2(CC1)CN(c1ccccc1NC(=O)Nc1csc(Cl)n1)c1c(O)cc(F)c(-c3ccc(Cl)cc3)c12] | 654.0 | 3.18 | C |
| 164 | 1-(2-(4-(4-Chlorophenyl)-5-fluoro-7-hydroxy-1'-neopentylspiro[indoline-3,4'-piperidin]-1-yl)phenyl)-3-(5-chlorothiazolo[5,4-b]pyridin-2-yl)urea | 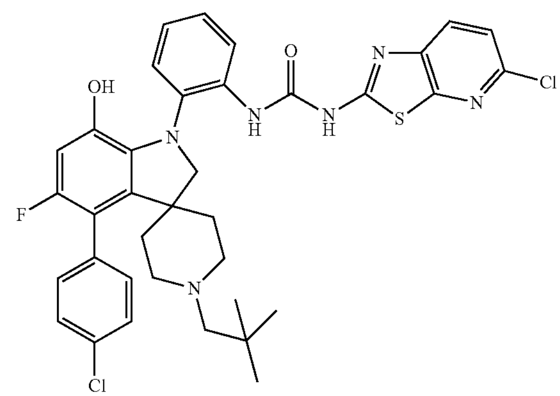 [SMILES: CC(C)(C)CN1CCC2(CC1)CN(c1ccccc1NC(=O)Nc1nc3ccc(Cl)nc3s1)c1c(O)cc(F)c(-c3ccc(Cl)cc3)c12] | 705.0 | 1.75 | D |
| 165 | 1-(2-(4-(4-Chlorophenyl)-5-fluoro-7-hydroxy-1'-neopentylspiro[indoline-3,4'-piperidin]-1-yl)phenyl)-3-(6-fluorobenzo[d]thiazol-2-yl)urea | 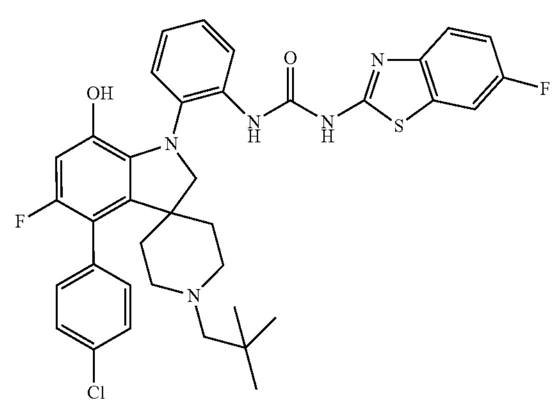 [SMILES: CC(C)(C)CN1CCC2(CC1)CN(c1ccccc1NC(=O)Nc1nc3ccc(F)cc3s1)c1c(O)cc(F)c(-c3ccc(Cl)cc3)c12] | 688.4 | 2.57 | E |

Example 166

1-(2-(4-Chloro-7-hydroxy-1'-neopentylspiro[indoline-3,4'-piperidine]-1-yl)phenyl)-3-(5-chlorothiazolo[5,4-b]pyridin-2-yl)urea

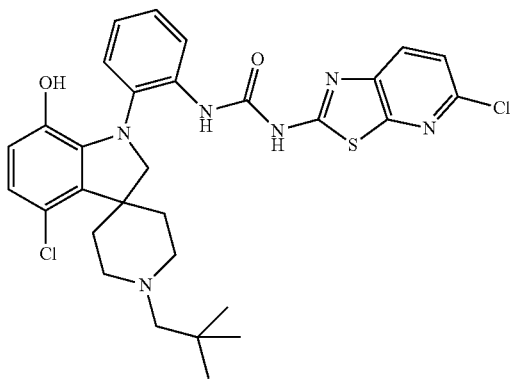 [SMILES: CC(C)(C)CN1CCC2(CC1)CN(c1ccccc1NC(=O)Nc1nc3ccc(Cl)nc3s1)c1c(O)ccc(Cl)c12]

166A 1-(2-(4-Chloro-7-methoxy-1'-neopentylspiro[indoline-3,4'-piperidine]-1-yl)phenyl)-3-(5-chlorothiazolo[5,4-b]pyridin-2-yl)urea: To a solution of Intermediate 7 (3.0 g, 7.3 mmol) and potassium carbonate (2.00 g, 14.5 mmol) in $CH_2Cl_2$ (100 mL) was added 4-nitrophenyl chloroformate (1.7 g, 8.2 mmol). The solution was stirred at room temperature for 3 h. To the solution was added Intermediate 22 (2.018 g, 10.87 mmol) and DMAP (0.089 g, 0.73 mmol) and the resulting solution was stirred at 80° C. for 5 h. The reaction mixture was diluted with dichloromethane (100 mL) and washed with 1N aq. NaOH (30 mL×4). The organic layer was dried over $MgSO_4$, concentrated and purified by flash chromatography (silica gel, eluting with EtOAc/Hexanes) to provide Example 166A (3.8 g, 84% yield) as a white solid. LCMS (ESI) m/z 625.3 (M+H)$^+$, RT=1.73 min (Method D). $^1$H NMR (400 MHz, tetrahydrofuran-$d_8$) δ ppm 10.59 (s, 1H), 8.77-9.07 (m, 1H), 8.33 (d, J=8.31 Hz, 1H), 7.66 (d, J=7.83 Hz, 1H), 7.28-7.36 (m, 1H), 7.17 (t, J=7.09 Hz, 1H), 6.99-7.04 (m, 1H), 6.95 (t, J=7.58 Hz, 1H), 6.78-6.84 (m, 1H), 6.69-6.77 (m, 1H), 4.08 (d, J=10.27 Hz, 1H), 3.41 (s, 3H), 3.35 (d, J=10.76 Hz, 1H), 3.26 (d, J=5.38 Hz, 2H), 2.99 (q, J=5.38 Hz, 1H), 2.91 (td, J=12.96, 4.40 Hz, 1H), 2.64-2.82 (m, 3H), 2.46-2.54 (m, 2H), 2.28-2.43 (m, 1H), 2.22 (t, J=11.25 Hz, 1H), 2.03 (s, 1H), 1.51-1.63 (m, 2H), 0.79-0.92 (m, 9H).

Example 166

To a solution of 166A (500 mg, 0.799 mmol) in $CH_2Cl_2$ (13 mL) was added aluminum chloride (1.07 g, 7.99 mmol). The mixture was heated by microwave for 10 min at 100° C. The reaction mixture was added in small portions to cold methanol. The reaction mixture was then diluted with dichloromethane (20 mL) and added aq. $NaHCO_3$ to pH=9. The aqueous solution was then extracted with dichloromethane and THF. The combined organic suspension was dried over $Na_2SO_4$, concentrated, and purified by flash chromatography (silica gel, eluting with EtOAc/Hexanes) to produce the title compound 1 (415 mg, 85.0% yield) as a white solid. LCMS (ESI) m/z 611.1 (M+H)$^+$, RT=1.53 min (Method D). $^1$H NMR (500 MHz, DMSO-$d_6$) δ ppm 11.68 (br. s., 1H), 9.22 (s, 1H), 9.00 (br. s., 1H), 8.11 (d, J=8.25 Hz, 1H), 8.03 (d, J=8.80 Hz, 1H), 7.51 (d, J=8.80 Hz, 1H), 7.15 (t, J=6.60 Hz, 1H), 6.90-7.04 (m, 2H), 6.71 (d, J=8.25 Hz, 1H), 6.60 (d, J=8.80 Hz, 1H), 4.10 (q, J=5.50 Hz, 2H), 4.05 (d, J=9.90 Hz, 1H), 3.33 (s, 2H), 3.17 (d, J=5.50 Hz, 5H), 2.72 (d, J=11.00 Hz, 1H), 2.58-2.68 (m, 2H), 2.55 (dd, J=12.92, 4.12 Hz, 1H), 2.27 (br. s., 1H), 2.15 (br. s., 1H), 1.98 (s, 2H), 1.68 (d, J=11.55 Hz, 1H), 1.46 (d, J=11.00 Hz, 1H), 0.82 (s, 9H).

Alternatively, Example 166 was prepared via a large-scale synthesis as following:

166A 1-(2-(4-Chloro-7-methoxy-1'-neopentylspiro[indoline-3,4'-piperidine]-1-yl)phenyl)-3-(5-chlorothiazolo[5,4-b]pyridin-2-yl)urea: To a solution of Intermediate 7 (67.0 g, 162 mmol) and potassium carbonate (44.7 g, 324 mmol) in DCE (1500 mL) was added 4-nitrophenyl carbonochloridate (35.9 g, 178 mmol) portionwise and the solution was stirred for 2 h at rt. Intermediate 22 (36.1 g, 194 mmol) and N,N-dimethylpyridin-4-amine (1.977 g, 16.18 mmol) were added and the mixture was stirred at 85° C. for 6.5 h. The solvent was removed and the residue was partitioned between EtOAc (3.5 L) and water. The organic layer was washed with water (1000 mL×3) and then 0.25N HCl water (1000 mL). The precipitate was filtered and washed with water. It was suspended in EtOAc (2000 mL) and extracted with 0.25N HCl (2000 mL) to remove the un-reacted Intermediate 22. The solid was again filtered and then washed with water. It was basified with Sat'd. $Na_2CO_3$ solution to give 90.2 g of the pure 166A as the free base. The ethyl acetate organic layer was washed with water and brine, dried over $Na_2SO_4$ and concentrated to give more of the crude product, which was purified by silica gel column (BIOTAGE® 40m, AcOEt/Hex=0-20%) to give additional pure 166A, which was crystallized from $CH_3OH$/EtOAc (30 mL, 30%) to give additional 6.7 g pure 166A. Total 166A obtained was 96.9 g (yield: 96%). $^1$H NMR (DMSO-$d_6$) δ 0.83 (s, 9H), 1.00 (m, 1H), 1.53 (m, 1H), 1.72 (m, 1H), 1.99 (s, 2H), 2.16 (m, 1H), 2.28 (m, 1H), 2.67 (m, 3H), 3.25 (m, 1H), 3.42 (s, 3H), 4.04 (m, 1H), 6.84 (s, 2H), 7.00 (d, 2H), 7.18 (dd, 1H), 7.50 (d, 1H), 8.02 (d, 1H), 8.12 (d, 1H), 8.98 (s, 1H), 11.63 (s, 1H). MS(ESI) m/z 626 (M+H)$^+$.

Example 166

1-(2-(4-Chloro-7-Hydroxy-1'-neopentylspiro[indoline-3,4'-piperidine]-1-yl)phenyl)-3-(5-chlorothiazolo[5,4-b]pyridin-2-yl)urea: Boron trichloride-methyl sulfide complex (427 mL, 854 mmol) was added to a solution of 1A (89.0 g, 142 mmol) in DCE (4000 mL), and mixture was refluxed for 24 h. The reaction mixture was cooled to 0° C. and methanol (400 mL) was carefully added. After stirring for 15 min at rt, the solvent was removed. The residue was partitioned between EtOAc and Sat. $Na_2CO_3$. The organic layer was washed with water and brine, dried over $MgSO_4$. The solvent was removed, and the residue was purified by crystallization (EtOAc+Product 400 g) to give white solid (LCMS showed 2% SM). The solid was recrystallized from EtOAc (P+EtOAc 440 g) to yield 21.49 g of white solid product (HPLC purity 99.85%) and second crop 24.1 g (HPLC purity 99.54%). The crude compound from mother liquid was purified by column (65i, AcOEt/hexane=10%-30%) to give title compound 166 (24.1 g). Total Example 166 obtained was 73.5 g (yield: 85%). MS (ESI) m/z 611 (M+H)$^+$.

Example 167

1-(2-(4-Chloro-7-hydroxy-1'-neopentylspiro[indoline-3,4'-piperidine]-1-yl)phenyl)-3-(5-chlorothiazolo[5,4-b]pyridin-2-yl)urea, methanesulfonic acid salt

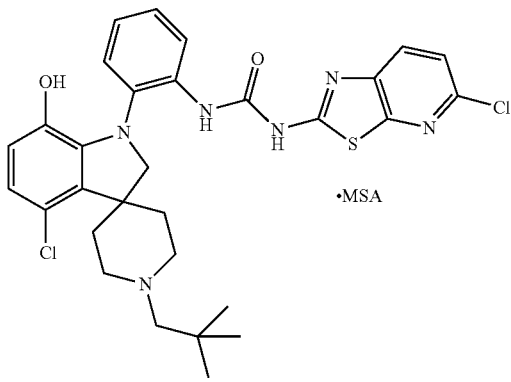

Example 166 (188 g, 308 mmol) was dissolved in ethyl acetate (9400 mL) and a solution of methanesulfonic acid (21.0 mL, 323 mmol) in EtOAc (1000 mL) was added in a portion. The resulting suspension was stirred at room temperature for 24 h. The white solid was collected by filtration and washed with EtOAc, and dried to provide Example 167 as a white solid (195 g 90.0%). MS (ESI) m/z 611 (M+H)$^+$.

Examples 168 to 180 were prepared following similar procedures described in Examples 1 to 166.

| Example | Name | Structure | [M + H]$^+$ | $t_R$ (min) | LC/MS Method |
|---|---|---|---|---|---|
| 168 | 1-(5-Chlorothiazolo[5,4-b]pyridin-2-yl)-3-(2-(4-fluoro-7-hydroxy-1'-neopentylspiro-[indoline-3,4'-piperidine]-1-yl)phenyl)urea | 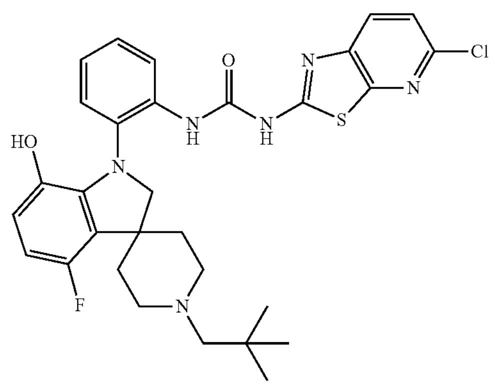 [SMILES: CC(C)(C)CN1CCC2(CC1)CN(c1ccccc1NC(=O)Nc1nc3ccc(Cl)nc3s1)c1c(O)ccc(F)c12] | 595.3 | 1.57 | D |
| 169 | 1-(2-(4-Chloro-7-hydroxy-1'-neopentylspiro[indoline-3,4'-piperidine]-1-yl)phenyl)-3-(5-methoxythiazolo[5,4-b]pyridin-2-yl)urea | 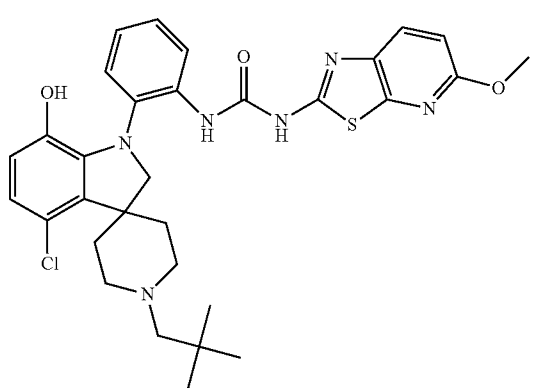 [SMILES: COc1ccc2nc(NC(=O)Nc3ccccc3N3CC4(CCN(CC(C)(C)C)CC4)c4c(Cl)ccc(O)c43)sc2n1] | 607.3 | 1.62 | D |

| Example | Name | Structure | [M + H]⁺ | $t_R$ (min) | LC/MS Method |
|---|---|---|---|---|---|
| 170 | | 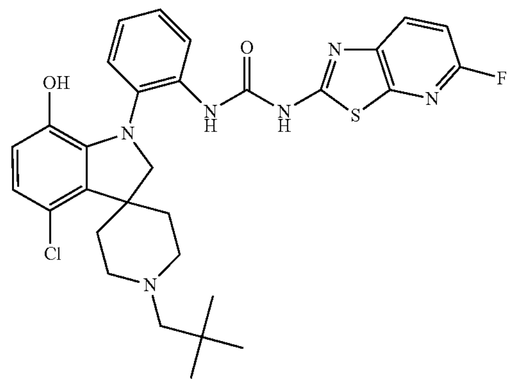 [SMILES: CC(C)(C)CN1CCC2(CC1)CN(c1ccccc1NC(=O)Nc1nc3ccc(F)nc3s1)c1c(O)ccc(Cl)c12] | 595.3 | 1.56 | D |
| 171 | 1-(5-Chlorothiazolo[5,4-b]pyridin-2-yl)-3-(2-(7-hydroxy-1'-isobutyl-4-(trifluoromethyl)spiro[indoline-3,4'-piperidine]-1-yl)phenyl)urea | 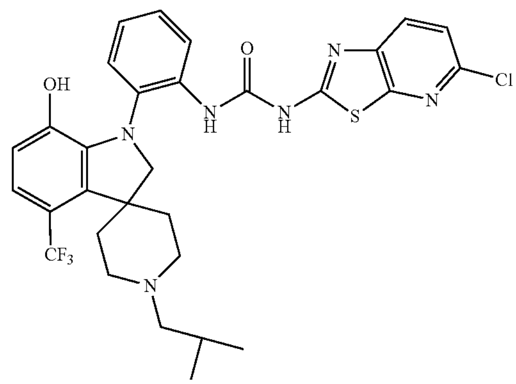 [SMILES: CC(C)CN1CCC2(CC1)CN(c1ccccc1NC(=O)Nc1nc3ccc(Cl)nc3s1)c1c(O)ccc(C(F)(F)F)c12] | 631.1 | 3.01 | C |
| 172 | 1-(5-Chlorothiazolo[5,4-b]pyridin-2-yl)-3-(2-(7-hydroxy-1'-neopentylspiro[indoline-3,4'-piperidine]-1-yl)phenyl)urea | 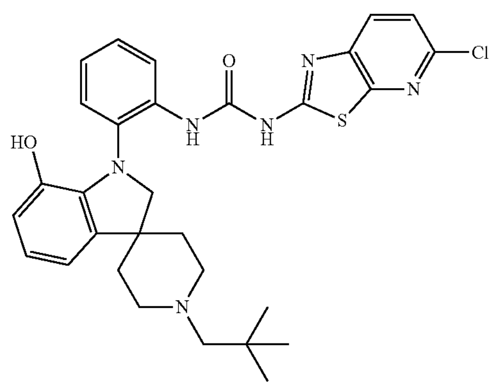 [SMILES: CC(C)(C)CN1CCC2(CC1)CN(c1ccccc1NC(=O)Nc1nc3ccc(Cl)nc3s1)c1c(O)cccc12] | 577.0 | 1.62 | B |
| 173 | 1-(2-(4-Fluoro-7-hydroxy-1'-neopentylspiro[indoline-3,4'-piperidine]-1-yl)phenyl)-3-(5-methoxythiazolo[5,4-b]pyridin-2-yl)urea | 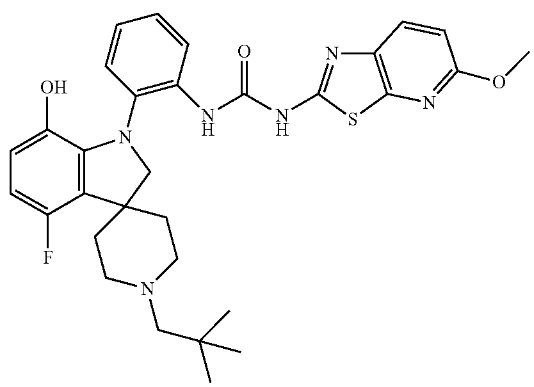 [SMILES: COc1ccc2nc(NC(=O)Nc3ccccc3N3CC4(CCN(CC(C)(C)C)CC4)c4c(F)ccc(O)c43)sc2n1] | 591.0 | 1.15 | B |

| Example | Name | Structure | [M + H]+ | t_R (min) | LC/MS Method |
|---|---|---|---|---|---|
| 174 | 1-(2-(4-Fluoro-7-hydroxy-1'-neopentylspiro[indoline-3,4'-piperidine]-1-yl)phenyl)-3-(5-fluorothiazolo[5,4-b]pyridin-2-yl)urea | 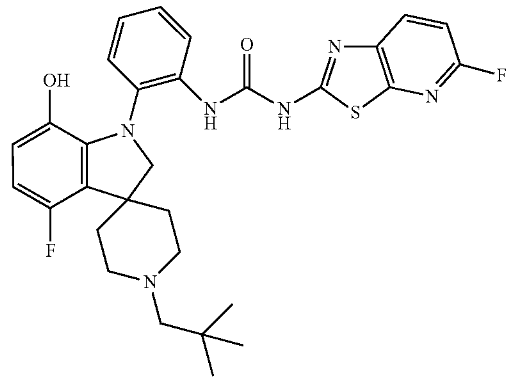 [SMILES: CC(C)(C)CN1CCC2(CC1)CN(c1ccccc1NC(=O)Nc1nc3ccc(F)nc3s1)c1c(O)ccc(F)c12] | 579.1 | 1.14 | B |
| 175 | 1-(5-Chlorothiazolo[5,4-b]pyridin-2-yl)-3-(2-(7-hydroxy-1'-neopentyl-4-(trifluoromethyl)spiro[indoline-3,4'-piperidine]-1-yl)phenyl)urea | 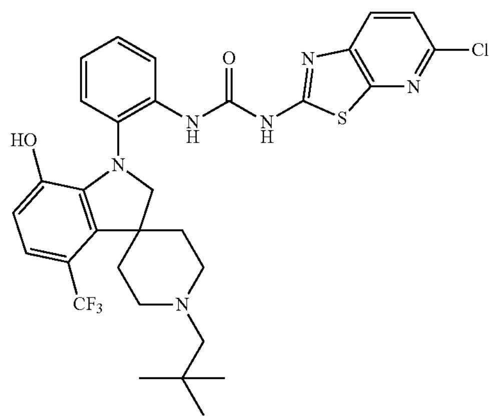 [SMILES: CC(C)(C)CN1CCC2(CC1)CN(c1ccccc1NC(=O)Nc1nc3ccc(Cl)nc3s1)c1c(O)ccc(C(F)(F)F)c12] | 645.1 | 3.05 | C |
| 176 | 1-(5-Chlorothiazolo[5,4-b]pyridin-2-yl)-3-(2-(7-hydroxy-1'-neopentyl-4-(trifluoromethyl)spiro[indoline-3,4'-piperidine]-1-yl)pyridin-3-yl)urea | 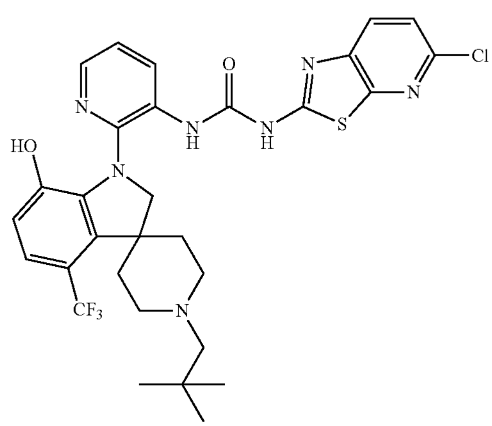 | 646.1 | 2.91 | C |

-continued

| Example | Name | Structure | [M + H]+ | t_R (min) | LC/MS Method |
|---|---|---|---|---|---|
| 177 | 1-(2-(4-Cyano-7-hydroxy-1'-neopentylspiro[indoline-3,4'-piperidine]-1-yl)phenyl)-3-(5-methoxythiazolo[5,4-b]pyridin-2-yl)urea | 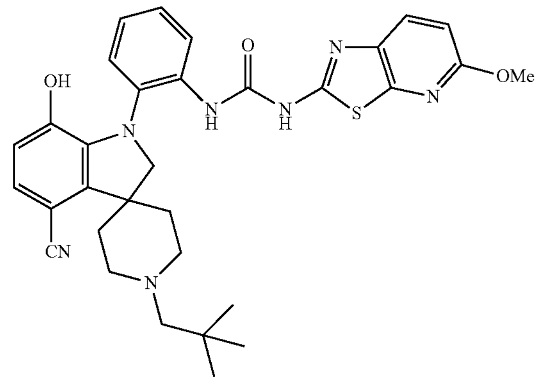 [SMILES: COc1ccc2nc(NC(=O)Nc3ccccc3N3CC4(CCN(CC(C)(C)C)CC4)c4c(C#N)ccc(O)c43)sc2n1] | 598.5 | 1.57 | D |
| 178 | 1-(2-(4-Chloro-5-fluoro-7-hydroxy-1'-neopentylspiro[indoline-3,4'-piperidine]-1-yl)phenyl)-3-(5-chlorothiazolo[5,4-b]pyridin-2-yl)urea | 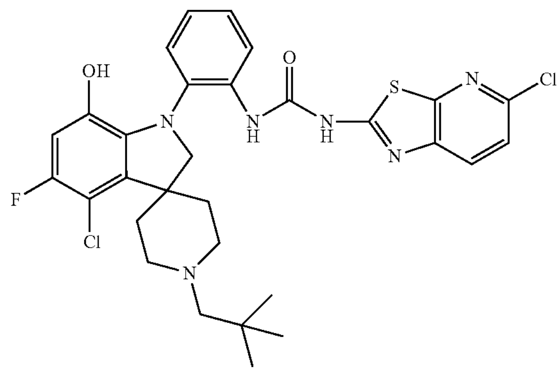 [SMILES: CC(C)(C)CN1CCC2(CC1)CN(c1ccccc1NC(=O)Nc1nc3ccc(Cl)nc3s1)c1c(O)cc(F)c(Cl)c12] | 629.3 | 1.64 | D |
| 179 | 1-(2-(4-Chloro-5-fluoro-7-hydroxy-1'-neopentylspiro[indoline-3,4'-piperidine]-1-yl)phenyl)-3-(5-fluorothiazolo[5,4-b]pyridin-2-yl)urea | 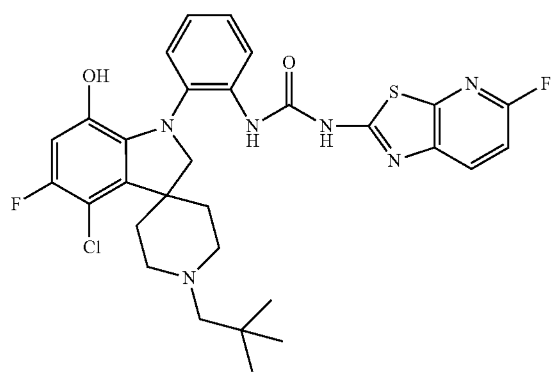 [SMILES: CC(C)(C)CN1CCC2(CC1)CN(c1ccccc1NC(=O)Nc1nc3ccc(F)nc3s1)c1c(O)cc(F)c(Cl)c12] | 613.3 | 2.95 | C |
| 180 | 1-(2-(4-Cyano-7-hydroxy-1'-neopentylspiro[indoline-3,4'-piperidine]-1-yl)phenyl)-3-(5-fluorothiazolo[5,4-b]pyridin-2-yl)urea | 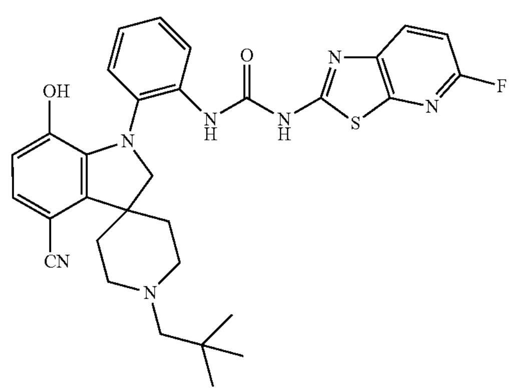 [SMILES: CC(C)(C)CN1CCC2(CC1)CN(c1ccccc1NC(=O)Nc1nc3ccc(F)nc3s1)c1c(O)ccc(C#N)c12] | 586.5 | 1.50 | D |

What is claimed is:
1. A compound selected from the group consisting of:
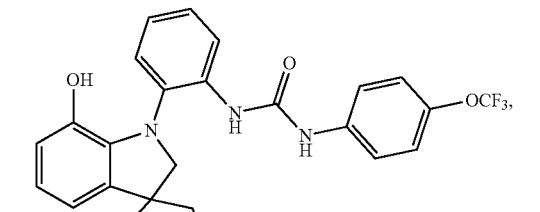
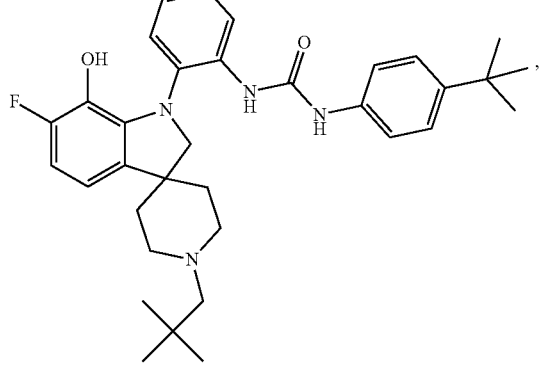
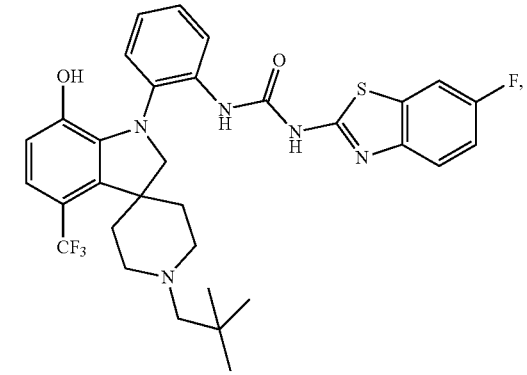
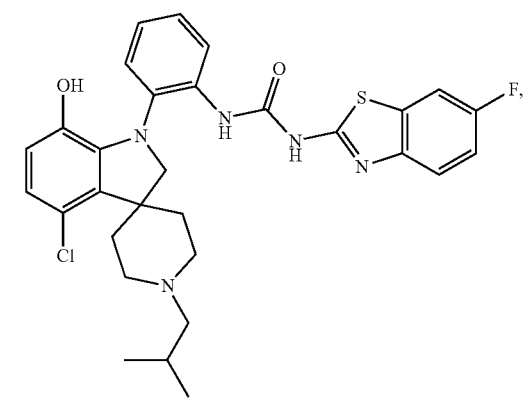
-continued
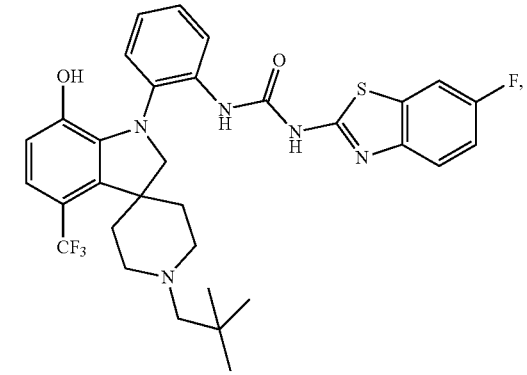

203
-continued
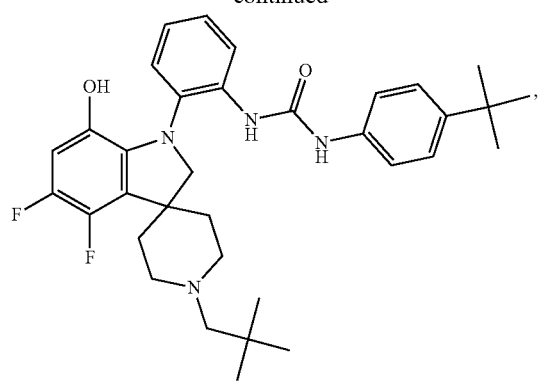
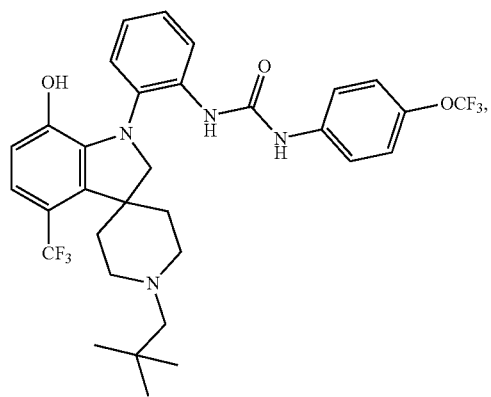
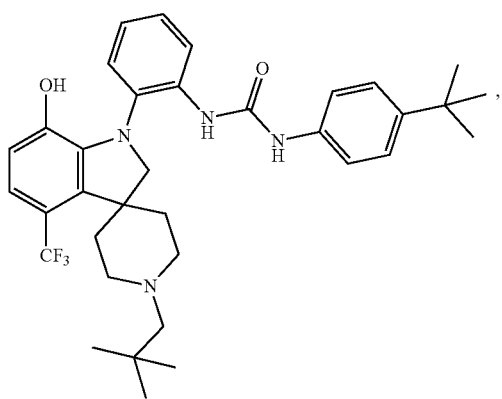
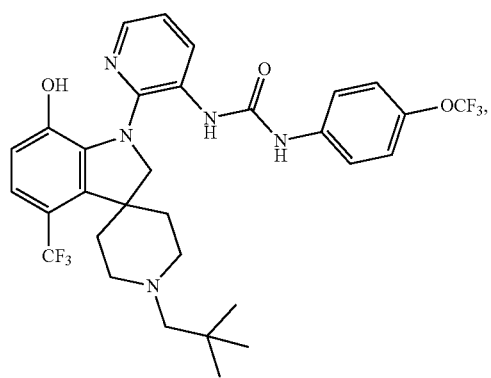
204
-continued
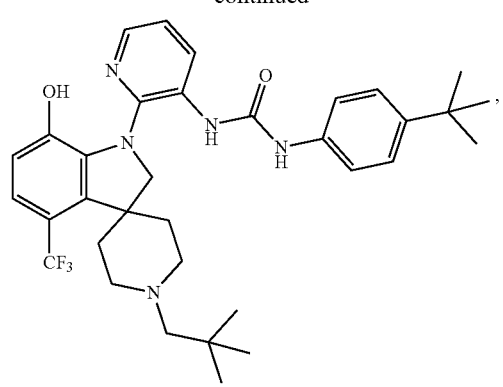
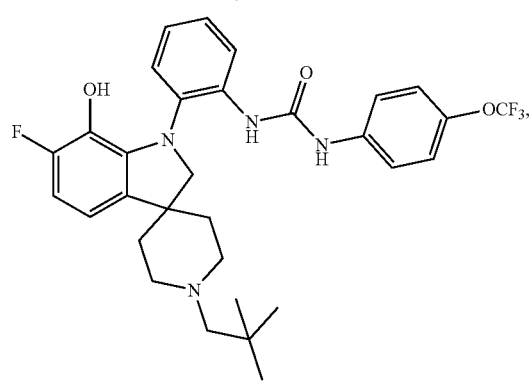
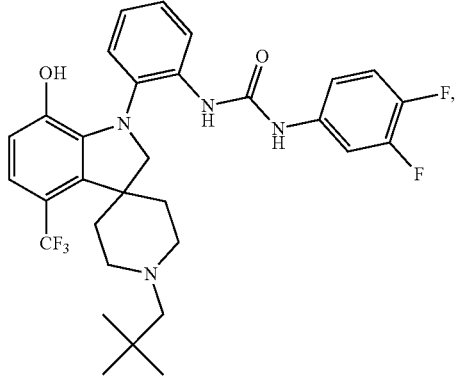
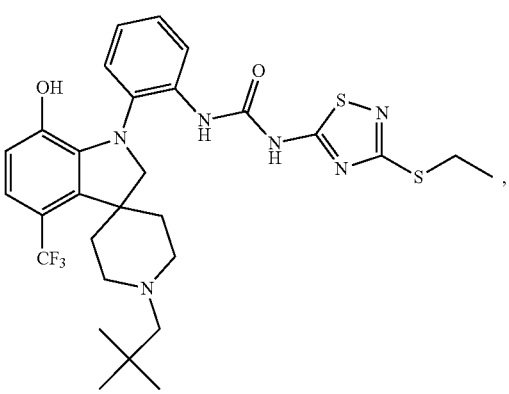

205
-continued
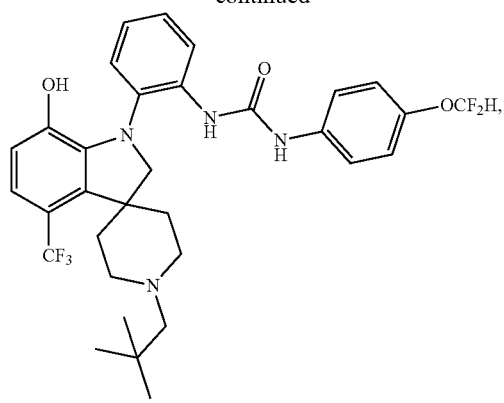
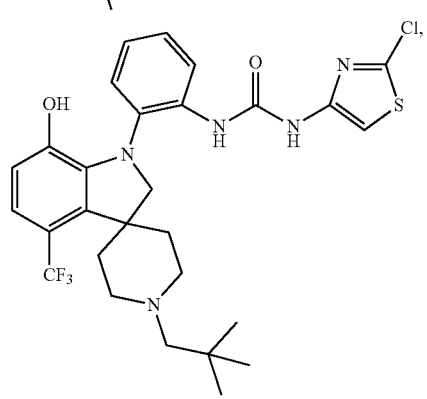
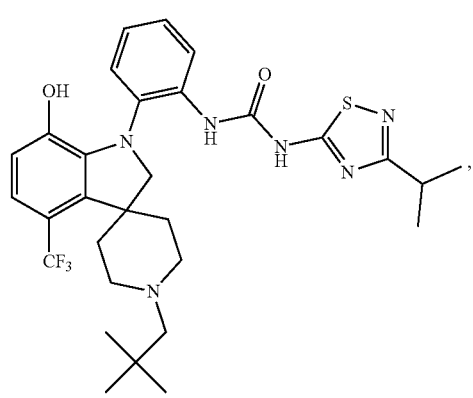
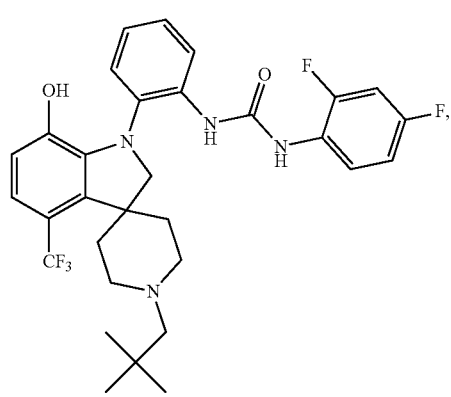
206
-continued
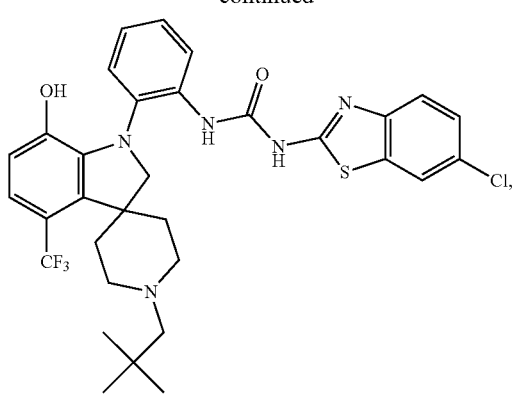
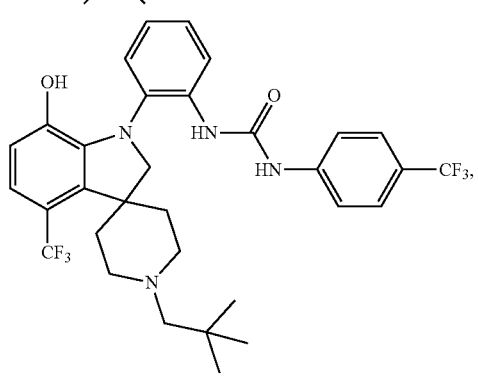
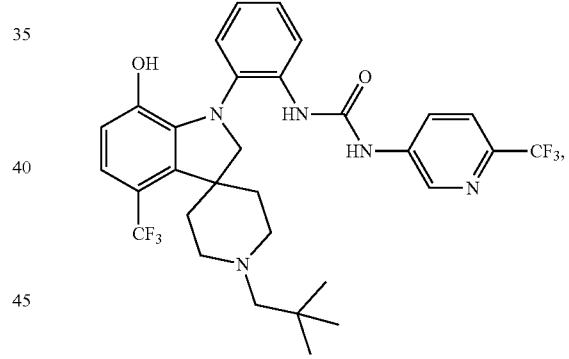
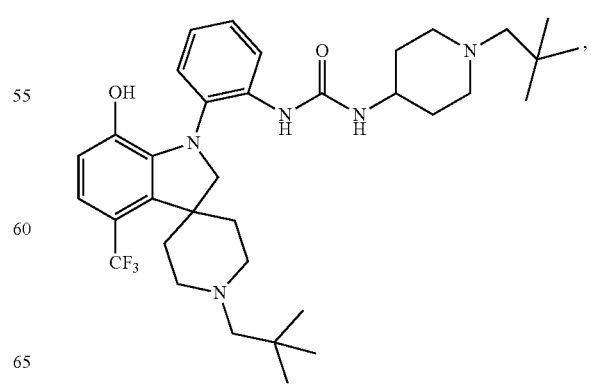

207
-continued
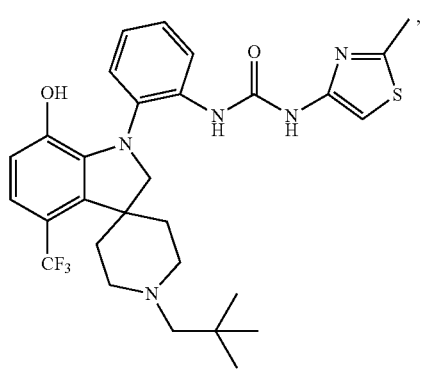
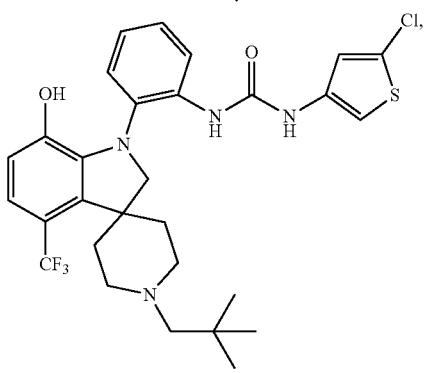
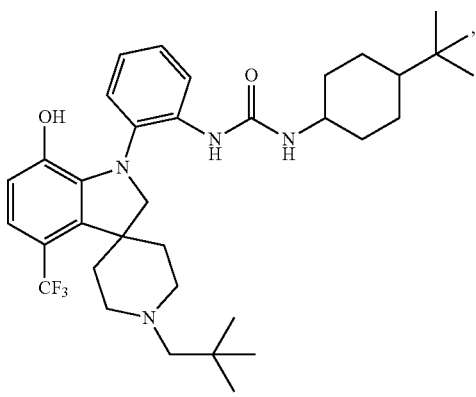
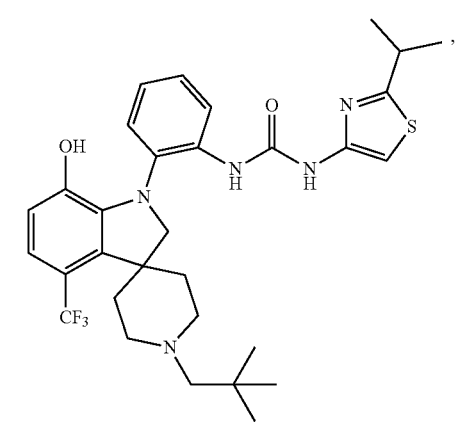
208
-continued
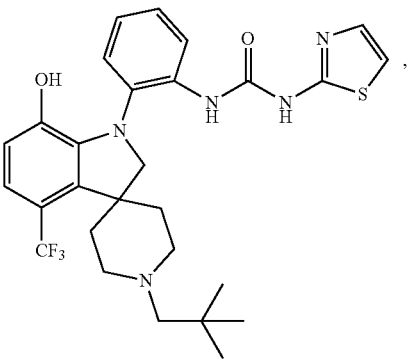
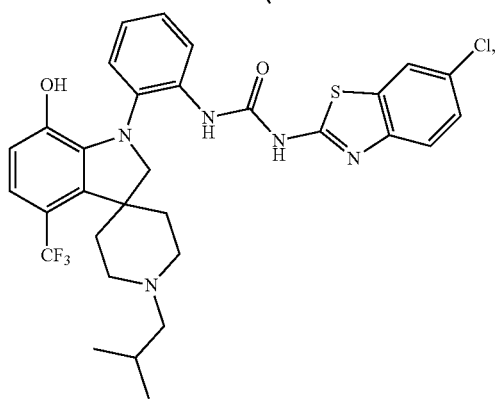
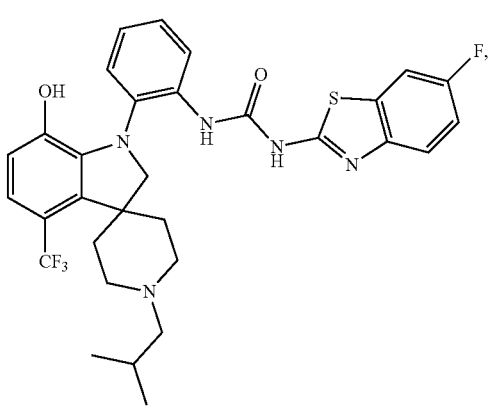
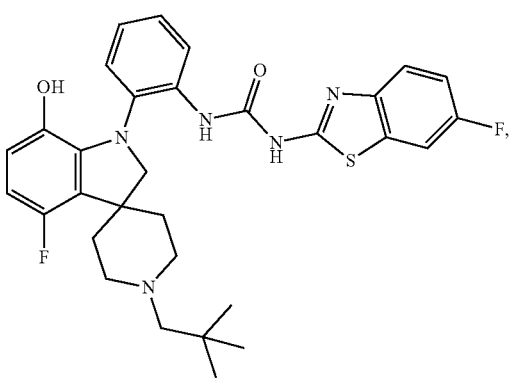

209
-continued
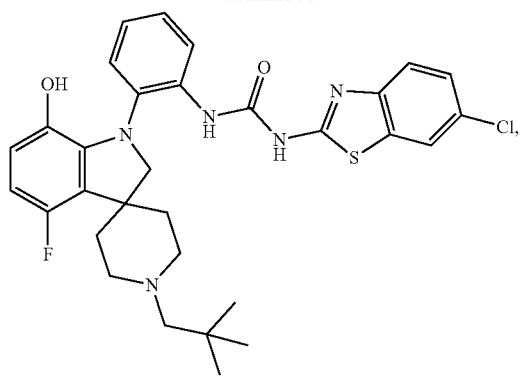
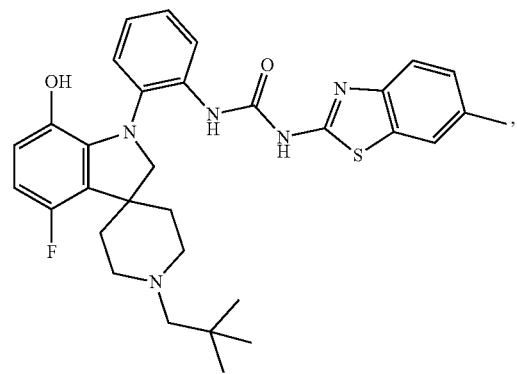
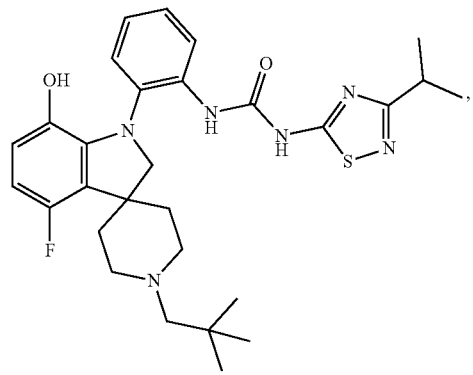
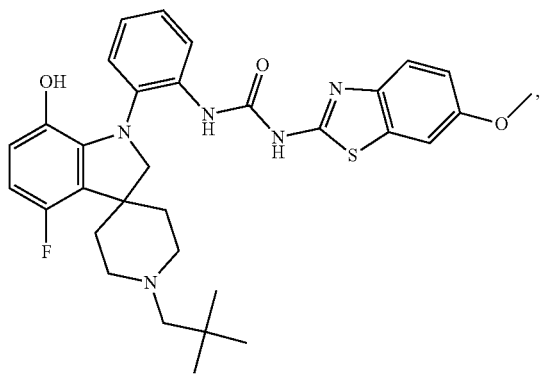
210
-continued
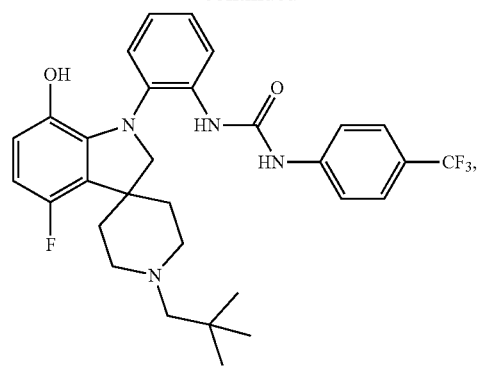
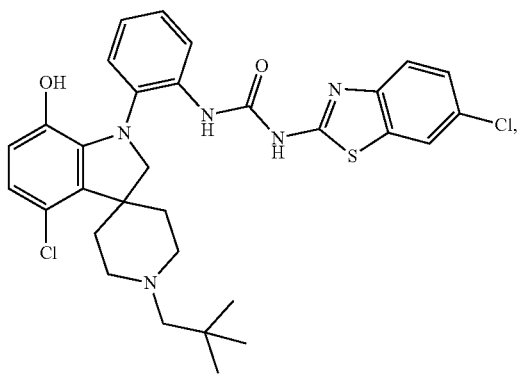
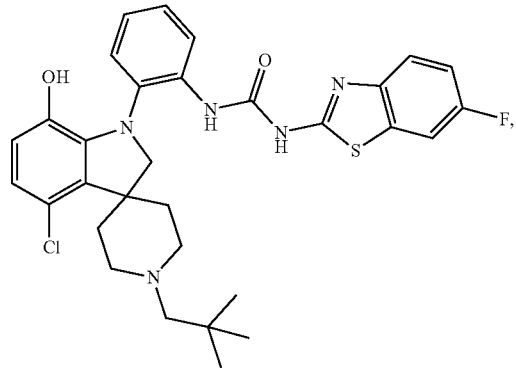
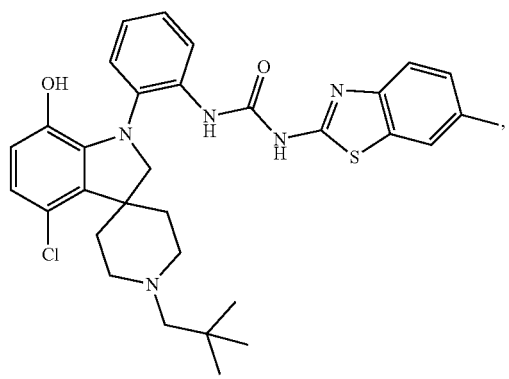

211
-continued
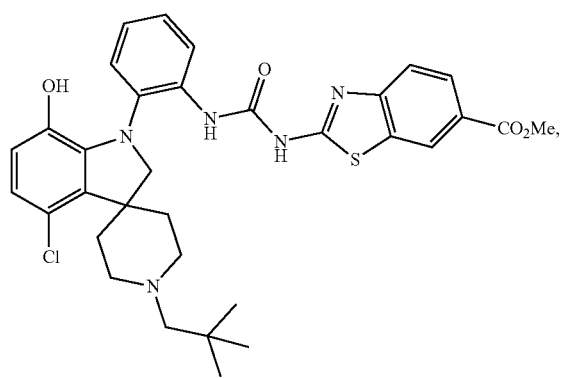
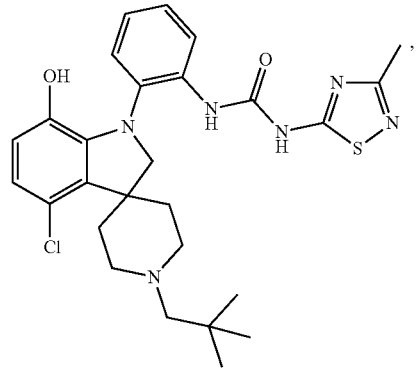
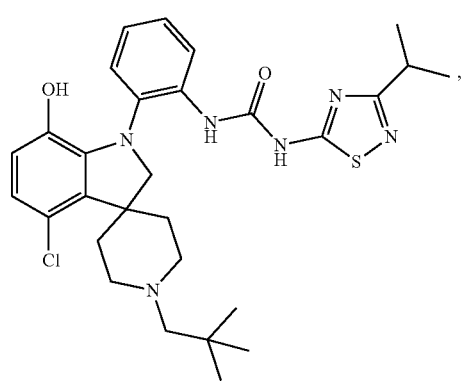
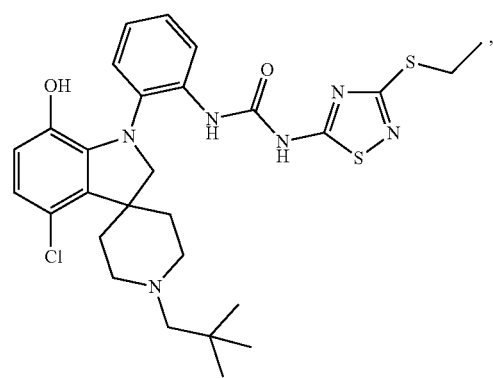
212
-continued
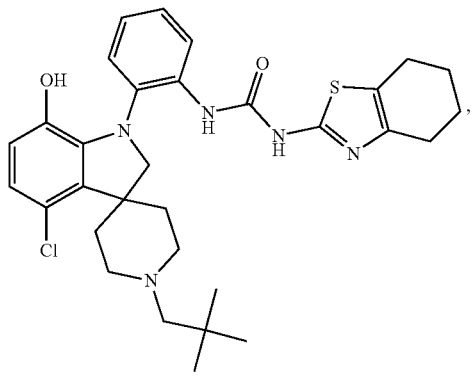
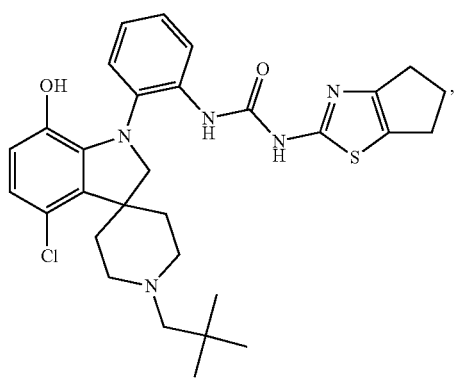
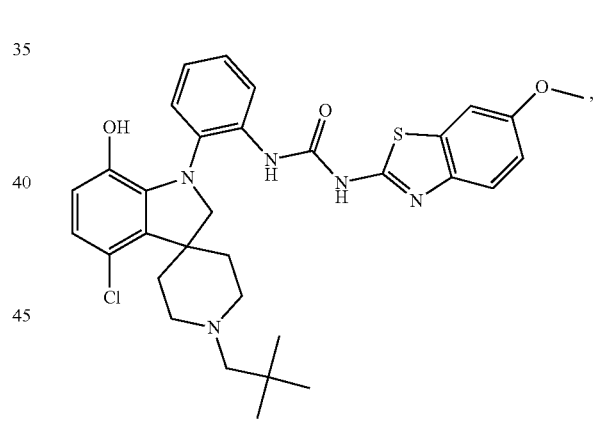
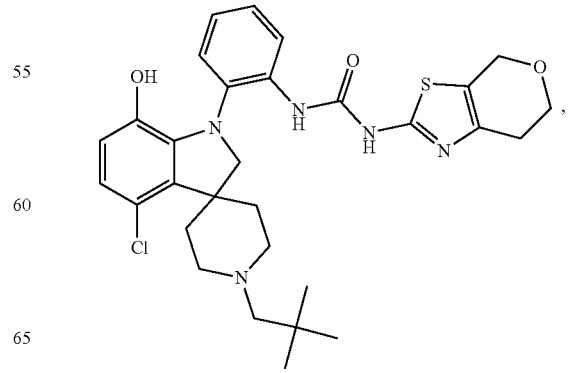

213
-continued
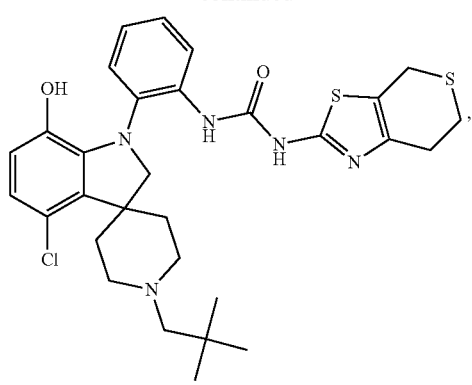
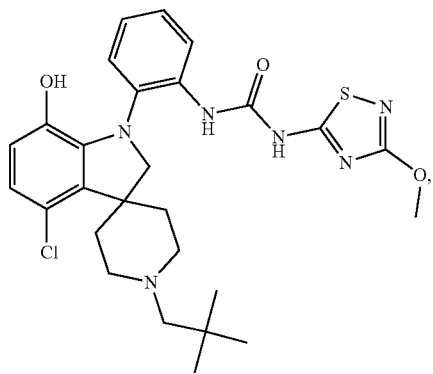
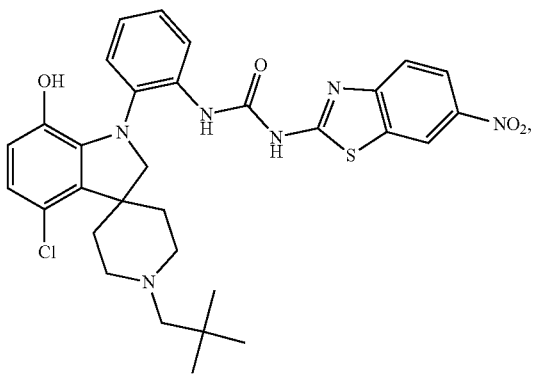
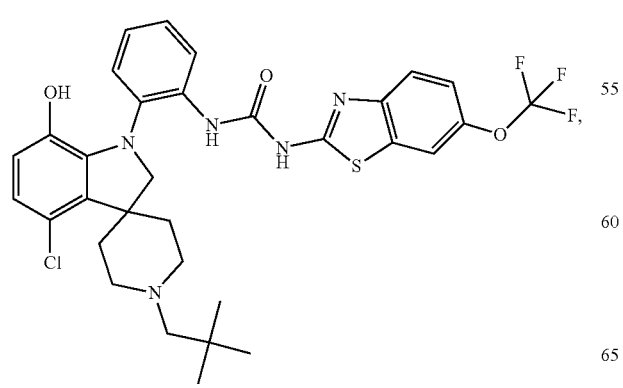
214
-continued
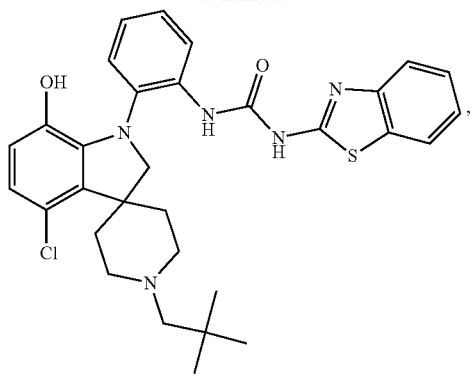
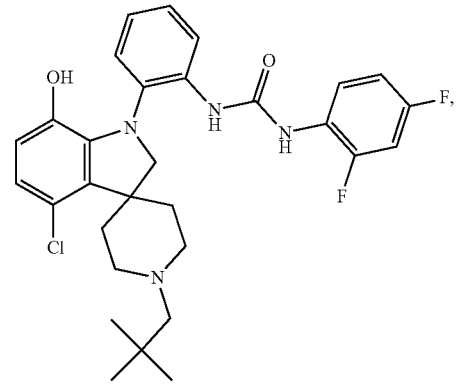
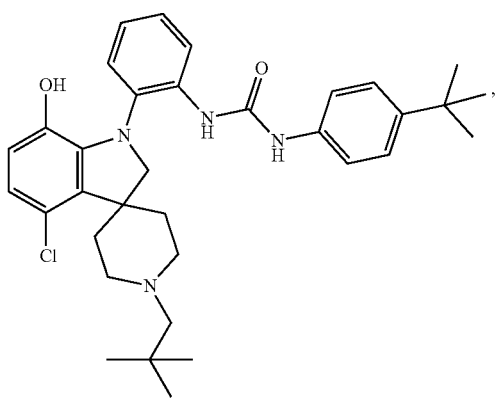
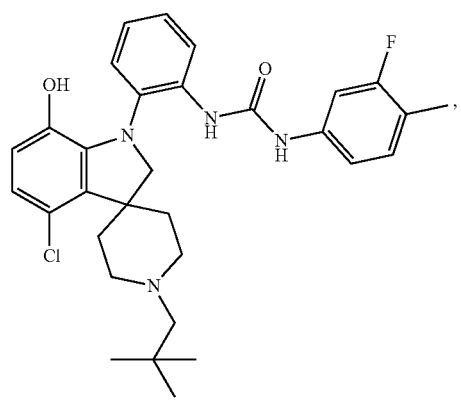

215
-continued
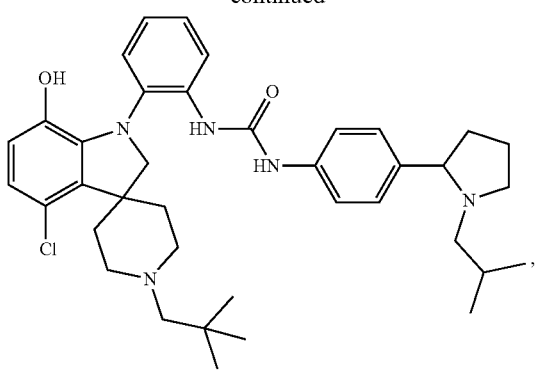
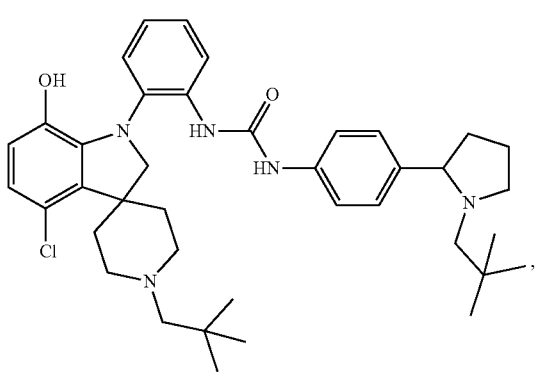
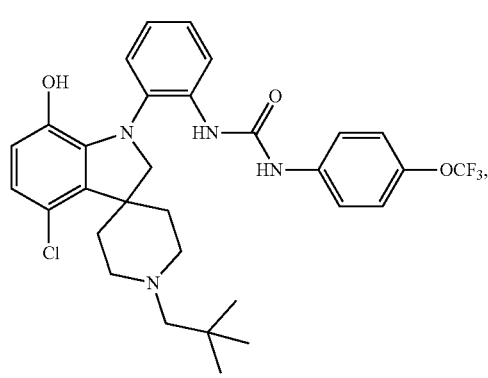
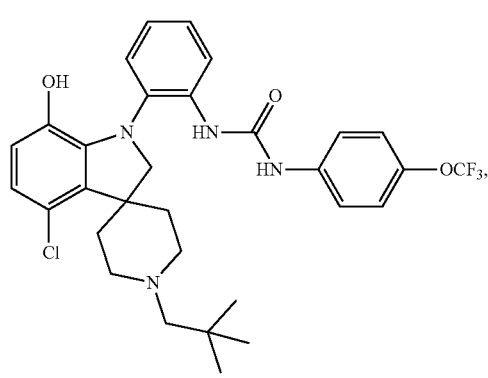
216
-continued
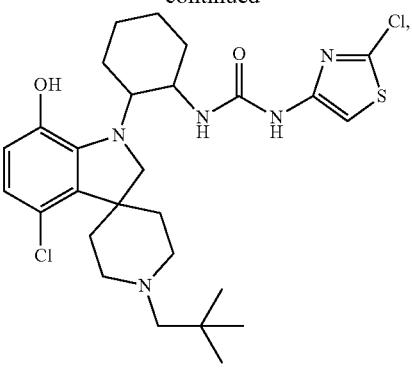
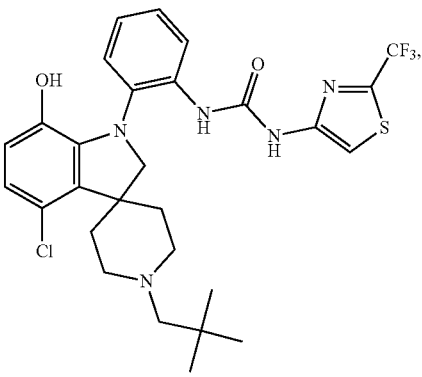
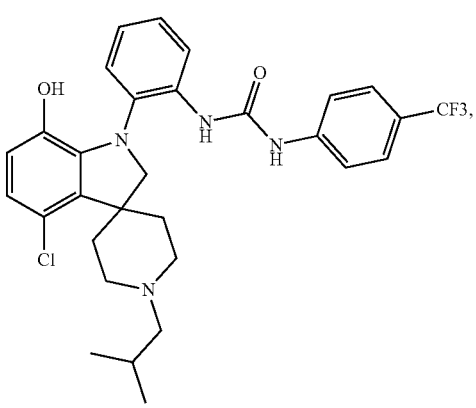

217
-continued
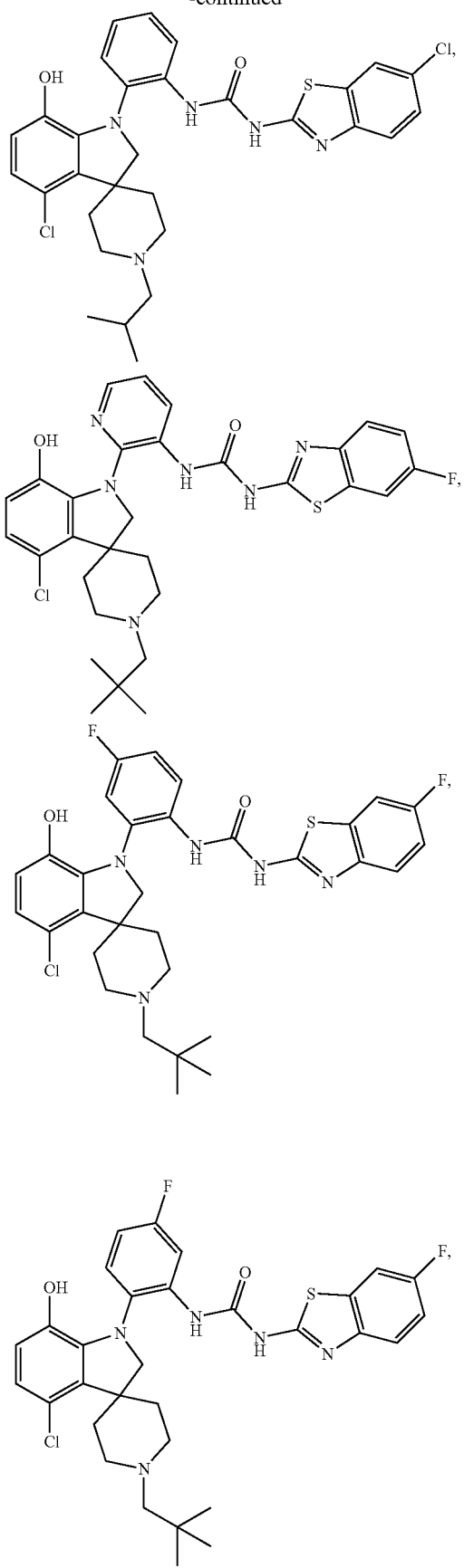
218
-continued
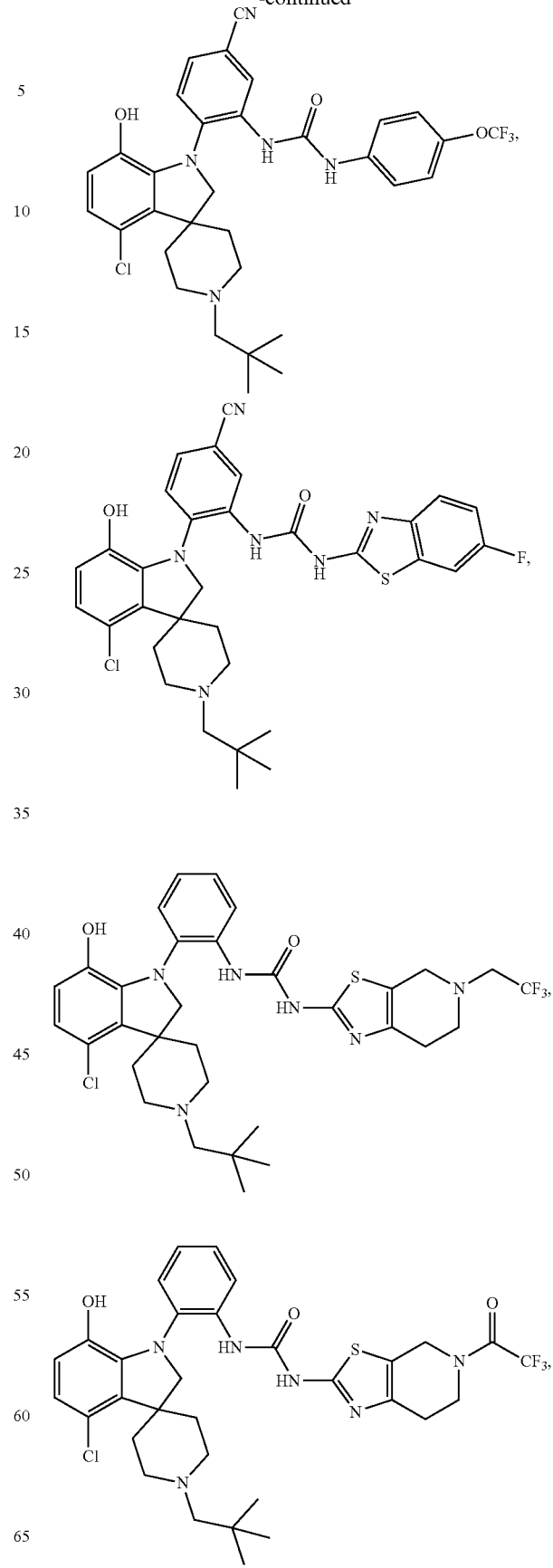

219
-continued
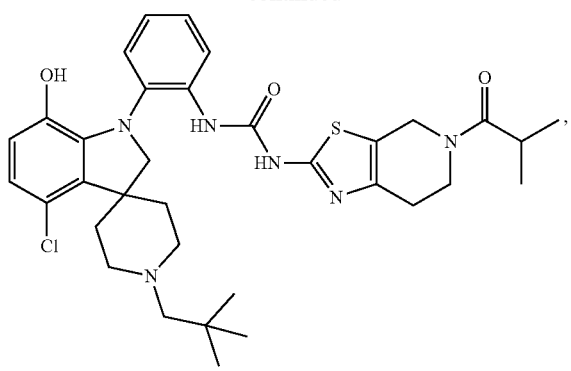
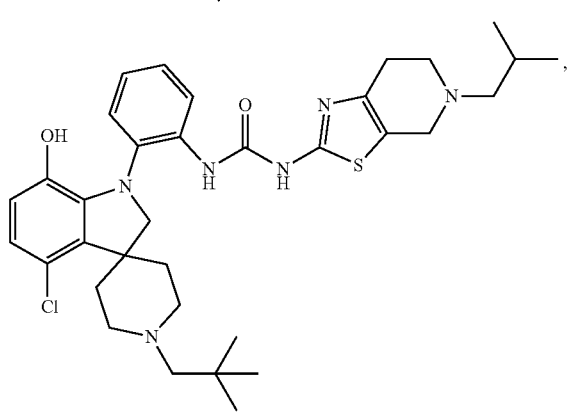
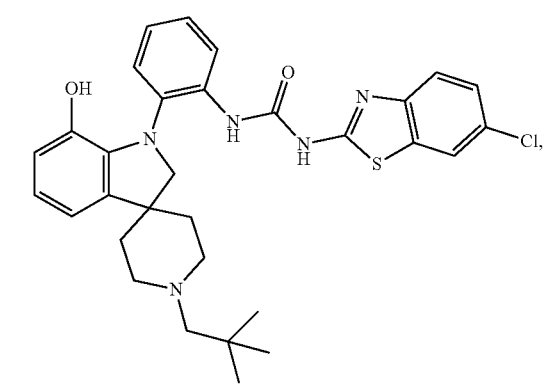
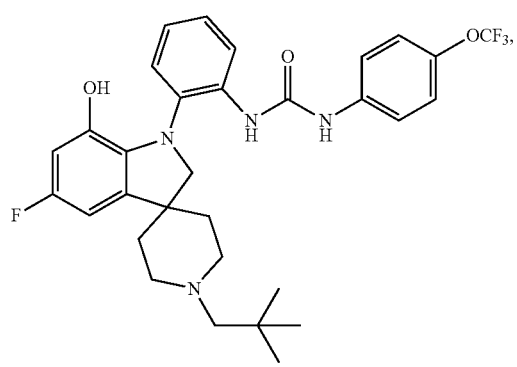
220
-continued
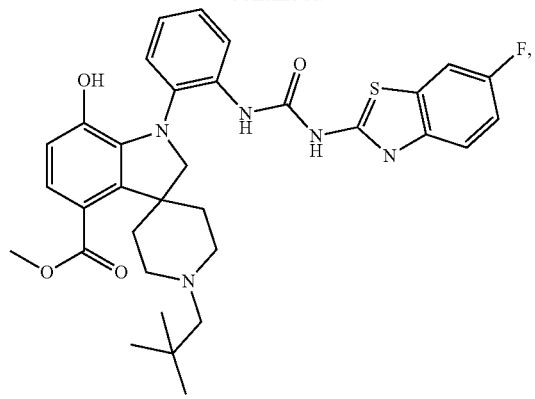
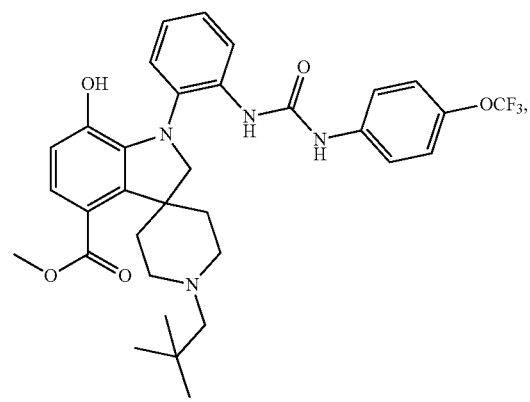
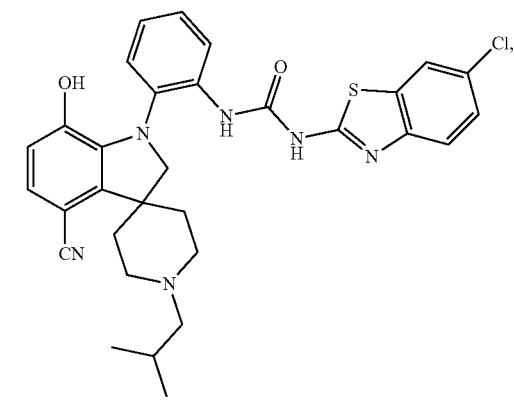

221
-continued
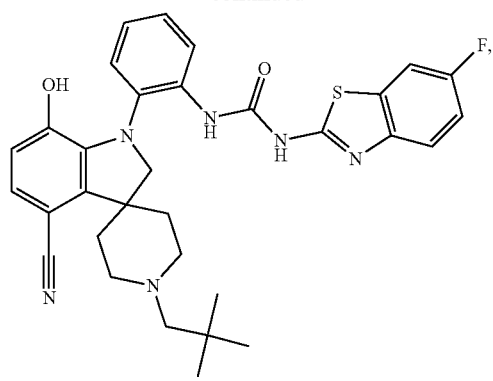
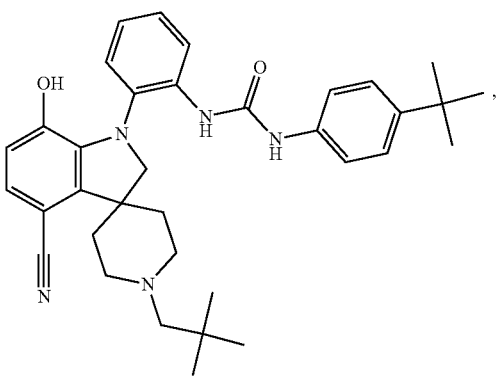
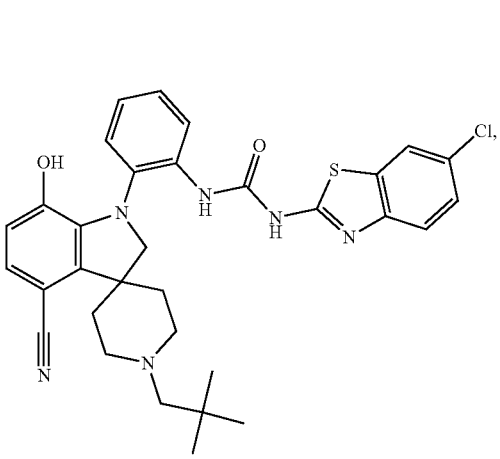
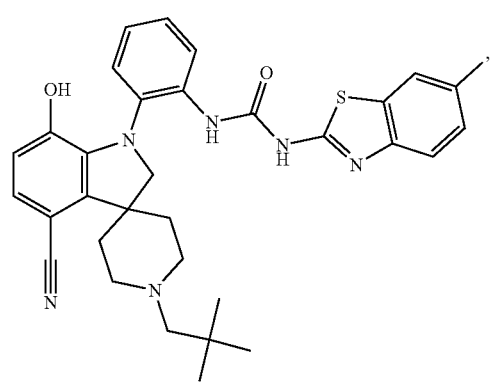
222
-continued
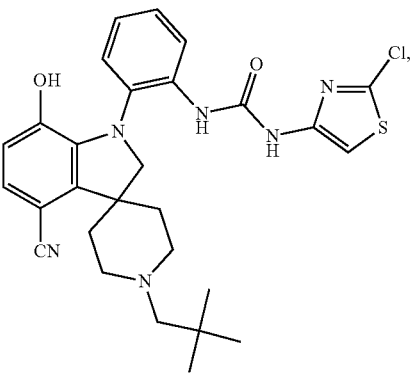
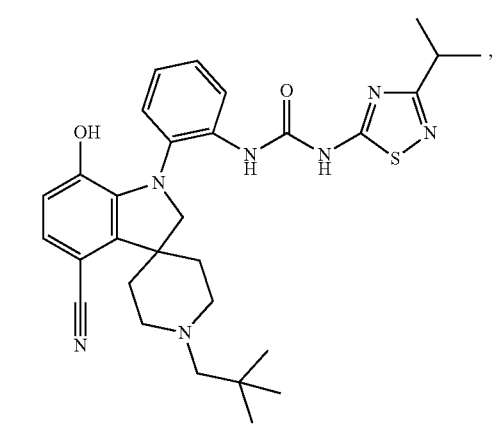

223
-continued
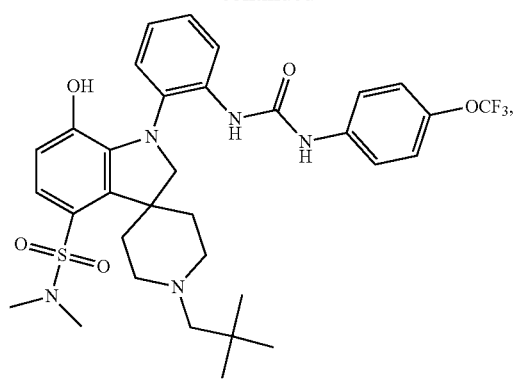
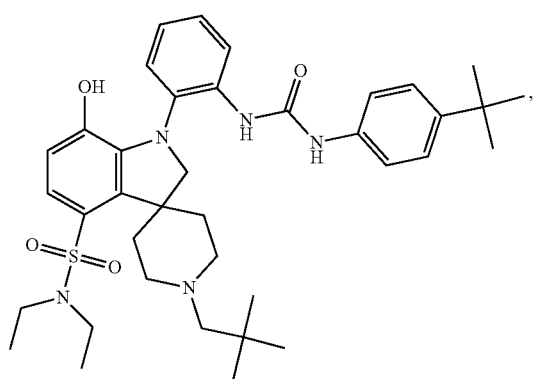
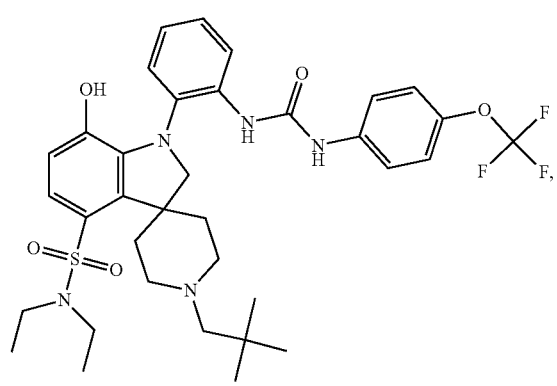
224
-continued
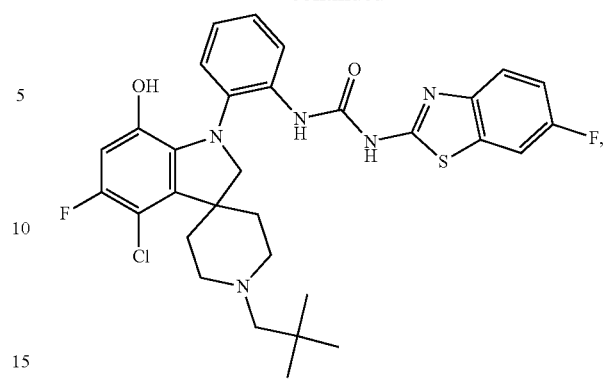
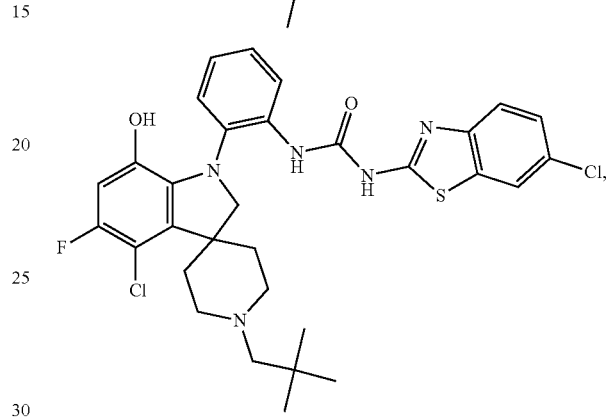
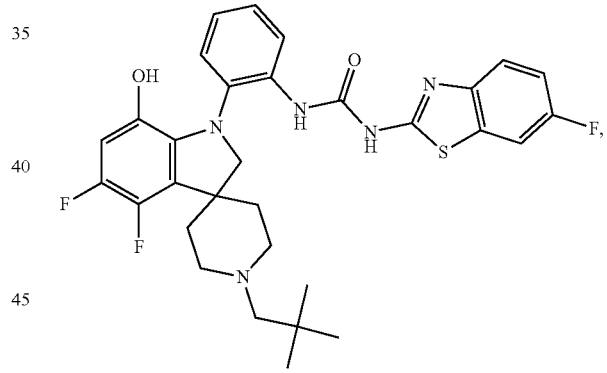
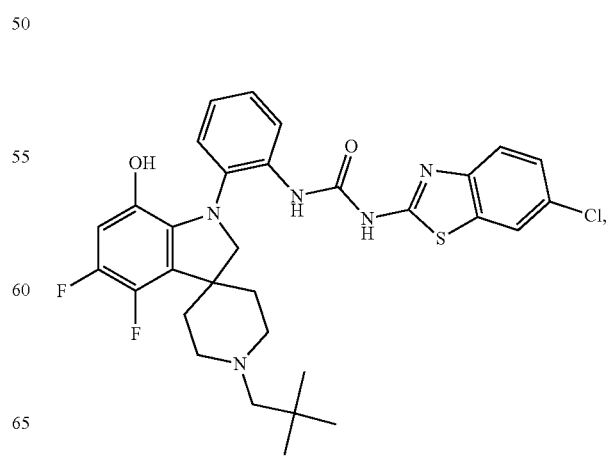

225
-continued
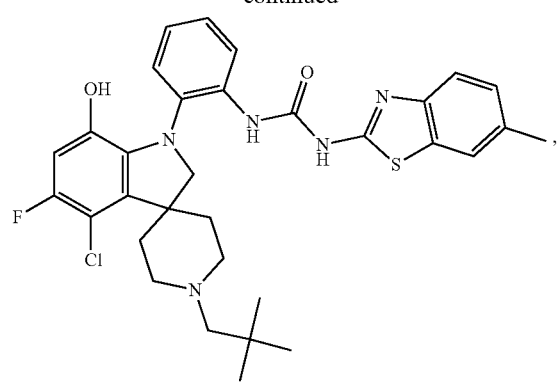
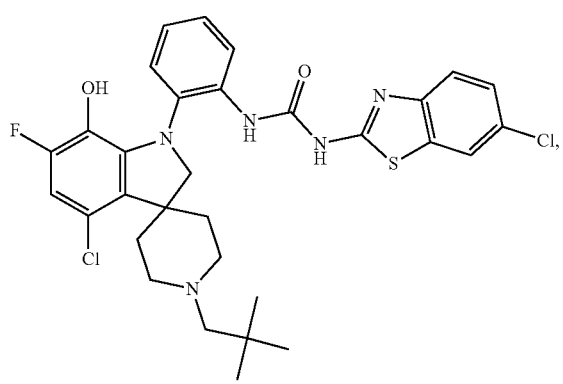
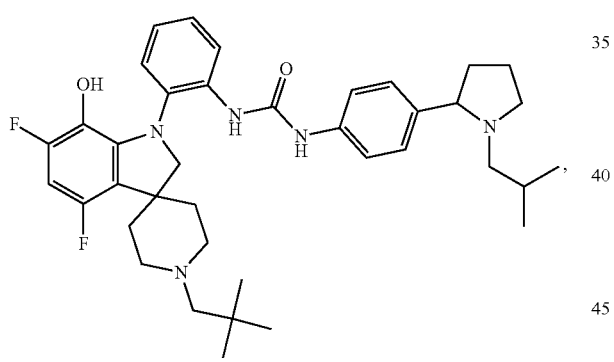
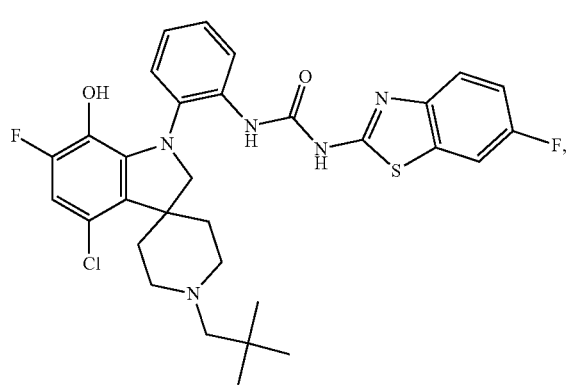
226
-continued
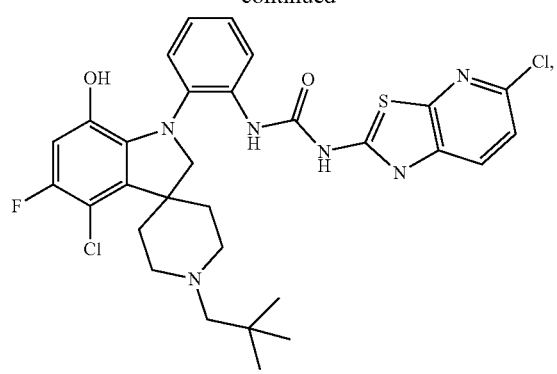
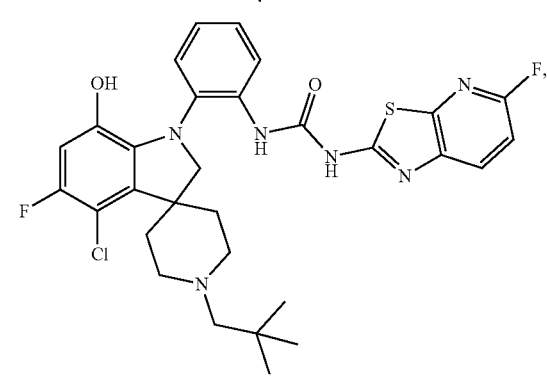
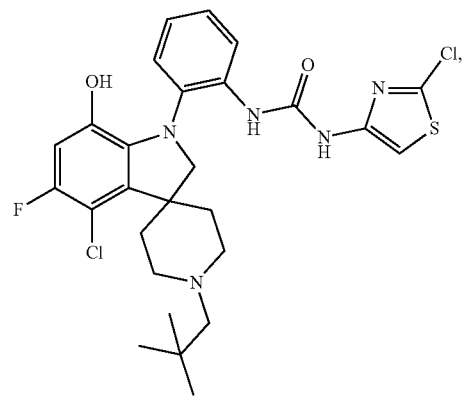
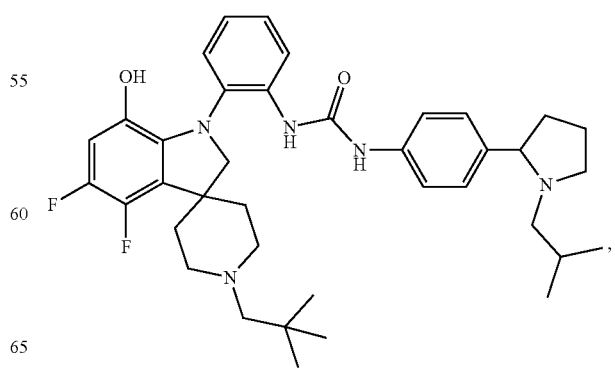

227
-continued
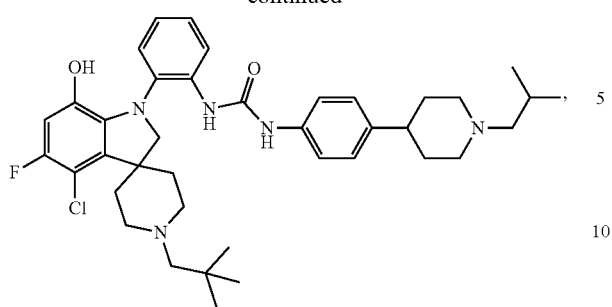
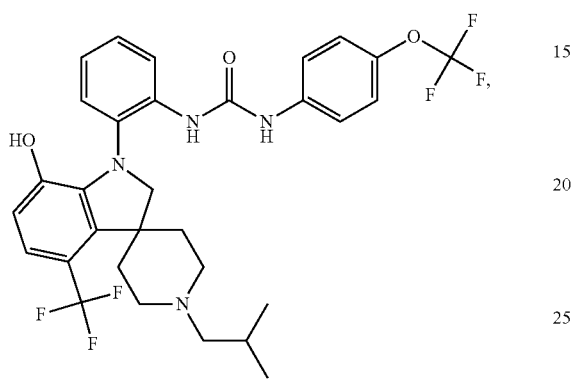
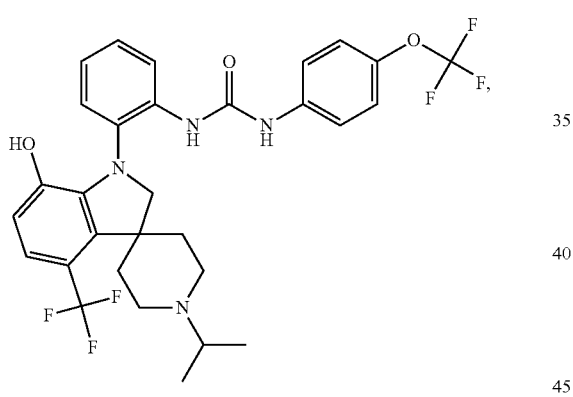
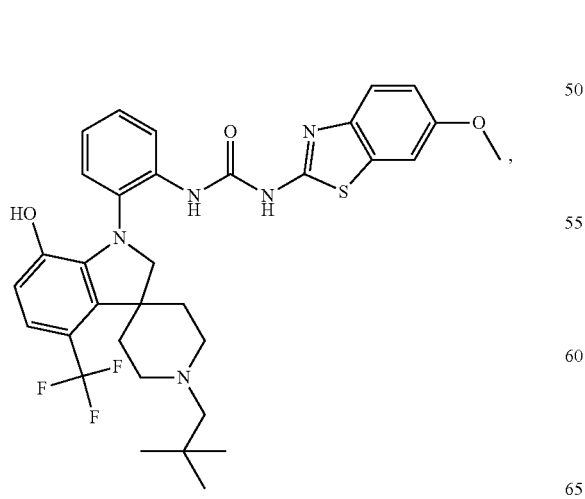
228
-continued
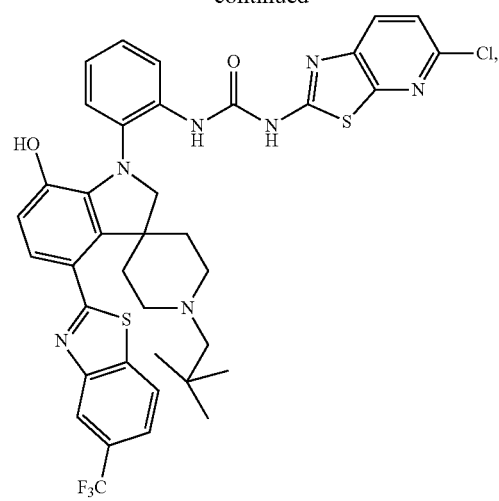
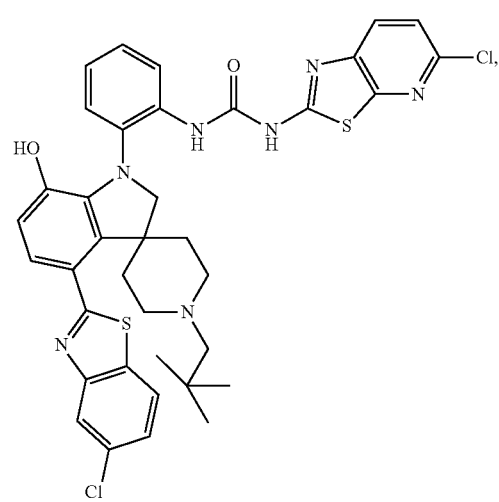
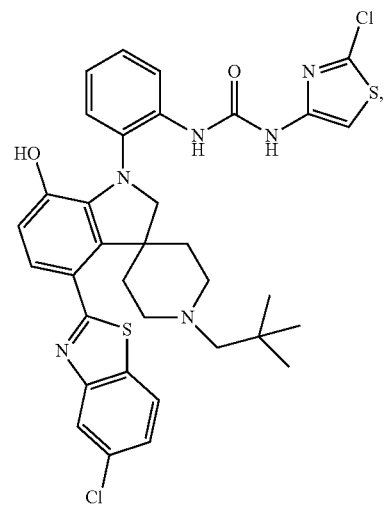

229
-continued
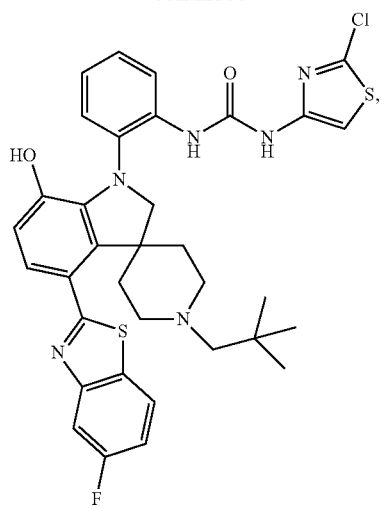
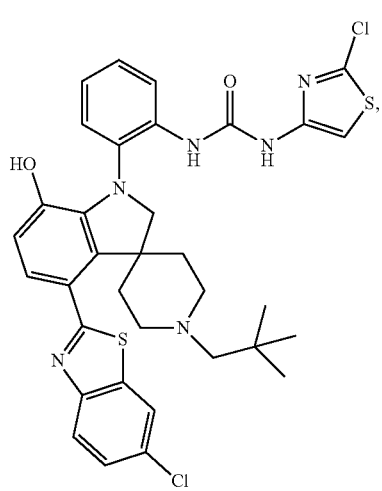
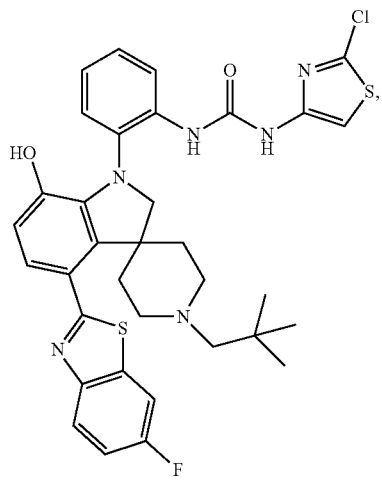
230
-continued
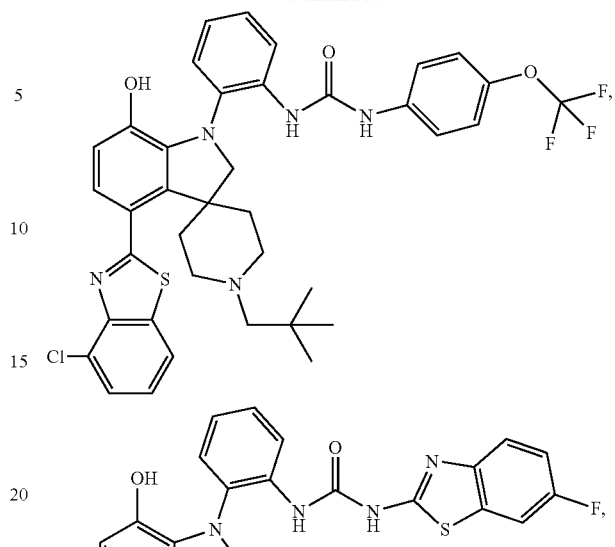
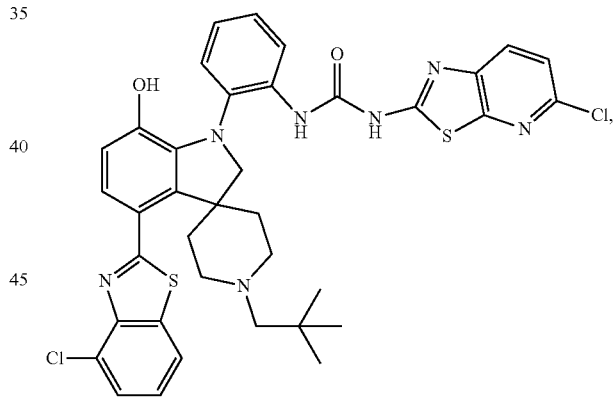
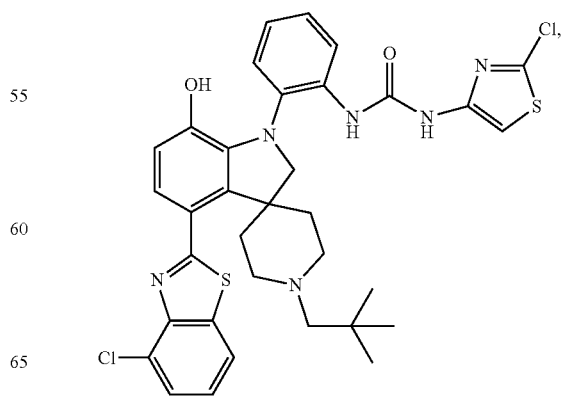

231
-continued
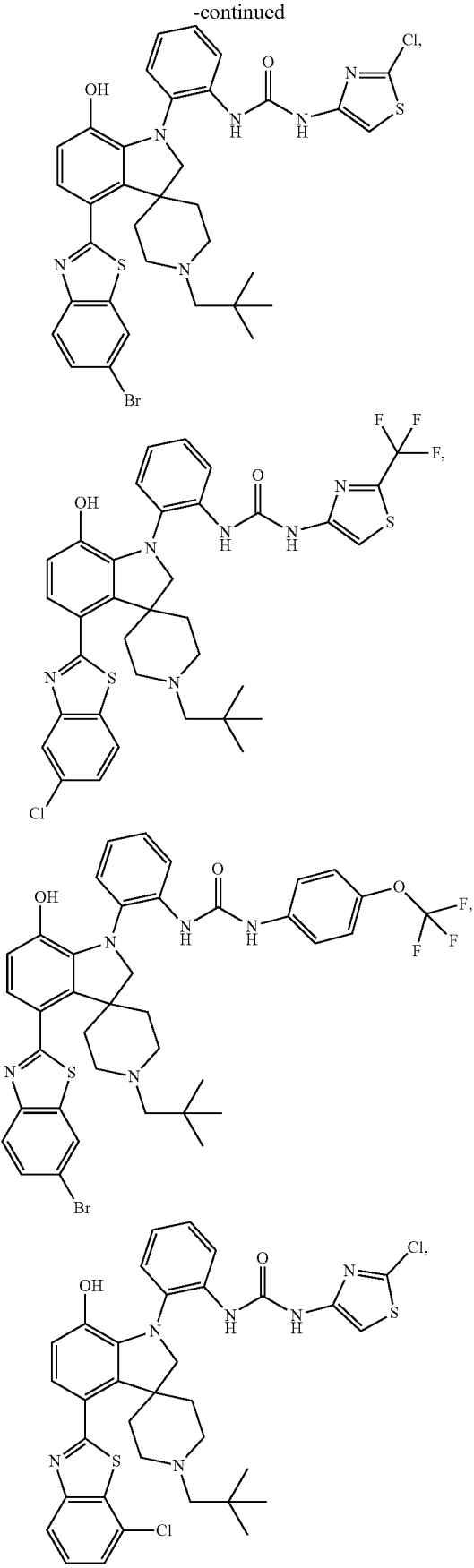
232
-continued
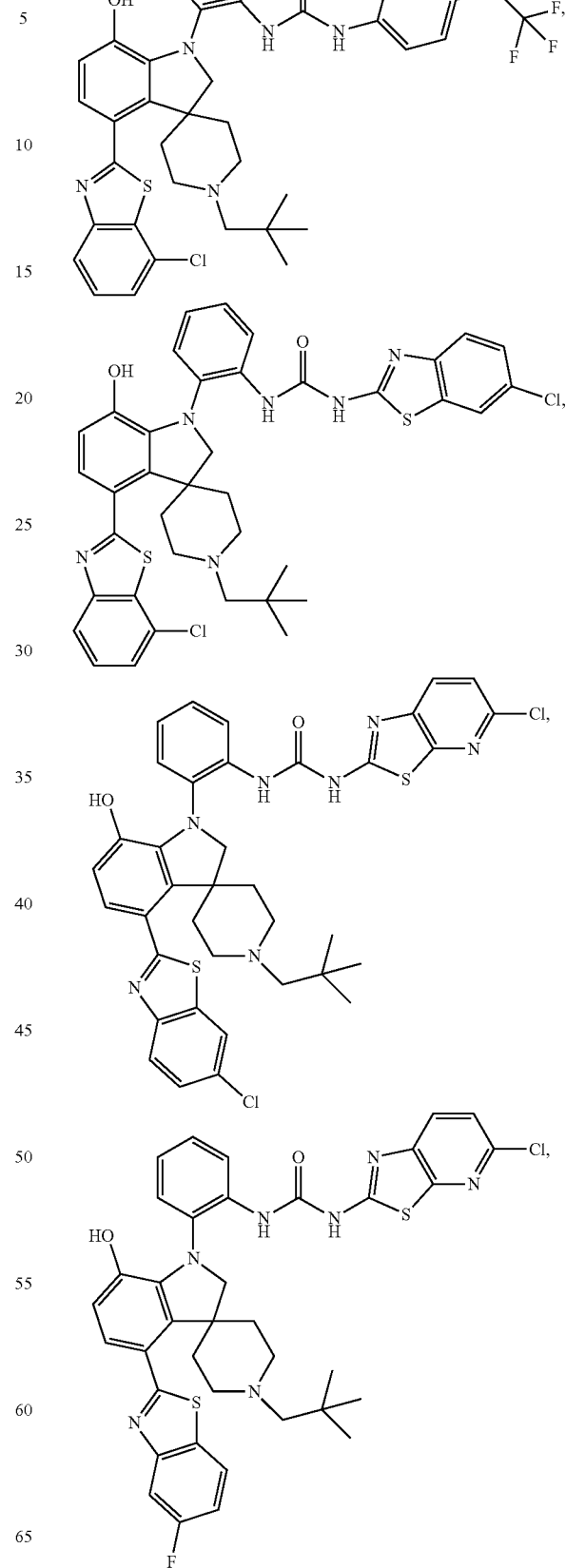

233
-continued
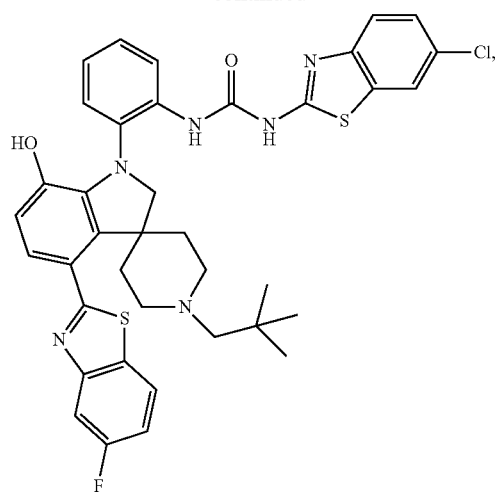
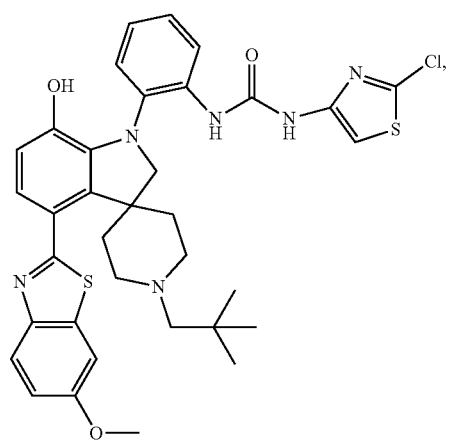
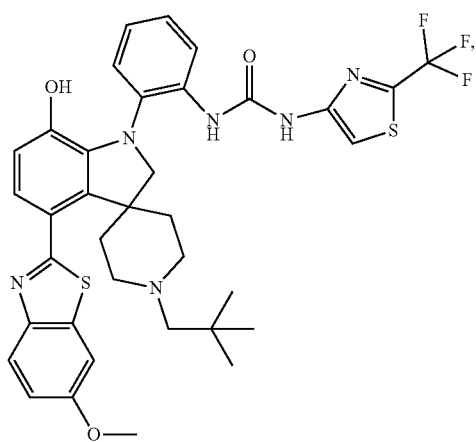
234
-continued
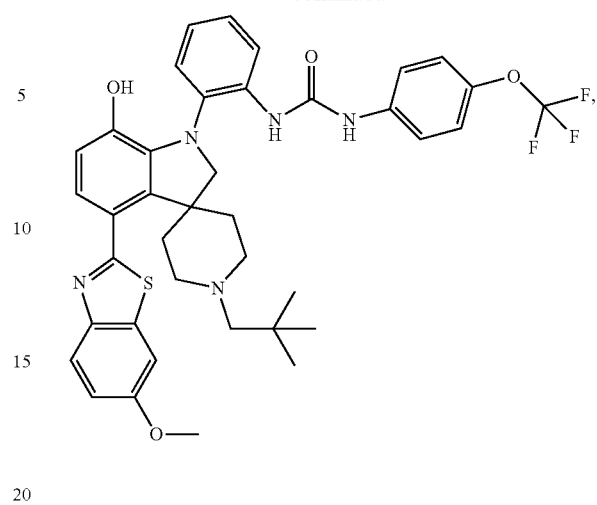
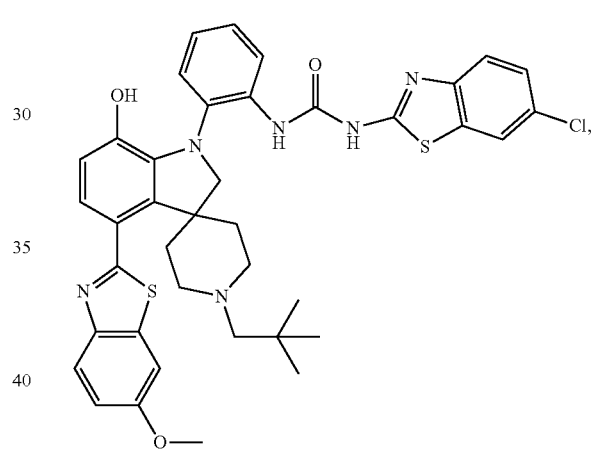
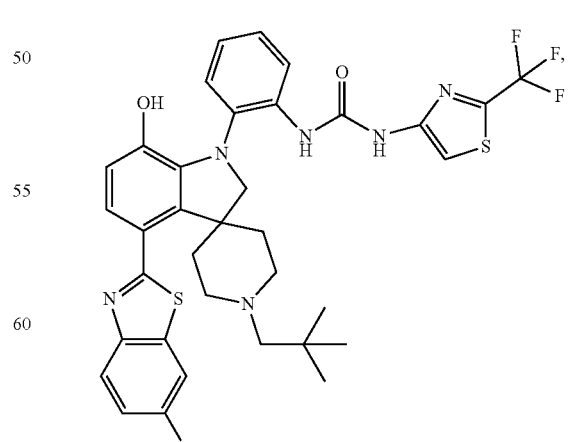

235 -continued
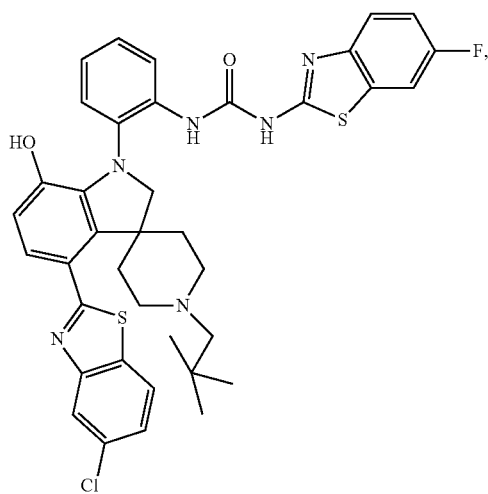
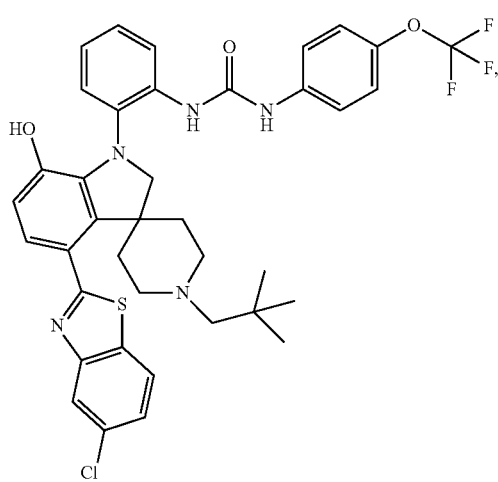
236 -continued
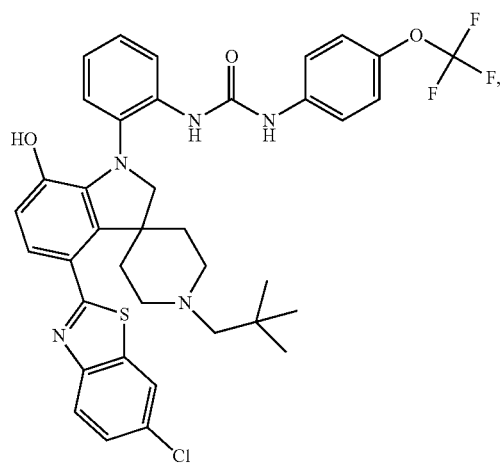
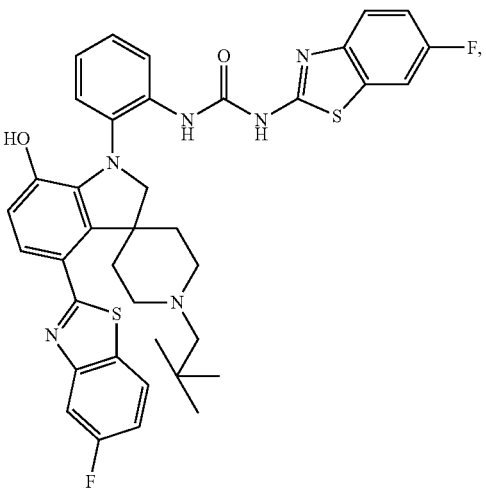

237
-continued
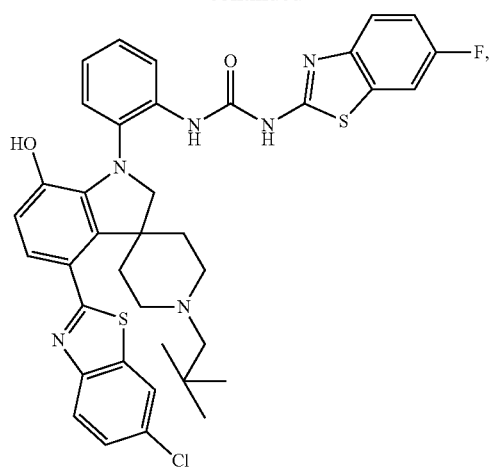
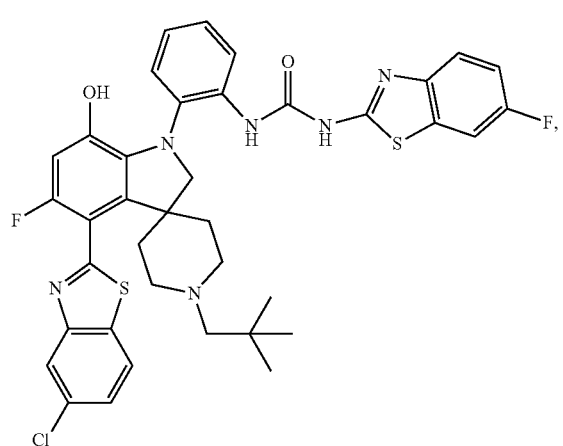
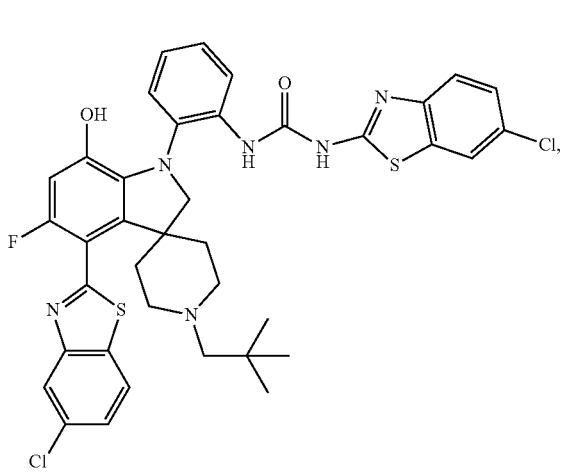
238
-continued
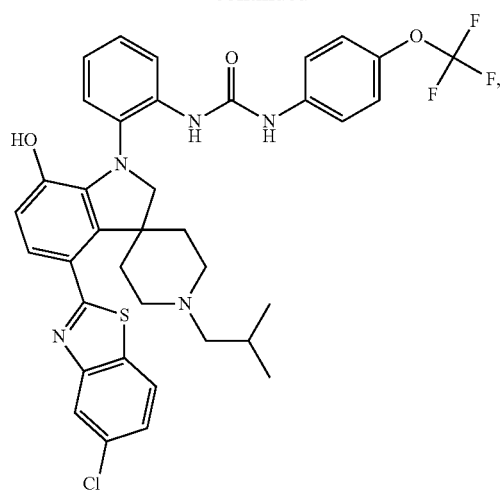
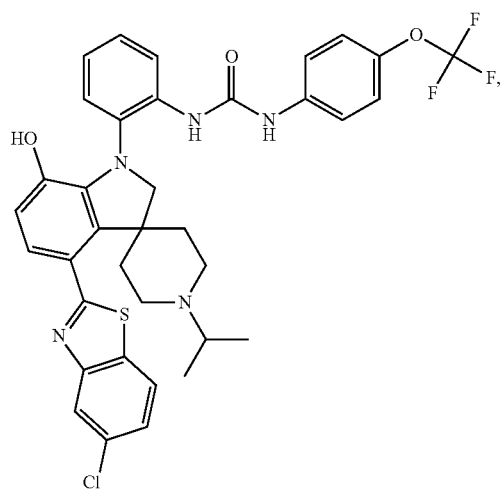
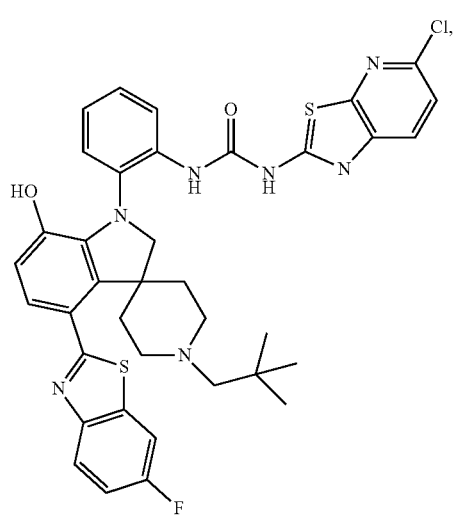

239
-continued
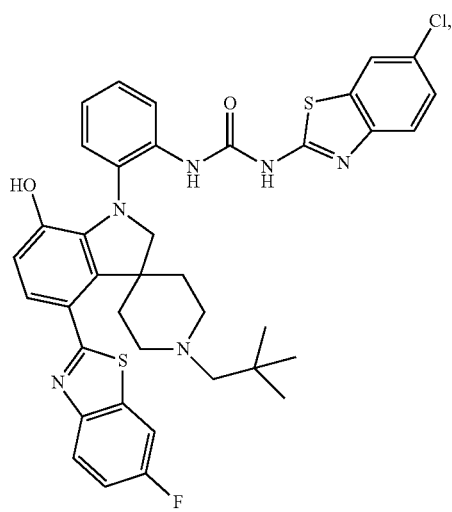
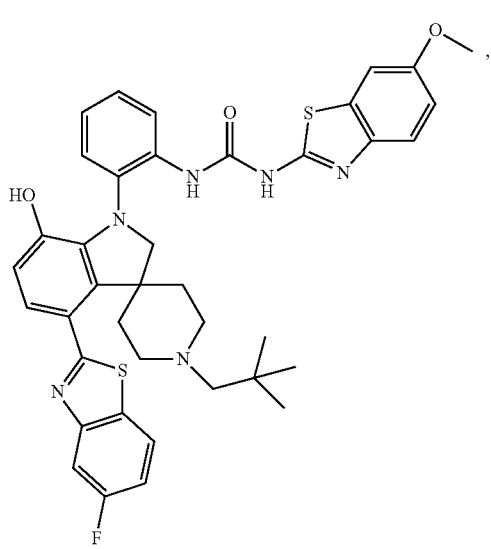
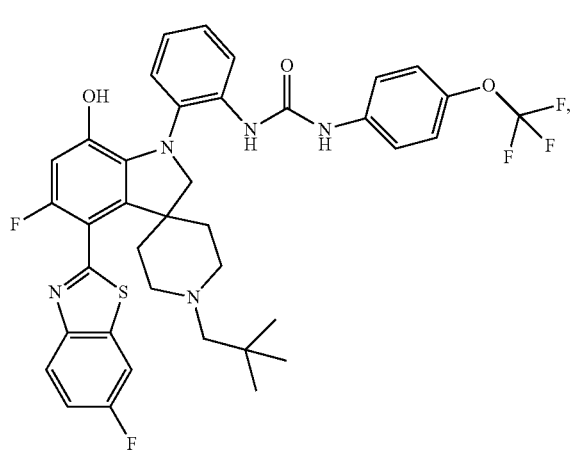
240
-continued
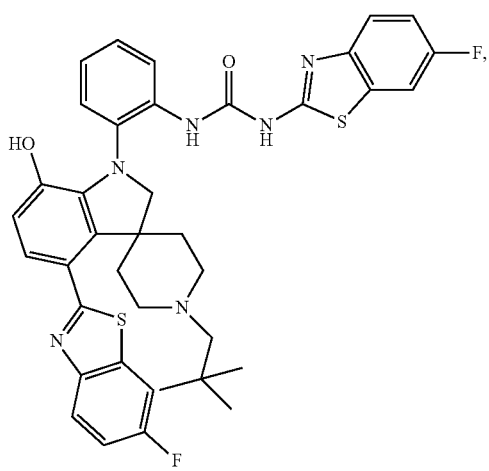
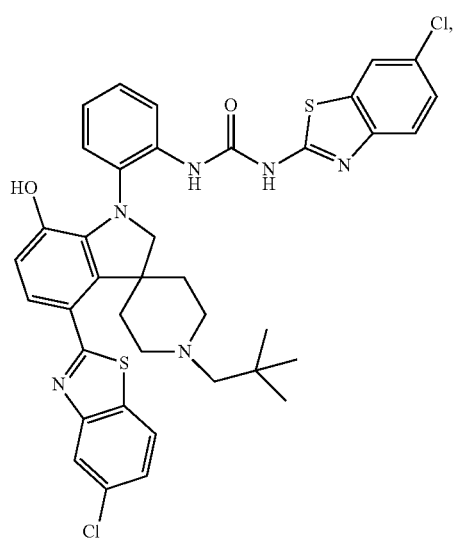
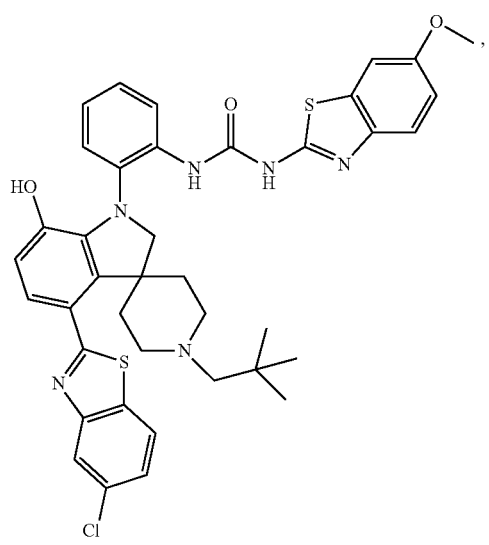

241
-continued
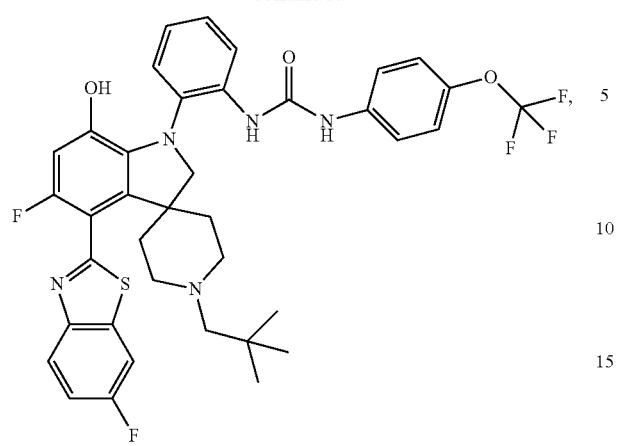
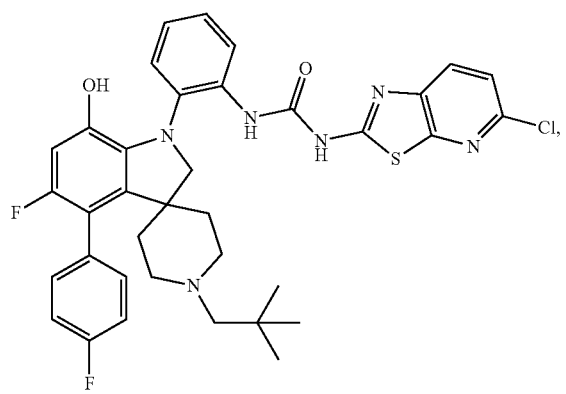
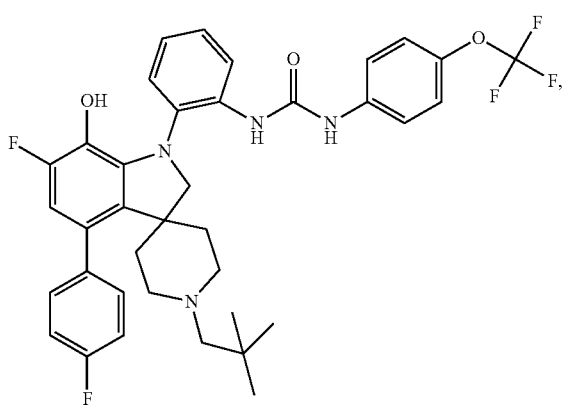
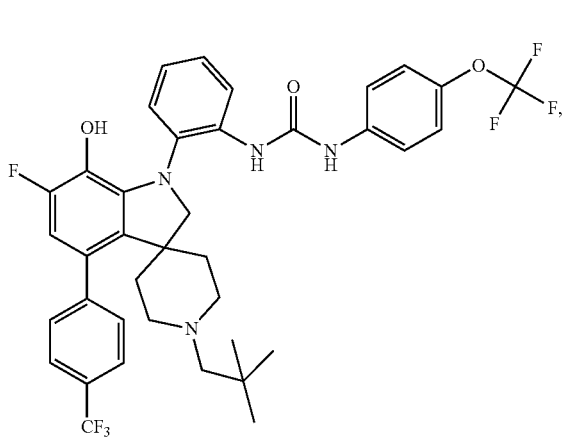
242
-continued
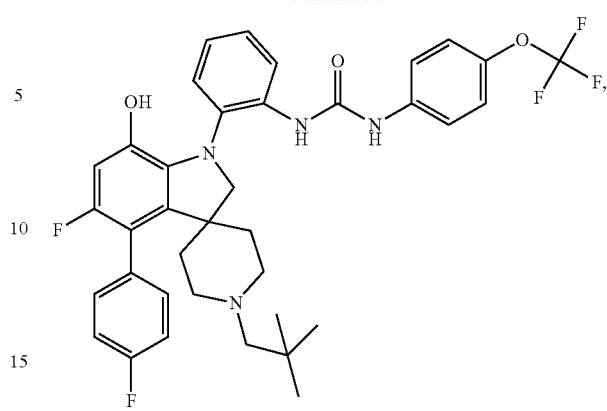
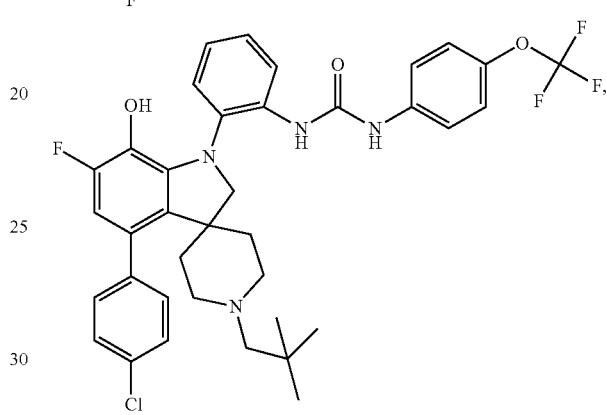
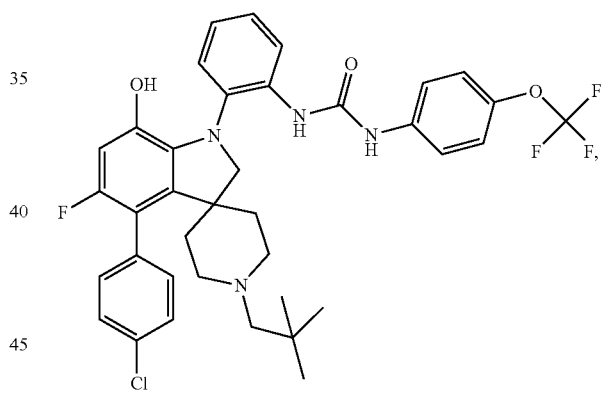
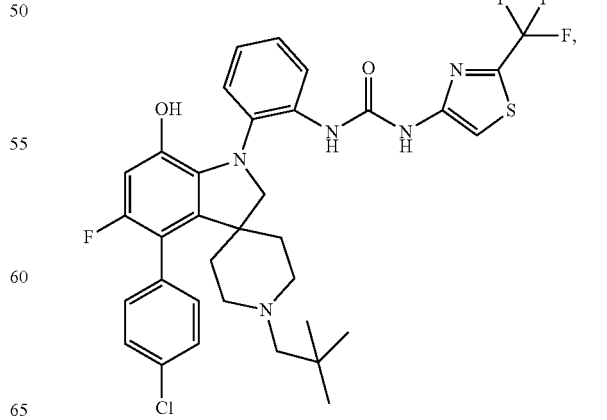

243
-continued
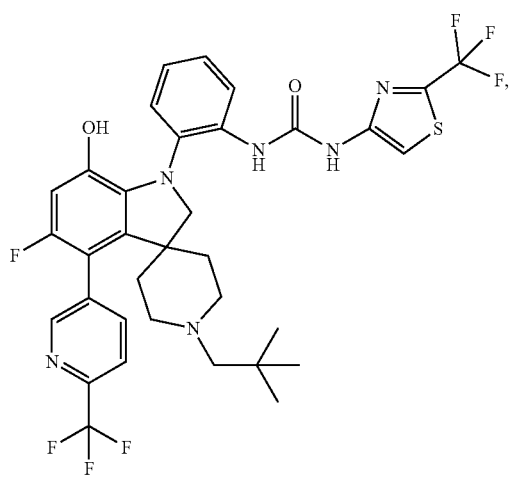
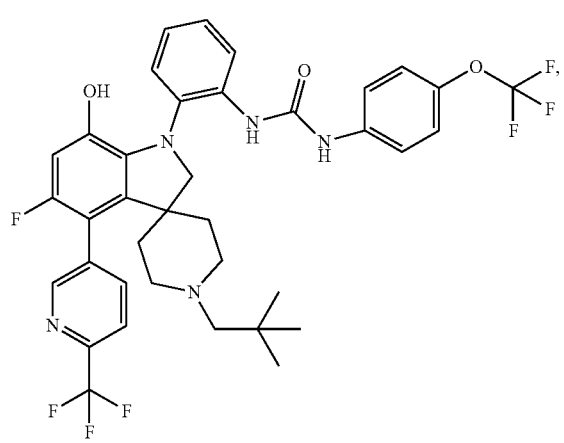
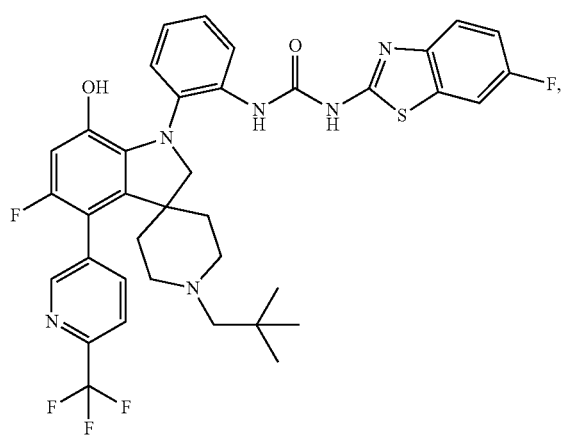
244
-continued
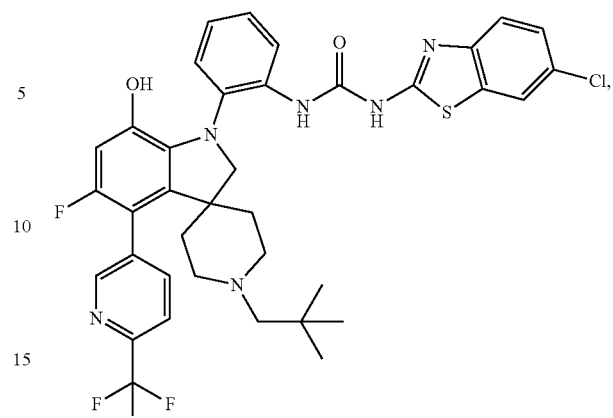
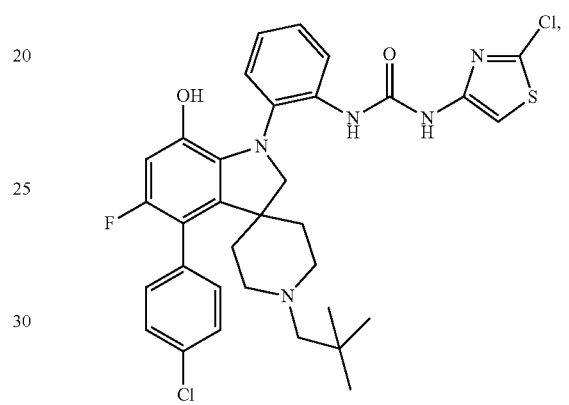
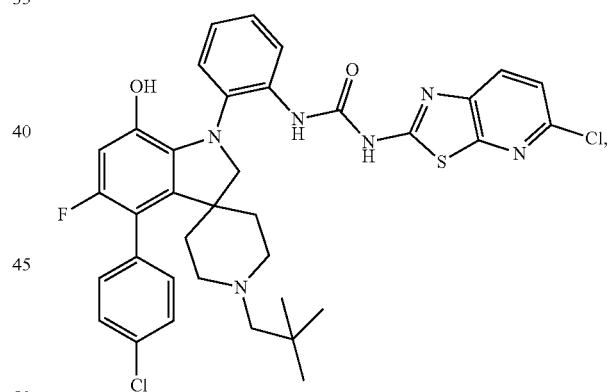
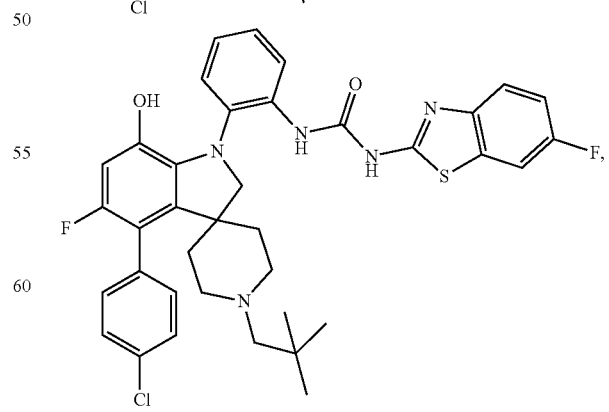

245
-continued
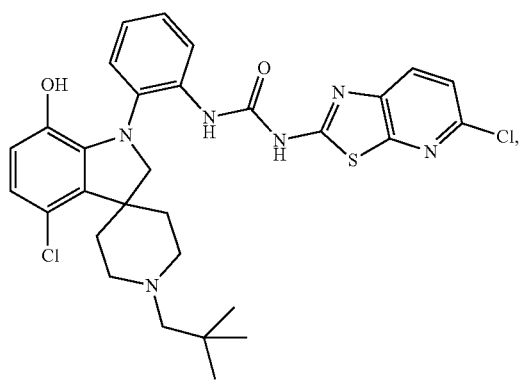
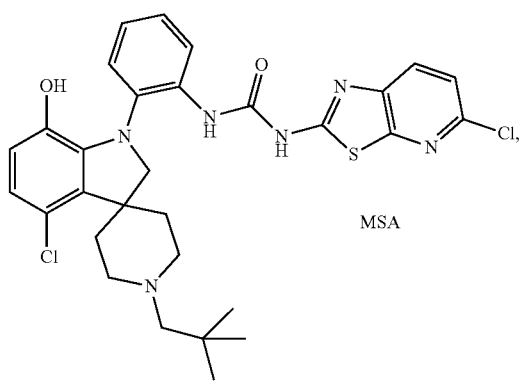
MSA
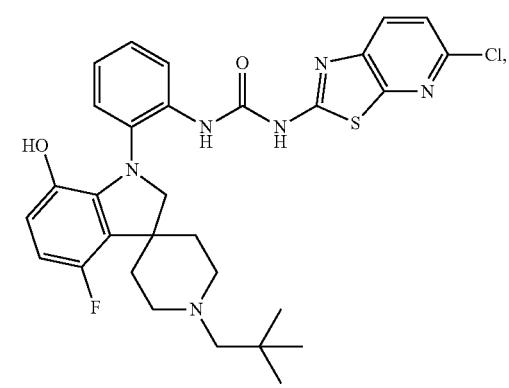
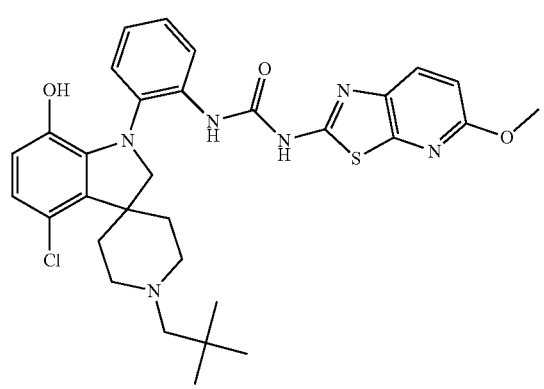
246
-continued
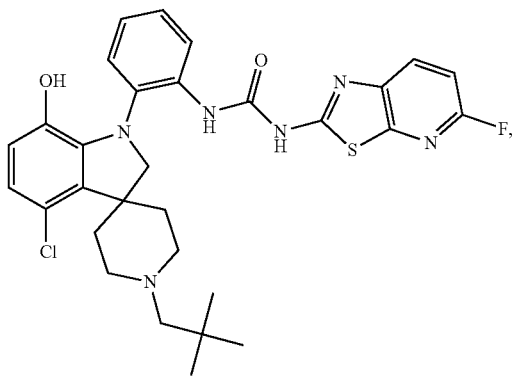
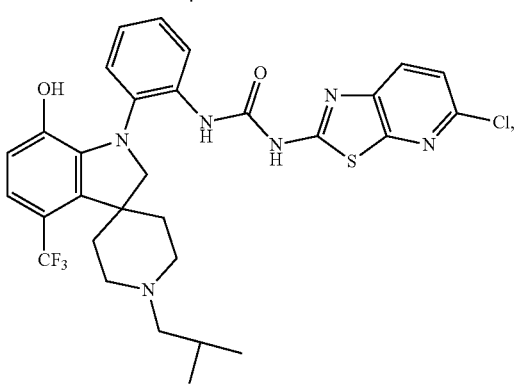
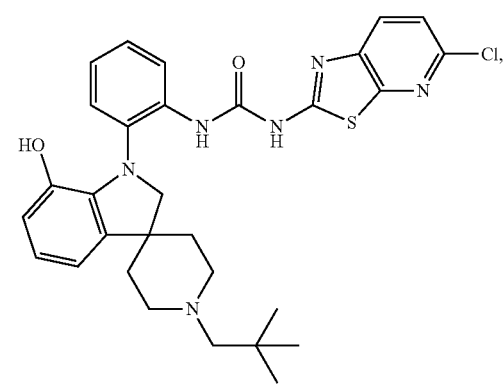
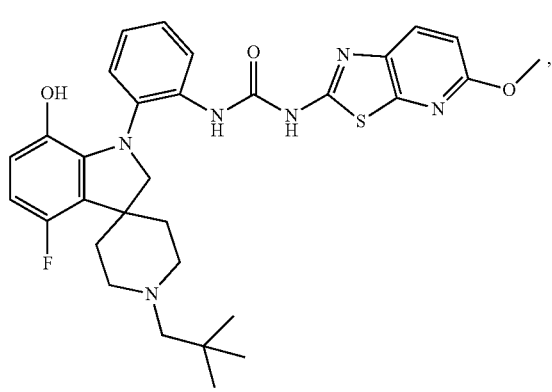

247
-continued
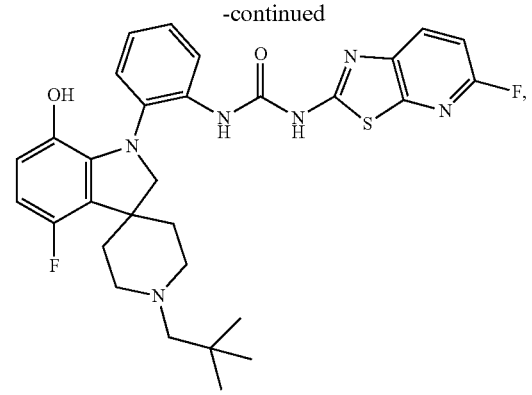
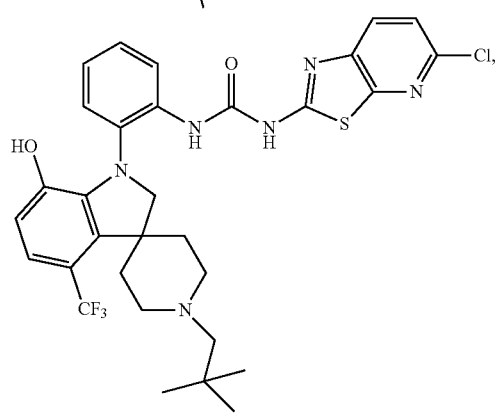
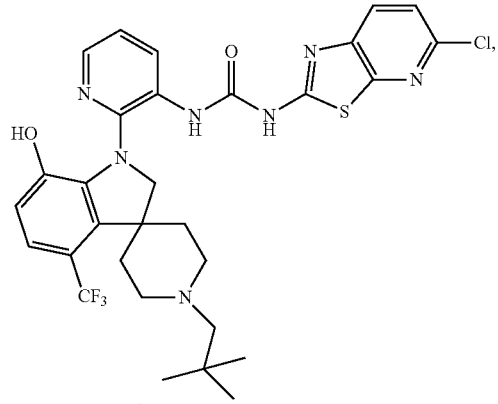
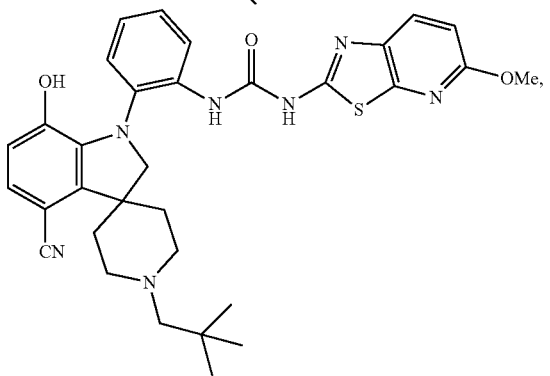
248
-continued
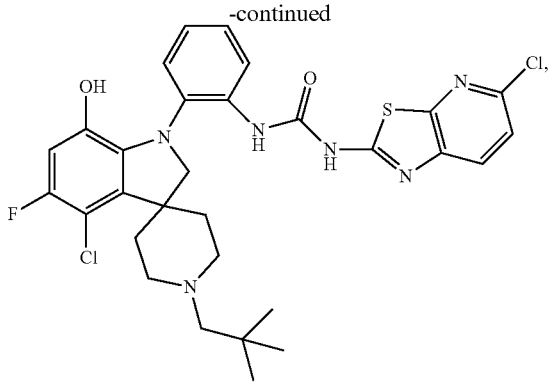
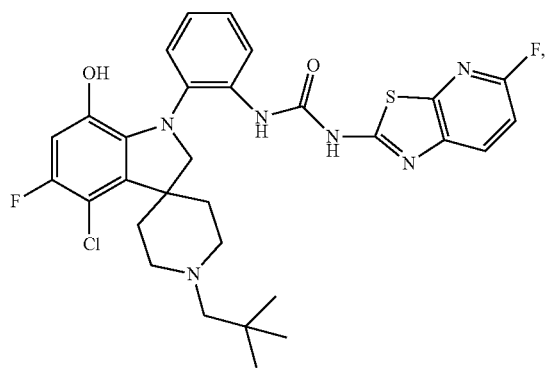
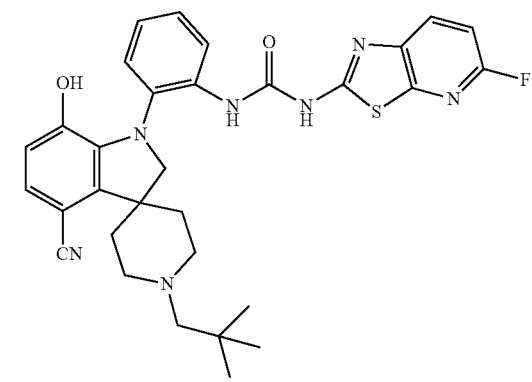
or a stereoisomer, a tautomer, or a pharmaceutically acceptable salt thereof.
2. A pharmaceutical composition, comprising a pharmaceutically acceptable carrier and a compound of claim 1.
* * * * *